US011981897B2

(12) United States Patent
Freier

(10) Patent No.: US 11,981,897 B2
(45) Date of Patent: May 14, 2024

(54) COMPOUNDS AND METHODS FOR MODULATION OF DYSTROPHIA MYOTONICA-PROTEIN KINASE (DMPK) EXPRESSION

(71) Applicant: Ionis Pharmaceuticals, Inc., Carlsbad, CA (US)

(72) Inventor: Susan M. Freier, San Diego, CA (US)

(73) Assignee: Ionis Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 17/173,139

(22) Filed: Feb. 10, 2021

(65) Prior Publication Data

US 2021/0403916 A1 Dec. 30, 2021

Related U.S. Application Data

(63) Continuation of application No. 16/167,783, filed on Oct. 23, 2018, now Pat. No. 10,954,519, which is a continuation of application No. 14/911,248, filed as application No. PCT/US2014/050481 on Aug. 11, 2014, now abandoned.

(60) Provisional application No. 61/889,337, filed on Oct. 10, 2013, provisional application No. 61/864,439, filed on Aug. 9, 2013.

(51) Int. Cl.
*C12N 15/113* (2010.01)

(52) U.S. Cl.
CPC .. *C12N 15/1137* (2013.01); *C12Y 207/11001* (2013.01); *C12N 2310/11* (2013.01); *C12N 2310/315* (2013.01); *C12N 2310/32* (2013.01); *C12N 2310/3231* (2013.01); *C12N 2310/3341* (2013.01); *C12N 2320/30* (2013.01)

(58) Field of Classification Search
CPC .............. C12N 15/113; C12N 2310/11; C12N 2310/315; C12N 2310/32; C12N 2310/3231; C12N 2310/3341
See application file for complete search history.

(56) References Cited

U.S. PATENT DOCUMENTS 3,687,808 A 8/1972 Merigan et al.
4,845,205 A 7/1989 Huynh Dinh et al.
5,034,506 A 7/1991 Summerton et al.
5,130,302 A 7/1992 Spielvogel et al.
5,134,066 A 7/1992 Rogers et al.
5,166,315 A 11/1992 Summerton et al.
5,175,273 A 12/1992 Bischofberger et al.
5,185,444 A 2/1993 Summerton et al.
5,367,066 A 11/1994 Urdea et al.
5,432,272 A 7/1995 Benner
5,434,257 A 7/1995 Matteucci
5,457,187 A 10/1995 Gmelner et al.
5,459,255 A 10/1995 Cook et al.
5,484,908 A 1/1996 Froehler et al.
5,502,177 A 3/1996 Matteucci et al.
5,525,711 A 6/1996 Hawkins et al.
5,552,282 A 9/1996 College
5,552,540 A 9/1996 Haralambidis
5,587,469 A 12/1996 Cook et al.
5,594,121 A 1/1997 Froehler et al.
5,596,091 A 1/1997 Switzer
5,614,617 A 3/1997 Cook et al.
5,645,985 A 7/1997 Froehler et al.
5,646,269 A 7/1997 Matteucci
5,681,941 A 10/1997 Cook et al.
5,698,685 A 12/1997 Summerton et al.
5,750,692 A 5/1998 Cook et al.
5,763,588 A 6/1998 Matteucci et al.
5,801,154 A 9/1998 Baracchini et al.
5,830,653 A 11/1998 Froehler et al.
5,955,265 A 9/1999 Brook et al.
6,005,096 A 12/1999 Matteucci et al.
6,007,992 A 12/1999 Lin et al.
6,028,183 A 2/2000 Lin et al.
6,268,490 B1 7/2001 Imanishi et al.
6,329,501 B1 12/2001 Smith
6,525,191 B1 2/2003 Ramasamy
6,582,908 B2 6/2003 Fodor et al.
6,670,461 B1 12/2003 Wengel et al.
6,770,748 B2 8/2004 Imanishi et al.
6,794,499 B2 9/2004 Wengel et al.
7,034,133 B2 4/2006 Wengel et al.
(Continued)

FOREIGN PATENT DOCUMENTS

WO 1991004753 A1 4/1991
WO WO 1999/014226 3/1999
(Continued)

OTHER PUBLICATIONS

Bennett et al., "RNA Targeting Therapeutics: Molecular Mechanisms of Antisense Oligonucleotides as a Therapeutic Platform" Ann Rev Pharmacol Toxicol (2010) 50: 259-293.
Cenik et al., "Argonaute proteins" Current Biology (2011) 21: R446-R449.
Doucet et al., "RNA-based gene therapy for myotonic dystrophy type 1 (DM1)" Abstract 150 for the Ottawa Conference on New Directions in Biology & Disease of Skeleta (May 5-8, 2010) Ottawa, Canada, 6 pages.
European Search Report for application EP 21187583.6 dated Jun. 22, 2022, 28 pages.
Furling et al., "Therapeutic RNA strategies for myotonic dystrophy with CTG repeats" Abstract for Nucleotide Repeat Expansion Disorders I: Poster Presentations (2004) Neuromuscular Disorders 14, 2 pages.
(Continued)

*Primary Examiner* — Brian Whiteman
(74) *Attorney, Agent, or Firm* — McNeill Baur PLLC

(57) ABSTRACT

Provided herein are methods, compounds, and compositions for reducing expression of a DMPK mRNA and protein in an animal. Also provided herein are methods, compounds, and compositions for preferentially reducing CUGexp DMPK RNA, reducing myotonia or reducing spliceopathy in an animal. Such methods, compounds, and compositions are useful to treat, prevent, delay, or ameliorate type 1 myotonic dystrophy, or a symptom thereof.

26 Claims, No Drawings

Specification includes a Sequence Listing.

(56) References Cited

U.S. PATENT DOCUMENTS

| | | | | |
|---|---|---|---|---|
| 7,053,207 | B2 | 5/2006 | Wengel | |
| 7,208,174 | B2 | 4/2007 | Huwyler et al. | |
| 7,374,927 | B2 | 5/2008 | Palma et al. | |
| 7,399,845 | B2 | 7/2008 | Seth et al. | |
| 7,427,672 | B2 | 9/2008 | Imanishi et al. | |
| 7,973,019 | B1 | 7/2011 | Chatterton et al. | |
| 8,158,354 | B2 | 4/2012 | Sarkar | |
| RE44,779 | E | 2/2014 | Imanishi et al. | |
| 9,012,421 | B2 | 4/2015 | Migawa et al. | |
| 9,592,250 | B2 | 3/2017 | Woolf et al. | |
| 9,765,338 | B2 * | 9/2017 | Bennett | A61P 25/14 |
| 10,954,519 | B2 * | 3/2021 | Swayze | A61P 21/02 |
| 2001/0053519 | A1 | 12/2001 | Fodor et al. | |
| 2003/0158403 | A1 | 8/2003 | Manoharan et al. | |
| 2003/0207804 | A1 | 11/2003 | Manoharan et al. | |
| 2003/0228597 | A1 | 12/2003 | Cowsert et al. | |
| 2004/0147023 | A1 | 7/2004 | Crooke et al. | |
| 2004/0171570 | A1 | 9/2004 | Allerson et al. | |
| 2004/0241651 | A1 | 12/2004 | Olek et al. | |
| 2005/0019746 | A1 | 1/2005 | Seery et al. | |
| 2005/0075306 | A1 | 4/2005 | Schreiber et al. | |
| 2005/0130923 | A1 | 6/2005 | Bhat et al. | |
| 2007/0031844 | A1 | 2/2007 | Khvorova et al. | |
| 2007/0031940 | A1 | 2/2007 | Van Rompaey et al. | |
| 2007/0134697 | A1 | 6/2007 | Khvorova et al. | |
| 2007/0287831 | A1 | 12/2007 | Seth et al. | |
| 2008/0015158 | A1 | 1/2008 | Ichiro et al. | |
| 2008/0039618 | A1 | 2/2008 | Allerson et al. | |
| 2008/0242629 | A1 | 10/2008 | Crooke et al. | |
| 2010/0016215 | A1 | 1/2010 | Moulton et al. | |
| 2010/0047289 | A1 | 2/2010 | Fakhari et al. | |
| 2010/0190837 | A1 | 7/2010 | Migawa et al. | |
| 2011/0229880 | A1 | 9/2011 | Wood et al. | |
| 2013/0059902 | A1 | 3/2013 | Corey et al. | |
| 2013/0225659 | A1 | 8/2013 | Bennett | |
| 2013/0237585 | A1 | 9/2013 | Bennett et al. | |
| 2015/0099791 | A1 * | 4/2015 | Krieg | C12N 15/113 530/300 |
| 2015/0191727 | A1 | 7/2015 | Migawa et al. | |
| 2016/0068845 | A1 | 3/2016 | Bennett et al. | |
| 2016/0304877 | A1 | 10/2016 | Swayze et al. | |
| 2019/0276832 | A1 | 9/2019 | Swayze et al. | |
| 2021/0052631 | A1 | 2/2021 | Prakash et al. | |
| 2023/0114429 | A1 | 4/2023 | Rigo et al. | |
| 2023/0174987 | A1 | 6/2023 | Bennett et al. | |

FOREIGN PATENT DOCUMENTS

| | | | |
|---|---|---|---|
| WO | WO 2000/058332 | | 10/2000 |
| WO | WO 2001/019161 | | 3/2001 |
| WO | WO 2002/001953 | | 1/2002 |
| WO | WO 2003/013437 | | 2/2003 |
| WO | WO 2004/028458 | | 4/2004 |
| WO | WO 2004/093783 | | 11/2004 |
| WO | WO 2004/106356 | | 12/2004 |
| WO | 2005116204 | A1 | 12/2005 |
| WO | WO 2005/121368 | | 12/2005 |
| WO | WO 2006/034348 | | 3/2006 |
| WO | WO 2007/089584 | | 8/2007 |
| WO | WO 2007/089611 | | 8/2007 |
| WO | WO 2007/121272 | | 10/2007 |
| WO | WO 2007/134181 | | 11/2007 |
| WO | WO 2008/018795 | | 2/2008 |
| WO | WO 2008/036406 | | 3/2008 |
| WO | WO 2008/049085 | | 4/2008 |
| WO | WO 2008/150729 | | 12/2008 |
| WO | WO 2008/154401 | | 12/2008 |
| WO | WO 2009/006478 | | 1/2009 |
| WO | WO 2009/099326 | | 8/2009 |
| WO | WO 2010/014592 | | 2/2010 |
| WO | 2010029303 | A1 | 3/2010 |
| WO | WO 2010/115993 | | 10/2010 |
| WO | WO 2011/097388 | | 8/2011 |
| WO | WO 2011/097641 | | 8/2011 |
| WO | 2011113889 | A1 | 9/2011 |
| WO | WO 2012/012443 | | 1/2012 |
| WO | WO 2012/012467 | | 1/2012 |
| WO | 2013173637 | A1 | 11/2013 |
| WO | 2014120861 | A2 | 8/2014 |
| WO | 2023034868 | A1 | 3/2023 |
| WO | 2023034870 | A2 | 3/2023 |

OTHER PUBLICATIONS

Furling et al., “Viral vector producing antisense RNA restores myotonic dystrophy myoblast functions” Gene Ther (2003) 10: 795-802.

Gagnon et al., “RNAi Factors are Present and Active in Human Cell Nuclei” Cell Rep (2014) 6: 211-221.

GenBank Accession No. NT_011109.16, 6 pages.

International Search Report for application PCT/US22/075768 dated Jan. 17, 2023, 13 pages.

Koshelev et al., “Therapeutic application for a cell culture model of myotonic dystrophy” Abstract 130 for New Directions in Biology & Disease of Skeletal Muscle (Apr. 27-30, 2008) New Orleans, 10 pages.

Kurreck et al., “Antisense technologies” Eur J Biochem (2003) 270: 1628-1644.

Langlois et al., “Cytoplasmic and Nuclear Retained DMPK mRNAs Are Targets for RNA Interference in Myotonic Dystrophy Cells” J Biol Chem (2005) 280: 16949-16954.

Langlois et al., “Hammerhead Ribozyme-Mediated Destruction of Nuclear Foci in Myotonic Dystrophy Myoblasts” Mol Ther (2003) 7: 670-680.

Langlois et al., “Ribozyme and Antisense RNA-Based Gene Therapies for Myotonic Dystrophy” Mol Ther (2003) 7:S320, 1 page.

Mignon et al., “Update on IONIS-DMPKRx Program” MDF Annual Conference (Sep. 14-15, 2018) Nashville, TN, 22 pages.

Monia et al., “Evaluation of 2'-Modified Oligonucleotides Containing 2'-Deoxy Gaps as Antisense Inhibitors of Gene Expression” J of Biol Chem (1993) 268: 14514-14522.

Mulders et al., “Molecular therapy in myotonic dystrophy: focus on RNA gain-of-function” Human Mol Genetics (2010) 19: R90-R97.

Partial Search Report for application EP 21187583.6 dated Mar. 21, 2022, 30 pages.

Sato et al., “In vivo gene delivery to tumor cells by transferrin-streptavidin-DNA conjugate” FASEB J (2000) 14:2108-2118.

Scanlon et al., “Anti-Genes: siRNA, Ribozymes and Antisense” Curr Pharma Biotech (2004) 56: 415-420.

Scherr et al., “Detection of Antisense and Ribozyme Accessible Sites on Native mRNAs: Application to NCOA3 mRNA” Mol Ther (2001) 4: 454-460.

Stein “The experimental use of antisense oligonucleotides: a guide for the perplexed” J Clin Invest (2001) 108:641-644.

Vickers et al., “Efficient Reduction of Target RNAs by Small Interfering RNA and Rnase H-dependent Antisense Agents” J Biol Chem (2003) 278: 7108-7118.

Wheeler et al., “Myotonic Dystrophy: Therapeutic Strategies for the Future” Neurotherapeutics: J Am Soc Exp Neurotherapeutics (2008) 5: 592-600.

International Search Report for PCT/US22/075772 dated Feb. 23, 2023, 13 pages.

GenBank NCBI Ref. No. XM_035463770.1, 2 pages.

GenBank NCBI Ref. No. XM_051814311.1, 2 pages.

Albaek et al., “Bi- and Tricyclic Nucleoside Derivatives Restricted in S-Type Conformations and Obtained by RCM-Reactions” Nucleosides, Nucleotides & Nucleic Acids (2003) 22(5-8):723-725.

Altmann et al., “Second Generation of Antisense Oligonucleotides: From Nuclease Resistance to Biological Efficacy in Animals” Chimia (1996) 50:168-176.

Altmann et al., “Second-generation antisense oligonucleotides: structure-activity relationships and the design of improved signal-transduction inhibitors” Biochem. Soc. Trans. (1996) 24:630-637.

Altmann et al., “Second Generation Antisense Oligonucleotides—Inhibition of PKC-a and c-RAF Kinase Expression by Chimeric Oligonucleotides Incorporating 6'-Subsituted Carbocyclic Nucleosides

(56) References Cited

OTHER PUBLICATIONS and 2'-O-Ethylene Glycol Substituted Ribonucleosides" Nucleosides & Nucleotides (1997) 16(7-9):917-926.
Aronin et al., "Expanded CAG repeats in the crosshairs" Nature Biotechnology (2009) 27(5): 451-452.
Ascoli et al., "Identification of a novel nuclear domain" J. Cell Biol. (1991) 112(5):785-795.
Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18):11944-12000.
Ballantyne et al., "Locked nucleic acids in PCR primers increase sensitivity and performance" Genomics (2008) 91: 301-305.
Braasch et al., "Locked nucleic acid (LNA): fine-tuning the recognition of DNA and RNA" Chem. Biol. (2001) 8:1-7.
Branch et al., "A good antisense molecule is hard to find," TIBS (1998) 23:45-50.
Brook et al., "Molecular basis of myotonic dystrophy: Expansion of a trinucleotide (CTG) repeat at the 3' end of a transcript encoding a protein kinase family member" Cell (1992) 68(4):799-808.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Cho et al., "Myotonic dystrophy: Emerging mechanisms for DM1 and DM2" Biochemica et Biophysica Acta (2007) 1772: 195-204.
Cleary et al., "The contribution of cis-elements to disease-associated repeat instability: clinical and experimental evidence" Cytogenet. Genome Res. (2003) 100:25-55.
Clemson et al., "An Architectural Role for a Nuclear Noncoding RNA: NEAT1 RNA Is Essential for the Structure of Paraspeckles" Mol. Cell (2009) 33:717-726.
Conte et al., "Conformational properties and thermodynamics of the RNA duplex r(CGCAAAUUUGCG)2: comparison with the DNA analogue d(CGCAAATTTGCG)2" Nucleic Acids Res. (1997) 25(13):2627-2634.
Cooper, "RNA and Disease" Cell (2009) 136:777-793.
Costa, "Non-coding RNAs and new opportunities for the private secotr" Drug Discovery today (2009) 14:446-452.
Cremer et al., "Chromosome Territories, Interchromatin Domain Compartment, and Nuclear Matrix: An Integrated View of the Functional Nuclear Architecture" Crit. Rev. Eukaroytic Gene Expr. (2000) 10:179-212.
Crooke et al., "Basic Principles of Antisense Therapeutics" Antisense Research and Application (1998) Chapter 1:1-50.
Davis et al., "Expansion of a CUG trinucleotide repeat in the 3 untranslated region of myotonic dystrophy protein kinase transcripts results in nuclear retention of transcripts" PNAS (1997) 94:7388-7393.
De Die-Smulders et al., "Age and causes of death in adult-onset myotonic dystrophy." *Brain* (1998) 121:1557-1563.
Denegri et al., "Human Chromosomes 9, 12, and 15 Contain the Nucleation Sites of Stress-Induced Nuclear Bodies" Mol. Biol. Cell (2002) 13:2069-2079.
Dong et al., "Implication of snoRNA U50 in human breast cancer" Journal of Genetics and Genomics (2009) 36(8): 447-454.
Doucas et al., "The PML nuclear compartment and cancer" Biochem. Biophys. Acta (1996) 1288(3):M25-M29.
Elayadi et al., "Application of PNA and LNA oligomers to chemotherapy" Curr. Opinion Invens. Drugs (2001) 2:558-561.
Englisch et al., "Chemically Modified Oligonucleotides as Probes and Inhibitors" Agnew Chem. Int. Ed. Engl. (1991) 30:613-629.
Fakan et al., "Ultrastructural Distribution of Nuclear Ribonucleoproteins as Visualized by Immunocytochemistry on Thin Sections" J. Cell Biol. (1984) 98:358-363.
Flanagan et al., "A cytosine analog that confers enhanced potency to antisense oligonucleotides" PNAS (1999) 96:3513-3518.
Fox et al., "P54nrb Forms a Heterodimer with PSP1 That Localizes to Paraspeckles in an RNA-dependent Manner" Mol. Biol. Cell (2005) 16:5304-5315.
Freier et al., "The ups and downs of nucleic acid duplex stability: structure-stability studies on chemically-modified DNA:RNA duplexes" Nucleic Acids Research (1997) 25(22): 4429-4443.
Frieden et al., "Expanding the design horizon of antisense oligonucleotides with alpha-L-LNA" Nucleic Acids Research (2003) 31(21):6365-6372.
Fu et al., "Factor required for mammalian spliceosome assembly is localized to discrete regions in the nucleus" Nature (1990) 343:437-441.
Galderisi et al., Biochem. Biophys. Res. Commun. (1996) 221(3):750-754.
Gautschi et al., "Activity of a Novel bcl-2/bcl-xL-Bispecific Antisense Oligonucleotide Against Tumors of Diverse Histologic Origins" J. Natl. Cancer Inst. (2001) 93:463-471.
Guo et al., "Inhibition of metastasis-associated lung adenocarcinoma transcript 1 in CaSki human cervical cancer cells suppresses cell proliferation and invasion" Acta Biochimica et Biophysica Sinica (2010) 42(3): 224-229.
Guttman et al., "Chromatin signature reveals over a thousand highly conserved large non-coding RNAs in mammals" Nature (2009) 458:223-227.
Hu et al., "Allele-specific silencing of mutant huntingtin and ataxin-3 genes by targeting expanded CAG repeats in mRNAs" Nature Biotechnology (2009) 27(5): 478-484.
Hu et al., "Allele-selective inhibition of mutant huntingtin by peptide nucleic acid-peptide conjugates, locked nucleic acid, and small interfering RNA" Annals of the New York Academy of Sciences (2009) 1175: 24-31.
Huang, "Review: Perinucleolar Structures" J. Struct. Biol. (2000) 129:233-240.
Ideue et al., "Efficient oligonucleotide-mediated degradation of nuclear noncoding RNAs in mammalian cultured cells" RNA (2009) 15(8): 1578-1587.
Ionis Pharmaceuticals, Inc. Press Release, Recently Published Preclinical Data Show Significant and Sustained Reduction of Muscle DMPK RNA with a Generation 2.5 Antisense Compound, Sep. 1, 2015, 1 Page.
Ji et al., "MALAT-1, a novel noncoding RNA, and thymosin b4 predict metastasis and survival in early-stage non-small cell lung cancer" Oncogene (2003) 22:8031-8041.
Jolly et al., "In vivo binding of active heat shock transcription factor 1 to human chromosome 9 heterochromatin during stress" J. Cell Biol. (2002) 156:775-781.
Kanadia et al., "Reversal of RNA missplicing and myotonia after muscleblind overexpression in a mouse poly(CUG) model for myotonic dystrophy" PNAS (2006) 103(31):11748-11753.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Krol et al., "Ribonuclease dicer cleaves triplet repeat hairpins into shorter repeats that silence specific targets" Molecular Cell (2007) 25:575-586.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Kurchavov et al., "A New Phosphoramidite Reagent for the Incorporation of Diazaphenoxazinone Nucleoside with Enhanced Base-Pairing Properties into Oligodeoxynucleotides" Nucleosides and Nucleotides (1997) 16)10 & 11):1837-1846.
Lavorgna et al., "In search of antisense" Trends Biochem. Sci. (2004) 29:88-94.
Lebedev at el., "Oligonucleotides containing 2-aminoadenine and 5-methylcytosine are more effective as primers for PCR amplification than their nonmodified counterparts," Genetic Analysis: Biomolecular Engineering (1996) 13:15-21.

(56) References Cited

OTHER PUBLICATIONS

Lee et al., "Targeted Degradation of Toxic RNA in Myotonic Dystrophy" p. 35, Abstracts of papers presented at the 2010 meeting on RNA & oligonucleotide therapeutics. Apr. 7-10, 2010.
Lehner et al., "Antisense transcripts in the human genome" Trends. Genet. (2002) 18:63-65.
Lesnik et al., "Relative Thermodynamic Stability of DNA, RNA, and DNA:RNA Hybried Duplexes: Relationship with Base Composition and Structure" Biochemistry (1995) 34:10807-10815.
Leumann, "DNA Analogues: From Supramolecular Principles to Biological Properties" Bioorg. & Med. Chem. (2002) 10:841-854.
Liang et al., "Efficient and specific knockdown of small non-coding RNAs in mammalian cells and in mice" Nucleic Acids Research (2010) 39(3): E13.
Lin et al., "Tricyclic 2'-Deoxycytidine Analogs: Synthesis and Incorporation into Oligodeoxynucleotides Which Have Enhanced Binding to Complementary RNA" J. Am. Chem. Soc. (1995) 117:3873-3874.
Lin et al., "A Cytosine Analogue Capable of Clamp-Like Binding to a Guanine in Helical Nucleic Acids" J. Am. Chem. Soc. (1998) 120:8531-8532.
Lin et al., "Failure of MBNL1-dependent post-natal splicing transitions in myotonic dystrophy" Human Mol. Genet. (2006) 15(13):2087-2097.
Liquori et al., "Myotonic Dystrophy Type 2 Caused by a CCTG Expansion in Intron 1 of ZNF9" Science (2001) 293:864-867.
Lolle, "Genome-wide non-mendelian inheritance of extra-genomic information in *Arabidopsis*" Nature (2005) 434:505-509.
Maher e tal., "Comparative hybrid arrest by tandem antisense oligodeoxyribonucleotides or oligodeoxyribonucleoside methylphosphonates in a cell-free system" Nuc. Acid. Res. (1988) 16:3341-3358.
Mankodi et al., "Expanding CUG Repeats Trigger Aberrant Splicing of CIC-1 Chloride Channel Pre-mRNA and Hyperexcitability of Skeletal Muscle in Myotonic Dystrophy" Mol. Cell. (2002) 10:35-44.
Martin, "Ein neuer Zugang zu 2'-O-Alkylribonucleosiden und Eigenschaften deren Oligonucleotide" Helv. Chim. Acta. (1995) 78:486-504.
Melone et al., "Antisense Oligonucleotides and Myotonin Gene Expression in C2 Mouse Cells" Antisense & Nucleic Acid Drug Development (1998) 8: 25-33.
Mercer et al., "Specific expression of long noncoding RNAs in the mouse brain" PNAS (2008) 105(2):716-721.
Miller et al., "Recruitment of human muscleblind proteins to (CUG)(n) expansions associated with myotonic dystrophy." EMBO J. (2000) 19:4439-4448.
Mouritzen et al., "ProbeLibrary: A new method for faster design and execution of quantitative real-time PCR" Nature Methods (2005) 2:313-317.
Mulders et al., "Triplet-repeat oligonucleotide-mediated reversal of RNA toxicity in myotonic dystrophy" Proceedings of the National Academy of Sciences (2009) 106: 13915-13928.
New England Biolabs 1998/1999 Catalog (cover page and pp. 121 and 284).
Noronha et al., "Amplimers with 1-15 3'-terminal phosphorothioate linkages resist degradation by Vent polymersase and reduce Taq polymerase mispriming," PCR Methods & Applicatio, Cold Spring Harbor Laboratory Press (1992) 2: 131-136.
Orum et al., "Locked nucleic acids: A promising molecular family for gene-function analysis and antisense drug development" Curr. Opinion Mol. Ther. (2001) 3:239-243.
O'Rourke, "Mechanisms of RNA-mediated Disease" J. Biol. Chem. (2009) 284(12):7419-7423.
Osborne et al., "RNA-dominant diseases." Hum Mol Genet. (2006) 15:R162-9.
Pandey et al., "Identification and Characterization of Modified Antisense Oligonucleotides Targeting DMPK in Mice and Nonhuman Primates for the Treatment of Myotonic Dystrophy Type 1," J Pharmacol Exp Ther (2015) 355: 329-340.
Peng et al., "The poly(A)-limiting element enhances mRNA accumulation by increasing the efficiency of pre-mRNA 3' processing" RNA (2005) 11:958-965.
Ploner et al., "Methodological obstacles in knocking down small noncoding RNAs" RNA (2009) 15(10):1797-1804.
Prasanth et al., "Regulating Gene Expression through RNA Nuclear Retention" Celll (2005) 123(2): 249-263.
Ranum et al., "RNA-mediated neuromuscular disorders." Annu Rev Neurosci (2006) 29:259-277.
Rassoulzadegan et al., "RNA-mediated non-mendelian inheritance of an epigenetic change in the mouse" Nature (2006) 441:469-474.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Sasaki et al., "MENε/β noncoding RNAs are essential for structural integrity of nuclear paraspeckles" PNAS (2009) 106(8):2525-2530.
Scholefield et al., "Therapeutic gene silencing strategies for polyglutamine disorders" Trends in Genetics (2010) 26(1): 29-38.
Searle et al., "On the stability of nucleic acid structures in solution: enthalpy-entropy compensations, internal rotations and reversibility" Nucleic Acids Res. (1993) 21:2051-2056.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Sunwoo et al., "MEN e/b nuclear-retained non-coding RNAs are up-regulated upon muscle differentiation and are essential components of paraspeckles" Genome Res. (2009) 19:347-359.
Swayze et al., "The Medicinal Chemistry of Oligonucleotides" in Antisense Drug Technology, 2nd Edition, Chapter 6, pp. 143-182, Crooke ed., 2008.
Thiry, "Birth of a nucleolus: the evolution of nucleolar compartments" Trends. Cell Biol. (2005) 15:194-199.
Van Der Burg et al., "Beyond the brain: widespread pathology in Huntington's disease", Lancet Neurology (2009) 8(8): 765-774.
Viegas et al., "Regulating the regulators: How ribonucleases dictate the rules in the control of small non-coding RNAs" RNA Biol. (2008) 5:230-243.
Wahlestedt et al., "Potent and nontoxic antisense oligonucleotide containing locked nucleic acids" Proc. Natl. Acad. Sci. USA (2000) 97: 5633-5638.
Wang et al., "Synthesis and binding property of an oligonucleotide containing tetraflurophenoxazine" Tetrahedron Lett. (1998) 39:8385-8388.
Watts e tal., "Chemically modified siRNAs: tools and applications" Drug Discovery Today (2008) 13(19-20):842-855.
Wheeler et al., "Reversal of RNA dominance by displacement of protein sequestered on triplet repeat RNA" Science (2009) 325:336-339.
Wheeler et al., "Myotonic dystrophy: RNA-mediated muscle disease." Curr Opin Neurol (2007) 20:572-576.
Wheeler et al., "Targeting Nuclear RNA for in vivo Correstoin of Myotonic Dystrophy," Nature (2012) 488:111-117.
Wilusz et al., "3' End Processing of a Long Nuclear-Retained Noncoding RNA Yields a tRNA-like Cytoplasmic RNA" Cell (2008) 135:919-932.
Woolf et al., "Specificity of antisense oligonucleotides in vivo" PNAS (1992) 89:7305-7309.
Yelin et al., "Widespread occurrence of antisense transcription in the human genome" Nat. Biotechnol. (2003) 21(4):379-386.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
European Seach Report for Application EP 16153949.9 dated May 11, 2016.

(56) References Cited

OTHER PUBLICATIONS

European Search Report for application EP 11740540.7 dated Aug. 19, 2014.
European Search Report for application EP 11810309.2 dated Aug. 19, 2014.
European Search Report for application EP 11810291.2 dated Feb. 4, 2014.
European Search Report for application EP 14834532.5 dated Feb. 20, 2017.
Partial Search Report for application EP 18199910.3 dated Apr. 11, 2019.
European Search Report for application EP 19191940.6 dated Jun. 26, 2020.
International Search Report for application PCT/US11/24099 dated Jun. 22, 2011.
International Search Report for application PCT/US11/44583 dated Mar. 1, 2012.
International Search Report for application PCT/US11/44555 dated Apr. 11, 2012.
International Search Report for application PCT/US14/050481 dated Feb. 2, 2015.
Henry et al., "Chemically modified oligonucleotides exhibit decreased immune stimulation in mice" J Pharmacol Exp Ther (2000) 292: 468-479.

* cited by examiner

SEQUENCE LISTING

```
<160> NUMBER OF SEQ ID NOS: 874

<210> SEQ ID NO 1
<211> LENGTH: 2877
<212> TYPE: DNA
<213> ORGANISM: homo sapiens

<400> SEQUENCE: 1

aggggggctg gaccaagggg tggggagaag gggaggaggc ctcggccggc cgcagagaga      60

agtggccaga gaggcccagg ggacagccag ggacaggcag acatgcagcc agggctccag     120

ggcctggaca ggggctgcca ggccctgtga caggaggacc ccgagccccc ggcccgggga     180

ggggccatgg tgctgcctgt ccaacatgtc agccgaggtg cggctgaggc ggctccagca     240

gctggtgttg gacccgggct tcctggggct ggagcccctg ctcgaccttc tcctgggcgt     300

ccaccaggag ctgggcgcct ccgaactggc ccaggacaag tacgtggccg acttcttgca     360
```

```
gtgggcggag cccatcgtgg tgaggcttaa ggaggtccga ctgcagaggg acgacttcga    420
gattctgaag gtgatcggac gcggggcgtt cagcgaggta gcggtagtga agatgaagca    480
gacgggccag gtgtatgcca tgaagatcat gaacaagtgg gacatgctga agaggggcga    540
ggtgtcgtgc ttccgtgagg agagggacgt gttggtgaat ggggaccggc ggtggatcac    600
gcagctgcac ttcgccttcc aggatgagaa ctacctgtac ctggtcatgg agtattacgt    660
gggcggggac ctgctgacac tgctgagcaa gtttggggag cggattccgg ccgagatggc    720
gcgcttctac ctggcggaga ttgtcatggc catagactcg gtgcaccggc ttggctacgt    780
gcacagggac atcaaacccg acaacatcct gctggaccgc tgtggccaca tccgcctggc    840
cgacttcggc tcttgcctca agctgcgggc agatggaacg gtgcggtcgc tggtggctgt    900
gggcacccca gactacctgt cccccgagat cctgcaggct gtgggcggtg ggcctgggac    960
aggcagctac gggcccgagt gtgactggtg ggcgctgggt gtattcgcct atgaaatgtt   1020
ctatgggcag acgcccttct acgcggattc cacggcggag acctatggca agatcgtcca   1080
ctacaaggag cacctctctc tgccgctggt ggacgaaggg gtccctgagg aggctcgaga   1140
cttcattcag cggttgctgt gtcccccgga gacacggctg ggccggggtg gagcaggcga   1200
cttccggaca catcccttct tctttggcct cgactgggat ggtctccggg acagcgtgcc   1260
cccctttaca ccggatttcg aaggtgccac cgacacatgc aacttcgact tggtggagga   1320
cgggctcact gccatggaga cactgtcgga cattcgggaa ggtgcgccgc taggggtcca   1380
cctgcctttt gtgggctact cctactcctg catggccctc agggacagtg aggtcccagg   1440
ccccacaccc atggaactgg aggccgagca gctgcttgag ccacacgtgc aagcgcccag   1500
cctggagccc tcggtgtccc cacaggatga aacagctgaa gtggcagttc cagcggctgt   1560
ccctgcggca gaggctgagg ccgaggtgac gctgcgggag ctccaggaag ccctggagga   1620
ggaggtgctc acccggcaga gcctgagccg ggagatggag gccatccgca cggacaacca   1680
gaacttcgcc agtcaactac gcgaggcaga ggctcggaac cgggacctag aggcacacgt   1740
ccggcagttg caggagcgga tggagttgct gcaggcagag ggagccacag ctgtcacggg   1800
ggtccccagt ccccgggcca cggatccacc ttcccatcta gatggccccc cggccgtggc   1860
tgtgggccag tgcccgctgg tggggccagg ccccatgcac cgccgccacc tgctgctccc   1920
tgccagggtc cctaggcctg gcctatcgga ggcgctttcc ctgctcctgt tcgccgttgt   1980
tctgtctcgt gccgccgccc tggctgcat tgggttggtg gcccacgccg gccaactcac   2040
cgcagtctgg cgccgcccag gagccgcccg cgctccctga accctagaac tgtcttcgac   2100
tccggggccc cgttggaaga ctgagtgccc ggggcacggc acagaagccg cgcccaccgc   2160
ctgccagttc acaaccgctc cgagcgtggg tctccgccca gctccagtcc tgtgatccgg   2220
gcccgccccc tagcggccgg ggagggaggg gccgggtccg cggccggcga acggggctcg   2280
aagggtcctt gtagccggga atgctgctgc tgctgctgct gctgctgctg ctgctgctgc   2340
tgctgctgct gctgctgctg ctgggggat cacagaccat ttctttcttt cggccaggct    2400
gaggccctga cgtggatggg caaactgcag gcctgggaag gcagcaagcc gggccgtccg   2460
tgttccatcc tccacgcacc cccacctatc gttggttcgc aaagtgcaaa gctttcttgt   2520
gcatgacgcc ctgctctggg gagcgtctgg cgcgatctct gcctgcttac tcgggaaatt   2580
tgcttttgcc aaacccgctt tttcggggat cccgcgcccc cctcctcact tgcgctgctc   2640
tcggagcccc agccggctcc gcccgcttcg gcggtttgga tatttattga cctcgtcctc   2700
```

-continued

```
cgactcgctg acaggctaca ggacccccaa caaccccaat ccacgttttg gatgcactga   2760

gaccccgaca ttcctcggta tttattgtct gtccccacct aggaccccca cccccgaccc   2820

tcgcgaataa aaggccctcc atctgcccaa aaaaaaaaaa aaaaaaaaaa aaaaaaa      2877
```

<210> SEQ ID NO 2
<211> LENGTH: 14411
<212> TYPE: DNA
<213> ORGANISM: homo sapiens

<400> SEQUENCE: 2

```
ctcccagccc agcgcctccc accccttttc atagcaggaa aagccggagc ccagggaggg     60

aacggacctg cgagtcacac aactggtgac ccacaccagc ggctggagca ggaccctctt    120

ggggagaaga gcatcctgcc cgcagccagg gcccctcatc aaagtcctcg gtgtttttta    180

aattatcaga actgcccagg accacgtttc ccaggccctg cccagctggg actcctcggt    240

ccttgcctcc tagtttctca ggcctggccc tctcaaggcc caggcacccc aggccggttg    300

gaggccccga cttccactct ggagaaccgt ccaccctgga aagaagagct cagattcctc    360

ttggctctcg gagccgcagg gagtgtgtct tcccgcgcca ccctccaccc cccgaaatgt    420

ttctgtttct aatcccagcc tgggcaggaa tgtggctccc cggccagggg ccaaggagct    480

attttggggt ctcgtttgcc cagggagggc ttggctccac cactttcctc ccccagcctt    540

tgggcagcag gtcacccctg ttcaggctct gagggtgccc cctcctggtc ctgtcctcac    600

cacccccttcc ccacctcctg ggaaaaaaaa aaaaaaaaaa aaaaaaagct ggtataaagc    660

agagagcctg agggctaaat ttaactgtcc gagtcggaat ccatctctga gtcacccaag    720

aagctgccct ggcctcccgt ccccttccca ggcctcaacc cctttctccc acccagcccc    780

aacccccagc cctcaccccc tagcccccag ttctggagct tgtcgggagc aaggggggtgg    840

ttgctactgg gtcactcagc ctcaattggc cctgtttcag caatgggcag gttcttcttg    900

aaattcatca cacctgtggc ttcctctgtg ctctaccttt ttattggggt gacagtgtga    960

cagctgagat tctccatgca ttccccctac tctagcactg aagggttctg aagggccctg   1020

gaaggaggga gcttgggggg ctggcttgtg aggggttaag gctgggaggc gggagggggg   1080

ctggaccaag gggtggggag aaggggagga ggcctcggcc ggccgcagag agaagtggcc   1140

agagaggccc aggggacagc cagggacagg cagacatgca gccagggctc cagggcctgg   1200

acaggggctg ccaggccctg tgacaggagg accccgagcc cccggcccgg ggaggggcca   1260

tggtgctgcc tgtccaacat gtcagccgag gtgcggctga ggcggctcca gcagctggtg   1320

ttggacccgg gcttcctggg gctggagccc ctgctcgacc ttctcctggg cgtccaccag   1380

gagctgggcg cctccgaact ggcccaggac aagtacgtgg ccgacttctt gcagtggggt   1440

gagtgcctac cctcggggct cctgcagatg gggtgggggt ggggcaggag acaggtctgg   1500

gcacagaggc ctggctgttg ggggggcagg atggcaggat gggcatgggg agatcctccc   1560

atcctggggc tcagagtgtg gacctgggcc ctggggcaac atttctctgt cctatgccac   1620

cactctggag gggcagagta aggtcagcag aggctagggt ggctgtgact cagagccatg   1680

gcttaggagt cacagcaggc taggctgcca acagcctccc atggcctctc tgcaccccgc   1740

ctcagggtca gggtcagggt catgctggga gctccctctc ctaggaccct ccccccaaaa   1800

gtgggctcta tggccctctc ccctggtttc ctgtggcctg gggcaagcca ggagggccag   1860

catggggcag ctgccagggg cgcagccgac aggcaggtgt tcggcgccag cctctccagc   1920

tgccccaaca ggtgcccagg cactgggagg gcggtgactc acgcgggccc tgtgggagaa   1980
```

-continued

```
ccagctttgc agacaggcgc caccagtgcc ccctcctctg cgatccagga gggacaactt   2040
tgggttcttc tgggtgtgtc tccttctttt gtaggttctg cacccacccc cacccccagc   2100
cccaaagtct cggttcctat gagccgtgtg ggtcagccac cattcccgcc accccgggtc   2160
cctgcgtcct ttagttctcc tggcccaggg cctccaacct tccagctgtc ccacaaaacc   2220
ccttcttgca agggctttcc agggcctggg gccagggctg gaaggaggat gcttccgctt   2280
ctgccagctg ccttgtctgc ccacctcctc cccaagccca ggactcgggc tcactggtca   2340
ctggtttctt tcattcccag caccctgccc ctctggccct catatgtctg gccctcagtg   2400
actggtgttt ggtttttggc ctgtgtgtaa caaactgtgt gtgacacttg tttcctgttt   2460
ctccgccttc ccctgcttcc tcttgtgtcc atctctttct gacccaggcc tggttccttt   2520
ccctcctcct cccatttcac agatgggaag gtggaggcca agaagggcca ggccattcag   2580
cctctggaaa aaccttctcc caacctccca cagcccctaa tgactctcct ggcctccctt   2640
tagtagagga tgaagttggg ttggcagggt aaactgagac cgggtggggt aggggtctgg   2700
cgctcccggg aggagcactc cttttgtggc ccgagctgca tctcgcggcc cctcccctgc   2760
caggcctggg gcgggggagg gggccagggt tcctgctgcc ttaaaagggc tcaatgtctt   2820
ggctctctcc tccctccccc gtcctcagcc ctggctggtt cgtccctgct ggcccactct   2880
cccggaaccc cccggaaccc ctctctttcc tccagaaccc actgtctcct ctccttccct   2940
cccctcccat acccatccct ctctccatcc tgcctccact tcttccaccc ccgggagtcc   3000
aggcctccct gtccccacag tccctgagcc acaagcctcc accccagctg gtcccccacc   3060
caggctgccc agtttaacat tcctagtcat aggaccttga cttctgagag gcctgattgt   3120
catctgtaaa taaggggtag gactaaagca ctcctcctgg aggactgaga gatgggctgg   3180
accggagcac ttgagtctgg gatatgtgac catgctacct ttgtctccct gtcctgttcc   3240
ttcccccagc cccaaatcca gggttttcca aagtgtggtt caagaaccac ctgcatctga   3300
atctagaggt actggataca accccacgtc tgggccgtta cccaggacat tctacatgag   3360
aacgtggggg tggggccctg gctgcacctg aactgtcacc tggagtcagg gtggaaggtg   3420
gaagaactgg gtcttatttc cttctcccct tgttctttag ggtctgtcct tctgcagact   3480
ccgttacccc accctaacca tcctgcacac ccttggagcc ctctgggcca atgccctgtc   3540
ccgcaaaggg cttctcaggc atctcacctc tatgggaggg catttttggc ccccagaacc   3600
ttacacggtg tttatgtggg gaagcccctg ggaagcagac agtcctaggg tgaagctgag   3660
aggcagagag aaggggagac agacagaggg tggggctttc cccctgtct ccagtgccct    3720
ttctggtgac cctcggttct tttcccccac caccccccca gcggagccca tcgtggtgag   3780
gcttaaggag gtccgactgc agagggacga cttcgagatt ctgaaggtga tcggacgcgg   3840
ggcgttcagc gaggtaagcc gaaccgggcg ggagcctgac ttgactcgtg gtgggcgggg   3900
catagggggtt ggggcggggc cttagaaatt gatgaatgac cgagccttag aacctagggc  3960
tgggctggag gcggggcttg ggaccaatgg gcgtggtgtg gcaggtgggg cggggccacg   4020
gctgggtgca gaagcgggtg gagttgggtc tgggcgagcc cttttgtttt cccgccgtct   4080
ccactctgtc tcactatctc gacctcaggt agcggtagtg aagatgaagc agacgggcca   4140
ggtgtatgcc atgaagatca tgaacaagtg ggacatgctg aagaggggcg aggtgagggg   4200
ctgggcggac gtggggggct ttgaggatcc gcgccccgtc tccggctgca gctcctccgg   4260
gtgccctgca ggtgtcgtgc ttccgtgagg agagggacgt gttggtgaat ggggaccggc   4320
```

-continued

```
ggtggatcac gcagctgcac ttcgccttcc aggatgagaa ctacctggtg agctccgggc   4380
cggggtgact aggaagaggg acaagagccc gtgctgtcac tggacgagga ggtggggaga   4440
ggaagctcta ggattggggg tgctgcccgg aaacgtctgt gggaaagtct gtgtgcggta   4500
agagggtgtg tcaggtggat gaggggcctt ccctatctga gacggggatg gtgtccttca   4560
ctgcccgttt ctggggtgat ctgggggact cttataaaga tgtctctgtt gcggggggtc   4620
tcttacctgg aatgggatag gtcttcagga attctaacgg ggccactgcc tagggaagga   4680
gtgtctggga cctattctct gggtgttggg tggcctctgg gttctctttc ccagaacatc   4740
tcagggggag tgaatctgcc cagtgacatc ccaggaaagt ttttttgttt gtgttttttt   4800
ttgaggggcg ggggcggggg ccgcaggtgg tctctgattt ggcccggcag atctctatgg   4860
ttatctctgg gctggggctg caggtctctg cccaaggatg gggtgtctct gggaggggtt   4920
gtcccagcca tccgtgatgg atcagggcct caggggacta ccaaccaccc atgacgaacc   4980
ccttctcagt acctggtcat ggagtattac gtgggcgggg acctgctgac actgctgagc   5040
aagtttgggg agcggattcc ggccgagatg gcgcgcttct acctggcgga gattgtcatg   5100
gccatagact cggtgcaccg gcttggctac gtgcacaggt gggtgcagca tggccgaggg   5160
gatagcaagc ttgttccctg gccgggttct tggaaggtca gagcccagag aggccagggc   5220
ctggagaggg accttcttgg ttggggccca ccggggggtg cctgggagta ggggtcagaa   5280
ctgtagaagc cctacagggg cggaacccga ggaagtgggg tcccaggtgg cactgcccgg   5340
aggggcggag cctggtggga ccacagaagg gaggttcatt tatcccaccc ttctcttttc   5400
ctccgtgcag ggacatcaaa cccgacaaca tcctgctgga ccgctgtggc cacatccgcc   5460
tggccgactt cggctcttgc ctcaagctgc gggcagatgg aacggtgagc cagtgccctg   5520
gccacagagc aactggggct gctgatgagg gatggaaggc acagagtgtg ggagcgggac   5580
tggatttgga ggggaaaaga ggtggtgtga cccaggctta agtgtgcatc tgtgtggcgg   5640
agtattagac caggcagagg gaggggctaa gcatttgggg agtggttgga aggagggccc   5700
agagctggtg ggcccagagg ggtgggccca agcctcgctc tgctcctttt ggtccaggtg   5760
cggtcgctgg tggctgtggg caccccagac tacctgtccc ccgagatcct gcaggctgtg   5820
ggcggtgggc ctgggacagg cagctacggg cccgagtgtg actggtgggc gctgggtgta   5880
ttcgcctatg aaatgttcta tgggcagacg cccttctacg cggattccac ggcggagacc   5940
tatggcaaga tcgtccacta caaggtgagc acggccgcag ggagacctgg cctctcccgg   6000
taggcgctcc caggctatcg cctcctctcc ctctgagcag gagcacctct ctctgccgct   6060
ggtggacgaa ggggtccctg aggaggctcg agacttcatt cagcggttgc tgtgtccccc   6120
ggagacacgg ctgggccggg gtggagcagg cgacttccgg acacatccct tcttctttgg   6180
cctcgactgg gatggtctcc gggacagcgt gccccccttt acaccggatt tcgaaggtgc   6240
caccgacaca tgcaacttcg acttggtgga ggacgggctc actgccatgg tgagcggggg   6300
cggggtaggt acctgtggcc cctgctcggc tgcgggaacc tccccatgct ccctccataa   6360
agttggagta aggacagtgc ctaccttctg ggtcctgaa tcactcattc cccagagcac    6420
ctgctctgtg cccatctact actgaggacc cagcagtgac ctagacttac agtccagtgg   6480
gggaacacag agcagtcttc agacagtaag gccccagagt gatcagggct gagacaatgg   6540
agtgcagggg gtgggggact cctgactcag caaggaaggt cctggagggc tttctggagt   6600
ggggagctat ctgagctgag acttggaggg atgagaagca ggagaggact cctcctccct   6660
taggccgtct ctcttcaccg tgtaacaagc tgtcatggca tgcttgctcg gctctgggtg   6720
```

-continued

```
ccctttgct gaacaatact ggggatccag cacggaccag atgagctctg gtccctgccc   6780
tcatccagtt gcagtctaga gaattagaga attatggaga gtgtggcagg tgccctgaag   6840
ggaagcaaca ggatacaaga aaaaatgatg gggccaggca cggtggctca cgcctgtaac   6900
cccagcaatt tggcaggccg aagtgggtgg attgcttgag cccaggagtt cgagaccagc   6960
ctgggcaatg tggtgagacc cccgtctcta caaaaatgtt ttaaaaattg gttgggcgtg   7020
gtggcgcatg cctgtatact cagctactag ggtggccgac gtgggcttga gcccaggagg   7080
tcaaggctgc agtgagctgt gattgtgcca ctgcactcca gcctgggcaa cggagagaga   7140
ctctgtctca aaaataagat aaactgaaat taaaaaatag gctgggctgg ccgggcgtgg   7200
tggctcacgc ctgtaatctc agcactttgg gaggccgagg cgggtggatc acgaggtcag   7260
gagatcgaga ccatcttggc taacacggtg aaaccccatc tctcctaaaa atacaaaaaa   7320
ttagccaggc gtggtggcgg gcgcctgtag tcccagctac tcaggaggct gaggcaggag   7380
aatggcgtga acccgggagg cagagtttgc agtgagccga gatcgtgcca ctgcactcca   7440
gcctgggcga cagagcgaga ctctgtctca gaaaaaaaaa aaaaaaaaaa aaaaaatagg   7500
ctggaccgcg gccgggcgct gtggctcatg cctgtaatcc cagcactttg ggagtccaag   7560
gccggtgggt catgagatca ggagttttga gactaggctg gccaacacgg tgaaaccccg   7620
tctctactaa aaatacaaga aaattagctg ggtgtggtct cgggtgcctg taattccagt   7680
tactggggaa gctgaggcag gagaattgct tgaacctggg aggcagagtt tgcagtgagc   7740
caagatcatg ccactacact ccagtctggg tgacagagtg agactctgtc tcaaaaaaaa   7800
aaaaaaaaaa aagggttggg caaggtggtt cacgcctgta atcccagaac tttgggaggc   7860
tgaggcaggc agatcactgg aagtcaggag ttcaagacca gcctggccaa catggtgaaa   7920
ccctgtgtct actaaaaata caaaatttag ccaggcttgg tggcgtatgc ctgtaatgcc   7980
agctactcag gaggctgagg caggagaatc gcttgattga acctgggagg cagagtttgc   8040
agtgggctgg ggttgtgcca ctgcactcta ggctgggaga cagcaagact ccatctaaaa   8100
aaaaaaaaca gaactgggct gggcacagtg gcttatattt gtaatcccag cactttggga   8160
ggctgaggtt ggaggactgc ttgagcccag agtttgggac tacaacagct gaggtaggcg   8220
gatcacttga ggtcagaaga tggagaccag cctggccagc gtggcgaaac cccgtctcta   8280
ccaaaaatat aaaaaattag ccaggcgtgg tagagggcgc ctgtaatctc agctactcag   8340
gacgctgagg caggagaatc gcctgaacct gggaggcgga ggttgcagtg agctgagatt   8400
gcaccactgc actccagcct gggtaacaga gcgagactcc gtatcaaaga aaaagaaaaa   8460
agaaaaaatg ctggaggggc cactttagat aagccctgag ttggggctgg tttgggggga   8520
acatgtaagc caagatcaaa aagcagtgag ggcccgccc tgacgactgc tgctcacatc   8580
tgtgtgtctt gcgcaggaga cactgtcgga cattcgggaa ggtgcgccgc taggggtcca   8640
cctgcctttt gtgggctact cctactcctg catggccctc aggtaagcac tgccctggac   8700
ggcctccagg ggccacgagg ctgcttgagc ttcctgggtc ctgctccttg gcagccaatg   8760
gagttgcagg atcagtcttg gaaccttact gttttgggcc caaagactcc taagaggcca   8820
gagttggagg accttaaatt ttcagatcta tgtacttcaa aatgttagat tgaattttaa   8880
aacctcagag tcacagactg ggcttcccag aatcttgtaa ccattaactt ttacgtctgt   8940
agtacacaga gccacaggac ttcagaactt ggaaaatatg aagtttagac ttttacaatc   9000
agttgtaaaa gaatgcaaat tctttgaatc agccatataa caataaggcc atttaaaagt   9060
```

```
attaatttag gcgggccgcg gtggctcacg cctgtaatcc tagcactttg ggaggccaag   9120
gcaggtggat catgaggtca ggagatcgag accatcctgg ctaacacggt gaaaccccgt   9180
ctctactaaa aatacaaaaa aattagccgg gcatggtggc gggcgcttgc ggtcccagct   9240
acttgggagg cgaggcagga gaatggcatg aacccgggag gcggagcttg cagtgagccg   9300
agatcatgcc actgcactcc agcctgggcg acagagcaag actccgtctc aaaaaaaaaa   9360
aaaaaaaagt atttatttag gccgggtgtg gtggctcacg cctgtaattc cagtgctttg   9420
ggaggatgag gtgggtggat cacctgaggt caggagttcg agaccagcct gaccaacgtg   9480
gagaaacctc atctctacta aaaaacaaaa ttagccaggc gtggtggcat atacctgtaa   9540
tcccagctac tcaggaggct gaggcaggag aatcagaacc caggaggggg aggttgtggt   9600
gagctgagat cgtgccattg cattccagcc tgggcaacaa gagtgaaact tcatctcaaa   9660
aaaaaaaaaa aaaaagtact aatttacagg ctgggcatgg tggctcacgc ttggaatccc   9720
agcactttgg gaggctgaag tggacggatt gcttcagccc aggagttcaa gaccagcctg   9780
agcaacataa tgagaccctg tctctacaaa aaattgaaaa aatcgtgcca ggcatggtgg   9840
tctgtgcctg cagtcctagc tactcaggag tctgaagtag gagaatcact tgagcctgga   9900
gtttgaggct tcagtgagcc atgatagatt ccagcctagg caacaaagtg agacctggtc   9960
tcaacaaaag tattaattac acaaataatg cattgcttat cacaagtaaa ttagaaaata  10020
cagataagga aaaggaagtt gatatctcgt gagctcacca gatggcagtg gtccctggct  10080
cacacgtgta ctgacacatg tttaaatagt ggagaacagg tgtttttttg gtttgttttt  10140
ttccccttcc tcatgctact ttgtctaaga gaacagttgg ttttctagtc agcttttatt  10200
actggacaac attacacata ctatacctta tcattaatga actccagctt gattctgaac  10260
cgctgcgggg cctgaacggt gggtcaggat tgaacccatc ctctattaga acccaggcgc  10320
atgtccagga tagctaggtc ctgagccgtg ttcccacagg agggactgct gggttggagg  10380
ggacagccac ttcatacccc agggaggagc tgtccccttc ccacagctga gtggggtgtg  10440
ctgacctcaa gttgccatct tggggtccca tgcccagtct taggaccaca tctgtggagg  10500
tggccagagc caagcagtct ccccatcagg tcggcctccc tgtcctgagg ccctgagaag  10560
aggggtctgc agcggtcaca tgtcaaggga ggagatgagc tgaccctaga acatgggggt  10620
ctggacccca agtccctgca gaaggtttag aaagagcagc tcccaggggc ccaaggccag  10680
gagaggggca gggcttttcc taagcagagg aggggctatt ggcctacctg ggactctgtt  10740
ctcttcgctc tgctgctccc cttcctcaaa tcaggaggtc ttggaagcag ctgcccctac  10800
ccacaggcca gaagttctgg ttctccacca gagaatcagc attctgtctc cctccccact  10860
ccctcctcct ctccccaggg acagtgaggt cccaggcccc acacccatgg aactggaggc  10920
cgagcagctg cttgagccac acgtgcaagc gcccagcctg gagccctcgg tgtccccaca  10980
ggatgaaaca gtaagttggt ggaggggagg gggtccgtca gggacaattg ggagagaaaa  11040
ggtgagggct tcccgggtgg cgtgcactgt agagccctct agggacttcc tgaacagaag  11100
cagacagaaa ccacggagag acgaggttac ttcagacatg ggacggtctc tgtagttaca  11160
gtggggcatt aagtaagggt gtgtgtgttg ctggggatct gagaagtcga tctttgagct  11220
gagcgctggt gaaggagaaa caagccatgg aaggaaaggt gccaagtggt caggcgagag  11280
cctccagggc aaaggccttg ggcaggtggg aatcctgatt tgttcctgaa aggtagtttg  11340
gctgaatcat tcctgagaag gctggagagg ccagcaggaa acaaaaccca gcaaggcctt  11400
ttgtcgtgag ggcattaggg agctggaggg attttgagca gcagagggac ataggttgtg  11460
```

ttagtgtttg agcaccagcc ctctggtccc tgtgtagatt tagaggacca gactcaggga 11520
tggggctgag ggaggtaggg aagggagggg gcttggatca ttgcaggagc tatggggatt 11580
ccagaaatgt tgaggggacg gaggagtagg ggataaacaa ggattcctag cctggaacca 11640
gtgcccaagt cctgagtctt ccaggagcca caggcagcct taagcctggt ccccatacac 11700
aggctgaagt ggcagttcca gcggctgtcc ctgcggcaga ggctgaggcc gaggtgacgc 11760
tgcgggagct ccaggaagcc ctggaggagg aggtgctcac ccggcagagc ctgagccggg 11820
agatggaggc catccgcacg gacaaccaga acttcgccag gtcgggatcg gggccggggc 11880
cggggccggg atgcgggccg gtggcaaccc ttggcatccc ctctcgtccg gcccggacgg 11940
actcaccgtc cttacctccc cacagtcaac tacgcgaggc agaggctcgg aaccgggacc 12000
tagaggcaca cgtccggcag ttgcaggagc ggatggagtt gctgcaggca gagggagcca 12060
caggtgagtc cctcatgtgt ccccttcccc ggaggaccgg gaggaggtgg gccgtctgct 12120
ccgcggggcg tgtatagaca cctggaggag ggaagggacc cacgctgggg cacgccgcgc 12180
caccgccctc cttcgcccct ccacgcgccc tatgcctctt tcttctcctt ccagctgtca 12240
cgggggtccc cagtccccgg gccacggatc caccttccca tgtaagaccc ctctctttcc 12300
cctgcctcag acctgctgcc cattctgcag atcccctccc tggctcctgg tctccccgtc 12360
cagatatagg gctcacccta cgtctttgcg actttagagg gcagaagccc tttattcagc 12420
cccagatctc cctccgttca ggcctcacca gattccctcc gggatctccc tagataacct 12480
ccccaacctc gattcccctc gctgtctctc gccccaccgc tgagggctgg gctgggctcc 12540
gatcgggtca cctgtccctt ctctctccag ctagatggcc ccccggccgt ggctgtgggc 12600
cagtgcccgc tggtggggcc aggccccatg caccgccgcc acctgctgct ccctgccagg 12660
gtacgtccgg ctgcccacgc ccccctccgc cgtcgcgccc cgcgctccac ccgccccttg 12720
ccacccgctt agctgcgcat ttgcggggct gggcccacgg caggagggcg gatcttcggg 12780
cagccaatca acacaggccg ctaggaagca gccaatgacg agttcggacg ggattcgagg 12840
cgtgcgagtg gactaacaac agctgtaggc tgttggggcg ggggcggggc gcagggaaga 12900
gtgcgggccc acctatgggc gtaggcgggg cgagtcccag gagccaatca gaggcccatg 12960
ccgggtgttg acctcgccct ctccccgcag gtccctaggc ctggcctatc ggaggcgctt 13020
tccctgctcc tgttcgccgt tgttctgtct cgtgccgccg ccctgggctg cattgggttg 13080
gtggcccacg ccggccaact caccgcagtc tggcgccgcc caggagccgc ccgcgctccc 13140
tgaaccctag aactgtcttc gactccgggg ccccgttgga agactgagtg cccggggcac 13200
ggcacagaag ccgcgcccac cgcctgccag ttcacaaccg ctccgagcgt gggtctccgc 13260
ccagctccag tcctgtgatc cggcccgccc ccctagcggc cggggaggga ggggccgggt 13320
ccgcggccgg cgaacggggc tcgaagggtc cttgtagccg ggaatgctgc tgctgctgct 13380
gctgctgctg ctgctgctgc tgctgctgct gctgctgctg ctgctggggg gatcacagac 13440
catttctttc tttcggccag gctgaggccc tgacgtggat gggcaaactg caggcctggg 13500
aaggcagcaa gccgggccgt ccgtgttcca tcctccacgc acccccacct atcgttggtt 13560
cgcaaagtgc aaagctttct tgtgcatgac gccctgctct ggggagcgtc tggcgcgatc 13620
tctgcctgct tactcgggaa atttgctttt gccaaacccg ctttttcggg gatcccgcgc 13680
ccccctcctc acttgcgctg ctctcggagc cccagccggc tccgcccgct tcggcggttt 13740
ggatatttat tgacctcgtc ctccgactcg ctgacaggct acaggacccc caacaacccc 13800
aatccacgtt ttggatgcac tgagaccccg acattcctcg gtatttattg tctgtcccca 13860
cctaggaccc ccaccccega ccctcgcgaa taaaaggccc tccatctgcc caaagctctg 13920
gactccacag tgtccgcggt ttgcgttgtg ggccggaggc tccgcagcgg gccaatccgg 13980
aggcgtgtgg aggcggccga aggtctggga ggagctagcg ggatgcgaag cggccgaatc 14040
agggttgggg gaggaaaagc cacggggcgg ggctttggcg tccggccaat aggagggcga 14100
gcgggccacc cggaggcacc gccccgccc agctgtggcc cagctgtgcc accgagcgtc 14160
gagaagaggg ggctgggctg gcagcgcgcg cggccatcct ccttccactg cgcctgcgca 14220
cgccacgcgc atccgctcct gggacgcaag ctcgagaaaa gttgctgcaa actttctagc 14280
ccgttccccg cccctcctcc cggccagacc cgcccccct gcggagccgg gaattccgag 14340
gggcggagcg caggccgaga tggggaatgt gggggcctgc agaggaccct ggagacggag 14400
gcgtgcagaa g 14411

<210> SEQ ID NO 3
<211> LENGTH: 15000
<212> TYPE: DNA
<213> ORGANISM: mus musculus

<400> SEQUENCE: 3
cagtgtcccc actgcccaag gctggctcca tcacgtaccg ctttggctca gctggccagg 60
acacacagtt ctgcctgtgg gacctcacag aagatgtgct ctcccctcat ccgtctctgg 120
cccgtacccg caccottccg ggcacacctg gtgccacccc accagcttct ggtagttctc 180
gggccggaga gacaggtgca ggccccctgc cccgctccct gtctcgttcc aacagtctcc 240
cacacccagc tggtggtggc aaggctggtg ggcctagtgc atcgatggag cctggcatac 300
cattcagcat tggccgcttt gccacactga ccctgcagga gcggcgggac cggggagctg 360
agaaggaaca caaacgctac catagcctgg gaaacatcag ccgcggtggc agtgggggca 420
atagcagcaa tgacaagctc agtggtcctg ccccccgaag ccgattggac ccagctaagg 480
tgctgggcac ggcactgtgc cctcggatcc atgaggtgcc actgctggag cctctcgtgt 540
gcaagaagat tgctcaggaa cgcctgaccg tgctactgtt cctggaggat tgtatcatca 600
ctgcctgcca agagggcctc atctgcacct gggcccggcc aggcaaggcg gtgagtccgc 660
acctgcccaa gcgctgaggg gcaccagttc tgtccctacc ggatgccagt tatccgtcag 720
cagaaaggtc aggtatagga gacagaatgg ggggaaccac agctaacgtc tttagagcct 780
ctgctggccc atatggctca tccttagtac ttcacactca aggcagaacc tgtgtttata 840
ggaaatctga agtgtagatg gtgaaacttt attcaggtct agggatgtga ttgagctggg 900
ggcccacttc tggcctgcct cttagacact gtttctgagc cagctgctga aggcctggat 960
gggaattagc cagggtccag gcctgcactt cctcttgctg ctgtgtggtc ctggtcattg 1020
ggtctcacag atgggctgtg cagtggctgt gctcttagtt ggtgaggtgc aggcctgtca 1080
cctggtcagg cttgagcatg tggtctcagt gtctaggacc ctactctgcc ctcagtcctt 1140
cagtcccttg ctttggaagg ctagagtcca gaagccttag aacgtcaggc agttgcagag 1200
ccactgccag gctagtaggg ctgcgggagt tgactgagtt ctcacagaca cccctctgtc 1260
tccctagttc acagacgagg agaccgaggc ccaggcaggg caagcaagtt ggcccaggtc 1320
acccagcaag tcagttgtag aggtaggaca acccctgaag ctgcaagtgg accccagttt 1380
cttttctctc cactgtcgtc ccctgtatgc ccaggacacc tggggccaca ttactgtgga 1440
agtgctactc tgggtcagtg gagacggccg agctgtttgt tcctagctag gacagcagct 1500

-continued

```
ttaggcctgg ggggcagatc ccagctgggg cagcagctcc aaggcctttg ggtggctcct   1560
tctccgggtt ctggcagaag cccaggtgct gtctaatcca cctttctcct cttgttctcc   1620
ccagggcatc tcctcccaac caggcagctc ccccagtggc actgtggtgt gaaatgtgga   1680
tgtcccatgt tcccggcctc ctagccataa ccctccccgc tgacctcaag aatcactgta   1740
ttaacaagac taatcatgat ggaaggactg ctccaagccc cacgctgcac acatactggg   1800
ggtcccctag gttggcccag ccatggggat gtagtgtcct gtgtggcctt ggccctgtcc   1860
tccacccact gccaagtaca atgacctgtt ctctgaaaca tcagtgttaa ccatatccct   1920
gtcccagcat gtgactgttc actcctggga gagacttagc ccacagtacc cctgggtgag   1980
agggcagggc aggggccatc cccactcctg cccaaactcc acccccttgct atggtctgtg   2040
atttgaaag tgttaaatta tggaagccct gagggccctc cttgttcccc tggacctctt   2100
atttatacta aagtccttgt ttgcacagtg tttctgttcc ctggggcagg gtagggtggg   2160
ggttgcagta cttggcctcc aagctgtgct ctgaccaaag gaagcccaat cttagctgtt   2220
tccccatccc tagccccgag cagagagccc tctgaaagat gagtctcgac ccccaaagtc   2280
aagaggctga gatggccttc ctactaggtc cttggagatg tttgaaactt gttttaaaca   2340
ccaggactat ccaagcatgc tctccttggg gagaggagga tgctggaatt gactgcactc   2400
cctgcctcct ctgaacatgc ctttgcagtc tgctgcccct ggcccattta tgactggcca   2460
tctagtgcca gctggaggtc atgatttcct ccccagagaa ctggccaccc tagaaagaag   2520
ctaacttgtc gcctggcttg ctgtccaggc agctccgccc tcaacccccta aaatgtttct   2580
gtctctaatc ctagcccagg caggaatgtg gctgccccgg cctgtggcca aggagctatt   2640
ttggggttct cttttgctta aggagggcct ggatccacca cttgcctccc ccaggctggg   2700
gccagcaggt caccccctggc cctggcggct gagcaaactc tctcctgatc ttccttctac   2760
ctcctgccaa aaaatggggg ggcgggtaat acagcaggca caggggctaa atttaactgt   2820
cccaaagtcg gaatccattg ctgagtcacg aagaagctgc ccctggcctt tgcccccccc   2880
actacccccct caccccctgt tgcccaggca tcagcccttt cccccaaccc ctcccagctc   2940
tgagtctata gactggctct cctgggcact gacacctccc acctgtaact ccctgtgctc   3000
tctttatggg tgggtagagt caatgggggg gggcaaccct ggagtattac tctgtcccct   3060
gacattgggc tctgaagagt tttgaggggc cctggaagaa gggagttggg gtgttggctc   3120
aggaggggtt aaaaactggg aggcgggagg ggggctgggc caaggggtgg agaaaagagg   3180
aggaggcctt aagcatagaa ctggccagag agacccaagg gatagtcagg gacgggcaga   3240
catgcagcta gggttctggg gcctggacag gggcagccag gccctgtgac gggaagaccc   3300
cgagctccgg cccggggagg ggccatggtg ttgcctgccc aacatgtcag ccgaagtgcg   3360
gctgaggcag ctccagcagc tggtgctgga cccaggcttc ctgggactgg agcccctgct   3420
cgaccttctc ctgggcgtcc accaggagct gggtgcctct cacctagccc aggacaagta   3480
tgtggccgac ttcttgcagt ggggtgagta tggataggaa gcctggggtt gggtgcaagg   3540
cagaggtggg tctacagggc aagaatgggc tatggagggg caggagggcc tggaaagggc   3600
tttttgtaag ggagccaagc agagctcatg acctgacccc aagctcccct ggtgaggcac   3660
cagggtcagt gaggccacct atgactcagc cagtgcaggc tggggtgggc atagcctcct   3720
gctatctcag cacccacact aggacctggc agctttctct tttaggaccc ttggctcctc   3780
aaactggctt catagccctc cccagtttcc cagagtgtgg ggagggacag cgtggggcag   3840
```

-continued

```
ctgccagggt gtggcccata ggcaggtgtt tggcgtctgc ctccccagct gccctgacag   3900
gtgtccagga gctatgaggg cactgtgact cacagaggcc ctgggggaga accagcccgg   3960
cagacaggcg ccaccgagca ccctttctgt tccccaaatt aagaggaagg aacaacttca   4020
gcttctgagt gtgcccatcc ctagcactct gatcccgccc agcctttgtg ggccagattg   4080
gtcatccctc ctggcttctc atctgctttt gtggttctag ctcaagacct ctaattcctc   4140
tgctgactta aatgcccttc cccagaggtc ttctcaggcc tagtggacaa gcttggagcc   4200
ttatctgctc ctgcccaaca ttgagccaaa gctccagctt accccagctt ccttacaagt   4260
aacgacctgt tttgttgctc tgtgcctatt attaagggtc caggtcttga ttcttggctg   4320
tctgcccatg tgtgtgaccc tagtgcattc tcccctcctc cccgtttca cagatggaaa   4380
ggttgaggcc atcggttaga ctgctaagcc tgtgaaagac tttttctcct ctccagtctt   4440
tagtgtctcc ctcaaccttt cttttgaagg atggggtttg ggctggcagg gtaaactgag   4500
aactggggtg ggggcagggg gtctgaccct ctgggaagga gcagtccttt tgtggcctga   4560
gcagcatcct gtgggcccct cccctgccag gcctgggcgg gggagggggc ctgggttccc   4620
gctgccttaa aagggctcaa cgccttggct ctctcctcct ccccaccccc cagccttggc   4680
cctagctgta tcttccccgg ctgcccactt tcccaaaccc ctttcttctc tgtgacccca   4740
tctccccgct tccccacacg tccctcctcc atccttactc cccggcctta gaacttccct   4800
aagggagatc tgacctccct ctgcccaccc cgcaccccca gtcgccagcc tcagacctag   4860
ctgctctccc ctctggctga accaccctag cacaggacct tataccctgg agctttggtt   4920
ataagaagac tctccttcac cctttggaaa ccaagaaagc ccttccaaca gtgtccagga   4980
tgctggaggg cagtgaccct cccccacttc ttcttcgtgc tggctgtgct gacacagctc   5040
cagttcgagg ttgtggcccg agacattaag tgagagcccc gggtgacctg acttagcacc   5100
ctgatcatca catgggagtg aaaggcctga tgcgccagct tctcccactg cctccctttc   5160
tgccctgcaa ccctgtggaa acaggcagtt ctgggtccca caaacatcac agaggttttg   5220
aaagcagaat cctaaagccg atttaagggg cagaaggaag gaggctataa agtcactacc   5280
cttaccgcta gtgttctgat gacccttggt tcttcttccc ccacccccgc ccagtggagc   5340
ccattgcagc aaggcttaag gaggtccgac tgcagaggga tgattttgag attttgaagg   5400
tgatcgggcg tggggcgttc agcgaggtga gtcttcagtg gcctgggaat ggaactttac   5460
ttgatgtggg tggggcataa cagctggggc agagccttaa aaattgatga atgagcttga   5520
atttaaggct ggaggggtgg gggcggagct tgtggtcagt gggcggtgtg cacgtgaggg   5580
cggggctaag gttgggtgga gataagggtg gagtcctgtc tgggtgagcc ttgctggttt   5640
tccctgccac ctcttgctgt catctcggtt ccgtatttag gtagcggtgg tgaagatgaa   5700
acagacgggc caagtgtatg ccatgaagat tatgaataag tgggacatgc tgaagagagg   5760
cgaggtgagg gccagggatt agggcagcgc cctcatctct ccaactcacc tcctgtagct   5820
tctctcctac ctcacaggtg tcgtgcttcc gggaagaaag ggatgtatta gtgaaagggg   5880
accggcgctg gatcacacag ctgcactttg ccttccagga tgagaactac ctggtaagct   5940
ccgggttcag gtgactagga aagagtgaca gttacatcgc cccaagtcaa gaaggctgga   6000
gaagggagaa gctgctgtag atcggggggg tgggggtggg ggggacacac acaggggatg   6060
ggggacgggg gtaggattgt gtctcaagta taggagagac cttccttgag acaggagtga   6120
tatctggttt ggcctttgga tggggcgctc tctcactgtg cgggggtcct ctgtgcttgg   6180
gaacggggtg tctttgggag tcttgggggc taccaaaccc ctgtgacaca cccgctccca   6240
```

```
gtacctggtc atggaatact acgtgggcgg ggacctgcta acgctgctga gcaagtttgg   6300
ggagcggatc cccgccgaga tggctcgctt ctacctggcc gagattgtca tggccataga   6360
ctccgtgcac cggctgggct acgtgcacag gtgggcgtgg cggggccctt ggagggttag   6420
cagaatttgt gtgggaagga agggtacctg aaggtcagat cccattgggg acagaatcgg   6480
ggtctagaat tgtagaatcc tgggtggggt ggaagtggat cgagctgacg ggccctaaga   6540
gggaaggttt tcaagaaagc acactttccc tcttctctct atgcacaggg acatcaaacc   6600
agataacatt ctgctggacc gatgtgggca cattcgcctg gcagacttcg gctcctgcct   6660
caaactgcag cctgatggaa tggtaagaag agcctggcga aactctcctc attggtgaag   6720
gaccggatta gggggcgggg ctgggttgag gagcaggagg ggagcttggt ctgggatgtc   6780
ctgcgcacca tatttggaca gtcaagggaa aggttttaag cattcaggtc tgattggcac   6840
aggtgaggtc gctggtggct gtgggcaccc cggactacct gtctcctgag attctgcagg   6900
ccgttggtgg agggcctggg gcaggcagct acgggccaga gtgtgactgg tgggcactgg   6960
gcgtgttcgc ctatgagatg ttctatgggc agacccccttt ctacgcggac tccacagccg   7020
agacatatgc caagattgtg cactacaggg tgagcacaag caccatgcag gggggctgac   7080
ttagtggctt gtgctcccag actgtctttt ttaaaagata tttatttata tgtgtgtgtt   7140
ttctgtgtat gtatatctgt gcactgagta ggtgtgcgaa ggtcagaggg catgggatcc   7200
cctggaactg gagtcacaga ctattgtgtg ctgccatgct gagtgctggg aaacagaacc   7260
ttgatcactc tgcaagagca gccagtgcac tgaaacgaca gagccagctc tgcagcccag   7320
ggctaactgt tgcttttctt tctaaatagg aacacttgtc gctgccgctg gcagacacag   7380
ttgtccccga ggaagctcag gacctcattc gtgggctgct gtgtcctgct gagataaggc   7440
taggtcgagg tggggcaggt gatttccaga aacatccttt cttctttggc cttgattggg   7500
agggtctccg agacagtgta cccccccttta caccagactt cgagggtgcc acggacacat   7560
gcaatttcga tgtggtggag gaccggctca ctgccatggt gagcgggggc ggggtacgta   7620
cctgcagttc ctgatccgtt gaggggactt ccctagcctc ttccataaaa ttggggtgat   7680
tggccaggtg tggtggtgca tacctttaat cgtagaactt cataggcaga ggcaggtggc   7740
tctctggtaa atcaaggcca tcttggtcta catagtgact tctaggccag tcaggagtga   7800
gatcctccct tgaaaaataa aaaagggggt gttgaccttc ctgggtccca aattattatc   7860
ctagagcact gctatgtatc cactcaggta tgaggacaca caggtgacca gtcccaaaga   7920
cagtgagtga ggcctcactc ttggcagtac taaaattgat tgtagggggc tgggctcttg   7980
acccagcctg gaaagtgctg gagggcttcc tggaggagga gactagctga gcccagaagg   8040
atgcaggaga tcctttctcg ggtgagtgct ctcagcattt taacaagctc taggccctgc   8100
agagagaagt ctggtgtggg cagagcccca atagaaagca acaagataga agagaaaatg   8160
gtggagtttg ttagtggggg cagttatgcc gtgaacatag aggggcgaag ggccatctcg   8220
gataactgct agccacaaga gccctgtctg tcttcctagg agacgctgtc agacatgcag   8280
gaagacatgc cccttggggt gcgcctgccc ttcgtgggct actcctactg ctgcatggcc   8340
ttcaggtgag cacgactgcc ccctgctggg gcctgtgtgc aggcccacca cagccactca   8400
attgaaggct cagtcttcaa accaagtatt cctaggagct gtctaagtta ggctttctgc   8460
tgctgcgatg aaccctgact aaaagcaagc tggggaggaa aaggcttatc gggcttacgt   8520
ttccacatgg gagcccatca ctgaaggaag ccaggacagg aactcacagc ggggcaggaa   8580
```

-continued

```
cgtggagctg atgcagaggc aatggagggg agctgcttac tgacttgatc cttatgtctt   8640
cctcagcctg tttccttgta gagcccagga ccaccaggcc agtgagggct ccactcacaa   8700
tgggctgagc tctcatctat gatcactagt tatgaaaatg cccgataggc ttgcctgcag   8760
cttcagtttt tgaggcactt tccttccttc cttccttcct tccttccttc cttccttcct   8820
ttctttcttt ctttctttct ttctttcttt ctttctttct ttctttcttt ctttctttct   8880
tagtctttta gagacagggt ctttctatgt agctctggct gtcttggaat tcattctgta   8940
gaccaggctg gtcttattta tttattttat gtatgtgagt ccactatcac tgtcctcaga   9000
cacaccagaa gagggcatca gatcccatta cagatggctg tgagccacca tgtggttgct   9060
gggaattgaa ctcaggacct ctggaagagc agccagtgct cctgccctgt agaggcattt   9120
tcttcatgaa ggctgtctcc tctctgatga cttgatgact ctagcttgtt gtgtcaagtg   9180
gacataagac taggaaagca gctacacatg cactttgttt atttttgttt tgctttttga   9240
gactgggtct ctccatctca tagctctggc catcctgcct ggtgacattc cagtccagtt   9300
gtataaccta agaatctgag actcagcctt gcagaatcct gctattaacg ggtctaggac   9360
actccataga atccaggatc ttagaaaaac aaacctgaag tgtgacagtt tattttaaga   9420
acacaattgg agcacataac aataatacaa cttttcagtt ttaaaaagtt ttctgtcttg   9480
tttttgagg caggagctcc ttaatatagt ctaagccgcc ctgcgagtgc tgtgattgat   9540
gggcatgtac caccatgcct agtcaataaa gcctttaaaa agcatccgtt atgctggctg   9600
tggtgccaca aacctgtaat cccagcactt agaaggtaga ggcaagatta tcagaaattc   9660
aaggccatcc tgggctatac agtaatctaa ggctagcctg gtctacaaga gactctgtct   9720
aaagaaacaa aagataaata gcacccacta ttgctaggca atataaccct ataaccccac   9780
cattgaggag gctgaggctg gagcatcact gcaaatttga ggccaggatg gtcaacaaat   9840
aagtcccaga gctggcatag aggaactctg tctcaacaat aaagagaact tatctagcat   9900
ttatgagggt aaataaaaat ttaccattgc cacaaaaaat gtaaatgaag agactgcttt   9960
taggagtgaa ctgggaagca gggaacactt agaggatgct cactcacaca ggtatccacc  10020
atcaggcatg cctcaggcct gcacagggaa ggacaacttg tttcatgatt tgcaagcagc  10080
atcccatgct ccttagagcg ggttgggccc agcccaccct ctgtggagtt atcgctcagc  10140
caggcagcaa ggcagccaag gtgctgaggc cctggcagtc tgctctcttc tctgctctga  10200
acctccttta gctttagcct aggagcctgg cctggtgccc acaggctagg gagtccctag  10260
cctcttcctc ttctcagaga caatcaggtc ccggacccca cccctatgga actagaggcc  10320
ctgcagttgc ctgtgtcaga cttgcaaggg cttgacttgc agccccagt gtccccaccg  10380
gatcaagtgg tgagtagact gagaggtggg caaagcttcc tgggtgggtg tacctgcagt  10440
gccaactgcc aggctgttaa ttcagtagga cactgtcccc aactggccca actgcacatc  10500
ctgtagtcag gaggcacagg cagaaaaatc ccaaattcaa ggcttgctcc cgttatgtaa  10560
tgagatcctg tcttggagta aaaaacaaag aagagaacta gggatagctc agaggtagat  10620
gctctcctgg catgggggtg gggtcagaaa gcaacaccaa ccggggcctg ggagggaggg  10680
actgccaacc acctggagga gtctggggta gacttggtga acaaagttca gaggccatca  10740
ggtgggatgc tggtttctta aaagccacag ataggtgggt agcattggaa agaggagtgg  10800
ggggttgcag aaagtgacaa gacacaaact ggggaggcct aagggtaaag ccagggttgt  10860
ctgaagcact gtggagctgg gaggaacacg ctaaacttct gacttcagcc cttcagttcc  10920
cctgttgact acactgtccc cagggaccca gggatgggga gaggtggacg ggggagggaa  10980
```

gtacgggact gatccagctc caggtcccaa ctctgatccc caccgacagg ctgaagaggc 11040
tgacctagtg gctgtccctg cccctgtggc tgaggcagag accacggtaa cgctgcagca 11100
gctccaggaa gccctggaag aagaggttct cacccggcag agcctgagcc gcgagctgga 11160
ggccatccgg accgccaacc agaacttctc caggtcaggg tcacagtgct ggggtgaggg 11220
gagaggagag cagcaaccct cgcagtctcc tcaccgatag gtcggctcac tcccctatct 11280
ttcccagcca actacaggag gccgaggtcc gaaaccgaga cctggaggcg catgttcggc 11340
agctacagga acggatggag atgctgcagg ccccaggagc cgcaggcgag tccctcacct 11400
gcttccagcc aagggggcac tgggtggaga tggggggcat gttgggtgtg tgaaccctcg 11460
gggcagggga ggagtccagg ctggggcacc gcagccgcgc cactgccttt ctcctccatc 11520
ctccacactc catacacctc tctcttctcc ttccagccat cacgggggtc cccagtcccc 11580
gggccacgga tccaccttcc catgtaagac ccctctctcc cctccccgat ccccatctta 11640
gatatgctac ccacagccct tctcccgtcc acgtttaggg tccattctcc ttgggggttc 11700
cagaagaaag ctgcccttca ctcatccatt cagcatgcac tatctaccag ctctccctcg 11760
tttcaggctt ctcgccaaat cctccccaag ggaactccct atactcccgt tctggcctcg 11820
actagattcc cgcactgcct ctcgccctgc tgctgggctc cgatcgggtc acctgtccct 11880
tctctctcca gctagatggc cccccggccg tggctgtggg ccagtgcccg ctggtggggc 11940
caggccccat gcaccgccgt cacctgctgc tccctgccag ggtatgtccc acgtccgccc 12000
accacgggcc tctgcctagc tctgcccact gagtgtcacc actgcttgct gtgcctctgt 12060
ggagctcggc ccaccgcagg gagggggggt attcgggcgg ccaatcaaca caggctgctg 12120
ctaagtagcc aatgacgagt tccaacagga gctctttctt gcgagcagac caactttagc 12180
tgcgggctgt ggggaccaga gatgcgctca gaggcccatc tatgggtata ggctgggcgg 12240
ctcccaggag ccagtgggcc cctgtagcct agtgctaatc caaccttctc tcctgcagat 12300
ccctaggcct ggcctatccg aggcgcgttg cctgctcctg ttcgccgctg ctctggctgc 12360
tgccgccaca ctgggctgca ctgggttggt ggcctatacc ggcggtctca ccccagtctg 12420
gtgtttcccg ggagccacct tcgccccctg aaccctaaga ctccaagcca tctttcattt 12480
aggcctccta ggaaggtcga gcgaccaggg agcgacccaa agcgtctctg tgcccatcgc 12540
gccccccccc cccccccacc gctccgctcc acacttctgt gagcctgggt ccccacccag 12600
ctccgctcct gtgatccagg cctgccacct ggcggccggg gagggaggaa cagggctcgt 12660
gcccagcacc cctggttcct gcagagctgg tagccaccgc tgctgcagca gctgggcatt 12720
cgccgacctt gctttactca gccccgacgt ggatgggcaa actgctcagc tcatccgatt 12780
tcactttttc actctcccag ccatcagtta caagccataa gcatgagccc cctatttcca 12840
gggacatccc attcccatag tgatggatca gcaagacctc tgccagcaca cacggagtct 12900
ttggcttcgg acagcctcac tcctgggggt tgctgcaact ccttccccgt gtacacgtct 12960
gcactctaac aacggagcca cagctgcact ccccccctccc ccaaagcagt gtgggtattt 13020
attgatcttg ttatctgact cactgacaga ctccgggacc cacgttttag atgcattgag 13080
actcgacatt cctcggtatt tattgtctgt ccccacctac gacctccact cccgaccctt 13140
gcgaataaaa tacttctggt ctgccctaaa tcccgcgcaa tatctctgtt gtggaaagga 13200
aaccgccccg caggccaatg gagagtccaa tagagacaac caatggcttg agtgggagct 13260
agaggggagg caaagcgcac gaatcaggtt gaagggtggg gcttaggcat ccagccagta 13320
ggagagaagc aacaagccac cagagacacc accgcccccc accctccccc ccagctgtga 13380
cccagctgtg ccactcaagt ttggaaaaaa gtagggggtt gggccagcag cgggcacacc 13440
atcttcccac tgcgcctgcg caagccacgc gcatccgctt tttggaccga cactccagaa 13500
aagttgctgc aaactttcta gcgcgattcc ccgcccctcc tcccagctag atccaccgcc 13560
tacccgcggg gccgggaatt ccgaggggcg gagcacggcg cggagatggg aagggagggg 13620
gcccttcaag ggacccggga gatgggagcg gcttcgcgcc cttaaccctc cggacggccc 13680
attaccttct ccgttgctct gatagggaaa ctgaggccct gagtcagagg cacacaaggg 13740
gggaaggcca aaagcgcggc cagagacgga gggaaaacaa agaatcctga cagcccggga 13800
ggggggcgga cacacaggga caaggacaga cccgagtgca gagctgggtc tagtctttgg 13860
gagggggcca gaagactgca aggggaccgg gggggggggc ggcgaggagg actgggcgga 13920
ggagggggct ggggaagccc gcgggaggcg gcaaaggagg gaggaacttt ccaaagttgc 13980
caaacatggc tacctcgcct gcggagccga gcgcggggcc cgcggctcgg ggggaggcgg 14040
cggcggcgac cgaggagcag gaggaggaag cgcgccagct tctgcagact ctgcaggcag 14100
ccgaggggga ggcggcggcg gccggggcgg gagatgcggc ggcggcggcg gactctgggt 14160
ccccgagtgg cccggggtct ccccgggaga ccgtgaccga ggtgcccact ggccttcgct 14220
tctcgcccga acaggtggca tgcgtgtgcg aggcgctgct gcaggcgggc cacgccggcc 14280
gcttgagccg cttcctgggc gcgctgcccc cggccgagcg cctacgtggc agcgatccgg 14340
tgctgcgcgc gcgggcccta gtggccttcc agcggggtga atacgccgag ctctaccaac 14400
ttctcgagag ccgccctttc cccgccgccc accacgcctt cctgcaggac ctctacctgc 14460
gcgcgcgcta ccacgaggcc gagcgggccc gtggccgtgc gctgggcgct gtggacaaat 14520
accggctgcg caagaagttc cctctgccca agaccatctg ggatggcgag gagaccgtct 14580
attgcttcaa ggagcgctcg cgagcggcgc tcaaggcctg ctaccgcggc aaccgctatc 14640
ccacgcctga cgagaagcgc cgcctggcca cgctcaccgg cctctcgctt acacaggtca 14700
gcaactggtt caagaaccgg cgacagcgcg accgcactgg gaccggcggt ggagcgcctt 14760
gcaaaaggtg agggggggaac cgaccctcct tcctcggtgg ccgctggagt ctgcgcaagt 14820
gacccttcac atccctcttc ggtggcgtcg gcgagtgcat aggctgagcg tggagagacc 14880
aggcacaccc tgggttctct gggcatcact gcctcagggg cagaggttgt tccagctact 14940
tctaagctgg gaacgcagtg ccaggaatgg gggggggggc gggggcggga cgggcagtga 15000

<210> SEQ ID NO 4
<211> LENGTH: 1896
<212> TYPE: DNA
<213> ORGANISM: mus musculus

<400> SEQUENCE: 4
atgtcagccg aagtgcggct gaggcagctc cagcagctgg tgctggaccc aggcttcctg 60
ggactggagc ccctgctcga ccttctcctg ggcgtccacc aggagctggg tgcctctcac 120
ctagcccagg acaagtatgt ggccgacttc ttgcagtggg tggagcccat tgcagcaagg 180
cttaaggagg tccgactgca gagggatgat tttgagattt tgaaggtgat cgggcgtggg 240
gcgttcagcg aggtagcggt ggtgaagatg aaacagacgg gccaagtgta tgccatgaag 300
attatgaata agtgggacat gctgaagaga ggcgaggtgt cgtgcttccg ggaagaaagg 360
gatgtattag tgaaagggga ccggcgctgg atcacacagc tgcactttgc cttccaggat 420
gagaactacc tgtacctggt catggaatac tacgtgggcg gggacctgct aacgctgctg 480

```
agcaagtttg gggagcggat ccccgccgag atggctcgct tctacctggc cgagattgtc     540
atggccatag actccgtgca ccggctgggc tacgtgcaca gggacatcaa accagataac     600
attctgctgg accgatgtgg gcacattcgc ctggcagact tcggctcctg cctcaaactg     660
cagcctgatg gaatggtgag gtcgctggtg gctgtgggca ccccggacta cctgtctcct     720
gagattctgc aggccgttgg tggagggcct ggggcaggca gctacgggcc agagtgtgac     780
tggtgggcac tgggcgtgtt cgcctatgag atgttctatg ggcagacccc cttctacgcg     840
gactccacag ccgagacata tgccaagatt gtgcactaca gggaacactt gtcgctgccg     900
ctggcagaca cagttgtccc cgaggaagct caggacctca ttcgtgggct gctgtgtcct     960
gctgagataa ggctaggtcg aggtggggca ggtgatttcc agaaacatcc tttcttcttt    1020
ggccttgatt gggagggtct ccgagacagt gtaccccct ttacaccaga cttcgagggt    1080
gccacggaca catgcaattt cgatgtggtg gaggaccggc tcactgccat ggtgagcggg    1140
ggcggggaga cgctgtcaga catgcaggaa gacatgcccc ttggggtgcg cctgcccttc    1200
gtgggctact cctactgctg catggccttc agagacaatc aggtcccgga ccccacccct    1260
atggaactag aggccctgca gttgcctgtg tcagacttgc aagggcttga cttgcagccc    1320
ccagtgtccc caccggatca agtggctgaa gaggccgacc tagtggctgt ccctgcccct    1380
gtggctgagg cagagaccac ggtaacgctg cagcagctcc aggaagccct ggaagaagag    1440
gttctcaccc ggcagagcct gagccgcgag ctggaggcca tccggaccgc caaccagaac    1500
ttctccagcc aactacagga ggccgaggtc cgaaaccgag acctggaggc gcatgttcgg    1560
cagctacagg aacggatgga gatgctgcag gccccaggag ccgcagccat cacgggggtc    1620
cccagtcccc gggccacgga tccaccttcc catctagatg gccccccggc cgtggctgtg    1680
ggccagtgcc cgctggtggg gccaggcccc atgcaccgcc gtcacctgct gctccctgcc    1740
aggatcccta ggcctggcct atccgaggcg cgttgcctgc tcctgttcgc cgctgctctg    1800
gctgctgccg ccacactggg ctgcactggg ttggtggcct ataccggcgg tctcacccca    1860
gtctggtgtt tcccgggagc caccttcgcc ccctga                              1896
```

<210> SEQ ID NO 5
<211> LENGTH: 771
<212> TYPE: DNA
<213> ORGANISM: mus musculus
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t

<400> SEQUENCE: 5

```
cctgcccctg tggctgaggc agagaccacg gtaacgctgc agcagctcca ggaagccctg      60
gaagaagagg ttctcacccg gcagagctng agccgcgagc tggaggccat ccggaccgcc     120
aaccagaact tctccagcca actacaggag gccgaggtcc gaaaccgaga cctggaggcg     180
catgttcggc agctacagga acggatggag atgctgcagg ccccaggagc cgccggantc     240
cctcacctgc ttccagccaa gggggcactg ggtggagatg gggggcatgt tgggtgtgtg     300
```

```
aaccctcggg gcaggggagg agtccaggct ggggcaccgc gccgcgccac tgcctttctc    360

ctccatcctc cacactccat acacctctct cttctccttc cagccatcac gggggtccca    420

gtccccgggc cacggatcca ccttcccatc tagatggccc cccggcggtg gctgtgggcc    480

agtgcccgct ggtggggcca ggacantgtc accgccgtca cctgctgctc cctgccagga    540

ttcctaggcc tggctatccg aggcgcgttg ctgctcctgt tcgccgctgc tctggctgct    600

gcgccacact gggctgcact gggttggttg gctataccgg cggtcttcac ccagtctggt    660

gtttcccgtg agcacccttc gcccctgaaa cctaagactt caagccatct ttcatttagg    720

ccttctagga aggtcgagcg acaggggagc gacccaaagc gtctctgtgc c             771
```

<210> SEQ ID NO 6
<211> LENGTH: 434
<212> TYPE: DNA
<213> ORGANISM: mus musculus

<400> SEQUENCE: 6

```
gagagaccca aggggtagtc agggacgggc agacatgcag ctagggttct ggggcctgga     60

caggggcagc caggccctgt gacgggaaga ccccgagctc cggcccgggg aggggccatg    120

gtgttgcctg cccaacatgt cagccgaagt gcggctgagg cagctccagc agctggtgct    180

ggacccaggc ttcctgggac tggagcccct gctcgacctt ctcctgggcg tccaccagga    240

gctgggtgcc tctcacctag cccaggacaa gtatgtggcc gacttcttgc agtgggtgga    300

gcccattgca gcaaggctta aggaggtccg actgcagagg gatgattttg agattttgaa    360

ggtgatcggg cgtggggcgt tcagcgaggt agcggtggtg aagatgaaac acacggagtc    420

tttggcttcg gaca                                                      434
```

<210> SEQ ID NO 7
<211> LENGTH: 2688
<212> TYPE: DNA
<213> ORGANISM: mus musculus

<400> SEQUENCE: 7

```
ccacgcgtcc gcccacgcgt ccggggcaga catgcagcta gggttctggg gcctggacag     60

gggcagccag gccctgtgac gggaagaccc cgagctccgg cccggggagg ggccatggtg    120

ttgcctgccc aacatgtcag ccgaagtgcg gctgaggcag ctccagcagc tggtgctgga    180

cccaggcttc ctgggactgg agcccctgct cgaccttctc ctgggcgtcc accaggagct    240

gggtgcctct cacctagccc aggacaagta tgtggccgac ttcttgcagt gggtggagcc    300

cattgcagca aggcttaagg aggtccgact gcagagggat gattttgaga ttttgaaggt    360

gatcgggcgt ggggcgttca gcgaggtagc ggtggtgaag atgaaacaga cgggccaagt    420

gtatgccatg aagattatga ataagtggga catgctgaag agaggcgagg tgtcgtgctt    480

ccgggaagaa agggatgtat tagtgaaagg ggaccggcgc tggatcacac agctgcactt    540

tgccttccag gatgagaact acctgtacct ggtcatggaa tactacgtgg gcggggacct    600

gctaacgctg ctgagcaagt ttggggagcg gatccccgcc gagatggctc gcttctacct    660

ggccgagatt gtcatggcca tagactccgt gcaccggctg ggctacgtgc acagggacat    720

caaaccagat aacattctgc tggaccgatg tgggcacatt cgcctggcag acttcggctc    780

ctgcctcaaa ctgcagcctg atggaatggt gaggtcgctg gtggctgtgg gcaccccgga    840

ctacctgtct cctgagattc tgcaggccgt tggtggaggg cctggggcag gcagctacgg    900

gccagagtgt gactggtggg cactgggcgt gttcacctat gagatgttct atggcagac     960
```

ccccttctac gcggactcca cagccgagac atatgccaag attgtgcact acagggaaca 1020
cttgtcgctg ccgctggcag acacagttgt ccccgaggaa gctcaggacc tcattcgtgg 1080
gctgctgtgt cctgctgaga taaggctagg tcgaggtggg gcaggtgatt tccagaaaca 1140
tcctttcttc tttggccttg attgggaggg tctccgagac agtgtacccc cctttacacc 1200
agacttcgag ggtgccacgg acacatgcaa tttcgatgtg gtggaggacc ggctcactgc 1260
catggtgagc gggggcgggg agacgctgtc agacatgcag gaagacatgc cccttggggt 1320
gcgcctgccc ttcgtgggct actcctactg ctgcatggcc ttcagagaca atcaggtccc 1380
ggaccccacc cctatggaac tagaggccct gcagttgcct gtgtcagact tgcaagggct 1440
tgacttgcag cccccagtgt ccccaccgga tcaagtggct gaagaggctg acctagtggc 1500
tgtccctgcc cctgtggctg aggcagagac cacggtaacg ctgcagcagc tccaggaagc 1560
cctggaagaa gaggttctca cccggcagag cctgagccgc gagctggagg ccatccggac 1620
cgccaaccag aacttctcca gccaactaca ggaggccgag gtccgaaacc gagacctgga 1680
ggcgcatgtt cggcagctac aggaacggat ggagatgctg caggccccag gagccgcaga 1740
tccctaggcc tggcctatcc gaggcgcgtt gcctgctcct gttcgccgct gctctggctg 1800
ctgccgccac actgggctgc actgggttgg tggcctatac cggcggtctc accccagtct 1860
ggtgtttccc gggagccacc ttcgccccct gaaccctaag actccaagcc atctttcatt 1920
taggcctcct aggaaggtcg agcgaccagg gagcgaccca aagcgtctct gtgcccatcg 1980
cccccccccc cccccccacc gctccgctcc acacttctgt gagcctgggt ccccacccag 2040
ctccgctcct gtgatccagg cctgccacct ggcggccggg gagggaggaa cagggctcgt 2100
gcccagcacc cctggttcct gcagagctgg tagccaccgc tgctgcagca gctgggcatt 2160
cgccgacctt gctttactca gccccgacgt ggatgggcaa actgctcagc tcatccgatt 2220
tcactttttc actctcccag ccatcagtta caagccataa gcatgagccc cctatttcca 2280
gggacatccc attcccatag tgatggatca gcaagacctc tgccagcaca cacggagtct 2340
ttggcttcgg acagcctcac tcctgggggt tgctgcaact ccttccccgt gtacacgtct 2400
gcactctaac aacggagcca cagctgcact ccccccctccc ccaaagcagt gtgggtattt 2460
attgatcttg ttatctgact cactgacaga ctccgggacc cacgttttag atgcattgag 2520
actcgacatt cctcggtatt tattgtctgt ccccacctac gacctccact cccgaccctt 2580
gcgaataaaa tacttctggt ctgccctaaa aaaaaaaaaa aaaaaaaaaa aaaaaaaaaa 2640
aaaaaaaaaa aaaaaaaaaa aaaaaaaaaa aaaaaaaaaa aaaaaaaa 2688

<210> SEQ ID NO 8
<211> LENGTH: 2862
<212> TYPE: DNA
<213> ORGANISM: mus musculus

<400> SEQUENCE: 8
gggatagtca gggacgggca gacatgcagc tagggttctg gggcctggac aggggcagcc 60
aggccctgtg acgggaagac cccgagctcc ggcccgggga ggggccatgg tgttgcctgc 120
ccaacatgtc agccgaagtg cggctgaggc agctccagca gctggtgctg gacccaggct 180
tcctgggact ggagcccctg ctcgaccttc tcctgggcgt ccaccaggag ctgggtgcct 240
ctcacctagc ccaggacaag tatgtggccg acttcttgca gtgggtggag cccattgcag 300
caaggcttaa ggaggtccga ctgcagaggg atgattttga gattttgaag gtgatcgggc 360

-continued gtggggcgtt cagcgaggta gcggtggtga agatgaaaca gacgggccaa gtgtatgcca 420
tgaagattac gaataagtgg gacatgctga agagaggcga ggtgtcgtgc ttccgggaag 480
aaagggatgt attagtgaaa ggggaccggc gctggatcac acagctgcac tttgccttcc 540
aggatgagaa ctacctgtac ctggtcatgg aatactacgt gggcggggac ctgctaacgc 600
tgctgagcaa gtttggggag cggatccccg ccgagatggc tcgcttctac ctggccgaga 660
ttgtcatggc catagactcc gtgcaccggc tgggctacgt gcacagggac atcaaaccag 720
ataacattct gctggaccga tgtgggcaca ttcgcctggc agacttcggc tcctgcctca 780
aactgcagcc tgatggaatg gtgaggtcgc tggtggctgt gggcaccccg gactacctgt 840
ctcctgagat tctgcaggcc gttggtggag ggcctggggc aggcagctac gggccagagt 900
gtgactggtg ggcactgggc gtgttcacct atgagatgtt ctatgggcag acccccttct 960
acgcggactc cacagccgag acatatgcca agattgtgca ctacagggaa cacttgtcgc 1020
tgccgctggc agacacagtt gtccccgagg aagctcagga cctcattcgt gggctgctgt 1080
gtcctgctga gataaggcta ggtcgaggtg gggcaggtga tttccagaaa catcctttct 1140
tctttggcct tgattgggag ggtctccgag acagtgtacc cccctttaca ccagacttcg 1200
agggtgccac ggacacatgc aatttcgatg tggtggagga ccggctcact gccatggaga 1260
cgctgtcaga catgcaggaa gacatgcccc ttggggtgcg cctgcccttc gtgggctact 1320
cctactgctg catggccttc agagacaatc aggtcccgga ccccacccct atggaactag 1380
aggccctgca gttgcctgtg tcagacttgc aagggcttga cttgcagccc ccagtgtccc 1440
caccggatca agtggctgaa gaggctgacc tagtggctgt ccctgcccct gtggctgagg 1500
cagagaccac ggtaacgctg cagcagctcc aggaagccct ggaagaagag gttctcaccc 1560
ggcagagcct gagccgcgag ctggaggcca tccggaccgc caaccagaac ttctccagcc 1620
aactacagga ggccgaggtc cgaaaccgag acctggaggc gcatgttcgg cagctacagg 1680
aacggatgga gatgctgcag gccccaggag ccgcagccat cacgggggtc cccagtcccc 1740
gggccacgga tccaccttcc catgcttctc gccaaatcct ccccaaggga actccctaga 1800
ctcccgttct ggcctcgact agattcccgc actgcctctc gccctgctgc tgggctccga 1860
tcgggtcacc tgtcccttct ctctccagct agatggcccc ccggccgtgg ctgtgggcca 1920
gtgcccgctg gtggggccag gccccatgca ccgccgtcac ctgctgctcc ctgccaggat 1980
ccctaggcct ggcctatccg aggcgcgttg cctgctcctg ttcgccgctg ctctggctgc 2040
tgccgccaca ctgggctgca ctgggttggt ggcctatacc ggcggtctca ccccagtctg 2100
gtgtttcccg ggagccacct tcgccccctg aaccctaaga ctccaagcca tctttcattt 2160
aggcctccta ggaaggtcga gcgaccaggg agcgacccaa agcgtctctg tgcccatcgc 2220
cccccccccc ccccccaccg ctccgctcca cacttctgtg agcctgggtc cccacccagc 2280
tccgctcctg tgatccaggc ctgccacctg gcggccgggg agggaggaac agggctcgtg 2340
cccagcaccc ctggttcctg cagagctggt agccaccgct gctgcagcag ctgggcattc 2400
gccgaccttg ctttactcag ccccgacgtg gatgggcaaa ctgctcagct catccgattt 2460
cactttttca ctctcccagc catcagttac aagccataag catgagcccc ctatttccag 2520
ggacatccca ttcccatagt gatggatcag caagacctct gccagcacac acggagtctt 2580
tggcttcgga cagcctcact cctgggggtt gctgcaactc cttccccgtg tacacgtctg 2640
cactctaaca acggagccac agctgcactc ccccctcccc caaagcagtg tgggtattta 2700
ttgatcttgt tatctgactc actgacagac tccgggaccc acgttttaga tgcattgaga 2760
ctcgacattc ctcggtattt attgtctgtc cccacctacg acctccactc ccgacccttg 2820
cgaataaaat acttctggtc tgccctaaaa aaaaaaaaaa aa 2862

<210> SEQ ID NO 9
<211> LENGTH: 2611
<212> TYPE: DNA
<213> ORGANISM: mus musculus

<400> SEQUENCE: 9
cgggaagacc ccgagctccg gcccggggag gggccatggt gttgcctgcc caacatgtca 60
gccgaagtgc ggctgaggca gctccagcag ctggtgctgg acccaggctt cctgggactg 120
gagcccctgc tcgaccttct cctgggcgtc caccaggagc tgggtgcctc tcacctagcc 180
caggacaagt atgtggccga cttcttgcag tgggtggagc ccattgcagc aaggcttaag 240
gaggtccgac tgcagaggga tgattttgag attttgaagg tgatcgggcg tggggcgttc 300
agcgaggtag cggtggtgaa gatgaaacag acgggccaag tgtatgccat gaagattatg 360
aataagtggg acatgctgaa gagaggcgag gtgtcgtgct tccgggaaga aagggatgta 420
ttagtgaaag gggaccggcg ctggatcaca cagctgcact ttgccttcca ggatgagaac 480
tacctgtacc tggtcatgga atactacgtg ggcggggacc tgctaacgct gctgagcaag 540
tttggggagc ggatccccgc cgagatggct cgcttctacc tggccgagat tgtcatggcc 600
atagactccg tgcaccggct gggctacgtg cacagggaca tcaaaccaga taacattctg 660
ctggaccgat gtgggcacat tcgcctggca gacttcggct cctgcctcaa actgcagcct 720
gatggaatgg tgaggtcgct ggtggctgtg ggcaccccgg actacctgtc tcctgagatt 780
ctgcaggccg ttggtggagg gcctggggca ggcagctacg ggccagagtg tgactggtgg 840
gcactgggcg tgttcaccta tgagatgttc tatgggcaga ccccc ttcta cgcggactcc 900 acagccgaga catatgccaa gattgtgcac tacagggaac acttgtcgct gccgctggca 960
gacacagttg tccccgagga agctcaggac ctcattcgtg ggctgctgtg tcctgctgag 1020
ataaggctag gtcgaggtgg ggcagacttc gagggtgcca cggacacatg caatttcgat 1080
gtggtggagg accggctcac tgccatggtg agcgggggcg gggagacgct gtcagacatg 1140
caggaagaca tgccccttgg ggtgcgcctg cccttcgtgg gctactccta ctgctgcatg 1200
gccttcagag acaatcaggt cccggacccc accccctatgg aactagaggc cctgcagttg 1260
cctgtgtcag acttgcaagg gcttgacttg cagcccccag tgtccccacc ggatcaagtg 1320
gctgaagagg ctgacctagt ggctgtccct gcccctgtgg ctgaggcaga gaccacggta 1380
acgctgcagc agctccagga agccctggaa gaagaggttc tcacccggca gagcctgagc 1440
cgcgagctgg aggccatccg gaccgccaac cagaacttct ccagccaact acaggaggcc 1500
gaggtccgaa accgagacct ggaggcgcat gttcggcagc tacaggaacg gatggagatg 1560
ctgcaggccc caggagccgc agccatcacg ggggtcccca gtccccgggc cacggatcca 1620
ccttcccatc tagatggccc cccggccgtg gctgtgggcc agtgcccgct ggtggggcca 1680
ggccccatgc accgccgtca cctgctgctc cctgccagga tccctaggcc tggcctatcc 1740
gaggcgcgtt gcctgctcct gttcgccgct gctctggctg ctgccgccac actgggctgc 1800
actgggttgg tggcctatac cggcggtctc accccagtct ggtgtttccc gggagccacc 1860 ttcgcccccct gaaccctaag actccaagcc atctttcatt taggcctcct aggaaggtcg 1920
agcgaccagg gagcgaccca aagcgtctct gtgcccatcg cccccccccc cccccccacc 1980
gctccgctcc acacttctgt gagcctgggt ccccacccag ctccgctcct gtgatccagg 2040
cctgccacct ggcggccggg gagggaggaa cagggctcgt gcccagcacc cctggttcct 2100
gcagagctgg tagccaccgc tgctgcagca gctgggcatt cgccgacctt gctttactca 2160
gccccgacgt ggatgggcaa actgctcagc tcatccgatt tcactttttc actctcccag 2220
ccatcagtta caagccataa gcatgagccc cctatttcca gggacatccc attcccatag 2280
tgatggatca gcaagacctc tgccagcaca cacggagtct ttggcttcgg acagcctcac 2340
tcctgggggt tgctgcaact ccttccccgt gtacacgtct gcactctaac aacggagcca 2400
cagctgcact cccccctccc ccaaagcagt gtgggtattt attgatcttg ttatctgact 2460
cactgacaga ctccgggacc cacgttttag atgcattgag actcgacatt cctcggtatt 2520
tattgtctgt ccccacctac gacctccact cccgaccctt gcgaataaaa tacttctggt 2580
ctgccctaaa aaaaaaaaaa aaaaaaaaaa a 2611

<210> SEQ ID NO 10
<211> LENGTH: 988
<212> TYPE: DNA
<213> ORGANISM: mus musculus
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (942)..(942)
<223> OTHER INFORMATION: n is a, c, g, or t

<400> SEQUENCE: 10
gctggaccgg tccggaattc tccggatcgc cagcctttgt gggccatatt cgtcatccct 60
cctggcttct catctgcttt tgtggtccta gctcaagacc tctaattcct ctgctgactt 120
aaatgccctt ccccagaggt cttctcaggc ctagtggaca agcttggagc cttatctgct 180
cctgcccaac attgagccaa agctccagct taccccagct tccttacaat ggaccccatt 240
gcagcaaggc ttaaggaggt ccgactgcag agggatgatt ttgagatttt gaaggtgatc 300
gggcgtgggg cgttcagcga ggtagcggtg gtgaagatga aacagacggg ccaagtgtat 360
gccatgaaga ttatgaataa gtgggacatg ctgaagagag gcgaggtgtc gtgcttccgg 420
gaagaaaggg atgtattagt gaaaggggac cggcgctgga tcacacagct gcactttgcc 480
ttccaggatg agaactacct gtacctggtc atggaatact acgtgggcgg ngacctgcta 540
acgctgctga gcaagttttg gggagcggat ccccgccgag atggctcgct tctacctggc 600
cgagattgtc atggccatag actccgtgca ccggctgggc tacgtgcaca gggacatcaa 660
accagataac attctgctgg accgatgtgg gcacattcgc ctggcagact tcggctcctg 720
gcctcaactg cagcctgatg gaatggtgga gtcccctggt ggctgtgggc acccccggac 780
tacctgtctc ctgaaattct gcagggcctt ggtgggaggc cctggggaag gcaactacgg 840
gccaaaagtt ggaagggggg ggcctggggg gggttcccct atgaaaagtt ctatggggag 900 gaccccccttt aagcggaatc ccaggccgaa aaatatgccc angattgggc cctaacaggg 960
aaaacttttc ccctgcccct gggacaat 988

<210> SEQ ID NO 11
<211> LENGTH: 649
<212> TYPE: DNA
<213> ORGANISM: mus musculus

<400> SEQUENCE: 11

```
ggcgtgttcg cctatgagat gttctatggg cagaccccct tctacgcgga ctccacagcc     60

gagacatatg ccaagattgt gcactacagg gaacacttgt cgctgccgct ggcagacaca    120

gttgtccccg aggaagctca ggacctcatt cgtgggctgc tgtgtcctgc tgagataagg    180

ctaggtcgag gtggggcagg tgatttccag aaacatcctt tcttctttgg ccttgattgg    240

gagggtctcc gagacagtgt acccccccttt acaccagact tcgagggtgc cacggacaca    300

tgcaatttcg atgtggtgga ggaccggctc actgccatgg agacgctgtc agacatgcag    360

gaagacatgc cccttggggt gcgcctgccc ttcgtgggct actcctactg ctgcatggcc    420

ttcagagaca atcaggtccc ggaccccacc cctatggaac tagaggccct gcagttgcct    480

gtgtcagact tgcaagggct tgacttgcag cccccagtgt ccccaccgga tcaagtggtc    540

ccaactctga tccccaccga caggctgaag aggctgacct agtggctgtc cctgcccctg    600

tggctgaggc agagccacgg taacgctgca gcagctccag gaagccctg                649
```

<210> SEQ ID NO 12
<211> LENGTH: 527
<212> TYPE: DNA
<213> ORGANISM: mus musculus

<400> SEQUENCE: 12

```
atttcgatgt ggtggaggac cggctcactg ccatggtgag cgggggcggg gagacgctgt     60

cagacatgca ggaagacatg ccccttgggg tgcgcctgcc cttcgtgggc tactcctact    120

gctgcatggc cttcagagac aatcaggtcc cggaccccac ccctatggaa ctagaggccc    180

tgcagttgcc tgtgtcagac ttgcaagggc ttgacttgca gcccccagtg tccccaccgg    240

atcaagtggc tgaagaggct gacctagtgg ctgtccctgc ccctgtggct gaggcagaga    300

ccacggtaac gctgcagcag ctccaggaag ccctggaaga agaggttctc acccggcaga    360

gcctgagccg cgagctggag gccatccgga ccgccaacca gaacttctcc aggaggccga    420

ggtccgaaac cgagacctgg aggcgcatgt tcggcagcta caggaacgga tggagatgct    480

gcaggcccca ggaaccgcag ccatcacggg ggtccccagt cccccgg                  527
```

<210> SEQ ID NO 13
<211> LENGTH: 567
<212> TYPE: DNA
<213> ORGANISM: mus musculus

<400> SEQUENCE: 13

```
atggtgaggt cgctggtggc tgtgggcacc ccggactacc tgtctcctga gattctgcag     60

gccgttggtg gagggcctgg ggcaggcagc tacgggccag agtgtgactg gtgggcactg    120

ggcgtgttcg cctatgagat gttctatggg cagacccccct tctacgcgga ctccacagcc   180

gagacatatg ccaagattgt gcactacagg gaacacttgt cgctgccgct ggcagacaca    240

gttgtccccg aggaagctca ggacctcatt cgtgggctgc tgtgtcctgc tgagataagg    300

ctaggtcgag gtggggcagg tgatttccag aaacatcctt tcttctttgg ccttgattgg    360

gagggtctcc gagacagtgt acccccccttt acaccagact tcgagggtgc cacggacaca   420

tgcaatttcg atgtggtgga ggaccggctc actgccatgg tgagcggggg cggggtatga    480

ggacacacag gtgaccagtc cccaagacag tgagtgaggc ttcactcttg gcagtactaa    540

aattgaatgt agggggctgg gctcttg                                        567
```

<210> SEQ ID NO 14

<211> LENGTH: 2474
<212> TYPE: DNA
<213> ORGANISM: mus musculus

<400> SEQUENCE: 14
ccgggaagaa agggatgtat tagtgaaagg ggaccggcgc tggatcacac agctgcactt 60
tgccttccag gatgagaact acctgtacct ggtcatggaa tactacgtgg gcggggacct 120
gctaacgctg ctgagcaagt ttggggagcg gatccccgcc gagatggctc gcttctacct 180
ggccgagatt gtcatggcca tagactccgt gcaccggctg ggctacgtgc acagggacat 240
caaaccagat aacattctgc tggaccgatg tgggcacatt cgcctggcag acttcggctc 300
ctgcctcaaa ctgcagcctg atggaatggt gaggtcgctg gtggctgtgg gcaccccgga 360
ctacctgtct cctgagattc tgcaggccgt tggtggaggg cctggggcag gcagctacgg 420
gccagagtgt gactggtggg cactgggcgt gttcgcctat gagatgttct atgggcagac 480 cccctctac gcggactcca cagccgagac atatgccaag attgtgcact acagggaaca 540
cttgtcgctg ccgctggcag acacagttgt ccccgaggaa gctcaggacc tcattcgtgg 600
gctgctgtgt cctgctgaga taaggctagg tcgagacttc gagggtgcca cggacacatg 660
caatttcgat gtggtggagg accggctcac tgccatggtg agcgggggcg gggagacgct 720
gtcagacatg caggaagaca tgccccttgg ggtgcgcctg cccttcgtgg gctactccta 780
ctgctgcatg gccttcagag acaatcaggt cccggacccc acccctatgg aactagaggc 840
cctgcagttg cctgtgtcag acttgcaagg gcttgacttg cagcccccag tgtccccacc 900
ggatcaagtg gctgaagagg ccgacctagt ggctgtccct gcccctgtgg ctgaggcaga 960
gaccacggta acgctgcagc agctccagga agccctggaa gaagaggttc tcacccggca 1020
gagcctgagc cgcgagctgg aggccatccg gaccgccaac cagaacttct ccagccaact 1080
acaggaggcc gaggtccgaa accgagacct ggaggcgcat gttcggcagc tacaggaacg 1140
gatggagatg ctgcaggccc caggagccgc aggcgagtcc ctcacctgct tccagccaag 1200
ggggcactgg gtggagatgg ggggcatgtt gggtgtgtga accctcgggg caggggagga 1260
gtccaggctg gggcaccgca gccgcgccac tgcctttctc ctccatcctc cacactccat 1320
acacctctct cttctccttc cagccatcac gggggtcccc agtccccggg ccacggatcc 1380
accttcccat gcttctcgcc aaatcctccc caagggaact ccctagactc ccgttctggc 1440
ctcgactaga ttcccgcact gcctctcgcc ctgctgctgg gctccgatcg ggtcacctgt 1500
cccttctctc tccagctaga tggcccccg gccgtggctg tgggccagtg cccgctggtg 1560
gggccaggcc ccatgcaccg ccgtcacctg ctgctccctg ccaggatccc taggcctggc 1620
ctatccgagg cgcgttgcct gctcctgttc gccgctgctc tggctgctgc cgccacactg 1680
ggctgcactg ggttggtggc ctataccggc ggtctcaccc cagtctggtg tttcccggga 1740
gccaccttcg cccccctgaac cctaagactc caagccatct ttcatttagg cctcctagga 1800
agatcgagcg accagggagc gacccaaagc gtctctgtgc ccatcgcccc cccccccccc 1860
cccaccgctc cgctccacac ttctgtgagc ctgggtcccc acccagctcc gctcctgtga 1920
tccaggcctg ccacctggcg gccggggagg gaggaacagg gctcgtgccc agcacccctg 1980
gttcctgcag agctggtagc caccgctgct gcagcagctg ggcattcgcc gaccttgctt 2040
tactcagccc tgacgtggat gggctaactg ctcagctcat ccgatttcac tttttcactc 2100
tcccagccat cagttacaag ccataagcat gagcccccta tttccaggga catcccattc 2160
ccatagtgat ggatcagcaa gacctctgcc agcacacacg gagtctttgg cttcggacag 2220
cctcactcct gggggttgct gcaactcctt ccccgtgtac acgtctgcac tctaacaacg 2280
gagccacagc tgcactcccc cctcccccaa agcagtgtgg gtatttattg atcttgttat 2340
ctgactcact gacagactcc gggacccacg ttttagatgc attgagactc gacattcctc 2400
ggtatttatt gtctgtcccc acctacgacc tccactcccg acccttgcga ataaaatact 2460
tctggtctgc ccta 2474

<210> SEQ ID NO 15
<211> LENGTH: 2135
<212> TYPE: DNA
<213> ORGANISM: mus musculus

<400> SEQUENCE: 15
ccgggaagaa agggatgtat tagtgaaagg ggaccggcgc tggatcacac agctgcactt 60
tgccttccag gatgagaact acctgtacct ggtcatggaa tactacgtgg gcggggacct 120
gctaacgctg ctgagcaagt ttggggagcg gatccccgcc gagatggctc gcttctacct 180
ggccgagatt gtcatggcca tagactccgt gcaccggctg ggctacgtgc acagggacat 240
caaaccagat aacattctgc tggaccgatg tgggcacatt cgcctggcag acttcggctc 300
ctgcctcaaa ctgcagcctg atggaatggt gaggtcgctg gtggctgtgg gcaccccgga 360
ctacctgtct cctgagattc tgcaggccgt tggtggaggg cctggggcag gcagctacgg 420
gccagagtgt gactggtggg cactgggcgt gttcgcctat gagatgttct atgggcagac 480 cccctctac gcggactcca cagccgagac atatgccaag attgtgcact acagggaaca 540
cttgtcgctg ccgctggcag acacagttgt ccccgaggaa gctcaggacc tcattcgtgg 600
gctgctgtgt cctgctgaga taaggctagg tcgaggtggg gcaggtgatt tccagaaaca 660
tcctttcttc tttggccttg attgggaggg tctccgagac agtgtacccc cctttacacc 720
agacttcgag ggtgccacgg acacatgcaa tttcgatgtg gtggaggacc ggctcactgc 780
catggagacg ctgtcagaca tgcaggaaga catgcccctt ggggtgcgcc tgcccttcgt 840
gggctactcc tactgctgca tggccttcag agctgaagag gccgacctag tggctgtccc 900
tgcccctgtg gctgaggcag agaccacggt aacgctgcag cagctccagg aagccctgga 960
agaagaggtt ctcacccggc agagcctgag ccgcgagctg gaggccatcc ggaccgccaa 1020
ccagaacttc tccagccaac tacaggaggc cgaggtccga aaccgagacc tggaggcgca 1080
tgttcggcag ctacaggaac ggatggagat gctgcaggcc ccaggagccg cagccatcac 1140
gggggtcccc agtccccggg ccacggatcc accttcccat atggcccccc ggccgtggct 1200
gtgggccagt gcccgctggt ggggccaggc cccatgcacc gccgtcacct gctgctccct 1260
gccaggatcc ctaggcctgg cctatccgag gcgcgttgcc tgctcctgtt cgccgctgct 1320
ctggctgctg ccgccacact gggctgcact gggttggtgg cctataccgg cggtctcacc 1380
ccagtctggt gtttcccggg agccaccttc gccccctgaa ccctaagact ccaagccatc 1440
tttcatttag gcctcctagg aagatcgagc gaccagggag cgacccaaag cgtctctgtg 1500
cccatcgccc cccccccccc ccccaccgct ccgctccaca cttctgtgag cctgggtccc 1560
cacccagctc cgctcctgtg atccaggcct gccacctggc ggccggggag ggaggaacag 1620
ggctcgtgcc cagcacccct ggttcctgca gagctggtag ccaccgctgc tgcagcagct 1680
gggcattcgc cgaccttgct ttactcagcc ctgacgtgga tgggctaact gctcagctca 1740
tccgatttca ctttttcact ctcccagcca tcagttacaa gccataagca tgagcccct 1800

-continued

```
atttccaggg acatcccatt cccatagtga tggatcagca agacctctgc cagcacacac   1860

ggagtctttg gcttcggaca gcctcactcc tgggggttgc tgcaactcct tccccgtgta   1920

cacgtctgca ctctaacaac ggagccacag ctgcactccc ccctccccca aagcagtgtg   1980

ggtatttatt gatcttgtta tctgactcac tgacagactc cgggacccac gttttagatg   2040

cattgagact cgacattcct cggtatttat tgtctgtccc cacctacgac ctccactccc   2100

gacccttgcg aataaaatac ttctggtctg cccta                              2135


<210> SEQ ID NO 16
<211> LENGTH: 2873
<212> TYPE: DNA
<213> ORGANISM: homo sapiens

<400> SEQUENCE: 16

agggggGctg gaccaagggg tggggagaag gggaggaggc ctcggccggc cgcagagaga     60

agtggccaga gaggcccagg ggacagccag ggacaggcag acatgcagcc agggctccag    120

ggcctggaca ggggctgcca ggccctgtga caggaggacc ccgagccccc ggcccgggga    180

ggggccatgg tgctgcctgt ccaacatgtc agccgaggtg cggctgaggc ggctccagca    240

gctggtgttg gacccgggct tcctggggct ggagcccctg ctcgaccttc tcctgggcgt    300

ccaccaggag ctgggcgcct ccgaactggc ccaggacaag tacgtggccg acttcttgca    360

gtgggcggag cccatcgtgg tgaggcttaa ggaggtccga ctgcagaggg acgacttcga    420

gattctgaag gtgatcggac gcggggcgtt cagcgaggta gcggtagtga agatgaagca    480

gacgggccag gtgtatgcca tgaagatcat gaacaagtgg gacatgctga agaggggcga    540

ggtgtcgtgc ttccgtgagg agagggacgt gttggtgaat ggggaccggc ggtggatcac    600

gcagctgcac ttcgccttcc aggatgagaa ctacctgtac ctggtcatgg agtattacgt    660

gggcggggac ctgctgacac tgctgagcaa gtttggggag cggattccgg ccgagatggc    720

gcgcttctac ctggcggaga ttgtcatggc catagactcg gtgcaccggc ttggctacgt    780

gcacagggac atcaaacccg acaacatcct gctggaccgc tgtggccaca tccgcctggc    840

cgacttcggc tcttgcctca agctgcgggc agatggaacg gtgcggtcgc tggtggctgt    900

gggcacccca gactacctgt cccccgagat cctgcaggct gtgggcggtg ggcctgggac    960

aggcagctac gggcccgagt gtgactggtg ggcgctgggt gtattcgcct atgaaatgtt   1020

ctatgggcag acgcccttct acgcggattc cacggcggag acctatggca agatcgtcca   1080

ctacaaggag cacctctctc tgccgctggt ggacgaaggg gtccctgagg aggctcgaga   1140

cttcattcag cggttgctgt gtcccccgga gacacggctg ggccggggtg gagcaggcga   1200

cttccggaca catcccttct tctttggcct cgactgggat ggtctccggg acagcgtgcc   1260

cccctttaca ccggatttcg aaggtgccac cgacacatgc aacttcgact tggtggagga   1320

cgggctcact gccatggaga cactgtcgga cattcgggaa ggtgcgccgc taggggtcca   1380

cctgcctttt gtgggctact cctactcctg catggccctc agggacagtg aggtcccagg   1440

ccccacaccc atggaactgg aggccgagca gctgcttgag ccacacgtgc aagcgcccag   1500

cctggagccc tcggtgtccc cacaggatga aacagctgaa gtggcagttc cagcggctgt   1560

ccctgcggca gaggctgagg ccgaggtgac gctgcgggag ctccaggaag ccctggagga   1620

ggaggtgctc acccggcaga gcctgagccg ggagatggag gccatccgca cggacaacca   1680

gaacttcgcc agtcaactac gcgaggcaga ggctcggaac cgggacctag aggcacacgt   1740

ccggcagttg caggagcgga tggagttgct gcaggcagag ggagccacag ctgtcacggg   1800
```

```
ggtccccagt ccccgggcca cggatccacc ttcccatatg gccccccggc cgtggctgtg   1860

ggccagtgcc cgctggtggg gccaggcccc atgcaccgcc gccacctgct gctccctgcc   1920

agggtcccta ggcctggcct atcggaggcg ctttccctgc tcctgttcgc cgttgttctg   1980

tctcgtgccg ccgccctggg ctgcattggg ttggtggccc acgccggcca actcaccgca   2040

gtctggcgcc gcccaggagc cgcccgcgct ccctgaaccc tagaactgtc ttcgactccg   2100

gggccccgtt ggaagactga gtgcccgggg cacggcacag aagccgcgcc caccgcctgc   2160

cagttcacaa ccgctccgag cgtgggtctc cgcccagctc cagtcctgtg atccgggccc   2220

gccccctagc ggccggggag ggaggggccg ggtccgcggc cggcgaacgg ggctcgaagg   2280

gtccttgtag ccgggaatgc tgctgctgct gctgctgctg ctgctgctgc tgctgctgct   2340

gctgctgctg ctgctgctgg ggggatcaca gaccatttct ttctttcggc caggctgagg   2400

ccctgacgtg gatgggcaaa ctgcaggcct gggaaggcag caagccgggc cgtccgtgtt   2460

ccatcctcca cgcaccccca cctatcgttg gttcgcaaag tgcaaagctt tcttgtgcat   2520

gacgccctgc tctggggagc gtctggcgcg atctctgcct gcttactcgg gaaatttgct   2580

tttgccaaac ccgctttttc ggggatcccg cgccccctc ctcacttgcg ctgctctcgg   2640

agccccagcc ggctccgccc gcttcggcgg tttggatatt tattgacctc gtcctccgac   2700

tcgctgacag gctacaggac ccccaacaac cccaatccac gttttggatg cactgagacc   2760

ccgacattcc tcggtattta ttgtctgtcc ccacctagga cccccacccc cgaccctcgc   2820

gaataaaagg ccctccatct gcccaaaaaa aaaaaaaaaa aaaaaaaaaa aaa          2873
```

<210> SEQ ID NO 17
<211> LENGTH: 1509
<212> TYPE: DNA
<213> ORGANISM: homo sapiens

<400> SEQUENCE: 17

```
ccaccgcagc ggacagcgcc aagtgaagcc tcgcttcccc tccgcggcga ccagggcccg     60

agccgagagt agcagttgta gctacccgcc cagaaactag acacaatgtg cgacgaagac    120

gagaccaccg ccctcgtgtg cgacaatggc tccggcctgg tgaaagccgg cttcgccggg    180

gatgacgccc ctagggccgt gttcccgtcc atcgtgggcc gcccccgaca ccagggcgtc    240

atggtcggta tgggtcagaa agattcctac gtgggcgacg aggctcagag caagagaggt    300

atcctgaccc tgaagtaccc tatcgagcac ggcatcatca ccaactggga tgacatggag    360

aagatctggc accacacctt ctacaacgag cttcgcgtgg ctcccgagga gcaccccacc    420

ctgctcaccg aggcccccct caatcccaag gccaaccgcg agaagatgac ccagatcatg    480

tttgagacct tcaacgtgcc cgccatgtac gtggccatcc aggccgtgct gtccctctac    540

gcctccggca ggaccaccgg catcgtgctg gactccggcg acggcgtcac ccacaacgtg    600

cccatttatg agggctacgc gctgccgcac gccatcatgc gcctggacct ggcgggccgc    660

gatctcaccg actacctgat gaagatcctc actgagcgtg gctactcctt cgtgaccaca    720

gctgagcgcg agatcgtgcg cgacatcaag gagaagctgt gctacgtggc cctggacttc    780

gagaacgaga tggcgacggc cgcctcctcc tcctccctgg aaaagagcta cgagctgcca    840

gacgggcagg tcatcaccat cggcaacgag cgcttccgct gcccggagac gctcttccag    900

ccctccttca tcggtatgga gtcggcgggc attcacgaga ccacctacaa cagcatcatg    960

aagtgtgaca tcgacatcag gaaggacctg tatgccaaca acgtcatgtc gggggggcacc   1020
```

-continued

```
acgatgtacc ctgggatcgc tgaccgcatg cagaaagaga tcaccgcgct ggcacccagc   1080

accatgaaga tcaagatcat cgccccgccg gagcgcaaat actcggtgtg gatcggcggc   1140

tccatcctgg cctcgctgtc caccttccag cagatgtgga tcaccaagca ggagtacgac   1200

gaggccggcc cttccatcgt ccaccgcaaa tgcttctaga cacactccac ctccagcacg   1260

cgacttctca ggacgacgaa tcttctcaat ggggggcgg ctgagctcca gccaccccgc   1320

agtcactttc tttgtaacaa cttccgttgc tgccatcgta aactgacaca gtgtttataa   1380

cgtgtacata cattaactta ttacctcatt ttgttatttt tcgaaacaaa gccctgtgga   1440

agaaaatgga aaacttgaag aagcattaaa gtcattctgt taagctgcgt aaaaaaaaaa   1500

aaaaaaaaa                                                           1509
```

<210> SEQ ID NO 18

<400> SEQUENCE: 18

000

<210> SEQ ID NO 19

<400> SEQUENCE: 19

000

<210> SEQ ID NO 20
<211> LENGTH: 18
<212> TYPE: DNA
<213> ORGANISM: Artificial sequence
<220> FEATURE:
<223> OTHER INFORMATION: Primer

<400> SEQUENCE: 20
agcctgagcc gggagatg 18

<210> SEQ ID NO 21
<211> LENGTH: 21
<212> TYPE: DNA
<213> ORGANISM: Artificial sequence
<220> FEATURE:
<223> OTHER INFORMATION: Primer

<400> SEQUENCE: 21
gcgtagttga ctggcgaagt t 21

<210> SEQ ID NO 22
<211> LENGTH: 21
<212> TYPE: DNA
<213> ORGANISM: Artificial sequence
<220> FEATURE:
<223> OTHER INFORMATION: Probe

<400> SEQUENCE: 22
aggccatccg cacggacaac c 21

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 23
acaataaata ccgagg 16

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
cggagcggtt gtgaactggc 20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
gcgcaccttc ccgaatgtcc 20

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
cccgaatgtc cgacag 16

<210> SEQ ID NO 27
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 27
cggagcggtt gtgaact 17

<210> SEQ ID NO 28
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 28
acaataaata ccgagga 17

<210> SEQ ID NO 29
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 29
gacaatctcc gccagg 16

<210> SEQ ID NO 30
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 30
tcccgaatgt ccgaca 16

<210> SEQ ID NO 31
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 31
tgtaatgttg tccagt 16

<210> SEQ ID NO 32
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 32
gtgtaatgtt gtccag 16

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
ttgcactttg cgaaccaacg 20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
cgacacctcg cccctcttca 20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
acgacacctc gcccctcttc 20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
cacgacacct cgcccctctt 20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
gcacgacacc tcgcccctct 20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
agcacgacac ctcgcccctc 20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
aagcacgaca cctcgcccct 20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
gaagcacgac acctcgcccc 20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
ggaagcacga cacctcgccc 20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
cggaagcacg acacctcgcc 20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
acggaagcac gacacctcgc 20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
cacggaagca cgacacctcg 20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
tcacggaagc acgacacctc 20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
ctcacggaag cacgacacct 20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
cctcacggaa gcacgacacc 20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
tcctcacgga agcacgacac 20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
ctcctcacgg aagcacgaca 20

<210> SEQ ID NO 50
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 50
tctcctcacg gaagcacgac 20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
ctctcctcac ggaagcacga 20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
cctctcctca cggaagcacg 20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
ccctctcctc acggaagcac 20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
tccctctcct cacggaagca 20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
gtccctctcc tcacggaagc 20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
cgtccctctc ctcacggaag 20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
ggtccccatt caccaacacg 20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
cggtccccat tcaccaacac 20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
ccggtcccca ttcaccaaca 20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
gccggtcccc attcaccaac 20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
cgccggtccc cattcaccaa 20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
ccgccggtcc ccattcacca 20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
accgccggtc cccattcacc 20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
caccgccggt ccccattcac 20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
ccaccgccgg tccccattca 20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
tccaccgccg gtccccattc 20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
atccaccgcc ggtccccatt 20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
gatccaccgc cggtccccat 20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
tgatccaccg ccggtcccca 20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
gtgatccacc gccggtcccc 20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
cgtgatccac cgccggtccc 20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
ttctcatcct ggaaggcgaa 20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
gttctcatcc tggaaggcga 20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
agttctcatc ctggaaggcg 20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
gtagttctca tcctggaagg 20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
ggtagttctc atcctggaag 20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
aggtagttct catcctggaa 20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
caggtagttc tcatcctgga 20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
tacaggtagt tctcatcctg 20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
gtacaggtag ttctcatcct 20

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
ggtacaggta gttctcatcc 20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
aggtacaggt agttctcatc 20

<210> SEQ ID NO 83

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
ccaggtacag gtagttctca 20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
accaggtaca ggtagttctc 20

<210> SEQ ID NO 85
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 85
gaccaggtac aggtagttct 20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
tgaccaggta caggtagttc 20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
catgaccagg tacaggtagt 20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
ccatgaccag gtacaggtag 20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
tccatgacca ggtacaggta 20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
ctccatgacc aggtacaggt 20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
actccatgac caggtacagg 20

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
tactccatga ccaggtacag 20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
atactccatg accaggtaca 20

<210> SEQ ID NO 94
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 94
aatactccat gaccaggtac 20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
taatactcca tgaccaggta 20

<210> SEQ ID NO 96
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 96
cgtaatactc catgaccagg 20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
agcagtgtca gcaggtcccc 20

<210> SEQ ID NO 98
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 98
cagcagtgtc agcaggtccc 20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
tcagcagtgt cagcaggtcc 20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100
ctcagcagtg tcagcaggtc 20

<210> SEQ ID NO 101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 101
gctcagcagt gtcagcaggt 20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
tgctcagcag tgtcagcagg 20

-continued

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103
ttgctcagca gtgtcagcag 20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
cttgctcagc agtgtcagca 20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
acttgctcag cagtgtcagc 20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
aacttgctca gcagtgtcag 20

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
aaacttgctc agcagtgtca 20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
caaacttgct cagcagtgtc 20

<210> SEQ ID NO 109
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 109
ccaaacttgc tcagcagtgt 20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
cccaaacttg ctcagcagtg 20

<210> SEQ ID NO 111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 111
gtgagcccgt cctccaccaa 20

<210> SEQ ID NO 112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 112
agtgagcccg tcctccacca 20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 113
cagtgagccc gtcctccacc 20

<210> SEQ ID NO 114
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 114
gcagtgagcc cgtcctccac 20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
ggcagtgagc ccgtcctcca 20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
tggcagtgag cccgtcctcc 20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
catggcagtg agcccgtcct 20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 118
ccatggcagt gagcccgtcc 20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
tccatggcag tgagcccgtc 20

<210> SEQ ID NO 120
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 120
ctccatggca gtgagcccgt 20

<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 121
tctccatggc agtgagcccg 20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 122
gtctccatgg cagtgagccc 20

<210> SEQ ID NO 123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 123
ccttcccgaa tgtccgacag 20

<210> SEQ ID NO 124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 124
accttcccga atgtccgaca 20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
caccttcccg aatgtccgac 20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 126
gcaccttccc gaatgtccga 20

<210> SEQ ID NO 127
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 127
cgcaccttcc cgaatgtccg 20

<210> SEQ ID NO 128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 128
ggcgcacctt cccgaatgtc 20

<210> SEQ ID NO 129
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 129
acaaaaggca ggtggacccc 20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
cacaaaaggc aggtggaccc 20

<210> SEQ ID NO 131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 131
ccacaaaagg caggtggacc 20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 132
cccacaaaag gcaggtggac 20

<210> SEQ ID NO 133
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 133
gcccacaaaa ggcaggtgga 20

<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 134
agcccacaaa aggcaggtgg 20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135
tagcccacaa aaggcaggtg 20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 136
gtagcccaca aaaggcaggt 20

<210> SEQ ID NO 137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 137
agtagcccac aaaaggcagg 20

<210> SEQ ID NO 138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 138
gagtagccca caaaaggcag 20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
ggagtagccc acaaaaggca 20

<210> SEQ ID NO 140
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 140
aggagtagcc cacaaaaggc 20

<210> SEQ ID NO 141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 141
taggagtagc ccacaaaagg 20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
gtaggagtag cccacaaaag 20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
agtaggagta gcccacaaaa 20

<210> SEQ ID NO 144
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 144
gagtaggagt agcccacaaa 20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 145
ggagtaggag tagcccacaa 20

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146
aggagtagga gtagcccaca 20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 147
caggagtagg agtagcccac 20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 148
gcaggagtag gagtagccca 20

<210> SEQ ID NO 149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 149
tgcaggagta ggagtagccc 20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
atgcaggagt aggagtagcc 20

<210> SEQ ID NO 151
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 151
catgcaggag taggagtagc 20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
ccatgcagga gtaggagtag 20

<210> SEQ ID NO 153
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 153
gccatgcagg agtaggagta 20

<210> SEQ ID NO 154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 154
ggccatgcag gagtaggagt 20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 155
gggccatgca ggagtaggag 20

<210> SEQ ID NO 156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 156
agggccatgc aggagtagga 20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
gagggccatg caggagtagg 20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
ctgagggcca tgcaggagta 20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 159
cctgagggcc atgcaggagt 20

<210> SEQ ID NO 160
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 160
ccctgagggc catgcaggag 20

<210> SEQ ID NO 161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 161
tccctgaggg ccatgcagga 20

<210> SEQ ID NO 162

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 162
gtccctgagg gccatgcagg 20

<210> SEQ ID NO 163
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 163
tgtccctgag ggccatgcag 20

<210> SEQ ID NO 164
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 164
ctgtccctga gggccatgca 20

<210> SEQ ID NO 165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 165
actgtccctg agggccatgc 20

<210> SEQ ID NO 166
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 166
cactgtccct gagggccatg 20

<210> SEQ ID NO 167
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 167
tcactgtccc tgagggccat 20

<210> SEQ ID NO 168
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 168
ctcactgtcc ctgagggcca 20

<210> SEQ ID NO 169
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 169
cctcactgtc cctgagggcc 20

<210> SEQ ID NO 170
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 170
acctcactgt ccctgagggc 20

<210> SEQ ID NO 171
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 171
gacctcactg tccctgaggg 20

<210> SEQ ID NO 172
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 172
ggacctcact gtccctgagg 20

<210> SEQ ID NO 173
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 173
gggacctcac tgtccctgag 20

<210> SEQ ID NO 174
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 174
cctccagttc catgggtgtg 20

<210> SEQ ID NO 175
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 175
gcctccagtt ccatgggtgt 20

<210> SEQ ID NO 176
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 176
ggcctccagt tccatgggtg 20

<210> SEQ ID NO 177
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 177
cggcctccag ttccatgggt 20

<210> SEQ ID NO 178
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 178
tcggcctcca gttccatggg 20

<210> SEQ ID NO 179
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 179
ctcggcctcc agttccatgg 20

<210> SEQ ID NO 180
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 180
gctcggcctc cagttccatg 20

<210> SEQ ID NO 181
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 181
tgctcggcct ccagttccat 20

<210> SEQ ID NO 182
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 182
ctgctcggcc tccagttcca 20

<210> SEQ ID NO 183
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 183
gctgctcggc ctccagttcc 20

<210> SEQ ID NO 184
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 184
agctgctcgg cctccagttc 20

<210> SEQ ID NO 185
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 185
cagctgctcg gcctccagtt 20

<210> SEQ ID NO 186
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 186
gcagctgctc ggcctccagt 20

<210> SEQ ID NO 187
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 187
agcagctgct cggcctccag 20

<210> SEQ ID NO 188
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 188
aagcagctgc tcggcctcca 20

<210> SEQ ID NO 189
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 189
caagcagctg ctcggcctcc 20

<210> SEQ ID NO 190
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 190
tcaagcagct gctcggcctc 20

<210> SEQ ID NO 191
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 191
ctcaagcagc tgctcggcct 20

<210> SEQ ID NO 192
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 192
gctcaagcag ctgctcggcc 20

<210> SEQ ID NO 193
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 193
ggctcaagca gctgctcggc 20

<210> SEQ ID NO 194
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 194
tggctcaagc agctgctcgg 20

<210> SEQ ID NO 195
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 195
gtggctcaag cagctgctcg 20

<210> SEQ ID NO 196
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 196
tgtggctcaa gcagctgctc 20

<210> SEQ ID NO 197
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 197
gtgtggctca agcagctgct 20

<210> SEQ ID NO 198
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 198
ccacttcagc tgtttcatcc 20

<210> SEQ ID NO 199
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 199
tgccacttca gctgtttcat 20

<210> SEQ ID NO 200
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 200
ctgccacttc agctgtttca 20

<210> SEQ ID NO 201
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 201
actgccactt cagctgtttc 20

<210> SEQ ID NO 202
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 202
aactgccact tcagctgttt 20

<210> SEQ ID NO 203
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 203
gaactgccac ttcagctgtt 20

<210> SEQ ID NO 204
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 204
ggaactgcca cttcagctgt 20

<210> SEQ ID NO 205
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 205
tggaactgcc acttcagctg 20

<210> SEQ ID NO 206
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 206
ctggaactgc cacttcagct 20

<210> SEQ ID NO 207
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 207
gctggaactg ccacttcagc 20

<210> SEQ ID NO 208
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 208
cgctggaact gccacttcag 20

<210> SEQ ID NO 209
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 209
ccgctggaac tgccacttca 20

<210> SEQ ID NO 210
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 210
gccgctggaa ctgccacttc 20

<210> SEQ ID NO 211
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 211
agccgctgga actgccactt 20

<210> SEQ ID NO 212
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 212
ctcagcctct gccgcaggga 20

<210> SEQ ID NO 213
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 213
cctcagcctc tgccgcaggg 20

<210> SEQ ID NO 214
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 214
ggcctcagcc tctgccgcag 20

<210> SEQ ID NO 215
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 215
cggcctcagc ctctgccgca 20

<210> SEQ ID NO 216
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 216
tcggcctcag cctctgccgc 20

<210> SEQ ID NO 217
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 217
ctcggcctca gcctctgccg 20

<210> SEQ ID NO 218
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 218
cctcggcctc agcctctgcc 20

<210> SEQ ID NO 219
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 219
acctcggcct cagcctctgc 20

<210> SEQ ID NO 220
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 220
cacctcggcc tcagcctctg 20

<210> SEQ ID NO 221
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 221
tcacctcggc ctcagcctct 20

<210> SEQ ID NO 222
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 222
gtcacctcgg cctcagcctc 20

<210> SEQ ID NO 223
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 223
cgtcacctcg gcctcagcct 20

<210> SEQ ID NO 224
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 224
agcacctcct cctccagggc 20

<210> SEQ ID NO 225
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 225
gagcacctcc tcctccaggg 20

<210> SEQ ID NO 226
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 226
tgagcacctc ctcctccagg 20

<210> SEQ ID NO 227
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 227
gtgagcacct cctcctccag 20

<210> SEQ ID NO 228
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 228
ggtgagcacc tcctcctcca 20

<210> SEQ ID NO 229
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 229
gggtgagcac ctcctcctcc 20

<210> SEQ ID NO 230
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 230
cgggtgagca cctcctcctc 20

<210> SEQ ID NO 231
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 231
ccgggtgagc acctcctcct 20

<210> SEQ ID NO 232
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 232
gccgggtgag cacctcctcc 20

<210> SEQ ID NO 233
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 233
tgccgggtga gcacctcctc 20

<210> SEQ ID NO 234
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 234
ctgccgggtg agcacctcct 20

<210> SEQ ID NO 235
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 235
tctgccgggt gagcacctcc 20

<210> SEQ ID NO 236
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 236
gctctgccgg gtgagcacct 20

<210> SEQ ID NO 237
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 237
ggctctgccg ggtgagcacc 20

<210> SEQ ID NO 238
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 238
aggctctgcc gggtgagcac 20

<210> SEQ ID NO 239
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 239
caggctctgc cgggtgagca 20

<210> SEQ ID NO 240
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 240
tcaggctctg ccgggtgagc 20

<210> SEQ ID NO 241

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 241
gctcaggctc tgccgggtga 20

<210> SEQ ID NO 242
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 242
cggctcaggc tctgccgggt 20

<210> SEQ ID NO 243
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 243
ccggctcagg ctctgccggg 20

<210> SEQ ID NO 244
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 244
cccggctcag gctctgccgg 20

<210> SEQ ID NO 245
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 245
tcccggctca ggctctgccg 20

<210> SEQ ID NO 246
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 246
ctcccggctc aggctctgcc 20

<210> SEQ ID NO 247
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 247
tctcccggct caggctctgc 20

<210> SEQ ID NO 248
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 248
atctcccggc tcaggctctg 20

<210> SEQ ID NO 249
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 249
catctcccgg ctcaggctct 20

<210> SEQ ID NO 250
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 250
ccatctcccg gctcaggctc 20

<210> SEQ ID NO 251
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 251
tccatctccc ggctcaggct 20

<210> SEQ ID NO 252
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 252
ctccatctcc cggctcaggc 20

<210> SEQ ID NO 253
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 253
cctccatctc ccggctcagg 20

<210> SEQ ID NO 254
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 254
gcctccatct cccggctcag 20

<210> SEQ ID NO 255
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 255
ggcctccatc tcccggctca 20

<210> SEQ ID NO 256
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 256
tggcctccat ctcccggctc 20

<210> SEQ ID NO 257
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 257
atggcctcca tctcccggct 20

<210> SEQ ID NO 258
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 258
gatggcctcc atctcccggc 20

<210> SEQ ID NO 259
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 259
ggatggcctc catctcccgg 20

<210> SEQ ID NO 260
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 260
cggatggcct ccatctcccg 20

<210> SEQ ID NO 261
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 261
gcggatggcc tccatctccc 20

<210> SEQ ID NO 262
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 262
tgcggatggc ctccatctcc 20

<210> SEQ ID NO 263
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 263
gttccgagcc tctgcctcgc 20

<210> SEQ ID NO 264
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 264
gtcggaggac gaggtcaata 20

<210> SEQ ID NO 265
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 265
agggcctcag cctggccgaa 20

<210> SEQ ID NO 266
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 266
cagggcctca gcctggccga 20

<210> SEQ ID NO 267
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 267
gtcagggcct cagcctggcc 20

<210> SEQ ID NO 268
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 268
cgtcagggcc tcagcctggc 20

<210> SEQ ID NO 269
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 269
agcaaatttc ccgagtaagc 20

<210> SEQ ID NO 270
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 270
aagcaaattt cccgagtaag 20

<210> SEQ ID NO 271
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 271
aaaagcaaat ttcccgagta 20

<210> SEQ ID NO 272
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 272
caaaagcaaa tttcccgagt 20

<210> SEQ ID NO 273
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 273
gcaaaagcaa atttcccgag 20

<210> SEQ ID NO 274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 274
ggcaaaagca aatttcccga 20

<210> SEQ ID NO 275
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 275
tggcaaaagc aaatttcccg 20

<210> SEQ ID NO 276
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 276
tttggcaaaa gcaaatttcc 20

<210> SEQ ID NO 277
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 277
gtttggcaaa agcaaatttc 20

<210> SEQ ID NO 278
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 278
gggtttggca aaagcaaatt 20

<210> SEQ ID NO 279
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 279
cgggtttggc aaaagcaaat 20

<210> SEQ ID NO 280
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 280
aagcgggttt ggcaaaagca 20

<210> SEQ ID NO 281
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 281
aatatccaaa ccgccgaagc 20

<210> SEQ ID NO 282
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 282
aaatatccaa accgccgaag 20

<210> SEQ ID NO 283
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 283
ataaatatcc aaaccgccga 20

<210> SEQ ID NO 284
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 284
aataaatatc caaaccgccg 20

<210> SEQ ID NO 285
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 285
tcaataaata tccaaaccgc 20

<210> SEQ ID NO 286
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 286
gtcaataaat atccaaaccg 20

<210> SEQ ID NO 287
<211> LENGTH: 20

-continued

<212> TYPE: DNA
<213> ORGANISM: Artificial sequence
<220> FEATURE:
<223> OTHER INFORMATION: Synthetic oligonucleotide

<400> SEQUENCE: 287
ggtcaataaa tatccaaacc 20

<210> SEQ ID NO 288
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 288
aggtcaataa atatccaaac 20

<210> SEQ ID NO 289
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 289
gaggtcaata aatatccaaa 20

<210> SEQ ID NO 290
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 290
acgaggtcaa taaatatcca 20

<210> SEQ ID NO 291
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 291
gacgaggtca ataaatatcc 20

<210> SEQ ID NO 292
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 292
aggacgaggt caataaatat 20

<210> SEQ ID NO 293
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 293
gaggacgagg tcaataaata 20

<210> SEQ ID NO 294
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 294
cggaggacga ggtcaataaa 20

<210> SEQ ID NO 295
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 295
tcggaggacg aggtcaataa 20

<210> SEQ ID NO 296
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 296
agtcggagga cgaggtcaat 20

<210> SEQ ID NO 297
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 297
gagtcggagg acgaggtcaa 20

<210> SEQ ID NO 298
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 298
gcgagtcgga ggacgaggtc 20

<210> SEQ ID NO 299
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 299
agcgagtcgg aggacgaggt 20

<210> SEQ ID NO 300
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 300
cagcgagtcg gaggacgagg 20

<210> SEQ ID NO 301
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 301
tcagcgagtc ggaggacgag 20

<210> SEQ ID NO 302
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 302
gtcagcgagt cggaggacga 20

<210> SEQ ID NO 303
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 303
ctgtcagcga gtcggaggac 20

<210> SEQ ID NO 304
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 304
cctgtcagcg agtcggagga 20

<210> SEQ ID NO 305
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 305
agcctgtcag cgagtcggag 20

<210> SEQ ID NO 306
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 306
gtctcagtgc atccaaaacg 20

<210> SEQ ID NO 307
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 307
ggtctcagtg catccaaaac 20

<210> SEQ ID NO 308
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 308
gggtctcagt gcatccaaaa 20

<210> SEQ ID NO 309
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 309
ggagggcctt ttattcgcga 20

<210> SEQ ID NO 310
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 310
tggagggcct tttattcgcg 20

<210> SEQ ID NO 311
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 311
atggagggcc ttttattcgc 20

<210> SEQ ID NO 312
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 312
gatggagggc cttttattcg 20

<210> SEQ ID NO 313
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 313
agatggaggg ccttttattc 20

<210> SEQ ID NO 314
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 314
cagatggagg gccttttatt 20

<210> SEQ ID NO 315
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 315
gcagatggag ggccttttat 20

<210> SEQ ID NO 316
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 316
ccctcaggct ctctgcttta 20

<210> SEQ ID NO 317
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 317
gccctcaggc tctctgcttt 20

<210> SEQ ID NO 318
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 318
agccctcagg ctctctgctt 20

<210> SEQ ID NO 319
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 319
tagccctcag gctctctgct 20

<210> SEQ ID NO 320

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 320
ttagccctca ggctctctgc 20

<210> SEQ ID NO 321
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 321
tttagccctc aggctctctg 20

<210> SEQ ID NO 322
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 322
atttagccct caggctctct 20

<210> SEQ ID NO 323
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 323
aatttagccc tcaggctctc 20

<210> SEQ ID NO 324
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 324
aaatttagcc ctcaggctct 20

<210> SEQ ID NO 325
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 325
taaatttagc cctcaggctc 20

<210> SEQ ID NO 326
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 326
ttaaatttag ccctcaggct 20

<210> SEQ ID NO 327
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 327
gttaaattta gccctcaggc 20

<210> SEQ ID NO 328
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 328
agttaaattt agccctcagg 20

<210> SEQ ID NO 329
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 329
cagttaaatt tagccctcag 20

<210> SEQ ID NO 330
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 330
acagttaaat ttagccctca 20

<210> SEQ ID NO 331
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 331
gacagttaaa tttagccctc 20

<210> SEQ ID NO 332
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 332
ggacagttaa atttagccct 20

<210> SEQ ID NO 333
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 333
cggacagtta aatttagccc 20

<210> SEQ ID NO 334
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 334
tcggacagtt aaatttagcc 20

<210> SEQ ID NO 335
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 335
ctcggacagt taaatttagc 20

<210> SEQ ID NO 336
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 336
actcggacag ttaaatttag 20

<210> SEQ ID NO 337
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 337
gactcggaca gttaaattta 20

<210> SEQ ID NO 338
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 338
cgactcggac agttaaattt 20

<210> SEQ ID NO 339
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 339
ccgactcgga cagttaaatt 20

<210> SEQ ID NO 340
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 340
tccgactcgg acagttaaat 20

<210> SEQ ID NO 341
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 341
tctcctcacg gaagca 16

<210> SEQ ID NO 342
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 342
ctctcctcac ggaagc 16

<210> SEQ ID NO 343
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 343
cctctcctca cggaag 16

<210> SEQ ID NO 344
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 344
aaacttgctc agcagt 16

<210> SEQ ID NO 345
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 345
caaacttgct cagcag 16

<210> SEQ ID NO 346
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 346
ccaaacttgc tcagca 16

<210> SEQ ID NO 347
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 347
cccaaacttg ctcagc 16

<210> SEQ ID NO 348
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 348
ccccaaactt gctcag 16

<210> SEQ ID NO 349
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 349
tccccaaact tgctca 16

<210> SEQ ID NO 350
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 350
gtttgatgtc cctgtg 16

<210> SEQ ID NO 351
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 351
ggtttgatgt ccctgt 16

<210> SEQ ID NO 352
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 352
gggtttgatg tccctg 16

<210> SEQ ID NO 353
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 353
acagcctgca ggatct 16

<210> SEQ ID NO 354
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 354
cacagcctgc aggatc 16

<210> SEQ ID NO 355
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 355
ccacagcctg caggat 16

<210> SEQ ID NO 356
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 356
cccacagcct gcagga 16

<210> SEQ ID NO 357
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 357
gcccacagcc tgcagg 16

<210> SEQ ID NO 358
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 358
cgcccacagc ctgcag 16

<210> SEQ ID NO 359
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 359
ccgcccacag cctgca 16

<210> SEQ ID NO 360
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 360
accgcccaca gcctgc 16

<210> SEQ ID NO 361
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 361
caccgcccac agcctg 16

<210> SEQ ID NO 362
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 362
ccaccgccca cagcct 16

<210> SEQ ID NO 363
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 363
cccaccgccc acagcc 16

<210> SEQ ID NO 364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 364
gcccaccgcc cacagc 16

<210> SEQ ID NO 365
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 365
ccaggcccac cgccca 16

<210> SEQ ID NO 366
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 366
cccaggccca ccgccc 16

<210> SEQ ID NO 367
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 367
tcccaggccc accgcc 16

<210> SEQ ID NO 368
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 368
tgcctgtccc aggccc 16

<210> SEQ ID NO 369
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 369
ctgcctgtcc caggcc 16

<210> SEQ ID NO 370
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 370
gctgcctgtc ccaggc 16

<210> SEQ ID NO 371
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 371
ggtggcacct tcgaaa 16

<210> SEQ ID NO 372
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 372
cggtggcacc ttcgaa 16

<210> SEQ ID NO 373
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 373
tcggtggcac cttcga 16

<210> SEQ ID NO 374
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 374
agtgagcccg tcctcc 16

<210> SEQ ID NO 375
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 375
cagtgagccc gtcctc 16

<210> SEQ ID NO 376
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 376
gcagtgagcc cgtcct 16

<210> SEQ ID NO 377
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 377
tcccgaatgt ccgaca 16

<210> SEQ ID NO 378
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 378
ttcccgaatg tccgac 16

<210> SEQ ID NO 379
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 379
cttcccgaat gtccga 16

<210> SEQ ID NO 380
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 380
ccttcccgaa tgtccg 16

<210> SEQ ID NO 381
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 381
accttcccga atgtcc 16

<210> SEQ ID NO 382
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 382
caccttcccg aatgtc 16

<210> SEQ ID NO 383
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 383
gcaccttccc gaatgt 16

<210> SEQ ID NO 384
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 384
cgcaccttcc cgaatg 16

<210> SEQ ID NO 385
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 385
atccgctcct gcaact 16

<210> SEQ ID NO 386
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 386
catccgctcc tgcaac 16

<210> SEQ ID NO 387
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 387
ccatccgctc ctgcaa 16

<210> SEQ ID NO 388
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 388
gctccctctg cctgca 16

<210> SEQ ID NO 389
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 389
aggtggatcc gtggcc 16

<210> SEQ ID NO 390
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 390
gggaaggtgg atccgt 16

<210> SEQ ID NO 391
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 391
acaggagcag ggaaag 16

<210> SEQ ID NO 392
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 392
cagactgcgg tgagtt 16

<210> SEQ ID NO 393
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 393
ggctcctggg cggcgc 16

<210> SEQ ID NO 394
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 394
ggcggctcct gggcgg 16

<210> SEQ ID NO 395
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 395
cgcgggcggc tcctgg 16

<210> SEQ ID NO 396
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 396
gagcgcgggc ggctcc 16

<210> SEQ ID NO 397
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 397
ggttcaggga gcgcgg 16

<210> SEQ ID NO 398
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 398
agttctaggg ttcagg 16

<210> SEQ ID NO 399

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 399
cagttctagg gttcag 16

<210> SEQ ID NO 400
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 400
acagttctag ggttca 16

<210> SEQ ID NO 401
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 401
gacagttcta gggttc 16

<210> SEQ ID NO 402
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 402
agacagttct agggtt 16

<210> SEQ ID NO 403
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 403
aagacagttc tagggt 16

<210> SEQ ID NO 404
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 404
gaagacagtt ctaggg 16

<210> SEQ ID NO 405
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 405

-continued cgaagacagt tctagg 16

<210> SEQ ID NO 406
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 406
tcgaagacag ttctag 16

<210> SEQ ID NO 407
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 407
gtcgaagaca gttcta 16

<210> SEQ ID NO 408
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 408
agtcgaagac agttct 16

<210> SEQ ID NO 409
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 409
gagtcgaaga cagttc 16

<210> SEQ ID NO 410
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 410
ggagtcgaag acagtt 16

<210> SEQ ID NO 411
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 411
cggagtcgaa gacagt 16

<210> SEQ ID NO 412
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 412
ccggagtcga agacag 16

<210> SEQ ID NO 413
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 413
cccggagtcg aagaca 16

<210> SEQ ID NO 414
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 414
ccccggagtc gaagac 16

<210> SEQ ID NO 415
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 415
gccccggagt cgaaga 16

<210> SEQ ID NO 416
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 416
ggccccggag tcgaag 16

<210> SEQ ID NO 417
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 417
gggccccgga gtcgaa 16

<210> SEQ ID NO 418
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 418
cggttgtgaa ctggca 16

<210> SEQ ID NO 419
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 419
agcggttgtg aactgg 16

<210> SEQ ID NO 420
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 420
gcactttgcg aaccaa 16

<210> SEQ ID NO 421
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 421
tgcactttgc gaacca 16

<210> SEQ ID NO 422
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 422
actttgcgaa ccaacg 16

<210> SEQ ID NO 423
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 423
aaagctttgc actttg 16

<210> SEQ ID NO 424
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 424
tcccgagtaa gcaggc 16

<210> SEQ ID NO 425
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 425
gcagcgcaag tgagga 16

<210> SEQ ID NO 426
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 426
gtcagcgagt cggagg 16

<210> SEQ ID NO 427
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 427
cctgtcagcg agtcgg 16

<210> SEQ ID NO 428
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 428
gcctgtcagc gagtcg 16

<210> SEQ ID NO 429
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 429
agcctgtcag cgagtc 16

<210> SEQ ID NO 430
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 430
gggtctcagt gcatcc 16

<210> SEQ ID NO 431
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 431
aggtttttcc agaggc 16

```
<210> SEQ ID NO 432
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 432

aaggtttttc cagagg                                                       16

<210> SEQ ID NO 433
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 433

ggtcactgct gggtcc                                                       16

<210> SEQ ID NO 434
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 434

gtggtttctg tctgct                                                       16

<210> SEQ ID NO 435
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 435

cgtggtttct gtctgc                                                       16

<210> SEQ ID NO 436
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 436

gaactggcag gcggtg                                                       16

<210> SEQ ID NO 437
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 437

tgtgaactgg caggcg                                                       16

<210> SEQ ID NO 438
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 438
ggttgtgaac tggcag 16

<210> SEQ ID NO 439
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 439
gagcggttgt gaactg 16

<210> SEQ ID NO 440
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 440
actggagctg ggcgga 16

<210> SEQ ID NO 441
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 441
aggactggag ctgggc 16

<210> SEQ ID NO 442
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 442
tcacaggact ggagct 16

<210> SEQ ID NO 443
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 443
atcacaggac tggagc 16

<210> SEQ ID NO 444
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 444
ggatcacagg actgga 16

<210> SEQ ID NO 445
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 445
cagcctggcc gaaaga 16

<210> SEQ ID NO 446
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 446
ctcagcctgg ccgaaa 16

<210> SEQ ID NO 447
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 447
gtcagggcct cagcct 16

<210> SEQ ID NO 448
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 448
cgtcagggcc tcagcc 16

<210> SEQ ID NO 449
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 449
tttgcacttt gcgaac 16

<210> SEQ ID NO 450
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 450
gaaagctttg cacttt 16

<210> SEQ ID NO 451
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 451
aatttcccga gtaagc 16

<210> SEQ ID NO 452
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 452
gcaaatttcc cgagta 16

<210> SEQ ID NO 453
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 453
agcaaatttc ccgagt 16

<210> SEQ ID NO 454
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 454
aagcaaattt cccgag 16

<210> SEQ ID NO 455
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 455
aaagcaaatt tcccga 16

<210> SEQ ID NO 456
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 456
aaaagcaaat ttcccg 16

<210> SEQ ID NO 457
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 457
gcaaaagcaa atttcc 16

<210> SEQ ID NO 458
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 458
ggcaaaagca aatttc 16

<210> SEQ ID NO 459
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 459
ttggcaaaag caaatt 16

<210> SEQ ID NO 460
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 460
gtttggcaaa agcaaa 16

<210> SEQ ID NO 461
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 461
ggtttggcaa aagcaa 16

<210> SEQ ID NO 462
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 462
gggtttggca aaagca 16

<210> SEQ ID NO 463
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 463
gcgggtttgg caaaag 16

<210> SEQ ID NO 464
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 464
agcgggtttg gcaaaa 16

<210> SEQ ID NO 465
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 465
aagcgggttt ggcaaa 16

<210> SEQ ID NO 466
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 466
ctccgagagc agcgca 16

<210> SEQ ID NO 467
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 467
gctccgagag cagcgc 16

<210> SEQ ID NO 468
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 468
ggctccgaga gcagcg 16

<210> SEQ ID NO 469
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 469
taaatatcca aaccgc 16

<210> SEQ ID NO 470
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 470
gtcaataaat atccaa 16

<210> SEQ ID NO 471
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 471
aggtcaataa atatcc 16

<210> SEQ ID NO 472
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 472
cgaggtcaat aaatat 16

<210> SEQ ID NO 473
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 473
acgaggtcaa taaata 16

<210> SEQ ID NO 474
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 474
gacgaggtca ataaat 16

<210> SEQ ID NO 475
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 475
ggacgaggtc aataaa 16

<210> SEQ ID NO 476
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 476
aggacgaggt caataa 16

<210> SEQ ID NO 477
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 477
gaggacgagg tcaata 16

<210> SEQ ID NO 478

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 478
ggaggacgag gtcaat 16

<210> SEQ ID NO 479
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 479
cggaggacga ggtcaa 16

<210> SEQ ID NO 480
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 480
tcggaggacg aggtca 16

<210> SEQ ID NO 481
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 481
gtcggaggac gaggtc 16

<210> SEQ ID NO 482
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 482
agtcggagga cgaggt 16

<210> SEQ ID NO 483
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 483
gagtcggagg acgagg 16

<210> SEQ ID NO 484
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 484
cgagtcggag gacgag 16

<210> SEQ ID NO 485
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 485
agcgagtcgg aggacg 16

<210> SEQ ID NO 486
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 486
cagcgagtcg gaggac 16

<210> SEQ ID NO 487
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 487
tcagcgagtc ggagga 16

<210> SEQ ID NO 488
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 488
tgtcagcgag tcggag 16

<210> SEQ ID NO 489
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 489
ctgtcagcga gtcgga 16

<210> SEQ ID NO 490
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 490
cagtgcatcc aaaacg 16

<210> SEQ ID NO 491
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 491
tcagtgcatc caaaac 16

<210> SEQ ID NO 492
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 492
ctcagtgcat ccaaaa 16

<210> SEQ ID NO 493
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 493
tctcagtgca tccaaa 16

<210> SEQ ID NO 494
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 494
gtctcagtgc atccaa 16

<210> SEQ ID NO 495
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 495
caataaatac cgagga 16

<210> SEQ ID NO 496
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 496
agacaataaa taccga 16

<210> SEQ ID NO 497
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 497
cagacaataa ataccg 16

<210> SEQ ID NO 498
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 498
cacggaagca cgacac 16

<210> SEQ ID NO 499
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 499
tcacggaagc acgaca 16

<210> SEQ ID NO 500
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 500
ctcacggaag cacgac 16

<210> SEQ ID NO 501
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 501
gtccctctcc tcacgg 16

<210> SEQ ID NO 502
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 502
cgtccctctc ctcacg 16

<210> SEQ ID NO 503
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 503
cccattcacc aacacg 16

<210> SEQ ID NO 504
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 504
ccccattcac caacac 16

<210> SEQ ID NO 505
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 505
tccccattca ccaaca 16

<210> SEQ ID NO 506
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 506
gtccccattc accaac 16

<210> SEQ ID NO 507
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 507
ggtccccatt caccaa 16

<210> SEQ ID NO 508
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 508
cggtccccat tcacca 16

<210> SEQ ID NO 509
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 509
ccggtcccca ttcacc 16

<210> SEQ ID NO 510
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 510
gccggtcccc attcac 16

<210> SEQ ID NO 511
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 511
cgccggtccc cattca 16

<210> SEQ ID NO 512
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 512
ccgccggtcc ccattc 16

<210> SEQ ID NO 513
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 513
accgccggtc cccatt 16

<210> SEQ ID NO 514
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 514
caccgccggt ccccat 16

<210> SEQ ID NO 515
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 515
ccaccgccgg tcccca 16

<210> SEQ ID NO 516
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 516
tccaccgccg gtcccc 16

<210> SEQ ID NO 517
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 517
atccaccgcc ggtccc 16

<210> SEQ ID NO 518
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 518
gatccaccgc cggtcc 16

<210> SEQ ID NO 519
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 519
tgatccaccg ccggtc 16

<210> SEQ ID NO 520
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 520
gtgatccacc gccggt 16

<210> SEQ ID NO 521
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 521
cgtgatccac cgccgg 16

<210> SEQ ID NO 522
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 522
catcctggaa ggcgaa 16

<210> SEQ ID NO 523
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 523
tcatcctgga aggcga 16

<210> SEQ ID NO 524
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 524
agttctcatc ctggaa 16

<210> SEQ ID NO 525
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 525
tagttctcat cctgga 16

<210> SEQ ID NO 526
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 526
gtagttctca tcctgg 16

<210> SEQ ID NO 527
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 527
caggtacagg tagttc 16

<210> SEQ ID NO 528
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 528
ccaggtacag gtagtt 16

<210> SEQ ID NO 529
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 529
gaccaggtac aggtag 16

<210> SEQ ID NO 530
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 530
ctccatgacc aggtac 16

<210> SEQ ID NO 531
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 531
actccatgac caggta 16

<210> SEQ ID NO 532
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 532
tactccatga ccaggt 16

<210> SEQ ID NO 533
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 533
atactccatg accagg 16

<210> SEQ ID NO 534
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 534
aatactccat gaccag 16

<210> SEQ ID NO 535
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 535
taatactcca tgacca 16

<210> SEQ ID NO 536
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 536
gtaatactcc atgacc 16

<210> SEQ ID NO 537
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 537
cgtaatactc catgac 16

<210> SEQ ID NO 538
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 538
cttgctcagc agtgtc 16

<210> SEQ ID NO 539
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 539
acttgctcag cagtgt 16

<210> SEQ ID NO 540
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 540
aacttgctca gcagtg 16

<210> SEQ ID NO 541
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 541
gctccccaaa cttgct 16

<210> SEQ ID NO 542
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 542
cgctccccaa acttgc 16

<210> SEQ ID NO 543
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 543
ccgctcccca aacttg 16

<210> SEQ ID NO 544
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 544
tccgctcccc aaactt 16

<210> SEQ ID NO 545
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 545
atccgctccc caaact 16

<210> SEQ ID NO 546
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 546
aatccgctcc ccaaac 16

<210> SEQ ID NO 547
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 547
gaatccgctc cccaaa 16

<210> SEQ ID NO 548
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 548
ggaatccgct ccccaa 16

<210> SEQ ID NO 549
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 549
cggaatccgc tcccca 16

<210> SEQ ID NO 550
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 550
ccggaatccg ctcccc 16

<210> SEQ ID NO 551
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 551
gccggaatcc gctccc 16

<210> SEQ ID NO 552
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 552
agaagcgcgc catctc 16

<210> SEQ ID NO 553
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 553
tagaagcgcg ccatct 16

<210> SEQ ID NO 554
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 554
gtagaagcgc gccatc 16

<210> SEQ ID NO 555
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 555
ggtagaagcg cgccat 16

<210> SEQ ID NO 556
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 556
aggtagaagc gcgcca 16

<210> SEQ ID NO 557

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 557
caggtagaag cgcgcc 16

<210> SEQ ID NO 558
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 558
ccaggtagaa gcgcgc 16

<210> SEQ ID NO 559
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 559
gccaggtaga agcgcg 16

<210> SEQ ID NO 560
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 560
cgccaggtag aagcgc 16

<210> SEQ ID NO 561
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 561
ccgccaggta gaagcg 16

<210> SEQ ID NO 562
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 562
tccgccaggt agaagc 16

<210> SEQ ID NO 563
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 563
tgacaatctc cgccag 16

<210> SEQ ID NO 564
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 564
atgacaatct ccgcca 16

<210> SEQ ID NO 565
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 565
catgacaatc tccgcc 16

<210> SEQ ID NO 566
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 566
ccatgacaat ctccgc 16

<210> SEQ ID NO 567
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 567
gccatgacaa tctccg 16

<210> SEQ ID NO 568
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 568
ggccatgaca atctcc 16

<210> SEQ ID NO 569
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 569
ccaactgttc tcttag 16

<210> SEQ ID NO 570
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 570
aaccaactgt tctctt 16

<210> SEQ ID NO 571
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 571
ccagtaataa aagctg 16

<210> SEQ ID NO 572
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 572
gtccagtaat aaaagc 16

<210> SEQ ID NO 573
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 573
gttgtccagt aataaa 16

<210> SEQ ID NO 574
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 574
atgttgtcca gtaata 16

<210> SEQ ID NO 575
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 575
taatgttgtc cagtaa 16

<210> SEQ ID NO 576
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 576
ttcaatcctg acccac 16

<210> SEQ ID NO 577
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 577
ggttcaatcc tgaccc 16

<210> SEQ ID NO 578
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 578
tgggttcaat cctgac 16

<210> SEQ ID NO 579
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 579
gatgggttca atcctg 16

<210> SEQ ID NO 580
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 580
aggatgggtt caatcc 16

<210> SEQ ID NO 581
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 581
agaggatggg ttcaat 16

<210> SEQ ID NO 582
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 582
atagaggatg ggttca 16

<210> SEQ ID NO 583
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 583
ccctcctgtg ggaaca 16

<210> SEQ ID NO 584
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 584
gtccctcctg tgggaa 16

<210> SEQ ID NO 585
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 585
cagtccctcc tgtggg 16

<210> SEQ ID NO 586
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 586
agcagtccct cctgtg 16

<210> SEQ ID NO 587
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 587
actcagctgt gggaag 16

<210> SEQ ID NO 588
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 588
cccactcagc tgtggg 16

<210> SEQ ID NO 589
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 589
accccactca gctgtg 16

<210> SEQ ID NO 590
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 590
acaccccact cagctg 16

<210> SEQ ID NO 591
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 591
gcacacccca ctcagc 16

<210> SEQ ID NO 592
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 592
tcagcacacc ccactc 16

<210> SEQ ID NO 593
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 593
gtggtcctaa gactgg 16

<210> SEQ ID NO 594
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 594
gatgtggtcc taagac 16

<210> SEQ ID NO 595
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 595
cagatgtggt cctaag 16

<210> SEQ ID NO 596
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 596
cctccacaga tgtggt 16

<210> SEQ ID NO 597
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 597
cacctccaca gatgtg 16

<210> SEQ ID NO 598
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 598
ggccacctcc acagat 16

<210> SEQ ID NO 599
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 599
tgcttggctc tggcca 16

<210> SEQ ID NO 600
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 600
actgcttggc tctggc 16

<210> SEQ ID NO 601
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 601
agactgcttg gctctg 16

<210> SEQ ID NO 602
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 602
ggagactgct tggctc 16

<210> SEQ ID NO 603
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 603
tgcagacccc tcttct 16

<210> SEQ ID NO 604
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 604
ctcctccctt gacatg 16

<210> SEQ ID NO 605
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 605
ccagaccccc atgttc 16

<210> SEQ ID NO 606
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 606
gtccagaccc ccatgt 16

<210> SEQ ID NO 607
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 607
gggtccagac ccccat 16

<210> SEQ ID NO 608
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 608
accttctgca gggact 16

<210> SEQ ID NO 609
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 609
taaaccttct gcaggg 16

<210> SEQ ID NO 610
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 610
gaaaagccct gcccct 16

<210> SEQ ID NO 611
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 611
taggaaaagc cctgcc 16

<210> SEQ ID NO 612
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 612
cttaggaaaa gccctg 16

<210> SEQ ID NO 613
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 613
tgcttaggaa aagccc 16

<210> SEQ ID NO 614
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 614
tctgcttagg aaaagc 16

<210> SEQ ID NO 615
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 615
ctcctctgct taggaa 16

<210> SEQ ID NO 616
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 616
ccctcctctg cttagg 16

<210> SEQ ID NO 617
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 617
ctgatttgag gaaggg 16

<210> SEQ ID NO 618
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 618
tcctgatttg aggaag 16

<210> SEQ ID NO 619
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 619
cctcctgatt tgagga 16

<210> SEQ ID NO 620
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 620
gacctcctga tttgag 16

<210> SEQ ID NO 621
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 621
aagacctcct gatttg 16

<210> SEQ ID NO 622
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 622
ccaagacctc ctgatt 16

<210> SEQ ID NO 623
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 623
ctgcttccaa gacctc 16

<210> SEQ ID NO 624
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 624
agctgcttcc aagacc 16

<210> SEQ ID NO 625
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 625
gcagctgctt ccaaga 16

<210> SEQ ID NO 626
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 626
ctggtggaga accaga 16

<210> SEQ ID NO 627
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 627
ctctggtgga gaacca 16

<210> SEQ ID NO 628
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 628
ttctctggtg gagaac 16

<210> SEQ ID NO 629
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 629
gattctctgg tggaga 16

<210> SEQ ID NO 630
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 630
acttactgtt tcatcc 16

<210> SEQ ID NO 631
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 631
cggaccccct cccctc 16

<210> SEQ ID NO 632
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 632
gacggacccc ctcccc 16

<210> SEQ ID NO 633
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 633
ctgacggacc ccctcc 16

<210> SEQ ID NO 634
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 634
ccctgacgga cccccct 16

<210> SEQ ID NO 635
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 635
aagccctcac cttttc 16

<210> SEQ ID NO 636

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 636
ggaagccctc accttt 16

<210> SEQ ID NO 637
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 637
cgggaagccc tcacct 16

<210> SEQ ID NO 638
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 638
cccgggaagc cctcac 16

<210> SEQ ID NO 639
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 639
cacccgggaa gccctc 16

<210> SEQ ID NO 640
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 640
gccacccggg aagccc 16

<210> SEQ ID NO 641
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 641
acgccacccg ggaagc 16

<210> SEQ ID NO 642
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 642
ctgttcagga agtccc 16

<210> SEQ ID NO 643
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 643
ttctgttcag gaagtc 16

<210> SEQ ID NO 644
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 644
gcttctgttc aggaag 16

<210> SEQ ID NO 645
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 645
gcttgggccc acccct 16

<210> SEQ ID NO 646
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 646
aggcttgggc ccaccc 16

<210> SEQ ID NO 647
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 647
cgaggcttgg gcccac 16

<210> SEQ ID NO 648
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 648
agcgaggctt gggccc 16

<210> SEQ ID NO 649
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 649
agagcgaggc ttgggc 16

<210> SEQ ID NO 650
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 650
gcagagcgag gcttgg 16

<210> SEQ ID NO 651
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 651
gagcagagcg aggctt 16

<210> SEQ ID NO 652
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 652
aaaggagcag agcgag 16

<210> SEQ ID NO 653
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 653
caaaaggagc agagcg 16

<210> SEQ ID NO 654
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 654
tggaccaaaa ggagca 16

<210> SEQ ID NO 655
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 655
cctggaccaa aaggag 16

<210> SEQ ID NO 656
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 656
cacctggacc aaaagg 16

<210> SEQ ID NO 657
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 657
cgcacctgga ccaaaa 16

<210> SEQ ID NO 658
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 658
gaccgcacct ggacca 16

<210> SEQ ID NO 659
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 659
accttgtagt ggacga 16

<210> SEQ ID NO 660
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 660
tcaccttgta gtggac 16

<210> SEQ ID NO 661
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 661
gctcaccttg tagtgg 16

<210> SEQ ID NO 662
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 662
ggagaggagg cgatag 16

<210> SEQ ID NO 663
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 663
agggagagga ggcgat 16

<210> SEQ ID NO 664
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 664
ctcctgctca gaggga 16

<210> SEQ ID NO 665
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 665
gtgctcctgc tcagag 16

<210> SEQ ID NO 666
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 666
aggtgctcct gctcag 16

<210> SEQ ID NO 667
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 667
agaggtgctc ctgctc 16

<210> SEQ ID NO 668
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 668
agagaggtgc tcctgc 16

<210> SEQ ID NO 669
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 669
accccgcccc cgctca 16

<210> SEQ ID NO 670
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 670
ctaccccgcc cccgct 16

<210> SEQ ID NO 671
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 671
acctaccccg cccccg 16

<210> SEQ ID NO 672
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 672
gtacctaccc cgcccc 16

<210> SEQ ID NO 673
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 673
aggtacctac cccgcc 16

<210> SEQ ID NO 674
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 674
gggaggttcc cgcagc 16

<210> SEQ ID NO 675
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 675
gtccttactc caactt 16

<210> SEQ ID NO 676
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 676
ctgtccttac tccaac 16

<210> SEQ ID NO 677
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 677
cactgtcctt actcca 16

<210> SEQ ID NO 678
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 678
ggcactgtcc ttactc 16

<210> SEQ ID NO 679
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 679
taggcactgt ccttac 16

<210> SEQ ID NO 680
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 680
ggtaggcact gtcctt 16

<210> SEQ ID NO 681
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 681
gtcactgctg ggtcct 16

<210> SEQ ID NO 682
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 682
aggtcactgc tgggtc 16

<210> SEQ ID NO 683
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 683
ctaggtcact gctggg 16

<210> SEQ ID NO 684
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 684
gtctaggtca ctgctg 16

<210> SEQ ID NO 685
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 685
aagtctaggt cactgc 16

<210> SEQ ID NO 686
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 686
gcactccatt gtctca 16

<210> SEQ ID NO 687
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 687
ctgcactcca ttgtct 16

<210> SEQ ID NO 688
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 688
ccctgcactc cattgt 16

<210> SEQ ID NO 689
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 689
ccccctgcac tccatt 16

<210> SEQ ID NO 690
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 690
cttgctgagt caggag 16

<210> SEQ ID NO 691
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 691
tccttgctga gtcagg 16

<210> SEQ ID NO 692
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 692
cttccttgct gagtca 16

<210> SEQ ID NO 693
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 693
accttccttg ctgagt 16

<210> SEQ ID NO 694
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 694
ggaccttcct tgctga 16

<210> SEQ ID NO 695
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 695
caggaccttc cttgct 16

<210> SEQ ID NO 696
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 696
agccctccag gacctt 16

<210> SEQ ID NO 697
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 697
tagctcccca ctccag 16

<210> SEQ ID NO 698
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 698
gatagctccc cactcc 16

<210> SEQ ID NO 699
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 699
cagatagctc cccact 16

<210> SEQ ID NO 700
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 700
ctcagatagc tcccca 16

<210> SEQ ID NO 701
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 701
agctcagata gctccc 16

<210> SEQ ID NO 702
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 702
tcagctcaga tagctc 16

<210> SEQ ID NO 703
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 703
tctcagctca gatagc 16

<210> SEQ ID NO 704
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 704
gagtcctctc ctgctt 16

<210> SEQ ID NO 705
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 705
ggaggagtcc tctcct 16

<210> SEQ ID NO 706
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 706
gaggaggagt cctctc 16

<210> SEQ ID NO 707
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 707
caaaagggca cccaga 16

<210> SEQ ID NO 708
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 708
agcaaaaggg caccca 16

<210> SEQ ID NO 709
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 709
ggatccccag tattgt 16

<210> SEQ ID NO 710
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 710
ctggatcccc agtatt 16

<210> SEQ ID NO 711
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 711
tgctggatcc ccagta 16

<210> SEQ ID NO 712
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 712
attctctaga ctgcaa 16

<210> SEQ ID NO 713
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 713
taattctcta gactgc 16

<210> SEQ ID NO 714
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 714
tctaattctc tagact 16

<210> SEQ ID NO 715

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 715
tctctaattc tctaga 16

<210> SEQ ID NO 716
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 716
ctccataatt ctctaa 16

<210> SEQ ID NO 717
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 717
actctccata attctc 16

<210> SEQ ID NO 718
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 718
acactctcca taattc 16

<210> SEQ ID NO 719
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 719
ccacactctc cataat 16

<210> SEQ ID NO 720
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 720
tgccacactc tccata 16

<210> SEQ ID NO 721
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 721
cccatgccca tcctgc 16

<210> SEQ ID NO 722
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 722
ggacagagaa atgttg 16

<210> SEQ ID NO 723
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 723
ggcataggac agagaa 16

<210> SEQ ID NO 724
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 724
gtggcatagg acagag 16

<210> SEQ ID NO 725
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 725
tggtggcata ggacag 16

<210> SEQ ID NO 726
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 726
cttactctgc ccctcc 16

<210> SEQ ID NO 727
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 727
accttactct gcccct 16

<210> SEQ ID NO 728
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 728
tgaccttact ctgccc 16

<210> SEQ ID NO 729
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 729
gctgacctta ctctgc 16

<210> SEQ ID NO 730
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 730
ctgctgacct tactct 16

<210> SEQ ID NO 731
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 731
ctctgctgac cttact 16

<210> SEQ ID NO 732
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 732
gcctctgctg acctta 16

<210> SEQ ID NO 733
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 733
ccatggctct gagtca 16

<210> SEQ ID NO 734
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 734
agccatggct ctgagt 16

<210> SEQ ID NO 735
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 735
taagccatgg ctctga 16

<210> SEQ ID NO 736
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 736
tagcctgctg tgactc 16

<210> SEQ ID NO 737
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 737
atgggaggct gttggc 16

<210> SEQ ID NO 738
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 738
ccatgggagg ctgttg 16

<210> SEQ ID NO 739
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 739
ggccatggga ggctgt 16

<210> SEQ ID NO 740
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 740
gtgcagagag gccatg 16

<210> SEQ ID NO 741
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 741
gagctcccag catgac 16

<210> SEQ ID NO 742
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 742
agggagctcc cagcat 16

<210> SEQ ID NO 743
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 743
gccatagagc ccactt 16

<210> SEQ ID NO 744
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 744
gggccataga gcccac 16

<210> SEQ ID NO 745
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 745
atgctggccc tcctgg 16

<210> SEQ ID NO 746
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 746
agctgcccca tgctgg 16

<210> SEQ ID NO 747
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 747
cgcccctggc agctgc 16

<210> SEQ ID NO 748
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 748
tgcgcccctg gcagct 16

<210> SEQ ID NO 749
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 749
gctgcgcccc tggcag 16

<210> SEQ ID NO 750
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 750
cggctgcgcc cctggc 16

<210> SEQ ID NO 751
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 751
gtcggctgcg cccctg 16

<210> SEQ ID NO 752
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 752
ctgtcggctg cgcccc 16

<210> SEQ ID NO 753
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 753
gcctgtcggc tgcgcc 16

<210> SEQ ID NO 754
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 754
ctgcctgtcg gctgcg 16

<210> SEQ ID NO 755
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 755
acctgcctgt cggctg 16

<210> SEQ ID NO 756
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 756
acacctgcct gtcggc 16

<210> SEQ ID NO 757
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 757
gaacacctgc ctgtcg 16

<210> SEQ ID NO 758
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 758
ccgaacacct gcctgt 16

<210> SEQ ID NO 759
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 759
cgccgaacac ctgcct 16

<210> SEQ ID NO 760
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 760
cctgggcacc tgttgg 16

<210> SEQ ID NO 761
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 761
gtgcctgggc acctgt 16

<210> SEQ ID NO 762
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 762
cgccctccca gtgcct 16

<210> SEQ ID NO 763
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 763
accgccctcc cagtgc 16

<210> SEQ ID NO 764
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 764
tcaccgccct cccagt 16

<210> SEQ ID NO 765
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 765
agtcaccgcc ctccca 16

<210> SEQ ID NO 766
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 766
tgagtcaccg ccctcc 16

<210> SEQ ID NO 767
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 767
cgtgagtcac cgccct 16

<210> SEQ ID NO 768
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 768
caaagctggt tctccc 16

<210> SEQ ID NO 769
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 769
tgcaaagctg gttctc 16

<210> SEQ ID NO 770
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 770
tctgcaaagc tggttc 16

<210> SEQ ID NO 771
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 771
tgtctgcaaa gctggt 16

<210> SEQ ID NO 772
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 772
cctgtctgca aagctg 16

<210> SEQ ID NO 773
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 773
cgcctgtctg caaagc 16

<210> SEQ ID NO 774
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 774
ttgtccctcc tggatc 16

<210> SEQ ID NO 775
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 775
agttgtccct cctgga 16

<210> SEQ ID NO 776
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 776
aaagttgtcc ctcctg 16

<210> SEQ ID NO 777
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 777
ccaaagttgt ccctcc 16

<210> SEQ ID NO 778
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 778
acccaaagtt gtccct 16

<210> SEQ ID NO 779
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 779
gaacccaaag ttgtcc 16

<210> SEQ ID NO 780
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 780
gaagaaccca aagttg 16

<210> SEQ ID NO 781
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 781
ccagaagaac ccaaag 16

<210> SEQ ID NO 782
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 782
cacccagaag aaccca 16

<210> SEQ ID NO 783
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 783
gcagaaccta caaaag 16

<210> SEQ ID NO 784
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 784
gtgcagaacc tacaaa 16

<210> SEQ ID NO 785
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 785
gggtgcagaa cctaca 16

<210> SEQ ID NO 786
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 786
gtgggtgcag aaccta 16

<210> SEQ ID NO 787
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 787
ccacacggct catagg 16

<210> SEQ ID NO 788
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 788
acccacacgg ctcata 16

<210> SEQ ID NO 789
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 789
tgacccacac ggctca 16

<210> SEQ ID NO 790
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 790
gctgacccac acggct 16

<210> SEQ ID NO 791
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 791
tggctgaccc acacgg 16

<210> SEQ ID NO 792
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 792
ggtggctgac ccacac 16

<210> SEQ ID NO 793
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 793
atggtggctg acccac 16

<210> SEQ ID NO 794

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 794
gaatggtggc tgaccc 16

<210> SEQ ID NO 795
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 795
ctaaaggacg caggga 16

<210> SEQ ID NO 796
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 796
aactaaagga cgcagg 16

<210> SEQ ID NO 797
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 797
gagaactaaa ggacgc 16

<210> SEQ ID NO 798
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 798
attggtccca agcccc 16

<210> SEQ ID NO 799
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 799
ccattggtcc caagcc 16

<210> SEQ ID NO 800
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 800
gcccattggt cccaag 16

<210> SEQ ID NO 801
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 801
acgcccattg gtccca 16

<210> SEQ ID NO 802
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 802
ccacgcccat tggtcc 16

<210> SEQ ID NO 803
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 803
caccacgccc attggt 16

<210> SEQ ID NO 804
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 804
agacccaact ccaccc 16

<210> SEQ ID NO 805
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 805
tcacctcgcc cctctt 16

<210> SEQ ID NO 806
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 806
cctcacctcg cccctc 16

<210> SEQ ID NO 807
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 807
agcccctcac ctcgcc 16

<210> SEQ ID NO 808
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 808
ctcaaagccc cccacg 16

<210> SEQ ID NO 809
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 809
atcctcaaag cccccc 16

<210> SEQ ID NO 810
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 810
ggatcctcaa agcccc 16

<210> SEQ ID NO 811
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 811
gcggatcctc aaagcc 16

<210> SEQ ID NO 812
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 812
gcgcggatcc tcaaag 16

<210> SEQ ID NO 813
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 813
gggcgcggat cctcaa 16

<210> SEQ ID NO 814
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 814
gagctgcagc cggaga 16

<210> SEQ ID NO 815
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 815
aggagctgca gccgga 16

<210> SEQ ID NO 816
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 816
cggaggagct gcagcc 16

<210> SEQ ID NO 817
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 817
acccggagga gctgca 16

<210> SEQ ID NO 818
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 818
gcacccggag gagctg 16

<210> SEQ ID NO 819
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 819
gggcacccgg aggagc 16

<210> SEQ ID NO 820
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 820
cagggcaccc ggagga 16

<210> SEQ ID NO 821
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 821
tgcagggcac ccggag 16

<210> SEQ ID NO 822
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 822
cctgcagggc acccgg 16

<210> SEQ ID NO 823
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 823
cgacacctgc agggca 16

<210> SEQ ID NO 824
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 824
cacgacacct gcaggg 16

<210> SEQ ID NO 825
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 825
agcacgacac ctgcag 16

<210> SEQ ID NO 826
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 826
gaagcacgac acctgc 16

<210> SEQ ID NO 827
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 827
ccaggtagtt ctcatc 16

<210> SEQ ID NO 828
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 828
caccaggtag ttctca 16

<210> SEQ ID NO 829
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 829
ctcaccaggt agttct 16

<210> SEQ ID NO 830
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 830
agctcaccag gtagtt 16

<210> SEQ ID NO 831
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 831
ggagctcacc aggtag 16

<210> SEQ ID NO 832
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 832
ccggagctca ccaggt 16

<210> SEQ ID NO 833
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 833
gcccggagct caccag 16

<210> SEQ ID NO 834
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 834
tagagcttcc tctccc 16

<210> SEQ ID NO 835
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 835
cctagagctt cctctc 16

<210> SEQ ID NO 836
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 836
atcctagagc ttcctc 16

<210> SEQ ID NO 837
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 837
caatcctaga gcttcc 16

<210> SEQ ID NO 838
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 838
cccaatccta gagctt 16

<210> SEQ ID NO 839
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 839
cccccaatcc tagagc 16

<210> SEQ ID NO 840
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 840

cacccccaat cctaga                                                    16

<210> SEQ ID NO 841
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 841

agcaccccca atccta                                                    16

<210> SEQ ID NO 842
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 842

gcagcacccc caatcc                                                    16

<210> SEQ ID NO 843
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 843

gggcagcacc cccaat                                                    16

<210> SEQ ID NO 844
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 844

tgacacaccc tcttac                                                    16

<210> SEQ ID NO 845
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 845

cctgacacac cctctt                                                    16

<210> SEQ ID NO 846
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 846
```

cacctgacac accctc 16

<210> SEQ ID NO 847
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 847
tccacctgac acaccc 16

<210> SEQ ID NO 848
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 848
catccacctg acacac 16

<210> SEQ ID NO 849
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 849
ctcatccacc tgacac 16

<210> SEQ ID NO 850
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 850
ccctcatcca cctgac 16

<210> SEQ ID NO 851
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 851
gcccctcatc cacctg 16

<210> SEQ ID NO 852
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 852
aggcccctca tccacc 16

<210> SEQ ID NO 853
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 853
gaaggcccct catcca 16

<210> SEQ ID NO 854
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 854
aggtaagaga cccccc 16

<210> SEQ ID NO 855
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 855
ccaggtaaga gacccc 16

<210> SEQ ID NO 856
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 856
ttccaggtaa gagacc 16

<210> SEQ ID NO 857
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 857
ccattccagg taagag 16

<210> SEQ ID NO 858
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 858
tcccattcca ggtaag 16

<210> SEQ ID NO 859
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 859
tatcccattc caggta 16

<210> SEQ ID NO 860
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 860
cctatcccat tccagg 16

<210> SEQ ID NO 861
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 861
gacctatccc attcca 16

<210> SEQ ID NO 862
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 862
aagacctatc ccattc 16

<210> SEQ ID NO 863
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 863
tgaagaccta tcccat 16

<210> SEQ ID NO 864
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 864
tggccccgtt agaatt 16

<210> SEQ ID NO 865
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 865
agtggccccg ttagaa 16

<210> SEQ ID NO 866
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 866
gcagtggccc cgttag 16

<210> SEQ ID NO 867
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 867
aggcagtggc cccgtt 16

<210> SEQ ID NO 868
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 868
ctaggcagtg gccccg 16

<210> SEQ ID NO 869
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 869
ccctaggcag tggccc 16

<210> SEQ ID NO 870
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 870
aggtcccaga cactcc 16

<210> SEQ ID NO 871
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 871
ataggtccca gacact 16

<210> SEQ ID NO 872
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 872
gaataggtcc cagaca 16

<210> SEQ ID NO 873

-continued

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 873

gagaataggt cccaga                                                  16


<210> SEQ ID NO 874
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 874

cagagaatag gtccca                                                  16
```

COMPOUNDS AND METHODS FOR MODULATION OF DYSTROPHIA MYOTONICA-PROTEIN KINASE (DMPK) EXPRESSION

SEQUENCE LISTING

The present application is being filed along with a Sequence Listing in electronic format. The Sequence Listing is provided as a file entitled BIOL0171USC2SEQ_ST25.txt created Feb. 10, 2021, which is approximately 276 Kb in size. The information in the electronic format of the sequence listing is incorporated herein by reference in its entirety.

FIELD

Provided herein are methods, compounds, and compositions for reducing expression of DMPK mRNA and protein in an animal. Also, provided herein are methods, compounds, and compositions comprising a DMPK inhibitor for preferentially reducing CUGexp DMPK RNA, reducing myotonia, or reducing spliceopathy in an animal. Such methods, compounds, and compositions are useful, for example, to treat, prevent, or ameliorate type 1 myotonic dystrophy (DM1) in an animal.

BACKGROUND

Myotonic dystrophy type 1 (DM1) is the most common form of muscular dystrophy in adults with an estimated frequency of 1 in 7,500 (Harper P S., Myotonic Dystrophy. London: W.B. Saunders Company; 2001). DM1 is an autosomal dominant disorder caused by expansion of a non-coding CTG repeat in DMPK1. DMPK1 is a gene encoding a cytosolic serine/threonine kinase (Brook J D, et al., *Cell.,* 1992, 68(4):799-808). The physiologic functions and substrates of this kinase have not been fully determined. The expanded CTG repeat is located in the 3' untranslated region (UTR) of DMPK1. This mutation leads to RNA dominance, a process in which expression of RNA containing an expanded CUG repeat (CUGexp) induces cell dysfunction (Osborne R J and Thornton C A., *Human Molecular Genetics.,* 2006, 15(2): R162-R169).

The DMPK gene normally has 5-37 CTG repeats in the 3' untranslated region. In myotonic dystrophy type I, this number is significantly expanded and is, for example, in the range of 50 to greater than 3,500 (Harper, Myotonic Dystrophy (Saunders, London, ed. 3, 2001); Annu. Rev. Neurosci. 29: 259, 2006; EMBO J. 19: 4439, 2000; Curr Opin Neurol. 20: 572, 2007).

The CUGexp tract interacts with RNA binding proteins including muscleblind-like (MBNL) protein, a splicing factor, and causes the mutant transcript to be retained in nuclear foci. The toxicity of this RNA stems from sequestration of RNA binding proteins and activation of signaling pathways. Studies in animal models have shown that phenotypes of DM1 can be reversed if toxicity of CUGexp RNA is reduced (Wheeler T M, et al., *Science.,* 2009, 325(5938):336-339; Mulders S A, et al., *Proc Natl Acad Sci USA.,* 2009, 106(33):13915-13920).

In DM1, skeletal muscle is the most severely affected tissue, but the disease also has important effects on cardiac and smooth muscle, ocular lens, and brain. The cranial, distal limb, and diaphragm muscles are preferentially affected. Manual dexterity is compromised early, which causes several decades of severe disability. The median age at death is 55 years, usually from respiratory failure (de Die-Smulders C E, et al., *Brain.,* 1998, 121(Pt 8):1557-1563).

Antisense technology is emerging as an effective means for modulating expression of certain gene products and may therefore prove to be uniquely useful in a number of therapeutic, diagnostic, and research applications for the modulation of DMPK1. Intramuscular injection of fully modified oligonucleotides targeting with the CAG-repeat were shown in mice to block formation of CUGexp-MBNL1 complexes, disperse nuclear foci of CUGexp transcripts, enhance the nucleocytoplasmic transport and translation of CUGexp transcripts, release MBNL proteins to the nucleoplasm, normalize alternative splicing of MBNL-dependent exons, and eliminate myotonia in CUGexp-expressing transgenic mice (Wheeler T M, et al., *Science.,* 2009, 325(5938): 336-339; WO2008/036406).

Presently there is no treatment that can modify the course of DM1. The burden of disease, therefore, is significant. It is, therefore, an object herein to provide compounds, compositions, and methods for treating DM1

SUMMARY

Provided herein are methods, compounds, and compositions for inhibiting expression of DMPK and treating, preventing, delaying or ameliorating a DMPK related disease and or a symptom thereof. In certain embodiments, the compounds and compositions disclosed herein inhibit mutant DMPK or CUGexp DMPK.

Certain embodiments provide a method of reducing DMPK expression in an animal comprising administering to the animal a compound comprising a modified oligonucleotide as further described herein targeted to DMPK.

Certain embodiments provide a method of preferentially reducing CUGexp DMPK relative to wild-type DMPK, reducing myotonia, or reducing spliceopathy in an animal comprising administering to the animal a compound comprising a modified oligonucleotide, as further described herein, targeted to CUGexp DMPK. In certain instances, CUGexp DMPK transcripts are believed to be particularly sensitive to antisense knockdown via nuclear ribonucleases (such as RNase H), because of their longer residence time in the nucleus, and this sensitivity is thought to permit effective antisense inhibition of CUGexp DMPK transcripts in relevant tissues such as muscle despite the biodistribution barriers to tissue uptake of antisense oligonucleotides. Antisense mechanisms that do not elicit cleavage via nuclear ribonucleases, such as the CAG-repeat ASOs described in, for example, Wheeler T M, et al., Science., 2009, 325(5938): 336-339 and WO2008/036406, do not provide the same therapeutic advantage.

Certain embodiments provide a method of treating an animal having type 1 myotonic dystrophy. In certain embodiments, the method includes administering to the animal a therapeutically effective amount of a compound comprising a modified oligonucleotide as further described herein targeted to DMPK. In certain embodiments, the method includes identifying an animal with type 1 myotonic dystrophy.

Certain embodiments provide a method of treating, preventing, delaying, or ameliorating symptoms and outcomes associated with development of DM1 including muscle stiffness, myotonia, disabling distal weakness, weakness in face and jaw muscles, difficulty in swallowing, drooping of the eyelids (ptosis), weakness of neck muscles, weakness in arm and leg muscles, persistent muscle pain, hypersomnia, muscle wasting, dysphagia, respiratory insufficiency, irregular heartbeat, heart muscle damage, apathy, insulin resistance, and cataracts. Certain embodiments provide a method of treating, preventing, delaying, or ameliorating symptoms and outcomes associated with development of DM1 in children, including, developmental delays, learning problems, language and speech issues, and personality development issues.

Certain embodiments provide a method of administering an antisense oligonucleotide to counteract RNA dominance by directing the cleavage of pathogenic transcripts.

In certain embodiments, the DMPK has a sequence as set forth in GenBank Accession No. NM_001081560.1 (incorporated herein as SEQ ID NO: 1). In certain embodiments, the DMPK has the sequence as set forth in GenBank Accession No. NT_011109.15 truncated from nucleotides 18540696 to U.S. Pat. No. 18,555,106 (incorporated herein as SEQ ID NO: 2). In certain embodiments, the DMPK has the sequence as set forth in GenBank Accession No. NT 039413.7 truncated from nucleotides 16666001 to U.S. Pat. No. 16,681,000 (incorporated herein as SEQ ID NO: 3). In certain embodiments, the DMPK has the sequence as set forth in GenBank Accession No. NM_032418.1 (incorporated herein as SEQ ID NO: 4). In certain embodiments, the DMPK has the sequence as set forth in GenBank Accession No. AI007148.1 (incorporated herein as SEQ ID NO: 5). In certain embodiments, the DMPK has the sequence as set forth in GenBank Accession No. AI304033.1 (incorporated herein as SEQ ID NO: 6). In certain embodiments, the DMPK has the sequence as set forth in GenBank Accession No. BC024150.1 (incorporated herein as SEQ ID NO: 7). In certain embodiments, the DMPK has the sequence as set forth in GenBank Accession No. BC056615.1 (incorporated herein as SEQ ID NO: 8). In certain embodiments, the DMPK has the sequence as set forth in GenBank Accession No. BC075715.1 (incorporated herein as SEQ ID NO: 9). In certain embodiments, the DMPK has the sequence as set forth in GenBank Accession No. BU519245.1 (incorporated herein as SEQ ID NO: 10). In certain embodiments, the DMPK has the sequence as set forth in GenBank Accession No. CB247909.1 (incorporated herein as SEQ ID NO: 11). In certain embodiments, the DMPK has the sequence as set forth in GenBank Accession No. CX208906.1 (incorporated herein as SEQ ID NO: 12). In certain embodiments, the DMPK has the sequence as set forth in GenBank Accession No. CX732022.1 (incorporated herein as SEQ ID NO: 13). In certain embodiments, the DMPK has the sequence as set forth in GenBank Accession No. S60315.1 (incorporated herein as SEQ ID NO: 14). In certain embodiments, the DMPK has the sequence as set forth in GenBank Accession No. S60316.1 (incorporated herein as SEQ ID NO: 15). In certain embodiments, the DMPK has the sequence as set forth in GenBank Accession No. NM_001081562.1 (incorporated herein as SEQ ID NO: 16). In certain embodiments, the DMPK has the sequence as set forth in GenBank Accession No. NM_001100.3 (incorporated herein as SEQ ID NO: 17).

The present disclosure provides the following non-limiting numbered embodiments:

Embodiment 1. A compound comprising a modified oligonucleotide consisting of 10-30 linked nucleosides and having a nucleobase sequence comprising a complementary region comprising at least 8 contiguous nucleobases complementary to a target region of equal length of a DMPK nucleic acid.

Embodiment 2. The compound of embodiment 1, wherein at least one nucleoside of the modified oligonucleotide comprises a bicyclic sugar selected from among cEt, LNA, α-L-LNA, ENA and 2'-thio LNA.

Embodiment 3. The compound of any of embodiments 1 to 2, wherein the target region is exon 9 of a DMPK nucleic acid.

Embodiment 4. The compound of any of embodiments 1 to 3, wherein the complementary region comprises at least 10 contiguous nucleobases complementary to a target region of equal length of a DMPK transcript.

Embodiment 5. The compound of any of embodiments 1 to 3, wherein the complementary region comprises at least 12 contiguous nucleobases complementary to a target region of equal length of a DMPK nucleic acid.

Embodiment 6. The compound of any of embodiments 1 to 3, wherein the complementary region comprises at least 14 contiguous nucleobases complementary to a target region of equal length of a DMPK nucleic acid.

Embodiment 7. The compound of any of embodiments 1 to 3, wherein the complementary region comprises at least 16 contiguous nucleobases complementary to a target region of equal length of a DMPK nucleic acid.

Embodiment 8. The compound of any of embodiments 1 to 7, wherein the DMPK nucleic acid is a DMPK pre-mRNA Embodiment 9. The compound of any of embodiments 1 to 7, wherein the DMPK nucleic acid is a DMPK mRNA.

Embodiment 10. The compound of any of embodiments 1 to 9, wherein the DMPK nucleic acid has a nucleobase sequence selected from among SEQ ID NO: 1 and SEQ ID NO: 2.

Embodiment 11. The compound of any of embodiments 1 to 10, wherein the modified oligonucleotide has a nucleobase sequence comprising a complementary region comprising at least 10 contiguous nucleobases complementary to a target region of equal length of SEQ ID NO: 1 or SEQ ID NO: 2.

Embodiment 12. The compound of embodiments 1 to 10, wherein the modified oligonucleotide has a nucleobase sequence comprising a complementary region comprising at least 12 contiguous nucleobases complementary to a target region of equal length of SEQ ID NO: 1 or SEQ ID NO: 2.

Embodiment 13. The compound of embodiments 1 to 10, wherein the modified oligonucleotide has a nucleobase sequence comprising a complementary region comprising at least 14 contiguous nucleobases complementary to a target region of equal length of SEQ ID NO: 1 or SEQ ID NO: 2.

Embodiment 14. The compound of embodiments 1 to 10, wherein the modified oligonucleotide has a nucleobase sequence comprising a complementary region comprising at least 16 contiguous nucleobases complementary to a target region of equal length of SEQ ID NO: 1 or SEQ ID NO: 2.

Embodiment 15. The compound of any of embodiments 1 to 14, wherein the target region is from nucleobase 1343 to nucleobase 1368 of SEQ ID NO.: 1.

Embodiment 16. The compound of any of embodiments 1 to 14, wherein the target region is from nucleobase 1317 to nucleobase 1366 of SEQ ID NO.: 1.

Embodiment 17. The compound of any of embodiments 1 to 14, wherein the target region is from nucleobase 2748 to nucleobase 2791 of SEQ ID NO.: 1.

Embodiment 18. The compound of any of embodiments 1 to 14, wherein the target region is from nucleobase 730 to nucleobase 748 of SEQ ID NO.: 1.

Embodiment 19. The compound of any of embodiments 1 to 14, wherein the target region is from nucleobase 10195 to nucleobase 10294 of SEQ ID NO.: 2.

Embodiment 20. The compound of any of embodiments 1 to 14, wherein the target region is from nucleobase 10195 to nucleobase 10294 of SEQ ID NO.: 2.

Embodiment 21. The compound of any of embodiments 1 to 14, wherein the target region is from nucleobase 10201 to nucleobase 10216 of SEQ ID NO.: 2.

Embodiment 22. The compound of any of embodiments 1 to 14, wherein the target region is from nucleobase 10202 to nucleobase 10218 of SEQ ID NO.: 2.

Embodiment 23. The compound of any of embodiments 1 to 22, wherein the modified oligonucleotide has a nucleobase sequence that is at least 80% complementary to the target region over the entire length of the oligonucleotide.

Embodiment 24. The compound of any of embodiments 1 to 22, wherein the modified oligonucleotide has a nucleobase sequence that is at least 90% complementary to the target region over the entire length of the oligonucleotide.

Embodiment 25. The compound of any of embodiments 1 to 22, wherein the modified oligonucleotide has a nucleobase sequence that is at least 100% complementary to the target region over the entire length of the oligonucleotide.

Embodiment 26. The compound of any of embodiments 1-25 having a nucleobase sequence comprising at least 8 contiguous nucleobases of a sequence recited in any of SEQ ID NOs: 23-874.

Embodiment 27. The compound of any of embodiments 1 to 25, wherein the modified oligonucleotide has a nucleobase sequence comprising at least 10 contiguous nucleobases of sequence recited in SEQ ID NOs: 23-32.

Embodiment 28. The compound of any of embodiments 1 to 25, wherein the modified oligonucleotide has a nucleobase sequence comprising at least 12 contiguous nucleobases of sequence recited in SEQ ID NOs: 23-32.

Embodiment 29. The compound of any of embodiments 1 to 25, wherein the modified oligonucleotide has a nucleobase sequence comprising at least 14 contiguous nucleobases of sequence recited in SEQ ID NOs: 23-32.

Embodiment 30. The compound of any of embodiments 1 to 25, wherein the modified oligonucleotide has a nucleobase sequence comprising at least 16 contiguous nucleobases of sequence recited in SEQ ID NOs: 23-32.

Embodiment 31. The compound of any of embodiments 1 to 30, wherein the modified oligonucleotide has a nucleobase sequence that consists of the sequence recited in SEQ ID NO: 23.

Embodiment 32. The compound of any of embodiments 1 to 14, wherein the modified oligonucleotide has a nucleobase sequence that consists of the sequence recited in SEQ ID NO: 25.

Embodiment 33. The compound of any of embodiments 1 to 14, wherein the modified oligonucleotide has a nucleobase sequence that consists of the sequence recited in SEQ ID NO: 26.

Embodiment 34. The compound of any of embodiments 1 to 14, wherein the modified oligonucleotide has a nucleobase sequence that consists of the sequence recited in SEQ ID NO: 27.

Embodiment 35. The compound of any of embodiments 1 to 14, wherein the modified oligonucleotide has a nucleobase sequence that consists of the sequence recited in SEQ ID NO: 28.

Embodiment 36. The compound of any of embodiments 1 to 14, wherein the modified oligonucleotide has a nucleobase sequence that consists of the sequence recited in SEQ ID NO: 29.

Embodiment 37. The compound of any of embodiments 1 to 14, wherein the modified oligonucleotide has a nucleobase sequence that consists of the sequence recited in SEQ ID NO: 30.

Embodiment 38. The compound of any of embodiments 1 to 14, wherein the modified oligonucleotide has a nucleobase sequence that consists of the sequence recited in SEQ ID NO: 31.

Embodiment 39. The compound of any of embodiments 1 to 14, wherein the modified oligonucleotide has a nucleobase sequence that consists of the sequence recited in SEQ ID NO: 32.

Embodiment 40. The compound of any of embodiments 1 to 14, wherein the modified oligonucleotide has a nucleobase sequence comprising the sequence recited in SEQ ID NO: 23, 24, 25, 26, 27, 28, 29, 30, 31, or 32.

Embodiment 41. The compound of any of embodiments 1 to 14, wherein the modified oligonucleotide has a nucleobase sequence comprising the sequence recited in SEQ ID NO: 23, 25, 26, 27, 28, 29, 30, 31, or 32.

Embodiment 42. The compound of any of embodiments 1 to 14, wherein the modified oligonucleotide has a nucleobase sequence comprising the sequence recited in SEQ ID NO: 33-874.

Embodiment 43. The compound of any of embodiments 1 to 42, wherein the nucleobase sequence of the modified oligonucleotide is at least 90% complementary to SEQ ID NOs: 1-19.

Embodiment 44. The compound of any of embodiments 1 to 34, wherein the nucleobase sequence of the modified oligonucleotide is 100% complementary to SEQ ID NOs: 1-19.

Embodiment 45. The compound of any of embodiments 1 to 30, wherein the modified oligonucleotide consists of 16 linked nucleosides.

Embodiment 46. The compound of any of embodiments 1 to 30, wherein the modified oligonucleotide consists of 17 linked nucleosides.

Embodiment 47. The compound of any of embodiments 1 to 30, wherein the modified oligonucleotide consists of 18 linked nucleosides.

Embodiment 48. The compound of any of embodiments 1 to 30, wherein the modified oligonucleotide consists of 19 linked nucleosides.

Embodiment 49. The compound of any of embodiments 1 to 30, wherein the modified oligonucleotide consists of 20 linked nucleosides.

Embodiment 50. The compound of any of embodiments 1 to 49, wherein the modified oligonucleotide is a single-stranded oligonucleotide.

Embodiment 51. The compound of any of embodiments 1 to 50 wherein at least one nucleoside comprises a modified sugar.

Embodiment 52. The compound of any of embodiments 1 to 51 wherein at least two nucleosides comprise a modified sugar.

Embodiment 53. The compound of embodiment 52, wherein each of the modified sugars have the same modification.

Embodiment 54. The compound of embodiment 52, wherein at least one the modified sugars has a different modification.

Embodiment 55. The compound of any of embodiments 51 to 54, wherein at least one modified sugar is a bicyclic sugar.

Embodiment 56. The compound of embodiment 55, wherein the bicyclic sugar is selected from among cEt, LNA, α-L-LNA, ENA and 2'-thio LNA.

Embodiment 57. The compound of embodiment 56, wherein the bicyclic sugar comprises cEt.

Embodiment 58. The compound of embodiment 56, wherein the bicyclic sugar comprises LNA.

Embodiment 59. The compound of embodiment 56, wherein the bicyclic sugar comprises α-L-LNA.

Embodiment 60. The compound of embodiment 56, wherein the bicyclic sugar comprises ENA.

Embodiment 61. The compound of embodiment 56, wherein the bicyclic sugar comprises 2'-thio LNA.

Embodiment 62. The compound of any of embodiments 1 to 61, wherein at least one modified sugar comprises a 2'-substituted nucleoside.

Embodiment 63. The compound of embodiment 62, wherein the 2'-substituted nucleoside is selected from among: 2'-$OCH_3$, 2'-F, and 2'-O-methoxyethyl.

Embodiment 64. The compound of any of embodiments 1 to 63, wherein at least one modified sugar comprises a 2'-O-methoxyethyl.

Embodiment 65. The compound of any of embodiments 1 to 64, wherein at least one nucleoside comprises a modified nucleobase.

Embodiment 66. The compound of embodiment 65, wherein the modified nucleobase is a 5-methylcytosine.

Embodiment 67. The compound of any of embodiments 1 to 67, wherein each cytosine is a 5-methylcytosine.

Embodiment 68. The compound of any of embodiments 1 to 67, wherein the modified oligonucleotide comprises:
- a. a gap segment consisting of linked deoxynucleosides;
- b. a 5' wing segment consisting of linked nucleosides;
- c. a 3' wing segment consisting of linked nucleosides;
- d. wherein the gap segment is positioned between the 5' wing segment and the 3' wing segment and wherein each nucleoside of each wing segment comprises a modified sugar.

Embodiment 69. The compound of embodiment 68, wherein the modified oligonucleotide consists of 16 linked nucleosides.

Embodiment 70. The compound of embodiment 68, wherein the modified oligonucleotide consists of 17 linked nucleosides.

Embodiment 71. The compound of embodiment 68, wherein the modified oligonucleotide consists of 18 linked nucleosides.

Embodiment 72. The compound of embodiment 68, wherein the modified oligonucleotide consists of 19 linked nucleosides.

Embodiment 73. The compound of embodiment 68, wherein the modified oligonucleotide consists of 20 linked nucleosides.

Embodiment 74. The compound of any of embodiments 68 to 73, wherein the 5'-wing segment consists of two linked nucleosides.

Embodiment 75. The compound of any of embodiments 68 to 73, wherein the 5'-wing segment consists of three linked nucleosides.

Embodiment 76. The compound of any of embodiments 68 to 73, wherein the 5'-wing segment consists of four linked nucleosides.

Embodiment 77. The compound of any of embodiments 68 to 73, wherein the 5'-wing segment consists of five linked nucleosides.

Embodiment 78. The compound of any of embodiments 68 to 73, wherein the 5'-wing segment consists of six linked nucleosides.

Embodiment 79. The compound of any of embodiments 68 to 78, wherein the 3'-wing segment consists of two linked nucleosides.

Embodiment 80. The compound of any of embodiments 68 to 78, wherein the 3'-wing segment consists of three linked nucleosides.

Embodiment 81. The compound of any of embodiments 68 to 78, wherein the 3'-wing segment consists of four linked nucleosides.

Embodiment 82. The compound of any of embodiments 68 to 78, wherein the 3'-wing segment consists of five linked nucleosides.

Embodiment 83. The compound of any of embodiments 68 to 78, wherein the 3'-wing segment consists of six linked nucleosides.

Embodiment 84. The compound of any of embodiments 68 to 83, wherein the gap segment consists of six linked deoxynucleosides.

Embodiment 85. The compound of any of embodiments 68 to 83, wherein the gap segment consists of seven linked deoxynucleosides.

Embodiment 86. The compound of any of embodiments 68 to 83, wherein the gap segment consists of eight linked deoxynucleosides.

Embodiment 87. The compound of any of embodiments 68 to 83, wherein the gap segment consists of nine linked deoxynucleosides.

Embodiment 88. The compound of any of embodiments 68 to 83, wherein the gap segment consists of ten linked deoxynucleosides.

Embodiment 89. The compound of any of embodiments 1 to 31, 34, 37 to 45, or 53 to 88, wherein the modified oligonucleotide consists of 16 linked nucleosides and comprises:
- a. a gap segment consisting of ten linked deoxynucleosides;
- b. a 5' wing segment consisting of three linked nucleosides;
- c. a 3' wing segment consisting of three linked nucleosides;
- d. wherein the gap segment is positioned between the 5' wing segment and the 3' wing segment, and wherein each nucleoside of each wing segment comprises a bicyclic sugar.

Embodiment 90. The compound of any of embodiments 1 to 31, 34, 37 to 45, or 53 to 88, wherein the modified oligonucleotide consists of 16 linked nucleosides and comprises:
- a. a gap segment consisting of eight linked deoxynucleosides;
- b. a 5' wing segment consisting of four linked nucleosides and having an AABB 5'-wing motif;
- c. a 3' wing segment consisting of four linked nucleosides and having a BBAA 3'-wing motif;
- d. wherein the gap segment is positioned between the 5' wing segment and the 3' wing segment.

Embodiment 91. The compound of any of embodiments 1 to 30, 35, 36, 46, or 50 to 88, wherein the modified oligonucleotide consists of 17 linked nucleosides and comprises:
a. a gap segment consisting of seven linked deoxynucleosides;
b. a 5' wing segment consisting of five linked nucleosides and having an AAABB 5'-wing motif;
c. a 3' wing segment consisting of five linked nucleosides and having a BBAAA 3'-wing motif;
d. wherein the gap segment is positioned between the 5' wing segment and the 3' wing segment.

Embodiment 92. The compound of any of embodiments 1 to 31, 34, 37 to 45, or 53 to 88, wherein the modified oligonucleotide consists of 16 linked nucleosides and comprises:
a. a gap segment consisting of eight linked deoxynucleosides;
b. a 5' wing segment consisting of four linked nucleosides and having a E-E-K-K 5'-wing motif;
c. a 3' wing segment consisting of four linked nucleosides and having a K-K-E-E 3'-wing motif;
d. wherein the gap segment is positioned between the 5' wing segment and the 3' wing segment, and wherein each E represents 2'-O-methoxyethyl sugar and each K represents a cEt sugar.

Embodiment 93. The compound of any of embodiments 1 to 30, 35, 36, 46, or 50 to 88, wherein the modified oligonucleotide consists of 17 linked nucleosides and comprises:
a. a gap segment consisting of seven linked deoxynucleosides;
b. a 5' wing segment consisting of five linked nucleosides and having an E-E-E-K-K 5'-wing motif;
c. a 3' wing segment consisting of five linked nucleosides and having a K-K-E-E-E 3'-wing motif;
d. wherein the gap segment is positioned between the 5' wing segment and the 3' wing segment, and wherein each E represents 2'-O-methoxyethyl sugar and each K represents a cEt sugar.

Embodiment 94. The compound of any of embodiments 1 to 30, 32, 33, or 49 to 88, wherein the modified oligonucleotide consists of 20 linked nucleosides and comprises:
a. a gap segment consisting of ten linked deoxynucleosides;
b. a 5' wing segment consisting of five linked nucleosides;
c. a 3' wing segment consisting of five linked nucleosides;
d. wherein the gap segment is positioned between the 5' wing segment and the 3' wing segment, and wherein each nucleoside of each wing segment comprises a 2'-O-methoxyethyl sugar.

Embodiment 95. The compound of any of embodiments 1 to 31, 34, 37 to 45, or 53 to 88, wherein the modified oligonucleotide consists of 16 linked nucleosides and comprises:
a. a gap segment consisting of ten linked deoxynucleosides;
b. a 5' wing segment consisting of three linked nucleosides;
c. a 3' wing segment consisting of three linked nucleosides;
d. wherein the gap segment is positioned between the 5' wing segment and the 3' wing segment, and wherein each nucleoside of each wing segment comprises a cEt sugar.

Embodiment 96. The compound of any of embodiments 1 to 67, wherein the modified oligonucleotide comprises at least 8 contiguous nucleobases complementary to a target region within nucleobase 1343 and nucleobase 1368 of SEQ ID NO.: 1, and wherein the modified oligonucleotide comprises:
a. a gap segment consisting of linked deoxynucleosides;
b. a 5' wing segment consisting of linked nucleosides;
c. a 3' wing segment consisting of linked nucleosides;
d. wherein the gap segment is positioned between the 5' wing segment and the 3' wing segment and wherein each nucleoside of each wing segment comprises a modified sugar.

Embodiment 97. The compound of embodiment 96, wherein each modified sugar in the 5'-wing segment has the same modifications.

Embodiment 98. The compound of embodiment 96, wherein at least two modified sugars in the 5'-wing segment have different modifications.

Embodiment 99. The compound of any of embodiments 96 to 98 wherein each modified sugar in the 3'-wing segment has the same modifications.

Embodiment 100. The compound of any of embodiments 96 to 98, wherein at least two modified sugars in the 3'-wing segment have different modification.

Embodiment 101. The compound of embodiment 96, wherein at least one modified sugar is a bicyclic sugar selected from among cEt, LNA, α-L-LNA, ENA and 2'-thio LNAs.

Embodiment 102. The compound of embodiment 90 to 91, wherein each B represents a bicyclic sugar selected from among cEt, LNA, α-L-LNA, ENA and 2'-thio LNA.

Embodiment 103. The compound of embodiment 102, wherein the bicyclic sugar comprises BNA.

Embodiment 104. The compound of embodiment 102, wherein the bicyclic sugar comprises cEt.

Embodiment 105. The compound of embodiment 102, wherein the bicyclic sugar comprises LNA.

Embodiment 106. The compound of embodiment 102, wherein the bicyclic sugar comprises α-L-LNA.

Embodiment 107. The compound of embodiment 102, wherein the bicyclic sugar comprises ENA.

Embodiment 108. The compound of embodiment 102, wherein the bicyclic sugar comprises 2'-thio LNA.

Embodiment 109. The compound of embodiment 90 or 91, wherein each A represents a 2'-substituted nucleoside is selected from among: 2'-$OCH_3$, 2'-F, and 2'-O-methoxyethyl.

Embodiment 110. The compound of embodiment 109, wherein the 2'-substituted nucleoside comprises 2'-O-methoxyethyl.

Embodiment 111. The compound of any of embodiments 1 to 111, wherein at least one internucleoside linkage is a modified internucleoside linkage.

Embodiment 112. The compound of any of embodiments 1 to 111, wherein each internucleoside linkage is a phosphorothioate internucleoside linkage.

Embodiment 113. A compound consisting of ISIS 486178.

Embodiment 114. A compound consisting of ISIS 512497.

Embodiment 115. A compound consisting of ISIS 598768.

Embodiment 116. A compound consisting of ISIS 594300.

Embodiment 117. A compound consisting of ISIS 594292.

Embodiment 118. A compound consisting of ISIS 569473.

Embodiment 119. A compound consisting of ISIS 598769.

Embodiment 120. A compound consisting of ISIS 570808.

Embodiment 121. A compound consisting of ISIS 598777.

Embodiment 122. A compound having a nucleobase sequence as set forth in SEQ ID NO: 23, wherein the modified oligonucleotide consists of 16 linked nucleosides and comprises:

a. a gap segment consisting of ten linked deoxynucleosides;
b. a 5' wing segment consisting of three linked nucleosides;
c. a 3' wing segment consisting of three linked nucleosides;
d. wherein the gap segment is positioned between the 5' wing segment and the 3' wing segment;
e. wherein each nucleoside of each wing segment comprises a bicyclic sugar;
f. wherein each internucleoside linkage is a phosphorothioate internucleoside linkage; and
g. wherein each cytosine residue is a 5-methyl cytosine.

Embodiment 123. A compound having a nucleobase sequence as set forth in SEQ ID NO: 29, wherein the modified oligonucleotide consists of 16 linked nucleosides and comprises:

a. a gap segment consisting of ten linked deoxynucleosides;
b. a 5' wing segment consisting of three linked nucleosides;
c. a 3' wing segment consisting of three linked nucleosides;
d. wherein the gap segment is positioned between the 5' wing segment and the 3' wing segment;
e. wherein each nucleoside of each wing segment comprises a bicyclic sugar;
f. wherein each internucleoside linkage is a phosphorothioate internucleoside linkage; and
g. wherein each cytosine residue is a 5-methyl cytosine.

Embodiment 124. A compound having a nucleobase sequence as set forth in SEQ ID NO: 31, wherein the modified oligonucleotide consists of 16 linked nucleosides and comprises:

a. a gap segment consisting of ten linked deoxynucleosides;
b. a 5' wing segment consisting of three linked nucleosides;
c. a 3' wing segment consisting of three linked nucleosides;
d. wherein the gap segment is positioned between the 5' wing segment and the 3' wing segment;
e. wherein each nucleoside of each wing segment comprises a bicyclic sugar;
f. wherein each internucleoside linkage is a phosphorothioate internucleoside linkage; and
g. wherein each cytosine residue is a 5-methyl cytosine.

Embodiment 125. A compound having a nucleobase sequence as set forth in SEQ ID NO: 26, wherein the modified oligonucleotide consists of 16 linked nucleosides and comprises:

a. a gap segment consisting of eight linked deoxynucleosides;
b. a 5' wing segment consisting of four linked nucleosides and having a E-E-K-K 5'-wing motif;
c. a 3' wing segment consisting of four linked nucleosides and having a K-K-E-E 3'-wing motif;
d. wherein the gap segment is positioned between the 5' wing segment and the 3' wing segment;
e. wherein each E represents 2'-O-methoxyethyl sugar and each K represents a cEt sugar;
f. wherein each internucleoside linkage is a phosphorothioate internucleoside linkage; and
g. wherein each cytosine residue is a 5-methyl cytosine.

Embodiment 126. A compound having a nucleobase sequence as set forth in SEQ ID NO: 30, wherein the modified oligonucleotide consists of 16 linked nucleosides and comprises:

a. a gap segment consisting of eight linked deoxynucleosides;
b. a 5' wing segment consisting of four linked nucleosides and having a E-E-K-K 5'-wing motif;
c. a 3' wing segment consisting of four linked nucleosides and having a K-K-E-E 3'-wing motif;
d. wherein the gap segment is positioned between the 5' wing segment and the 3' wing segment;
e. wherein each E represents 2'-O-methoxyethyl sugar and each K represents a cEt sugar;
f. wherein each internucleoside linkage is a phosphorothioate internucleoside linkage; and
g. wherein each cytosine residue is a 5-methyl cytosine.

Embodiment 127. A compound having a nucleobase sequence as set forth in SEQ ID NO: 32, wherein the modified oligonucleotide consists of 16 linked nucleosides and comprises:

a. a gap segment consisting of eight linked deoxynucleosides;
b. a 5' wing segment consisting of four linked nucleosides and having a E-E-K-K 5'-wing motif;
c. a 3' wing segment consisting of four linked nucleosides and having a K-K-E-E 3'-wing motif;
d. wherein the gap segment is positioned between the 5' wing segment and the 3' wing segment;
e. wherein each E represents 2'-O-methoxyethyl sugar and each K represents a cEt sugar;
f. wherein each internucleoside linkage is a phosphorothioate internucleoside linkage; and
g. wherein each cytosine residue is a 5-methyl cytosine.

Embodiment 128. A compound having a nucleobase sequence as set forth in SEQ ID NO: 27, wherein the modified oligonucleotide consists of 17 linked nucleosides and comprises:

a. a gap segment consisting of seven linked deoxynucleosides;
b. a 5' wing segment consisting of five linked nucleosides and having an E-E-E-K-K 5'-wing motif;
c. a 3' wing segment consisting of five linked nucleosides and having a K-K-E-E-E 3'-wing motif;
d. wherein the gap segment is positioned between the 5' wing segment and the 3' wing segment;
e. wherein each E represents 2'-O-methoxyethyl sugar and each K represents a cEt sugar;
f. wherein each internucleoside linkage is a phosphorothioate internucleoside linkage; and g. wherein each cytosine residue is a 5-methyl cytosine.

Embodiment 129. A compound having a nucleobase sequence as set forth in SEQ ID NO: 28, wherein the modified oligonucleotide consists of 17 linked nucleosides and comprises:

a. a gap segment consisting of seven linked deoxynucleosides;

b. a 5' wing segment consisting of five linked nucleosides and having an E-E-E-K-K 5'-wing motif;

c. a 3' wing segment consisting of five linked nucleosides and having a K-K-E-E-E 3'-wing motif;

d. wherein the gap segment is positioned between the 5' wing segment and the 3' wing segment;

e. wherein each E represents 2'-O-methoxyethyl sugar and each K represents a cEt sugar;

f. wherein each internucleoside linkage is a phosphorothioate internucleoside linkage; and g. wherein each cytosine residue is a 5-methyl cytosine.

Embodiment 130. A compound having a nucleobase sequence as set forth in SEQ ID NO: 25, wherein the modified oligonucleotide consists of 20 linked nucleosides and comprises:

a. a gap segment consisting of ten linked deoxynucleosides;

b. a 5' wing segment consisting of five linked nucleosides;

c. a 3' wing segment consisting of five linked nucleosides;

d. wherein the gap segment is positioned between the 5' wing segment and the 3' wing segment;

e. wherein each nucleoside of each wing segment comprises a 2'-O-methoxyethyl sugar;

f. wherein each internucleoside linkage is a phosphorothioate internucleoside linkage; and g. wherein each cytosine residue is a 5-methyl cytosine.

Embodiment 131. The compound of any of embodiments 1 to 130 comprising a conjugate.

Embodiment 132. A composition comprising the compound of any of embodiments 1 to 131, and a pharmaceutically acceptable carrier or diluent.

Embodiment 133. A method of treating DM1 in an animal comprising administering to an animal in need thereof a compound according to any of embodiments 1 to 130, or a composition according to embodiment 132.

Embodiment 134. The method of embodiment 133, wherein the compound reduces DMPK mRNA levels.

Embodiment 135. The method of embodiment 133, wherein the compound reduces DMPK protein expression.

Embodiment 136. The method of embodiment 133, wherein the compound reduces CUGexp DMPK.

Embodiment 137. The method of embodiment 133, wherein the compound preferentially reduces CUGexp DMPK.

Embodiment 138. The method of embodiment 133, wherein the compound reduces CUGexp DMPK mRNA.

Embodiment 139. The method of embodiment 133, wherein the compound preferentially reduces CUGexp DMPK mRNA.

Embodiment 140. The method of embodiment 138 or 139, wherein the preferential reduction of CUGexp is in muscle tissue.

Embodiment 141. A method of reducing myotonia in an animal comprising administering to an animal in need thereof a compound according to any of embodiments 1 to 131, or a composition according to embodiment 132.

Embodiment 142. A method of reducing MBLN dependent spliceopathy in an animal comprising administering to an animal in need thereof a compound according to any of embodiments 1 to 131, or a composition according to embodiment 132.

Embodiment 143. The method of embodiment 138, wherein splicing of any of Serca1, m-Titin, Clcn1, and Zasp is corrected.

Embodiment 144. The method of any of embodiments 133 to 143, wherein the administering is systemic administration.

Embodiment 145. The method of any of embodiments 133 to 143, wherein the administering is parenteral administration.

Embodiment 146. The method of embodiment 144, wherein the systemic administration is any of subcutaneous administration, intravenous administration, intracerebroventricular administration, and intrathecal administration.

Embodiment 147. The method of any of embodiments 133 to 143, wherein the administration is not intramuscular administration.

Embodiment 148. The method of any of embodiments 133 to 143, wherein the animal is a human.

Embodiment 149. A method of reducing spliceopathy of Serca1 in an animal in need thereof by administering a compound according to any of embodiments 1 to 131, or a composition according to embodiment 132, and thereby causing Serca1 exon 22 inclusion.

Embodiment 150. A method of reducing spliceopathy of m-Titin in an animal in need thereof by administering a compound according to any of embodiments 1 to 131, or a composition according to embodiment 132, and thereby causing m-Titin exon 5 inclusion.

Embodiment 151. A method of reducing spliceopathy of Clcn1 in an animal in need thereof by administering a compound according to any of embodiments 1 to 131, or a composition according to embodiment 132, and thereby causing Clcn1 exon 7a inclusion.

Embodiment 152. A method of reducing spliceopathy of Zasp in an animal in need thereof by administering a compound according to any of embodiments 1 to 131, or a composition according to embodiment 132, and thereby causing Zasp exon 11 inclusion.

Embodiment 153. A method of reducing DMPK mRNA in a cell, comprising contacting a cell with a compound according to any of embodiments 1 to 131, or a composition according to embodiment 132.

Embodiment 154. A method of reducing DMPK protein in a cell, comprising contacting a cell with a compound according to any of embodiments 1 to 131, or a composition according to embodiment 132.

Embodiment 155. A method of reducing CUGexp mRNA in a cell, comprising contacting a cell with a compound according to any of embodiments 1 to 131, or a composition according to embodiment 132.

Embodiment 156. The method of any of embodiments 149 to 151, wherein the cell is in an animal.

Embodiment 157. The method of embodiment 156, wherein the animal is a human.

Embodiment 158. A method of achieving a preferential reduction of CUGexp DMPK RNA, comprising:

a. selecting a subject having type 1 myotonic dystrophy or having a CUGexp DMPK RNA; and b. administering to said subject a compound according to any of embodiments 1 to 131, or a composition according to embodiment 132;

wherein said compound according to any of embodiments 1 to 131, or a composition according to embodiment 132, when bound to said CUGexp DMPK RNA, activates a ribonuclease, thereby achieving a preferential reduction of said CUGexp DMPK RNA.

Embodiment 159. A method of achieving a preferential reduction of CUGexp DMPK RNA, comprising:

a. selecting a subject having type 1 myotonic dystrophy or having a CUGexp DMPK RNA; and b. systemically administering to said subject a compound according to any of embodiments 1 to 131, or a composition according to embodiment 132;

wherein said chemically-modified antisense oligonucleotide, when bound to said CUGexp DMPK RNA, achieves a preferential reduction of said CUGexp DMPK RNA.

Embodiment 160. A method of reducing spliceopathy in a subject suspected of having type 1 myotonic dystrophy or having a nuclear retained CUGexp DMPK RNA, comprising: administering to said subject a compound according to any of embodiments 1 to 131, or a composition according to embodiment 132, wherein the compound according to any of embodiments 1 to 131, or a composition according to embodiment 132, when bound to said mutant DMPK RNA, activates a ribonuclease, thereby reducing spliceopathy.

Embodiment 161. A method of preferentially reducing CUGexp DMPK RNA, reducing myotonia or reducing spliceopathy in an animal comprising administering to the animal a compound according to any of embodiments 1 to 131 or a pharmaceutical composition of embodiment 132, wherein the compound reduces DMPK expression in the animal, thereby preferentially reducing CUGexp DMPK RNA, reducing myotonia, or reducing spliceopathy in the animal.

Embodiment 162. A method for treating an animal with type 1 myotonic dystrophy comprising identifying said animal with type 1 myotonic dystrophy, administering to said animal a therapeutically effective amount of a compound according to any of embodiments 1 to 131 or a pharmaceutical composition of embodiment 132, wherein said animal with type 1 myotonic dystrophy is treated.

Embodiment 163. A method of reducing DMPK expression comprising administering to an animal a compound according to any of embodiments 1 to 131 or a pharmaceutical composition of embodiment 132, wherein expression of DMPK is reduced.

Embodiment 164. A compound according to any of embodiments 1 to 131 or a pharmaceutical composition of embodiment 132, for use in treating DM1 in an animal.

Embodiment 165. A compound according to any of embodiments 1 to 131 or a pharmaceutical composition of embodiment 132, for use in reducing myotonia in an animal.

Embodiment 166. A compound according to any of embodiments 1 to 131 or a pharmaceutical composition of embodiment 132, for use in reducing MBLN dependent spliceopathy in an animal.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. Herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques can be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O$(CH_2)_2$—$OCH_3$) refers to an O-methoxy-ethyl modification of the 2' position of a furanosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to position 5. A 5-methylcytosine is a modified nucleobase.

"About" means within ±7% of a value. For example, if it is stated, "the compound affected at least about 70% inhibition of DMPK", it is implied that the DMPK levels are inhibited within a range of 63% and 77%.

"Active pharmaceutical agent" means the substance or substances in a pharmaceutical composition that provide a therapeutic benefit when administered to an animal. For example, in certain embodiments an antisense oligonucleotide targeted to DMPK is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing an agent to an animal, and includes, but is not limited to, administering by a medical professional and self-administering.

"Agent" means an active substance that can provide a therapeutic benefit when administered to an animal. "First Agent" means a therapeutic compound of the invention. For example, a first agent can be an antisense oligonucleotide targeting DMPK. "Second agent" means a second therapeutic compound of the invention (e.g. a second antisense oligonucleotide targeting DMPK) and/or a non-DMPK therapeutic compound.

"Amelioration" refers to a lessening of at least one indicator, sign, or symptom of an associated disease, disorder, or condition. The severity of indicators can be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, snoRNAs, miRNAs, and satellite repeats.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furanosyl ring modified by the bridging of two non-geminal carbon ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"CUGexp DMPK" means mutant DMPK RNA containing an expanded CUG repeat (CUGexp). The wild-type DMPK gene has 5-37 CTG repeats in the 3' untranslated region. In a "CUGexp DMPK" (such as in a myotonic dystrophy type I patient) this number is significantly expanded and is, for example, in the range of 50 to greater than 3,500 (Harper, Myotonic Dystrophy (Saunders, London, ed. 3, 2001); Annu. Rev. Neurosci. 29: 259, 2006; EMBO J. 19: 4439, 2000; Curr Opin Neurol. 20: 572, 2007).

"Diluent" means an ingredient in a composition that lacks pharmacological activity, but is pharmaceutically necessary or desirable. For example, the diluent in an injected composition can be a liquid, e.g. saline solution.

"DMPK" means any nucleic acid or protein of distrophia myotonica protein kinase. DMPK can be a mutant DMPK including CUGexp DMPK nucleic acid.

"DMPK expression" means the level of mRNA transcribed from the gene encoding DMPK or the level of protein translated from the mRNA. DMPK expression can be determined by art known methods such as a Northern or Western blot.

"DMPK nucleic acid" means any nucleic acid encoding DMPK. For example, in certain embodiments, a DMPK nucleic acid includes a DNA sequence encoding DMPK, an RNA sequence transcribed from DNA encoding DMPK (including genomic DNA comprising introns and exons), and an mRNA or pre-mRNA sequence encoding DMPK. "DMPK mRNA" means an mRNA encoding a DMPK protein.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region can be referred to as a "gap segment" and the external regions can be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Identifying an animal with type 1 myotonic dystrophy" means identifying an animal having been diagnosed with a type 1 myotonic dystrophy, disorder or condition or identifying an animal predisposed to develop a type 1 myotonic dystrophy, disorder or condition. For example, individuals with a familial history can be predisposed to type 1 myotonic dystrophy, disorder or condition. Such identification can be accomplished by any method including evaluating an individual's medical history and standard clinical tests or assessments.

"Immediately adjacent" means there are no intervening elements between the immediately adjacent elements.

"Individual" means a human or non-human animal selected for treatment or therapy.

"Internucleoside linkage" refers to the chemical bond between nucleosides.

"Linked nucleosides" means adjacent nucleosides which are bonded or linked together by an internucleoside linkage.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleoside and/or modified internucleoside linkage.

"Modified sugar" refers to a substitution or change from a natural sugar moiety. Modified sugars include substituted sugar moeities and surrogate sugar moieties.

"Motif" means the pattern of chemically distinct regions in an antisense compound.

"Myotonia" means an abnormally slow relaxation of a muscle after voluntary contraction or electrical stimulation.

"Nuclear ribonuclease" means a ribonuclease found in the nucleus. Nuclear ribonucleases include, but are not limited to, RNase H including RNase H1 and RNase H2, the double stranded RNase drosha and other double stranded RNases.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid can also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar. In certain embodiments, a nucleoside is linked to a phosphate group.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" means a polymer of linked monomeric subunits which is capable of hybridizing to at least a region of a nucleic acid molecule.

"Oligonucleotide" means a polymer of linked nucleosides, wherein each nucleoside and each internucleoside linkage may be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition can comprise one or more active agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Preferentially reducing CUG exp DMPK RNA" refers to a preferential reduction of RNA transcripts from a CUGexp DMPK allele relative to RNA transcripts from a normal DMPK allele.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum can indicate liver toxicity or liver function abnormality. For example, increased bilirubin can indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Spliceopathy" means a change in the alternative splicing of one or more RNAs that leads to the expression of altered splice products in a particular tissue.

"Subcutaneous administration" means administration just below the skin.

"Substituted sugar moiety" means a furanosyl other than a natural sugar of RNA or DNA.

"Sugar" or "Sugar moiety" means a natural sugar moiety or a modified sugar.

"Sugar surrogate" overlaps with the slightly broader term "nucleoside mimetic" but is intended to indicate replacement of the sugar unit (furanose ring) only A sugar surrogate is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds. In certain embodiments, a target nucleic acid comprises a region of a DMPK nucleic acid.

"Target segment" means the sequence of nucleotides of a target nucleic acid to which an antisense compound is targeted. "5' target site" refers to the 5'-most nucleotide of a target segment.

"3' target site" refers to the 3'-most nucleotide of a target segment.

"Therapeutically effective amount" means an amount of an agent that provides a therapeutic benefit to an individual.

"Treat" refers to administering a pharmaceutical composition to effect an alteration or improvement of a disease, disorder, or condition.

"Type 1 myotonic dystrophy" or "DM1" means an autosomal dominant disorder caused by expansion of a noncoding CTG repeat in DMPK. This mutation leads to RNA dominance, a process in which expression of RNA containing an expanded CUG repeat (CUGexp) induced cell dysfunction. The CUGexp tract interacts with RNA binding proteins and causes the mutant transcript to be retained in nuclear foci. The toxicity of this RNA stems from sequestration of RNA binding proteins and activation of signaling pathways.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds, and compositions for inhibiting DMPK expression.

Certain embodiments provide a method of reducing DMPK expression in an animal comprising administering to the animal a compound comprising a modified oligonucleotide targeting DMPK.

Certain embodiments provide a method of preferentially reducing CUGexp DMPK RNA, reducing myotonia or reducing spliceopathy in an animal comprising administering to the animal a compound comprising a modified oligonucleotide targeted to DMPK, wherein the modified oligonucleotide preferentially reduces CUGexp DMPK RNA, reduces myotonia or reduces spliceopathy in the animal.

Certain embodiments provide a method of administering an antisense oligonucleotide to counteract RNA dominance by directing the cleavage of pathogenic transcripts.

Certain embodiments provide a method of reducing spliceopathy of Serca1. In certain embodiments, methods provided herein result in exon 22 inclusion. In certain embodiments, the corrective splicing occurs in the tibialis anterior, gastrocnemius, and quadriceps muscles.

Certain embodiments provide a method of reducing spliceopathy of m-Titin. In certain embodiments, methods provided herein result in exon 5 inclusion. In certain embodiments, the corrective splicing occurs in the tibialis anterior, gastrocnemius, and quadriceps muscles.

Certain embodiments provide a method of reducing spliceopathy of Clcn1. In certain embodiments, methods provided herein result in exon 7a inclusion. In certain embodiments, the corrective splicing occurs in the tibialis anterior, gastrocnemius, and quadriceps muscles.

Certain embodiments provide a method of reducing spliceopathy of Zasp. In certain embodiments, methods provided herein result in exon 11 inclusion. In certain embodiments, the corrective splicing occurs in the tibialis anterior, gastrocnemius, and quadriceps muscles.

Certain embodiments provide a method for treating an animal with type 1 myotonic dystrophy comprising: a) identifying said animal with type 1 myotonic dystrophy, and b) administering to said animal a therapeutically effective amount of a compound comprising a modified oligonucleotide targeted to DMPK. In certain embodiments, the therapeutically effective amount of the compound administered to the animal preferentially reduces CUGexp DMPK RNA, reduces myotonia or reduces spliceopathy in the animal.

Certain embodiments provide a method of achieving a preferential reduction of CUGexp DMPK RNA, including administering to the subject suspected of having type 1 myotonic dystrophy or having a CUGexp DMPK RNA a modified antisense oligonucleotide complementary to a non-repeat region of said CUGexp DMPK RNA. The modified antisense oligonucleotide, when bound to said CUGexp DMPK RNA, achieves a preferential reduction of the CUGexp DMPK RNA.

Certain embodiments provide a method of achieving a preferential reduction of CUGexp DMPK RNA, including selecting a subject having type 1 myotonic dystrophy or having a CUGexp DMPK RNA and administering to said subject a modified antisense oligonucleotide complementary to a non-repeat region of said CUGexp DMPK RNA. The modified antisense oligonucleotide, when bound to the CUGexp DMPK RNA, activates a ribonuclease or nuclear ribonuclease, thereby achieving a preferential reduction of the CUGexp DMPK RNA in the nucleus.

Certain embodiments provide a method of achieving a preferential reduction of CUGexp DMPK RNA, including selecting a subject having type 1 myotonic dystrophy or having a mutant or CUGexp DMPK RNA and systemically administering to said subject a modified antisense oligonucleotide complementary to a non-repeat region of said CUGexp DMPK RNA. The modified antisense oligonucleotide, when bound to the mutant or CUGexp DMPK RNA, achieves a preferential reduction of the mutant or CUGexp DMPK RNA.

Certain embodiments provide a method of reducing myotonia in a subject in need thereof. The method includes administering to the subject a modified antisense oligonucleotide complementary to a non-repeat region of a DMPK RNA, wherein the modified antisense oligonucleotide, when bound to the DMPK RNA, activates a ribonuclease or nuclear ribonuclease, thereby reducing myotonia. In certain embodiments, the subject has or is suspected of having type 1 myotonic dystrophy or having a mutant DMPK RNA or CUGexp DMPK RNA. In certain embodiments, the DMPK RNA is nuclear retained.

Certain embodiments provide a method of reducing spliceopathy in a subject in need thereof. The method includes administering to the subject a modified antisense oligonucleotide complementary to a non-repeat region of a DMPK RNA, wherein the modified antisense oligonucleotide, when bound to the DMPK RNA, activates a ribonuclease or nuclear ribonuclease, thereby reducing spliceopathy. In certain embodiments, the subject has or is suspected of having type 1 myotonic dystrophy or having a nuclear retained CUGexp DMPK RNA. In certain embodiments, the DMPK RNA is nuclear retained. In certain embodiments, the spliceopathy is MBNL dependent spliceopathy.

In certain embodiments, the modified antisense oligonucleotide of the methods is chimeric. In certain embodiments, the modified antisense oligonucleotide of the methods is a gapmer.

In certain embodiments of the methods provided herein, the administering is subcutaneous. In certain embodiments, the administering is intravenous.

In certain embodiments, the modified antisense oligonucleotide of the methods targets a non-coding sequence within the non-repeat region of a DMPK RNA. In certain embodiments, the oligonucleotide targets a coding region, an intron, a 5'UTR, or a 3'UTR of the mutant DMPK RNA.

In certain embodiments of the methods provided herein, the nuclear ribonuclease is RNase H1.

In certain embodiments of the methods, the DMPK RNA is reduced in muscle tissue. In certain embodiments, the mutant DMPK RNA CUGexp DMPK RNA is preferentially reduced.

In certain embodiments, the DMPK has the sequence as set forth in GenBank Accession No. NM_001081560.1 (incorporated herein as SEQ ID NO: 1). In certain embodiments, the DMPK has the sequence as set forth in GenBank Accession No. NT_011109.15 truncated from nucleotides 18540696 to U.S. Pat. No. 18,555,106 (incorporated herein as SEQ ID NO: 2). In certain embodiments, the DMPK has the sequence as set forth in GenBank Accession No. NT_039413.7 truncated from nucleotides 16666001 to U.S. Pat. No. 16,681,000 (incorporated herein as SEQ ID NO: 3). In certain embodiments, the DMPK has the sequence as set forth in GenBank Accession No. NM_032418.1 (incorporated herein as SEQ ID NO: 4). In certain embodiments, the DMPK has the sequence as set forth in GenBank Accession No. AI007148.1 (incorporated herein as SEQ ID NO: 5). In certain embodiments, the DMPK has the sequence as set forth in GenBank Accession No. AI304033.1 (incorporated herein as SEQ ID NO: 6). In certain embodiments, the DMPK has the sequence as set forth in GenBank Accession No. BC024150.1 (incorporated herein as SEQ ID NO: 7). In certain embodiments, the DMPK has the sequence as set forth in GenBank Accession No. BC056615.1 (incorporated herein as SEQ ID NO: 8). In certain embodiments, the DMPK has the sequence as set forth in GenBank Accession No. BC075715.1 (incorporated herein as SEQ ID NO: 9). In certain embodiments, the DMPK has the sequence as set forth in GenBank Accession No. BU519245.1 (incorporated herein as SEQ ID NO: 10). In certain embodiments, the DMPK has the sequence as set forth in GenBank Accession No. CB247909.1 (incorporated herein as SEQ ID NO: 11). In certain embodiments, the DMPK has the sequence as set forth in GenBank Accession No. CX208906.1 (incorporated herein as SEQ ID NO: 12). In certain embodiments, the DMPK has the sequence as set forth in GenBank Accession No. CX732022.1 (incorporated herein as SEQ ID NO: 13). In certain embodiments, the DMPK has the sequence as set forth in GenBank Accession No. S60315.1 (incorporated herein as SEQ ID NO: 14). In certain embodiments, the DMPK has the sequence as set forth in GenBank Accession No. S60316.1 (incorporated herein as SEQ ID NO: 15). In certain embodiments, the DMPK has the sequence as set forth in GenBank Accession No. NM_001081562.1 (incorporated herein as SEQ ID NO: 16). In certain embodiments, the DMPK has the sequence as set forth in GenBank Accession No. NM_001100.3 (incorporated herein as SEQ ID NO: 17).

In certain embodiments, the modified oligonucleotide has a nucleobase sequence comprising at least 8 contiguous nucleobases of a nucleobase sequence recited in any one of SEQ ID NOs: 23, 24, 25, 26, 27, 28, 29, 30, 31, 32, or 33-874. In certain embodiments, the modified oligonucleotide has a nucleobase sequence comprising at least 9, at least 10, or at least 11, contiguous nucleobases of a nucleobase sequence recited in any one of SEQ ID NOs: 23, 24, 25, 26, 27, 28, 29, 30, 31, 32, or 33-874.

In certain embodiments, the modified oligonucleotide has a nucleobase sequence comprising at least 12 contiguous nucleobases of a nucleobase sequence recited in any one of SEQ ID NOs: 23, 24, 25, 26, 27, 28, 29, 30, 31, 32, or 33-874. In certain embodiments, the modified oligonucleotide has a nucleobase sequence comprising at least 13, or at least 14, contiguous nucleobases of a nucleobase sequence recited in any one of SEQ ID NOs: 23, 24, 25, 26, 27, 28, 29, 30, 31, 32, or 33-874.

In certain embodiments, the modified oligonucleotide has a nucleobase sequence comprising at least 15 contiguous nucleobases of a nucleobase sequence recited in any one of SEQ ID NOs: 23, 24, 25, 26, 27, 28, 29, 30, 31, 32, or 33-874. In certain embodiments, the modified oligonucleotide has a nucleobase sequence comprising at least 16 contiguous nucleobases of a nucleobase sequence recited in any one of SEQ ID NOs: 23, 24, 25, 26, 27, 28, 29, 30, 31, 32, or 33-874.

In certain embodiments, the modified oligonucleotide has a nucleobase sequence comprising at least 17 contiguous nucleobases of a nucleobase sequence recited in any one of SEQ ID NOs: 24, 25, 27, or 28.

In certain embodiments, the modified oligonucleotide has a nucleobase sequence comprising at least 18 contiguous nucleobases of a nucleobase sequence recited in any one of SEQ ID NOs: 24 or 25. In certain embodiments, the modified oligonucleotide has a nucleobase sequence comprising at least 19 contiguous nucleobases of a nucleobase sequence recited in any one of SEQ ID NOs: 24 or 25.

In certain embodiments, the modified oligonucleotides provided herein are targeted to any one of the following regions of SEQ ID NO: 1: 1343-1368, 1317-1366, 2748-2791, 2155-2208, 2748-2791, 730-748, 528-547, 531-567, 636-697, 1311-1331, 1314-1339, 1446-1475, 1635-1670, 1610-1638, 1457-1486, 2773-1788, 931-948, 934-949, 937-952, 942-957, 937-957, 943-958, 937-953, 1346-1363, 1346-1361, 1347-1363, 2162-2179, 2492-2508, 2696-2717, and 2683-2703. In certain embodiments, the modified oligonucleotides provided herein are targeted to any one of the following regions of SEQ ID NO: 1: 2773-2788, 1343-1358, and 1344-1359.

In certain embodiments, the modified oligonucleotides provided herein have a nucleobase sequence comprising a complementary region comprising at least 8 contiguous nucleobases complementary to a target region. In certain embodiments, the modified oligonucleotides provided herein have a nucleobase sequence comprising a complementary region comprising at least 8 contiguous nucleobases complementary to a target region, wherein the target region is targeted to nucleobases 1343-1368, 1317-1366, 2748-2791, 2155-2208, 2748-2791, 730-748, 528-547, 531-567, 636-697, 1311-1331, 1314-1339, 1446-1475, 1635-1670, 1610-1638, 1457-1486, 2773-1788, 931-948, 934-949, 937-952, 942-957, 937-957, 943-958, 937-953, 1346-1363, 1346-1361, 1347-1363, 2162-2179, 2492-2508, 2696-2717, or 2683-2703 of SEQ ID NO: 1. In certain embodiments, the modified oligonucleotides provided herein have a nucleobase sequence comprising a complementary region comprising at least 8 contiguous nucleobases complementary to a target region, wherein the target region is targeted to nucleobases 2773-2788, 1343-1358, or 1344-1359 of SEQ ID NO: 1.

In certain embodiments, the modified oligonucleotides provided herein have a nucleobase sequence comprising a complementary region comprising at least 10 contiguous nucleobases complementary to a target region. In certain embodiments, the modified oligonucleotides provided herein have a nucleobase sequence comprising a complementary region comprising at least 10 contiguous nucleobases complementary to a target region, wherein the target region is targeted to nucleobases 1343-1368, 1317-1366, 2748-2791, 2155-2208, 2748-2791, 730-748, 528-547, 531-567, 636-697, 1311-1331, 1314-1339, 1446-1475, 1635-1670, 1610-1638, 1457-1486, 2773-1788, 931-948, 934-949, 937-952, 942-957, 937-957, 943-958, 937-953, 1346-1363, 1346-1361, 1347-1363, 2162-2179, 2492-2508, 2696-2717, or 2683-2703 of SEQ ID NO: 1. In certain embodiments, the modified oligonucleotides provided herein have a nucleobase sequence comprising a complementary region comprising at least 10 contiguous nucleobases complementary to a target region, wherein the target region is targeted to nucleobases 2773-2788, 1343-1358, or 1344-1359 of SEQ ID NO: 1.

In certain embodiments, the modified oligonucleotides provided herein have a nucleobase sequence comprising a complementary region comprising at least 12 contiguous nucleobases complementary to a target region. In certain embodiments, the modified oligonucleotides provided herein have a nucleobase sequence comprising a complementary region comprising at least 12 contiguous nucleobases complementary to a target region, wherein the target region is targeted to nucleobases 1343-1368, 1317-1366, 2748-2791, 2155-2208, 2748-2791, 730-748, 528-547, 531-567, 636-697, 1311-1331, 1314-1339, 1446-1475, 1635-1670, 1610-1638, 1457-1486, 2773-1788, 931-948, 934-949, 937-952, 942-957, 937-957, 943-958, 937-953, 1346-1363, 1346-1361, 1347-1363, 2162-2179, 2492-2508, 2696-2717, or 2683-2703 of SEQ ID NO: 1. In certain embodiments, the modified oligonucleotides provided herein have a nucleobase sequence comprising a complementary region comprising at least 12 contiguous nucleobases complementary to a target region, wherein the target region is targeted to nucleobases 2773-2788, 1343-1358, or 1344-1359 of SEQ ID NO: 1.

In certain embodiments, the modified oligonucleotides provided herein have a nucleobase sequence comprising a complementary region comprising at least 14 contiguous nucleobases complementary to a target region. In certain embodiments, the modified oligonucleotides provided herein have a nucleobase sequence comprising a complementary region comprising at least 14 contiguous nucleobases complementary to a target region, wherein the target region is targeted to nucleobases 1343-1368, 1317-1366, 2748-2791, 2155-2208, 2748-2791, 730-748, 528-547, 531-567, 636-697, 1311-1331, 1314-1339, 1446-1475, 1635-1670, 1610-1638, 1457-1486, 2773-1788, 931-948, 934-949, 937-952, 942-957, 937-957, 943-958, 937-953, 1346-1363, 1346-1361, 1347-1363, 2162-2179, 2492-2508, 2696-2717, or 2683-2703 of SEQ ID NO: 1. In certain embodiments, the modified oligonucleotides provided herein have a nucleobase sequence comprising a complementary region comprising at least 14 contiguous nucleobases complementary to a target region, wherein the target region is targeted to nucleobases 2773-2788, 1343-1358, or 1344-1359 of SEQ ID NO: 1.

In certain embodiments, the modified oligonucleotides provided herein have a nucleobase sequence comprising a complementary region comprising at least 16 contiguous nucleobases complementary to a target region. In certain embodiments, the modified oligonucleotides provided herein have a nucleobase sequence comprising a complementary region comprising at least 16 contiguous nucleobases complementary to a target region, wherein the target region is targeted to nucleobases 1343-1368, 1317-1366, 2748-2791, 2155-2208, 2748-2791, 730-748, 528-547, 531-567, 636-697, 1311-1331, 1314-1339, 1446-1475, 1635-1670, 1610-1638, 1457-1486, 2773-1788, 931-948, 934-949, 937-952, 942-957, 937-957, 943-958, 937-953, 1346-1363, 1346-1361, 1347-1363, 2162-2179, 2492-2508, 2696-2717, or 2683-2703 of SEQ ID NO: 1. In certain embodiments, the modified oligonucleotides provided herein have a nucleobase sequence comprising a complementary region comprising at least 16 contiguous nucleobases complementary to a target region, wherein the target region is targeted to nucleobases 2773-2788, 1343-1358, or 1344-1359 of SEQ ID NO: 1.

In certain embodiments, the modified oligonucleotides provided herein are targeted to any one of the following regions of SEQ ID NO: 2: 10195-10294, 13553-13572, 13748-13767, 13455-13475, 13628-13657, 13735-13760, 13746-13905, 13836-13851, 13553-13568, 13563-13578, 13624-13639, 13686-13701, 13760-13775, 13763-13779, 13765-13780, 2580-2595, 6446-6461, 11099-11115, 11082-11099, 1974-1993, 4435-4456, 6035-6052, 6360-6385, 6445-6468, 6807-6824, 6789-6806, and 6596-6615. In certain embodiments, the modified oligonucleotides provided herein are targeted to any one of the following regions of SEQ ID NO: 2: 13836-13831, 8603-8618, and 8604-8619.

In certain embodiments, the modified oligonucleotides provided herein have a nucleobase sequence comprising a complementary region comprising at least 8 contiguous nucleobases complementary to a target region. In certain embodiments, the modified oligonucleotides provided herein have a nucleobase sequence comprising a complementary region comprising at least 8 contiguous nucleobases complementary to a target region, wherein the target region is targeted to nucleobases 10195-10294, 13553-13572, 13748-13767, 13455-13475, 13628-13657, 13735-13760, 13746-13905, 13836-13851, 13553-13568, 13563-13578, 13624-13639, 13686-13701, 13760-13775, 13763-13779, 13765-13780, 2580-2595, 6446-6461, 11099-11115, 11082-11099, 1974-1993, 4435-4456, 6035-6052, 6360-6385, 6445-6468, 6807-6824, 6789-6806, or 6596-6615 of SEQ ID NO: 2. In certain embodiments, the modified oligonucleotides provided herein have a nucleobase sequence comprising a complementary region comprising at least 8 contiguous nucleobases complementary to a target region, wherein the target region is targeted to nucleobases 13836-13831, 8603-8618, or 8604-8619 of SEQ ID NO: 2.

In certain embodiments, the modified oligonucleotides provided herein have a nucleobase sequence comprising a complementary region comprising at least 10 contiguous nucleobases complementary to a target region. In certain embodiments, the modified oligonucleotides provided herein have a nucleobase sequence comprising a complementary region comprising at least 10 contiguous nucleobases complementary to a target region, wherein the target region is targeted to nucleobases 10195-10294, 13553-13572, 13748-13767, 13455-13475, 13628-13657, 13735-13760, 13746-13905, 13836-13851, 13553-13568, 13563-13578, 13624-13639, 13686-13701, 13760-13775, 13763-13779, 13765-13780, 2580-2595, 6446-6461, 11099-11115, 11082-11099, 1974-1993, 4435-4456, 6035-6052, 6360-6385, 6445-6468, 6807-6824, 6789-6806, or 6596-6615 of SEQ ID NO: 2. In certain embodiments, the modified oligonucleotides provided herein have a nucleobase sequence comprising a complementary region comprising at least 10 contiguous nucleobases complementary to a target region, wherein the target region is targeted to nucleobases 13836-13831, 8603-8618, or 8604-8619 of SEQ ID NO: 2.

In certain embodiments, the modified oligonucleotides provided herein have a nucleobase sequence comprising a complementary region comprising at least 12 contiguous nucleobases complementary to a target region. In certain embodiments, the modified oligonucleotides provided herein have a nucleobase sequence comprising a complementary region comprising at least 12 contiguous nucleobases complementary to a target region, wherein the target region is targeted to nucleobases 10195-10294, 13553-13572, 13748-13767, 13455-13475, 13628-13657, 13735-13760, 13746-13905, 13836-13851, 13553-13568, 13563-13578, 13624-13639, 13686-13701, 13760-13775, 13763-13779, 13765-13780, 2580-2595, 6446-6461, 11099-11115, 11082-11099, 1974-1993, 4435-4456, 6035-6052, 6360-6385, 6445-6468, 6807-6824, 6789-6806, or 6596-6615 of SEQ ID NO: 2. In certain embodiments, the modified oligonucleotides provided herein have a nucleobase sequence comprising a complementary region comprising at least 12 contiguous nucleobases complementary to a target region, wherein the target region is targeted to nucleobases 13836-13831, 8603-8618, or 8604-8619 of SEQ ID NO: 2.

In certain embodiments, the modified oligonucleotides provided herein have a nucleobase sequence comprising a complementary region comprising at least 14 contiguous nucleobases complementary to a target region. In certain embodiments, the modified oligonucleotides provided herein have a nucleobase sequence comprising a complementary region comprising at least 14 contiguous nucleobases complementary to a target region, wherein the target region is targeted to nucleobases 10195-10294, 13553-13572, 13748-13767, 13455-13475, 13628-13657, 13735-13760, 13746-13905, 13836-13851, 13553-13568, 13563-13578, 13624-13639, 13686-13701, 13760-13775, 13763-13779, 13765-13780, 2580-2595, 6446-6461, 11099-11115, 11082-11099, 1974-1993, 4435-4456, 6035-6052, 6360-6385, 6445-6468, 6807-6824, 6789-6806, or 6596-6615 of SEQ ID NO: 2. In certain embodiments, the modified oligonucleotides provided herein have a nucleobase sequence comprising a complementary region comprising at least 14 contiguous nucleobases complementary to a target region, wherein the target region is targeted to nucleobases 13836-13831, 8603-8618, or 8604-8619 of SEQ ID NO: 2.

In certain embodiments, the modified oligonucleotides provided herein have a nucleobase sequence comprising a complementary region comprising at least 16 contiguous nucleobases complementary to a target region. In certain embodiments, the modified oligonucleotides provided herein have a nucleobase sequence comprising a complementary region comprising at least 16 contiguous nucleobases complementary to a target region, wherein the target region is targeted to nucleobases 10195-10294, 13553-13572, 13748-13767, 13455-13475, 13628-13657, 13735-13760, 13746-13905, 13836-13851, 13553-13568, 13563-13578, 13624-13639, 13686-13701, 13760-13775, 13763-13779, 13765-13780, 2580-2595, 6446-6461, 11099-11115, 11082-11099, 1974-1993, 4435-4456, 6035-6052, 6360-6385, 6445-6468, 6807-6824, 6789-6806, or 6596-6615 of SEQ ID NO: 2. In certain embodiments, the modified oligonucleotides provided herein have a nucleobase sequence comprising a complementary region comprising at least 16 contiguous nucleobases complementary to a target region, wherein the target region is targeted to nucleobases 13836-13831, 8603-8618, or 8604-8619 of SEQ ID NO: 2.

In certain embodiments, the animal is a human.

In certain embodiments, the compounds or compositions of the invention are designated as a first agent and the methods of the invention further comprise administering a second agent. In certain embodiments, the first agent and the second agent are co-administered. In certain embodiments the first agent and the second agent are co-administered sequentially or concomitantly.

In certain embodiments, administration comprises parenteral administration.

In certain embodiments, the compound is a single-stranded modified oligonucleotide. In certain embodiments, the nucleobase sequence of the modified oligonucleotide is at least 95% complementary to any one of SEQ ID NOs: 1-19 as measured over the entirety of said modified oligonucleotide. In certain embodiments, the nucleobase sequence of the modified oligonucleotide is 100% complementary to any one of SEQ ID NOs: 1-19 as measured over the entirety of said modified oligonucleotide. In certain embodiments, the compound is a single-stranded modified oligonucleotide. In certain embodiments, the nucleobase sequence of the modified oligonucleotide is at least 95% complementary to any one of SEQ ID NO: 1 as measured over the entirety of said modified oligonucleotide. In certain embodiments, the nucleobase sequence of the modified oligonucleotide is 100% complementary to any one of SEQ ID NO: 1 as measured over the entirety of said modified oligonucleotide.

In certain embodiments, the nucleobase sequence of the modified oligonucleotide is at least 90% complementary to any one of SEQ ID NO: 1 as measured over the entirety of said modified oligonucleotide. In certain embodiments, the nucleobase sequence of the modified oligonucleotide is 85% complementary to any one of SEQ ID NOs: 1 as measured over the entirety of said modified oligonucleotide.

In certain embodiments, the nucleobase sequence of the modified oligonucleotide is at least 90% complementary to any one of SEQ ID NO: 2 as measured over the entirety of said modified oligonucleotide. In certain embodiments, the nucleobase sequence of the modified oligonucleotide is 85% complementary to any one of SEQ ID NO: 2 as measured over the entirety of said modified oligonucleotide.

In certain embodiments, at least one internucleoside linkage of said modified oligonucleotide is a modified internucleoside linkage. In certain embodiments, each internucleoside linkage is a phosphorothioate internucleoside linkage.

In certain embodiments, at least one nucleoside of said modified oligonucleotide comprises a modified sugar. In certain embodiments, at least one modified sugar is a bicyclic sugar. In certain embodiments, at least one modified sugar comprises a 2'-O-methoxyethyl or a 4'-$(CH_2)_n$—O-2' bridge, wherein n is 1 or 2.

In certain embodiments, at least one nucleoside of said modified oligonucleotide comprises a modified nucleobase. In certain embodiments, the modified nucleobase is a 5-methylcytosine.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl sugar, each internucleoside linkage of said modified oligonucleotide is a phosphorothioate linkage, and each cytosine in said modified oligonucleotide is a 5-methylcytosine.

In certain embodiments, the modified oligonucleotide consists of 20 linked nucleosides. In certain embodiments, the modified oligonucleotide consists of 19 linked nucleosides. In certain embodiments, the modified oligonucleotide consists of 18 linked nucleosides. In certain embodiments, the modified oligonucleotide consists of 17 linked nucleosides. In certain embodiments, the modified oligonucleotide consists of 16 linked nucleosides.

Certain embodiments provide a method of preferentially reducing CUGexp DMPK RNA, reducing myotonia or reducing spliceopathy in an animal comprising administering to the animal a compound comprising a modified oligonucleotide having a gap segment consisting of ten linked deoxynucleosides, a 5' wing segment consisting of five linked nucleosides and a 3' wing segment consisting of five linked nucleosides. The gap segment is positioned between the 5' wing segment and the 3' wing segment, each nucleoside of each wing segment comprises a 2'-O-methoxyethyl sugar, each internucleoside linkage of said modified oligonucleotide is a phosphorothioate linkage, each cytosine in said modified oligonucleotide is a 5-methylcytosine.

In certain embodiments, the modified oligonucleotide comprises: a) a gap segment consisting of eight linked deoxynucleosides; b) a 5' wing segment consisting of four linked nucleosides and having a E-E-K-K 5'-wing motif; c) a 3' wing segment consisting of four linked nucleosides and having a K-K-E-E 3'-wing motif; and d) wherein the gap segment is positioned between the 5' wing segment and the 3' wing segment, and wherein each E represents 2'-O-methoxyethyl sugar and each K represents a cEt sugar.

In certain embodiments, the modified oligonucleotide comprises: a) a gap segment consisting of seven linked deoxynucleosides; b) a 5' wing segment consisting of five linked nucleosides and having an E-E-E-K-K 5'-wing motif; c) a 3' wing segment consisting of five linked nucleosides and having a K-K-E-E-E 3'-wing motif; and d) wherein the gap segment is positioned between the 5' wing segment and the 3' wing segment, and wherein each E represents 2'-O-methoxyethyl sugar and each K represents a cEt sugar.

In certain embodiments, the modified oligonucleotide comprises: a) a gap segment consisting of ten linked deoxynucleosides; b) a 5' wing segment consisting of five linked nucleosides; c) a 3' wing segment consisting of five linked nucleosides; and d) wherein the gap segment is positioned between the 5' wing segment and the 3' wing segment, and wherein each nucleoside of each wing segment comprises a 2'-O-methoxyethyl sugar.

In certain embodiments, the modified oligonucleotide comprises: a) a gap segment consisting of ten linked deoxynucleosides; b) a 5' wing segment consisting of three linked nucleosides; c) a 3' wing segment consisting of three linked nucleosides; and d) wherein the gap segment is positioned between the 5' wing segment and the 3' wing segment, and wherein each nucleoside of each wing segment comprises a cEt sugar.

Certain embodiments provide a method of preferentially reducing CUGexp DMPK RNA, reducing myotonia or reducing spliceopathy in an animal comprising administering to the animal a compound comprising a modified oligonucleotide having: a) a gap segment consisting of eight linked deoxynucleosides; b) a 5' wing segment consisting of four linked nucleosides and having a E-E-K-K 5'-wing motif; c) a 3' wing segment consisting of four linked nucleosides and having a K-K-E-E 3'-wing motif; and d) wherein the gap segment is positioned between the 5' wing segment and the 3' wing segment, and wherein each E represents 2'-O-methoxyethyl sugar and each K represents a cEt sugar.

Certain embodiments provide a method of preferentially reducing CUGexp DMPK RNA, reducing myotonia or reducing spliceopathy in an animal comprising administering to the animal a compound comprising a modified oligonucleotide having: a) a gap segment consisting of seven linked deoxynucleosides; b) a 5' wing segment consisting of five linked nucleosides and having an E-E-E-K-K 5'-wing motif; c) a 3' wing segment consisting of five linked nucleosides and having a K-K-E-E-E 3'-wing motif; and d) wherein the gap segment is positioned between the 5' wing segment and the 3' wing segment, and wherein each E represents 2'-O-methoxyethyl sugar and each K represents a cEt sugar.

Certain embodiments provide a method of preferentially reducing CUGexp DMPK RNA, reducing myotonia or reducing spliceopathy in an animal comprising administering to the animal a compound comprising a modified oligonucleotide having: a) a gap segment consisting of ten linked deoxynucleosides; b) a 5' wing segment consisting of five linked nucleosides; c) a 3' wing segment consisting of five linked nucleosides; and d) wherein the gap segment is positioned between the 5' wing segment and the 3' wing segment, and wherein each nucleoside of each wing segment comprises a 2'-O-methoxyethyl sugar.

Certain embodiments provide a method of preferentially reducing CUGexp DMPK RNA, reducing myotonia or reducing spliceopathy in an animal comprising administering to the animal a compound comprising a modified oligonucleotide having: a) a gap segment consisting of ten linked deoxynucleosides; b) a 5' wing segment consisting of three linked nucleosides; c) a 3' wing segment consisting of three linked nucleosides; and d) wherein the gap segment is positioned between the 5' wing segment and the 3' wing segment, and wherein each nucleoside of each wing segment comprises a cEt sugar.

Certain embodiments provide the use of any compound as described herein in the manufacture of a medicament for use in any of the therapeutic methods described herein. For example, certain embodiments provide the use of a compound as described herein in the manufacture of a medicament for treating, ameliorating, or preventing type 1 myotonic dystrophy. Certain embodiments provide the use of a compound as described herein in the manufacture of a medicament for inhibiting expression of DMPK and treating, preventing, delaying or ameliorating a DMPK related disease and or a symptom thereof. Certain embodiments provide the use of a compound as described herein in the manufacture of a medicament for reducing DMPK expression in an animal. Certain embodiments provide the use of a compound as described herein in the manufacture of a medicament for preferentially reducing CUGexp DMPK, reducing myotonia, or reducing spliceopathy in an animal. Certain embodiments provide the use of a compound as described herein in the manufacture of a medicament for treating an animal with type 1 myotonic dystrophy. Certain embodiments provide the use of a compound as described herein in the manufacture of a medicament for treating, preventing, delaying, or ameliorating symptoms and outcomes associated with development of DM1 including muscle stiffness, myotonia, disabling distal weakness, weakness in face and jaw muscles, difficulty in swallowing, drooping of the eyelids (ptosis), weakness of neck muscles, weakness in arm and leg muscles, persistent muscle pain, hypersomnia, muscle wasting, dysphagia, respiratory insufficiency, irregular heartbeat, heart muscle damage, apathy, insulin resistance, and cataracts. Certain embodiments provide the use of a compound as described herein in the manufacture of a medicament for counteracting RNA dominance by directing the cleavage of pathogenic transcripts.

Certain embodiments provide a kit for treating, preventing, or ameliorating type 1 myotonic dystrophy as described herein wherein the kit comprises: a) a compound as described herein; and optionally b) an additional agent or therapy as described herein. The kit can further include instructions or a label for using the kit to treat, prevent, or ameliorate type 1 myotonic dystrophy.

Certain embodiments provide any compound or composition as described herein, for use in any of the therapeutic methods described herein. For example, certain embodiments provide a compound or composition as described herein for inhibiting expression of DMPK and treating, preventing, delaying or ameliorating a DMPK related disease and or a symptom thereof. Certain embodiments provide a compound or composition as described herein for use in reducing DMPK expression in an animal. Certain embodiments provide a compound or composition as described herein for use in preferentially reducing CUGexp DMPK, reducing myotonia, or reducing spliceopathy in an animal. Certain embodiments provide a compound or composition as described herein for use in treating an animal with type 1 myotonic dystrophy. Certain embodiments provide a compound or composition as described herein for use in treating, preventing, delaying, or ameliorating symptoms and outcomes associated with development of DM1 including muscle stiffness, myotonia, disabling distal weakness, weakness in face and jaw muscles, difficulty in swallowing, drooping of the eyelids (ptosis), weakness of neck muscles, weakness in arm and leg muscles, persistent muscle pain, hypersomnia, muscle wasting, dysphagia, respiratory insufficiency, irregular heartbeat, heart muscle damage, apathy, insulin resistance, and cataracts. Certain embodiments provide a compound or composition as described herein for use in counteracting RNA dominance by directing the cleavage of pathogenic transcripts. Certain embodiments provide compounds comprising a modified oligonucleotide consisting of 12 to 30 linked nucleosides having a nucleobase sequence comprising at least 12 contiguous nucleobases of any of the nucleobase sequences of SEQ ID NOs: 23, 24, 25, 26, 27, 28, 29, 30, 31, 32, or 33-874.

Other compounds which can be used in the methods described herein are also provided.

For example, certain embodiments provide compounds comprising a modified oligonucleotide consisting of 10 to 80, 12 to 50, 12 to 30, 15 to 30, 18 to 24, 19 to 22, or 20 linked nucleosides having a nucleobase sequence comprising at least 8, at least 9, at least 10, at least 11, at least 12, at least 13, at least 14, at least 15, at least 16, at least 17, at least 18, or at least 19, contiguous nucleobases of any of the nucleobase sequences of SEQ ID NOs: 23, 24, 25, 26, 27, 28, 29, 30, 31, 32, or 33-874.

Certain embodiments provide compounds comprising a modified oligonucleotide consisting of 10 to 80, 12 to 50, 12 to 30, 15 to 30, 18 to 24, 19 to 22, or 20, linked nucleosides having a nucleobase sequence comprising at least 8, at least 9, at least 10, at least 11, at least 12, at least 13, at least 14, at least 15, at least 16, at least 17, at least 18, at least 19, contiguous nucleobases of any of the nucleobase sequences of SEQ ID NOs: 23, 24, 25, 26, 27, 28, 29, 30, 31, 32, or 33-874.

Certain embodiments provide compounds comprising a modified oligonucleotide consisting of 10 to 80, 12 to 50, 12 to 30, 15 to 30, or 15 to 17, linked nucleosides having a nucleobase sequence comprising a portion of at least 8, at least 9, at least 10, at least 11, at least 12, at least 13, at least 14, at least 15, at least 16, at least 17, at least 18, or at least 19, or more, contiguous nucleobases complementary to an equal length portion of nucleobases 1343-1368, 1317-1366, 2748-2791, 2155-2208, 2748-2791, 730-748, 528-547, 531-567, 636-697, 1311-1331, 1314-1339, 1446-1475, 1635-1670, 1610-1638, 1457-1486, 2773-1788, 931-948, 934-949, 937-952, 942-957, 937-957, 943-958, 937-953, 1346-1363, 1346-1361, 1347-1363, 2162-2179, 2492-2508, 2696-2717, or 2683-2703 of SEQ ID NO: 1.

Certain embodiments provide compounds comprising a modified oligonucleotide consisting of 10 to 80, 12 to 50, 12 to 30, 15 to 30, 18 to 24, 19 to 22, or 20, linked nucleosides having a nucleobase sequence comprising a portion of at least 8, at least 9, at least 10, at least 11, at least 12, at least 13, at least 14, at least 15, at least 16, at least 17, at least 18, or at least 19, or more, contiguous nucleobases complementary to an equal length portion of nucleobases 10195-10294, 13553-13572, 13748-13767, 13455-13475, 13628-13657, 13735-13760, 13746-13905, 13836-13851, 13553-13568, 13563-13578, 13624-13639, 13686-13701, 13760-13775, 13763-13779, 13765-13780, 2580-2595, 6446-6461, 11099-11115, 11082-11099, 1974-1993, 4435-4456, 6035-6052, 6360-6385, 6445-6468, 6807-6824, 6789-6806, or 6596-6615 of SEQ ID NO: 2.

In certain embodiments, the modified oligonucleotide is a single-stranded oligonucleotide.

In certain embodiments, the nucleobase sequence of the modified oligonucleotide is at least 70%, at least 75%, at least 80%, at least 85%, at least 90%, at least 95%, or 100%, complementary to any of SEQ ID NOs: 23, 24, 25, 26, 27, 28, 29, 30, 31, 32, or 33-874.

In certain embodiments, at least one internucleoside linkage is a modified internucleoside linkage.

In certain embodiments, each internucleoside linkage is a phosphorothioate internucleoside linkage.

In certain embodiments, at least one nucleoside comprises a modified sugar.

In certain embodiments, at least one modified sugar is a bicyclic sugar.

In certain embodiments, at least one modified sugar is a cEt.

In certain embodiments, at least one modified sugar comprises a 2'-O-methoxyethyl.

In certain embodiments, at least one nucleoside comprises a modified nucleobase.

In certain embodiments, the modified nucleobase is a 5-methylcytosine. In certain embodiments, each cytosine residue comprises a 5-methylcytosine.

In certain embodiments, the modified oligonucleotide consists of 16 linked nucleosides.

In certain embodiments, the modified oligonucleotide consists of 17 linked nucleosides.

In certain embodiments, the modified oligonucleotide consists of 20 linked nucleosides.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound can be “antisense” to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to DMPK as described herein is 10 to 30 nucleotides in length. In other words, the antisense compounds are in some embodiments from 10 to 30 linked nucleobases. In other embodiments, the antisense compound comprises a modified oligonucleotide consisting of 8 to 80, 10 to 80, 12 to 30, 12 to 50, 15 to 30, 15 to 18, 15 to 17, 16 to 16, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values. In certain embodiments, antisense compounds of any of these lengths contain at least 8, at least 9, at least 10, at least 11, at least 12, at least 13, at least 14, at least 15, at least 16, at least 17, at least 18, or at least 19, contiguous nucleobases of the nucleobase sequence of any of the exemplary antisense compounds described herein (e.g., at least 8 contiguous nucleobases of a nucleobase sequence recited in any one of SEQ ID NOs: 23, 24, 25, 26, 27, 28, 29, 30, 31, 32, or 33-874.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide can have two nucleosides deleted from the 5' end, or alternatively can have two subunits deleted from the 3' end. Alternatively, the deleted nucleosides can be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside can be located at the 5' or 3' end of the oligonucleotide. When two or more additional nucleosides are present, the added nucleosides can be adjacent to each other, for example, in an oligonucleotide having two nucleosides added to the 5' end (5' addition), or alternatively to the 3' end (3' addition), of the oligonucleotide. Alternatively, the added nucleoside can be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Target Nucleic Acids, Target Regions and Nucleotide Sequences

Nucleotide sequences that encode DMPK include, without limitation, the following sequences as set forth in GenBank Accession No. NM_001081560.1 (incorporated herein as SEQ ID NO: 1), GenBank Accession No. NT_011109.15 truncated from nucleotides 18540696 to U.S. Pat. No. 18,555,106 (incorporated herein as SEQ ID NO: 2), GenBank Accession No. NT_039413.7 truncated from nucleotides 16666001 to U.S. Pat. No. 16,681,000 (incorporated herein as SEQ ID NO: 3), GenBank Accession No. NM_032418.1 (incorporated herein as SEQ ID NO: 4), GenBank Accession No. AI007148.1 (incorporated herein as SEQ ID NO: 5), GenBank Accession No. AI304033.1 (incorporated herein as SEQ ID NO: 6), GenBank Accession No. BC024150.1 (incorporated herein as SEQ ID NO: 7), GenBank Accession No. BC056615.1 (incorporated herein as SEQ ID NO: 8), GenBank Accession No. BC075715.1 (incorporated herein as SEQ ID NO: 9), GenBank Accession No. BU519245.1 (incorporated herein as SEQ ID NO: 10), GenBank Accession No. CB247909.1 (incorporated herein as SEQ ID NO: 11), GenBank Accession No. CX208906.1 (incorporated herein as SEQ ID NO: 12), GenBank Accession No. CX732022.1 (incorporated herein as SEQ ID NO: 13), GenBank Accession No. S60315.1 (incorporated herein as SEQ ID NO: 14), GenBank Accession No. S60316.1 (incorporated herein as SEQ ID NO: 15), GenBank Accession No. NM_001081562.1 (incorporated herein as SEQ ID NO: 16), and GenBank Accession No. NM_001100.3 (incorporated herein as SEQ ID NO: 17). It is understood that the sequence set forth in each SEQ ID NO in the Examples contained herein is independent of any modification to a sugar moiety, an internucleoside linkage, or a nucleobase. As such, antisense compounds defined by a SEQ ID NO can comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region can encompass a 3' UTR, a 5' UTR, an exon, an intron, an exon/intron junction, a coding region, a translation initiation region, translation termination region, or other defined nucleic acid region. The structurally defined regions for DMPK can be obtained by accession number from sequence databases such as NCBI and such information is incorporated herein by reference. In certain embodiments, a target region can encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region can contain one or more target segments. Multiple target segments within a target region can be overlapping. Alternatively, they can be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments can be found within a 5' UTR, a coding region, a 3' UTR, an intron, an exon, or an exon/intron junction. Target segments containing a start codon or a stop codon are also suitable target segments. A suitable target segment can specifically exclude a certain structurally defined region such as the start codon or stop codon.

The determination of suitable target segments can include a comparison of the sequence of a target nucleic acid to other sequences throughout the genome. For example, the BLAST algorithm can be used to identify regions of similarity amongst different nucleic acids. This comparison can prevent the selection of antisense compound sequences that can hybridize in a non-specific manner to sequences other than a selected target nucleic acid (i.e., non-target or off-target sequences).

There can be variation in activity (e.g., as defined by percent reduction of target nucleic acid levels) of the antisense compounds within an active target region. In certain embodiments, reductions in DMPK mRNA levels are indicative of inhibition of DMPK protein expression. Reductions in levels of a DMPK protein are also indicative of inhibition of target mRNA expression. Further, phenotypic changes, such as a reducing myotonia or reducing spliceopathy, can be indicative of inhibition of DMPK mRNA and/or protein expression.

Hybridization

In some embodiments, hybridization occurs between an antisense compound disclosed herein and a DMPK nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrooke and Russell, Molecular Cloning: A Laboratory Manual, $3^{rd}$ Ed., 2001). In certain embodiments, the antisense compounds provided herein are specifically hybridizable with a DMPK nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a DMPK nucleic acid).

An antisense compound can hybridize over one or more segments of a DMPK nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a DMPK nucleic acid, a target region, target segment, or specified portion thereof. In certain embodiments, the antisense compounds are at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to a DMPK nucleic acid, a target region, target segment, or specified portion thereof, and contain at least 8, at least 9, at least 10, at least 11, at least 12, at least 13, at least 14, at least 15, at least 16, at least 17, at least 18, or at least 19, contiguous nucleobases of the nucleobase sequence of any of the exemplary antisense compounds described herein (e.g., at least 8 contiguous nucleobases of a nucleobase sequence recited in any one of SEQ ID NOs: 23, 24, 25, 26, 27, 28, 29, 30, 31, 32, or 33-874). Percent complementarity of an antisense compound with a target nucleic acid can be determined using routine methods, and is measured over the entirety of the antisense compound.

For example, an antisense compound in which 18 of 20 nucleobases of the antisense compound are complementary to a target region, and would therefore specifically hybridize, would represent 90 percent complementarity. In this example, the remaining noncomplementary nucleobases can be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound can be fully complementary to a DMPK nucleic acid, or a target region, or a target segment or target sequence thereof. As used herein, “fully complementary” means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be “fully complementary” to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound can be fully complementary to the target sequence, depending on whether the remaining 10 nucleobases of the antisense compound are also complementary to the target sequence.

The location of a non-complementary nucleobase can be at the 5' end or 3' end of the antisense compound. Alternatively, the non-complementary nucleobase or nucleobases can be at an internal position of the antisense compound. When two or more non-complementary nucleobases are present, they can be either contiguous (i.e. linked) or non-contiguous. In one embodiment, a non-complementary nucleobase is located in the wing segment of a gapmer antisense oligonucleotide.

In certain embodiments, antisense compounds that are, or are up to 10, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a DMPK nucleic acid, or specified portion thereof.

In certain embodiments, antisense compounds that are, or are up to 10, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a DMPK nucleic acid, or specified portion thereof.

The antisense compounds provided herein also include those which are complementary to a portion of a target nucleic acid. As used herein, “portion” refers to a defined number of contiguous (i.e. linked) nucleobases within a region or segment of a target nucleic acid. A “portion” can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 10 nucleobase portion of a target segment. In certain embodiments, the antisense compounds are complementary to at least a 15 nucleobase portion of a target segment. Also contemplated are antisense compounds that are complementary to at least an 8, at least a 9, at least a 10, at least an 11, at least a 12, at least a 13, at least a 14, at least a 15, at least a 16, at least a 17, at least an 18, at least a 19, at least a 20, or more nucleobase portion of a target segment, or a range defined by any two of these values.

Identity

The antisense compounds provided herein can also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases can be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, at least 75%, at least 80%, at least 85%, at least 90%, at least 95%, at least 96%, at least 97%, at least 98%, at least 99% or 100% identical to one or more of the exemplary antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides can also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a DMPK nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(═O)—$N(R_m)(R_n)$, and O—$CH_2$—C(═O)—$N(R_l)$—$(CH_2)_2$—$N(R_m)(R_n)$, where each $R_l$, $R_m$ and $R_n$ is, independently, H or substituted or unsubstituted $C_1$-$C_{10}$ alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-$(CH_2)$—O-2' (LNA); 4'-$(CH_2)$—S-2'; 4'-$(CH_2)_2$—O-2' (ENA); 4'-$CH(CH_3)$—O-2' and 4'-$CH(CH_2OCH_3)$—O-2' (and analogs thereof see U.S. Pat. No.

7,399,845, issued on Jul. 15, 2008); 4'-$C(CH_3)(CH_3)$—O-2' (and analogs thereof see PCT/US2008/068922 published as WO/2009/006478, published Jan. 8, 2009); 4'-$CH_2$—N($OCH_3$)-2' (and analogs thereof see PCT/US2008/064591 published as WO/2008/150729, published Dec. 11, 2008); 4'-$CH_2$—O—N($CH_3$)-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2' (see Chattopadhyaya et al., *J. Org. Chem.*, 2009, 74, 118-134); and 4'-$CH_2$—C(=$CH_2$)-2' (and analogs thereof see PCT/US2008/066154 published as WO 2008/154401, published on Dec. 8, 2008).

Further bicyclic nucleosides have been reported in published literature (see for example: Srivastava et al., *J. Am. Chem. Soc.,* 2007, 129(26) 8362-8379; Frieden et al., *Nucleic Acids Research,* 2003, 21, 6365-6372; Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; Wahlestedt et al., *Proc. Natl. Acad. Sci. U.S.A,* 2000, 97, 5633-5638; Singh et al., *Chem. Commun.,* 1998, 4, 455-456; Koshkin et al., *Tetrahedron,* 1998, 54, 3607-3630; Kumar et al., *Bioorg. Med. Chem. Lett.,* 1998, 8, 2219-2222; Singh et al., *J. Org. Chem.,* 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618; US2007-0287831; US2004-0171570; U.S. patent application Ser. Nos. 12/129,154; 61/099,844; 61/097,787; 61/086,231; 61/056,564; 61/026,998; 61/026,995; 60/989,574; International applications WO 2007/134181; WO 2005/021570; WO 2004/106356; WO 94/14226; and PCT International Applications Nos.: PCT/US2008/068922; PCT/US2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic nucleosides comprise a bridge between the 4' and the 2' carbon atoms of the pentofuranosyl sugar moiety including without limitation, bridges comprising 1 or from 1 to 4 linked groups independently selected from —$[C(R_a)(R_b)]_n$—, —$C(R_a)$=$C(R_b)$—, —$C(R_a)$=N—, —C(=$NR_a$)—, —C(=O)—, —C(=S)—, —O—, —$Si(R_a)_2$—, —$S(=O)_x$—, and —$N(R_a)$—; wherein: x is 0, 1, or 2; n is 1, 2, 3, or 4; each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is, —$[C(R_a)(R_b)]_n$—, —$[C(R_a)(R_b)]_n$—O—, —$C(R_aR_b)$—N(R)—O— or —$C(R_aR_b)$—O—N(R)—. In certain embodiments, the bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-($CH_2$)—O-2' bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include those having a 4' to 2' bridge wherein such bridges include without limitation, α-L-4'-($CH_2$)—O-2', β-D-4'-$CH_2$—O-2', 4'-$(CH_2)_2$—O-2', 4'-$CH_2$—O—N(R)-2', 4'-$CH_2$—N(R)—O-2', 4'-CH($CH_3$)—O-2', 4'-$CH_2$—S-2', 4'-$CH_2$—N(R)-2', 4'-$CH_2$—CH($CH_3$)-2', and 4'-$(CH_2)_3$-2', wherein R is H, a protecting group or $C_1$-$C_{12}$ alkyl.

In certain embodiments, bicyclic nucleosides have the formula:

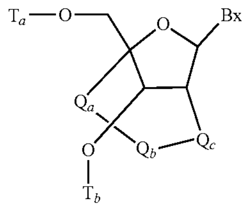

wherein:

Bx is a heterocyclic base moiety;

$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides have the formula:

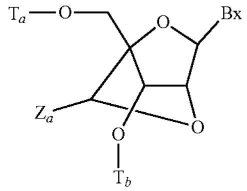

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides have the formula:

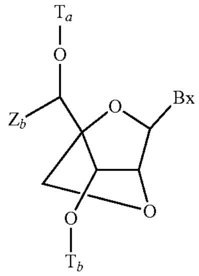

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides have the formula:

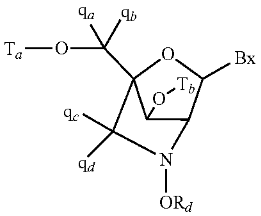

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

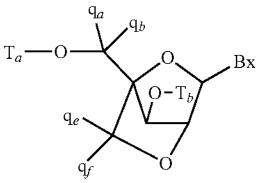

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-$CH_2$—O-2' bridge, along with their oligomerization, and nucleic acid recognition properties have been described (Koshkin et al., *Tetrahedron,* 1998, 54, 3607-3630). The synthesis of bicyclic nucleosides has also been described in WO 98/39352 and WO 99/14226.

Analogs of various bicyclic nucleosides that have 4' to 2' bridging groups such as 4'-$CH_2$—O-2' and 4'-$CH_2$—S-2', have also been prepared (Kumar et al., *Bioorg. Med. Chem. Lett.,* 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.,* 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

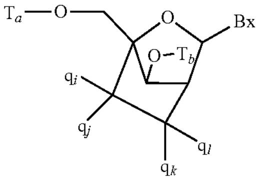

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(═O)$OJ_j$, C(═O)$NJ_jJ_k$, C(═O)$J_j$, O—C(═O)$NJ_jJ_k$, N(H)C(═NH)$NJ_jJ_k$, N(H)C(═O)$NJ_jJ_k$ or N(H)C(═S)$NJ_jJ_k$; and $q_i$ and $q_j$ or $q_l$ and $q_k$ together are ═C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH═CH—$CH_2$-2' have been described (Frier et al., *Nucleic Acids Research,* 1997, 25(22), 4429-4443 and Albaek et al., *J. Org. Chem.,* 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-$(CH_2)_2$—O-2') BNA, (D) aminooxy (4'-$CH_2$—O—N(R)-2') BNA, (E) oxyamino (4'-$CH_2$—N(R)—O-2') BNA, (F) methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, (J) propylene carbocyclic (4'-$(CH_2)_3$-2') BNA, and (K) vinyl BNA as depicted below.

(A)

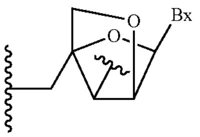

(B)

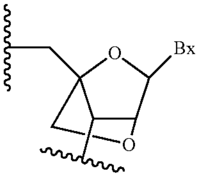

(C)

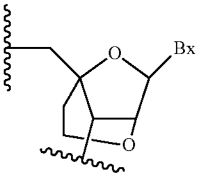

(D)

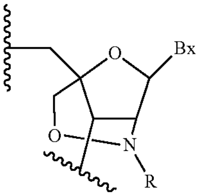

-continued (E)

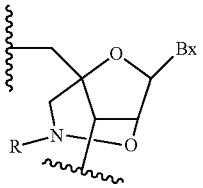

(F)

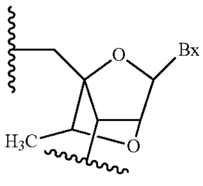

(G)

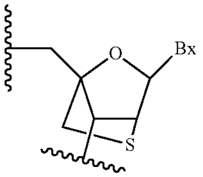

(H)

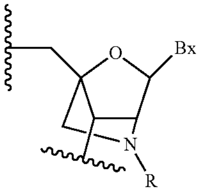

(I)

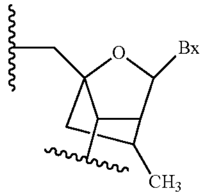

(J)

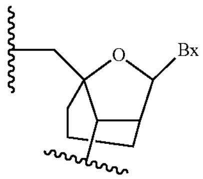

(K)

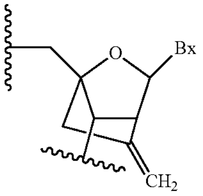

wherein Bx is the base moiety and R is, independently, H, a protecting group, $C_1$-$C_6$ alkyl or $C_1$-$C_6$ alkoxy.

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

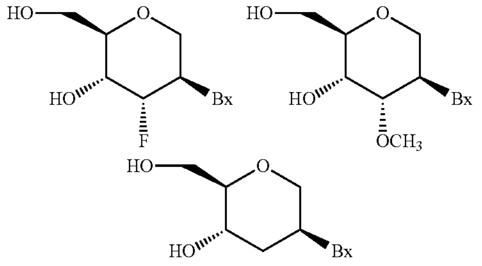

In certain embodiments, sugar surrogates are selected having the formula:

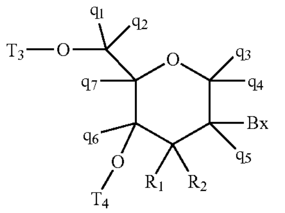

wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and q are each H. In certain embodiments, at least one of $q_1$, $q_2$, $q_3$, $q_4$, $q_5$, $q_6$ and q is other than H. In certain embodiments, at least one of $q_1$, $q_2$, $q_3$, $q_4$, $q_5$, $q_6$ and q is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

Such sugar surrogates include, but are not limited to, what is referred to in the art as hexitol nucleic acid (HNA), altritol nucleic acid (ANA), and mannitol nucleic acid (MNA) (see Leumann, C. J., *Bioorg. & Med. Chem.*, 2002, 10, 841-854).

In certain embodiments, sugar surrogates comprise rings having more than 5 atoms and more than one heteroatom. For example nucleosides comprising morpholino sugar moieties and their use in oligomenc compounds has been reported (see for example: Braasch et al., Biochemistry, 2002, 41, 4503-4510; and U.S. Pat. Nos. 5,698,685; 5,166,315; 5,185,444; and 5,034,506).

As used here, the term "morpholino" means a sugar surrogate having the following structure:

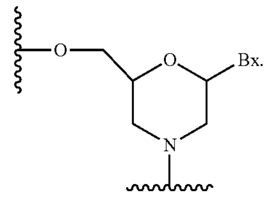

In certain embodiments, morpholinos may be modified, for example by adding or altering various substituent groups from the above morpholino structure. Such sugar surrogates are referred to herein as "modified morpholinos."

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvith et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., *J. Org. Chem.*, 2003, 68, 4499-4505; Verbeure et al., Nucleic Acids Research, 2001, 29(24), 4941-4947; Wang et al., *J Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have the formula:

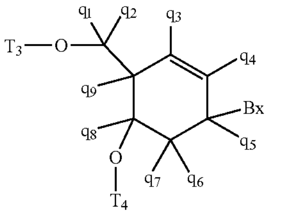

wherein:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other bicyclic and tricyclic sugar surrogate ring systems are also known in the art that can be used to modify nucleosides for incorporation into antisense compounds (see for example review article: Leumann, Christian J., *Bioorg. & Med. Chem.,* 2002, 10, 841-854). Such ring systems can undergo various additional substitutions to enhance activity.

Methods for the preparations of modified sugars are well known to those skilled in the art. Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds targeted to a DMPK nucleic acid comprise one or more nucleotides having modified sugar moieties. In certain embodiments, the modified sugar moiety is 2'-MOE. In certain embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and 0-6 substituted purines, including 2 aminopropyladenine, 5-propynyluracil and 5-propynylcytosine.

In certain embodiments, antisense compounds targeted to a DMPK nucleic acid comprise one or more modified nucleobases. In certain embodiments, gap-widened antisense oligonucleotides targeted to a DMPK nucleic acid comprise one or more modified nucleobases. In certain embodiments, the modified nucleobase is 5-methylcytosine. In certain embodiments, each cytosine is a 5-methylcytosine.

Certain Antisense Compound Motifs

In certain embodiments, antisense compounds targeted to a DMPK nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound can optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer can in some embodiments include β-D-ribonucleosides, β-D-deoxyribonucleosides, 2'-modified nucleosides (such 2'-modified nucleosides can include 2'-MOE, and $2'-O-CH_3$, among others), and bicyclic sugar modified nucleosides (such bicyclic sugar modified nucleosides can include those having a $4'-(CH_2)_n-O-2'$ bridge, where n=1 or n=2). The wing-gap-wing motif is frequently described as "X—Y—Z", where "X" represents the length of the 5' wing region, "Y" represents the length of the gap region, and "Z" represents the length of the 3' wing region. As used herein, a gapmer described as "X—Y—Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6, 5-8-5, 5-7-5, 1-8-1, or 2-6-2.

In certain embodiments, the antisense compound as a "wingmer" motif, having a wing-gap or gap-wing configuration, i.e. an X-Y or Y—Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13, or 5-13.

In certain embodiments, antisense compounds targeted to a DMPK nucleic acid possess a 5-10-5 gapmer motif. In certain embodiments, antisense compounds targeted to a DMPK nucleic acid possess a 5-7-5 gapmer motif. In certain embodiments, antisense compounds targeted to a DMPK nucleic acid possess a 3-10-3 gapmer motif. In certain embodiments, antisense compounds targeted to a DMPK nucleic acid possess a 4-8-4 gapmer motif.

In certain embodiments, an antisense compound targeted to a DMPK nucleic acid has a gap-widened motif.

In certain embodiments, antisense compounds of any of these gapmer or wingmer motifs contain at least 8, at least 9, at least 10, at least 11, at least 12, at least 13, at least 14, at least 15, at least 16, at least 17, at least 18, or at least 19, contiguous nucleobases of the nucleobase sequence of any of the exemplary antisense compounds described herein (e.g., at least 8 contiguous nucleobases of a nucleobase sequence recited in any one of SEQ ID NOs: 23, 24, 25, 26, 27, 28, 29, 30, 31, 32, or 33-874.

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer).

Certain 5'-Wings

In certain embodiments, the 5'-wing of a gapmer consists of 1 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside. In certain embodiments, the 5'-wing of a gapmer comprises at least one bicyclic nucleoside and at least one 2'-deoxynucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside. In certain embodiments, the 5'-wing of a gapmer comprises at least one constrained ethyl nucleoside and at least one 2'-deoxynucleoside.

In certain embodiments, the 5'-wing of a gapmer comprises at least one LNA nucleoside and at least one non-bicyclic modified nucleoside. In certain embodiments, the 5'-wing of a gapmer comprises at least one LNA nucleoside and at least one 2'-substituted nucleoside. In certain embodiments, the 5'-wing of a gapmer comprises at least one LNA nucleoside and at least one 2'-MOE nucleoside. In certain embodiments, the 5'-wing of a gapmer comprises at least one LNA nucleoside and at least one 2'-OMe nucleoside. In certain embodiments, the 5'-wing of a gapmer comprises at least one LNA nucleoside and at least one 2'-deoxynucleoside.

In certain embodiments, the 5'-wing of a gapmer comprises three constrained ethyl nucleosides. In certain embodiments, the 5'-wing of a gapmer comprises two bicyclic nucleosides and two non bicyclic modified nucleosides. In certain embodiments, the 5'-wing of a gapmer comprises two constrained ethyl nucleosides and two 2'-MOE nucleosides. In certain embodiments, the 5'-wing of a gapmer comprises two bicyclic nucleosides and two non bicyclic modified nucleosides. In certain embodiments, the 5'-wing of a gapmer comprises two constrained ethyl nucleosides and two 2'-MOE nucleosides. In certain embodiments, the 5'-wing of a gapmer comprises two constrained ethyl nucleosides and three 2'-MOE nucleosides.

In certain embodiments, the 5'-wing of a gapmer comprises three LNA nucleosides. In certain embodiments, the 5'-wing of a gapmer comprises two LNA nucleosides and two non bicyclic modified nucleosides. In certain embodiments, the 5'-wing of a gapmer comprises two LNA nucleosides and two 2'-MOE nucleosides. In certain embodiments, the 5'-wing of a gapmer comprises two LNA and two non bicyclic modified nucleosides. In certain embodiments, the 5'-wing of a gapmer comprises two LNA nucleosides and two 2'-MOE nucleosides. In certain embodiments, the 5'-wing of a gapmer comprises two LNA nucleosides and three 2'-MOE nucleosides.

In certain embodiments, the 5'-wing of a gapmer comprises three constrained ethyl nucleosides. In certain embodiments, the 5'-wing of a gapmer comprises two bicyclic nucleosides and two non bicyclic modified nucleosides. In certain embodiments, the 5'-wing of a gapmer comprises two constrained ethyl nucleosides and two 2'-OMe nucleosides. In certain embodiments, the 5'-wing of a gapmer comprises two bicyclic nucleosides and two non bicyclic modified nucleosides. In certain embodiments, the 5'-wing of a gapmer comprises two constrained ethyl nucleosides and two 2'-OMe nucleosides. In certain embodiments, the 5'-wing of a gapmer comprises two constrained ethyl nucleosides and three 2'-OMe nucleosides.

In certain embodiments, the 5'-wing of a gapmer comprises three LNA nucleosides. In certain embodiments, the 5'-wing of a gapmer comprises two LNA nucleosides and two non bicyclic modified nucleosides. In certain embodiments, the 5'-wing of a gapmer comprises two LNA nucleosides and two 2'-OMe nucleosides. In certain embodiments, the 5'-wing of a gapmer comprises two LNA and two non bicyclic modified nucleosides. In certain embodiments, the 5'-wing of a gapmer comprises two LNA nucleosides and two 2'-OMe nucleosides. In certain embodiments, the 5'-wing of a gapmer comprises two LNA nucleosides and three 2'-OMe nucleosides.

In certain embodiments, the 5'-wing of a gapmer has an AABB motif, wherein each A is selected from among a 2'-MOE nucleoside and a 2'OMe nucleoside. In certain embodiments, the 5'-wing of a gapmer has an AABB motif, wherein each B is selected from among a cEt, LNA, α-L-LNA, ENA and 2'-thio LNA nucleoside. In certain embodiments, the 5'-wing of a gapmer has an AABB motif, wherein each A represents a 2'-MOE nucleoside and each B represents a constrained ethyl nucleoside.

In certain embodiments, the 5'-wing of a gapmer has an AAABB motif, wherein each A is selected from among a 2'-MOE nucleoside and a 2'OMe nucleoside. In certain embodiments, the 5'-wing of a gapmer has an AABB motif, wherein each B is selected from among a cEt, LNA, α-L-LNA, ENA and 2'-thio LNA nucleoside. In certain embodiments, the 5'-wing of a gapmer has an AABB motif, wherein each A represents a 2'-MOE nucleoside and each B represents a constrained ethyl nucleoside.

Certain 3'-Wings

In certain embodiments, the 3'-wing of a gapmer consists of 1 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside. In certain embodiments, the 3'-wing of a gapmer comprises at least one bicyclic nucleoside and at least one 2'-deoxynucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside. In certain embodiments, the 3'-wing of a gapmer comprises at least one constrained ethyl nucleoside and at least one 2'-deoxynucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside. In certain embodiments, the 3'-wing of a gapmer comprises at least one LNA nucleoside and at least one 2'-deoxynucleoside.

In certain embodiments, the 3'-wing of a gapmer comprises three constrained ethyl nucleosides. In certain embodiments, the 3'-wing of a gapmer comprises two bicyclic nucleosides and two non bicyclic modified nucleosides. In certain embodiments, the 3'-wing of a gapmer comprises two constrained ethyl nucleosides and two 2'-MOE nucleosides. In certain embodiments, the 3'-wing of a gapmer comprises two bicyclic nucleosides and two non bicyclic modified nucleosides. In certain embodiments, the 3'-wing of a gapmer comprises two constrained ethyl nucleosides and two 2'-MOE nucleosides. In certain embodiments, the 5'-wing of a gapmer comprises two constrained ethyl nucleosides and three 2'-MOE nucleosides.

In certain embodiments, the 3'-wing of a gapmer comprises three LNA nucleosides. In certain embodiments, the 3'-wing of a gapmer comprises two LNA nucleosides and two non bicyclic modified nucleosides. In certain embodiments, the 3'-wing of a gapmer comprises two LNA nucleosides and two 2'-MOE nucleosides. In certain embodiments, the 3'-wing of a gapmer comprises two LNA and two non bicyclic modified nucleosides. In certain embodiments, the 3'-wing of a gapmer comprises two LNA nucleosides and two 2'-MOE nucleosides. In certain embodiments, the 3'-wing of a gapmer comprises two LNA nucleosides and three 2'-MOE nucleosides.

In certain embodiments, the 3'-wing of a gapmer comprises three constrained ethyl nucleosides. In certain embodiments, the 3'-wing of a gapmer comprises two bicyclic nucleosides and two non bicyclic modified nucleosides. In certain embodiments, the 3'-wing of a gapmer comprises two constrained ethyl nucleosides and two 2'-OMe nucleosides. In certain embodiments, the 3'-wing of a gapmer comprises two bicyclic nucleosides and two non bicyclic modified nucleosides. In certain embodiments, the 3'-wing of a gapmer comprises two constrained ethyl nucleosides and two 2'-OMe nucleosides. In certain embodiments, the 3'-wing of a gapmer comprises two constrained ethyl nucleosides and three 2'-OMe nucleosides.

In certain embodiments, the 3'-wing of a gapmer comprises three LNA nucleosides. In certain embodiments, the 3'-wing of a gapmer comprises two LNA nucleosides and two non bicyclic modified nucleosides. In certain embodiments, the 3'-wing of a gapmer comprises two LNA nucleosides and two 2'-OMe nucleosides. In certain embodiments, the 3'-wing of a gapmer comprises two LNA and two non bicyclic modified nucleosides. In certain embodiments, the 3'-wing of a gapmer comprises two LNA nucleosides and two 2'-OMe nucleosides. In certain embodiments, the 3'-wing of a gapmer comprises two LNA nucleosides and three 2'-OMe nucleosides.

In certain embodiments, the 3'-wing of a gapmer has a BBAA motif, wherein each A is selected from among a 2'-MOE nucleoside and a 2'OMe nucleoside. In certain embodiments, the 3'-wing of a gapmer has an BBAA motif, wherein each B is selected from among a cEt, LNA, α-L-LNA, ENA and 2'-thio LNA nucleoside. In certain embodiments, the 3'-wing of a gapmer has a BBAA motif, wherein each A represents a 2'-MOE nucleoside and each B represents a constrained ethyl nucleoside.

In certain embodiments, the 3'-wing of a gapmer has a BBAAA motif, wherein each A is selected from among a 2'-MOE nucleoside and a 2'OMe nucleoside. In certain embodiments, the 3'-wing of a gapmer has a BBAA motif, wherein each B is selected from among a cEt, LNA, α-L-LNA, ENA and 2'-thio LNA nucleoside. In certain embodiments, the 3'-wing of a gapmer has a BBAA motif, wherein each A represents a 2'-MOE nucleoside and each B represents a constrained ethyl nucleoside.

Compositions and Methods for Formulating Pharmaceutical Compositions

Antisense oligonucleotides can be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a DMPK nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a DMPK nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds can be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of DMPK nucleic acids can be tested in vitro in a variety of cell types. Cell types used for such analyses are available from commercial vendors (e.g. American Type Culture Collection, Manassas, VA; Zen-Bio, Inc., Research Triangle Park, NC; Clonetics Corporation, Walkersville, MD) and cells are cultured according to the vendor's instructions using commercially available reagents (e.g. Invitrogen Life Technologies, Carlsbad, CA). Illustrative cell types include, but are not limited to, HepG2 cells, Hep3B cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, CA). Antisense oligonucleotides are mixed with LIPOFECTIN® in OPTI-MEM® 1 (Invitrogen, Carlsbad, CA) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, CA). Antisense oligonucleotide is mixed with LIPOFECTAMINE 2000® in OPTI-MEM® 1 reduced serum medium (Invitrogen, Carlsbad, CA) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, CA). Antisense oligonucleotide is mixed with Cytofectin® in OPTI-MEM® 1 reduced serum medium (Invitrogen, Carlsbad, CA) to achieve the desired concentration of antisense oligonucleotide and a Cytofectin® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, CA) according to the manufacturer's recommended protocols.

Analysis of Inhibition of Target Levels or Expression

Inhibition of levels or expression of a DMPK nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, CA and used according to manufacturer's instructions.

Quantitative Real-Time PCR Analysis of Target RNA Levels

Quantitation of target RNA levels can be accomplished by quantitative real-time PCR using the ABI PRISM® 7600, 7700, or 7900 Sequence Detection System (PE-Applied Biosystems, Foster City, CA) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, CA). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, CA). Cyclophilin A expression is quantified by real time PCR, by being run simultaneously with the target, multiplexing, or separately. Total RNA is quantified using RIBOGREEN® RNA quantification reagent (Invitrogen, Inc. Eugene, OR). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a DMPK nucleic acid. Methods for designing real-time PCR probes and primers are well known in the art, and can include the use of software such as PRIMER EXPRESS® Software (Applied Biosystems, Foster City, CA).

Analysis of Protein Levels

Antisense inhibition of DMPK nucleic acids can be assessed by measuring DMPK protein levels. Protein levels of DMPK can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, MI), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of DMPK and produce phenotypic changes. Testing can be performed in normal animals, or in experimental disease models, for example, the $HSA^{LR}$ mouse model of myotonic dystrophy (DM1).

The $HSA^{LR}$ mouse model is an established model for DM1 (Mankodi, A. et al. Science. 289: 1769, 2000). The mice carry a human skeletal actin (hACTA1) transgene with 220 CTG repeats inserted in the 3' UTR of the gene. The hACTA1-$CUG^{exp}$ transcript accumulates in nuclear foci in skeletal muscles and results in myotonia similar to that in human DM1 (Mankodi, A. et al. Mol. Cell 10: 35, 2002; Lin, X. et al. Hum. Mol. Genet. 15: 2087, 2006). Hence, it is expected that amelioration of DM1 symptoms in the $HSA^{LR}$ mouse by antisense inhibition of the hACTA1 transgene would predict amelioration of similar symptoms in human patients by antisense inhibition of the DMPK transcript.

Expression of $CUG^{exp}$ RNA in mice causes extensive remodeling of the muscle transcriptome, much of which is reproduced by ablation of MBNL1. Hence, it is expected that normalization of the transcriptome in $HSA^{LR}$ mice would predict normalization of the human transcriptome in DM1 patients by antisense inhibition of the DMPK transcript.

For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in DMPK nucleic acid expression are measured. Changes in DMPK protein levels are also measured.

Splicing

Myotonic dystrophy (DM1) is caused by CTG repeat expansions in the 3' untranslated region of the DMPK gene (Brook, J. D. et al. Cell. 68: 799, 1992). This mutation leads to RNA dominance, a process in which expression of RNA containing an expanded CUG repeat (CUGexp) induces cell dysfunction (Osborne R J and Thornton C A., *Human Molecular Genetics.,* 2006, 15(2): R162-R169). Such CUGexp are retained in the nuclear foci of skeletal muscles (Davis, B. M. et al. Proc. Natl. Acad. Sci. U.S.A. 94:7388, 1997). The accumulation of CUGexp in the nuclear foci leads to the sequestration of poly(CUG)-binding proteins, such as, Muscleblind-like 1 (MBLN1) (Miller, J. W. et al. EMBO J. 19: 4439, 2000). MBLN1 is a splicing factor and regulates the splicing of genes such as Serca1, CIC-1, Titin, and Zasp. Therefore, sequestration of MBLN1 by CUGexp triggers misregulated alternative splicing of the exons of genes that MBLN1 normally controls (Lin, X. et al. Hum. Mol. Genet. 15: 2087, 2006). Correction of alternative splicing in an animal displaying such disregulation, such as, for example, in a DM1 patient and the HSALR mouse model, is a useful indicator for the efficacy of a treatment, including treatment with an antisense oligonucleotide.

Certain Antisense Mechanisms

Myotonic dystrophy (DM1) is caused by CTG repeat expansions in the 3' untranslated region of the DMPK gene. In certain embodiments, expansions in the 3' untranslated region of the DMPK gene results in the transcription of RNA containing an expanded CUG repeat, and RNA containing an expanded CUG repeat (CUGexp) is retained in the nuclear foci of skeletal muscles. In certain instances, the cellular machinery responsible for exporting mRNA from the nucleus into the cytoplasm does not export RNA containing an expanded CUG repeat from the nucleus or does so less efficiently. In certain embodiments, cells do not export DMPK CUGexp mRNA from the nucleus or such export is reduced. Accordingly, in certain embodiments, DMPK CUGexp mRNA accumulates in the nucleus. In certain embodiments, more copies of DMPK CUGexp mRNA are present in the nucleus of a cell than are copies of wild-type DMPK mRNA, which is exported normally. In such embodiments, antisense compounds that reduce target in the nucleus will preferentially reduce mutant DMPK CUGexp mRNA relative to wild type DMPK mRNA, due to their relative abundences in the nucleus, even if the antisense compound does not otherwise distinguish between mutant and wild type. Since RNase H dependent antisense compounds are active in the nucleus, such compounds are particularly well suited for such use.

In certain instances, wild-type DMPK pre-mRNA and mutant CUGexp DMPK pre-mRNA are expected to be processed into mRNA at similar rate. Accordingly, approximately the same amount of wild-type DMPK pre-mRNA and mutant CUGexp DMPK pre-mRNA are expected to be present in the nucleus of a cell. However, after processing, wild type DMPK mRNA is exported from the nucleus relatively quickly, and mutant CUGexp DMPK mRNA is exported slowly or not at all. In certain such embodiments, mutant CUGexp DMPK mRNA accumulates in the nucleus in greater amounts than wild-type DMPK mRNA. In certain such embodiments, an antisense oligonucleotide targeted to the mRNA, will preferentially reduce the expression of the mutant CUGexp DMPK mRNA compared to the wild-type DMPK mRNA because more copies of the mutant CUGexp DMPK mRNA are present in the nucleus of the cell. In certain embodiments, antisense compounds targeted to pre-mRNA and not mRNA (e.g., targeting an intron) are not expected to preferentially reduce mutant DMPK relative to wild type, because the nuclear abundance of the two pre-mRNAs is likely to be similar. In certain embodiments, antisense compounds described herein are not targeted to introns of DMPK pre-mRNA. In certain embodiments, antisense compounds described herein are targeted to exons or exon-exon junctions present in DMPK mRNA. In certain embodiments, use of an antisense oligonucleotide to target the mRNA is therefore preferred because an antisense oligonucleotide having one or more features described herein (i) has activity in the nucleus of a cell and (2) will preferentially reduce mutant CUGexp DMPK mRNA compared to wild-type DMPK mRNA.

Certain Biomarkers

DM1 severity in mouse models is determined, at least in part, by the level of $CUG^{exp}$ transcript accumulation in the nucleus or nuclear foci. A useful physiological marker for DM1 severity is the development of high-frequency runs of involuntary action potentials (myotonia).

Certain Indications

In certain embodiments, provided herein are methods of treating an individual comprising administering one or more pharmaceutical compositions as described herein. In certain embodiments, the individual has type 1 myotonic dystrophy (DM1).

Accordingly, provided herein are methods for ameliorating a symptom associated with type 1 myotonic dystrophy in a subject in need thereof. In certain embodiments, provided is a method for reducing the rate of onset of a symptom associated with type 1 myotonic dystrophy. In certain embodiments, provided is a method for reducing the severity of a symptom associated with type 1 myotonic dystrophy. In certain embodiments, symptoms associated with DM1 include muscle stiffness, myotonia, disabling distal weakness, weakness in face and jaw muscles, difficulty in swallowing, drooping of the eyelids (ptosis), weakness of neck muscles, weakness in arm and leg muscles, persistent muscle pain, hypersomnia, muscle wasting, dysphagia, respiratory insufficiency, irregular heartbeat, heart muscle damage, apathy, insulin resistance, and cataracts. In children, the symptoms may also be developmental delays, learning problems, language and speech issues, and personality development issues.

In certain embodiments, the methods comprise administering to an individual in need thereof a therapeutically effective amount of a compound targeted to a DMPK nucleic acid.

In certain embodiments, administration of an antisense compound targeted to a DMPK nucleic acid results in reduction of DMPK expression by at least about 15%, by at least about 20%, by at least about 25%, by at least about 30%, by at least about 35%, by at least about 40%, by at least about 45%, by at least about 50%, by at least about 55%, by at least about 60%, by least about 65%, by least about 70%, by least about 75%, by least about 80%, by at least about 85%, by at least about 90%, by at least about 95% or by at least about 99%, or a range defined by any two of these values.

In certain embodiments, pharmaceutical compositions comprising an antisense compound targeted to DMPK are used for the preparation of a medicament for treating a patient suffering or susceptible to type 1 myotonic dystrophy.

In certain embodiments, the methods described herein include administering a compound comprising a modified oligonucleotide having a contiguous nucleobases portion as described herein of a sequence recited in SEQ ID NOs: 23, 24, 25, 26, 27, 28, 29, 30, 31, 32, or 33-874.

Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection (e.g., bolus injection). The injection can be delivered with a syringe.

Parenteral administration includes subcutaneous administration, intravenous administration, intramuscular administration, intraarterial administration, intraperitoneal administration, or intracranial administration, e.g., intrathecal or intracerebroventricular administration. Administration can be continuous, or chronic, or short, or intermittent.

In certain embodiments, the administering is subcutaneous, intravenous, intracerebral, intracerebroventricular, intrathecal or another administration that results in a systemic effect of the oligonucleotide (systemic administration is characterized by a systemic effect, i.e., an effect in more than one tissue) or delivery to the CNS or to the CSF.

The duration of action as measured by inhibition of alpha 1 actin and reduction of myotonia in the $HSA^{LR}$ mouse model of DM1 is prolonged in muscle tissue including quadriceps, gastrocnemius, and the tibialis anterior (see Examples, below). Subcutaneous injections of antisense oligonucleotide for 4 weeks results in inhibition of alpha 1 actin by at least 70% in quadriceps, gastrocnemius, and the tibialis anterior in $HSA^{LR}$ mice for at least 11 weeks (77 days) after termination of dosing. Subcutaneous injections of antisense oligonucleotide for 4 weeks results in elimination of myotonia in quadriceps, gastrocnemius, and the tibialis anterior in $HSA^{LR}$ mice for at least 11 weeks (77 days) after termination of dosing.

In certain embodiments, delivery of a compound of composition, as described herein, results in at least 70% down-regulation of a target mRNA and/or target protein for at least 77 days. In certain embodiments, delivery of a compound or composition, as described herein, results in 50%, 55%, 60%, 65%, 70%, 75%, 80%, 85%, 90%, 95%, or 100% down-regulation of a target mRNA and/or target protein for at least 30 days, at least 35 days, at least 40 days, at least 45 days, at least 50 days, at least 55 days, at least 60 days, at least 65 days, at least 70 days, at least 75 days, at least 76 days, at least 77 days, at least 78 days, at least 79 days, at least 80 days, at least 85 days, at least 90 days, at least 95 days, at least 100 days, at least 105 days, at least 110 days, at least 115 days, at least 120 days, at least 1 year.

In certain embodiments, an antisense oligonucleotide is delivered by injection or infusion once every 77 days. In certain embodiments, an antisense oligonucleotide is delivered by injection or infusion once every month, every two months, every three months, every 6 months, twice a year or once a year.

Certain Combination Therapies

In certain embodiments, a first agent comprising the modified oligonucleotide of the invention is co-administered with one or more secondary agents. In certain embodiments, such second agents are designed to treat the same type 1 myotonic dystrophy as the first agent described herein. In certain embodiments, such second agents are designed to treat a different disease, disorder, or condition as the first agent described herein. In certain embodiments, such second agents are designed to treat an undesired side effect of one or more pharmaceutical compositions as described herein. In certain embodiments, second agents are co-administered with the first agent to treat an undesired effect of the first agent. In certain embodiments, second agents are co-administered with the first agent to produce a combinational effect. In certain embodiments, second agents are co-administered with the first agent to produce a synergistic effect.

In certain embodiments, a first agent and one or more second agents are administered at the same time. In certain embodiments, the first agent and one or more second agents are administered at different times. In certain embodiments, the first agent and one or more second agents are prepared together in a single pharmaceutical formulation. In certain embodiments, the first agent and one or more second agents are prepared separately.

Certain Comparator Compounds

In certain embodiments, the compounds disclosed herein benefit from one or more improved in vitro and/or in vivo properties relative to an appropriate comparator compound.

In certain embodiments, ISIS 445569, a 5-10-5 MOE gapmer, having a sequence of (from 5' to 3') CGGAGCGGTTGTGAACTGGC (incorporated herein as SEQ ID NO: 24), wherein each internucleoside linkage is a phosphorothioate linkage, each cytosine is a 5-methylcytosine, and each of nucleosides 1-5 and 16-20 comprise a 2'-O-methoxyethyl moiety, which was previously described in WO 2012/012443, incorporated herein by reference, is a comparator compound.

ISIS 445569 is an appropriate representative comparator compound because ISIS 445569 demonstrates statistically significant reduction of human DMPK in vitro as measured using a plurality of primer probe sets (see e.g. Example 1 and Example 2 of WO 2012/012443). Additionally, ISIS 445569 demonstrates statistically significant dose-dependent inhibition of human DMPK in vitro in both human skeletal muscle cells and DM1 fibroblasts (see e.g. Example 4 and Example 5 of WO 2012/012443 and Example 28 of WO 2012/012467). ISIS 445569 also reduces human DMPK transcript expression in transgenic mice (Examples 23 and 24 of WO 2012/012443 and Examples 29 and 30 of WO 2012/012467). ISIS 445569 was a preferred human DMPK antisense compound in WO 2012/012443 and WO 2012/012467.

Certain Compounds

In certain embodiments, the compounds disclosed herein benefit from improved activity and/or improved tolerability relative to appropriate comparator compounds, such as ISIS 445569. For example, in certain embodiments, ISIS 598769, ISIS 598768, and/or ISIS 486178 have more activity and/or tolerability than appropriate comparator compounds, such as ISIS 445569.

In certain embodiments, the compounds disclosed herein are more potent than appropriate comparator compounds, such as ISIS 445569. For example, as provided in Example 10 (described herein), ISIS 598769 achieved an $IC_{50}$ of 1.9 μM, ISIS 598768 achieved an $IC_{50}$ of 1.2 μM, and ISIS 486178 achieved an $IC_{50}$ of 0.7 μM in a 6 point dose response curve (61.7 nM, 185.2 nM, 555.6 nM, 1666.7 nM, 5000.0 nM, and 15000.0 nM) in cultured in HepG2 cells when transfected using electroporation, whereas ISIS 445569 achieved an $IC_{50}$ of 2.3 μM. Thus, ISIS 598769, ISIS 598768, and ISIS 486178 are more potent than the comparator compound, ISIS 445569.

In certain embodiments, the compounds disclosed herein have greater activity than appropriate comparator compounds, such as ISIS 445569, at achieving dose-dependent inhibition of DMPK across multiple different muscle tissues. In another example, as provided in Example 16 (described herein), ISIS 598768 and ISIS 598769 achieved greater dose-dependent inhibition than the comparator compound ISIS 445569 across several different muscle tissues when administered subcutaneously to DMSXL transgenic mice twice a week for 4 weeks with 25 mg/kg/week, 50 mg/kg/wk, or 100 mg/kg/wk. In some muscle tissues, for example, in the tibialis anterior, both ISIS 598768 and ISIS 598769 achieved greater inhibition of DMPK at 25, 50 and 100 mg/kg/wk than ISIS 445569 achieved at 200 mg/kg/wk. In the quadriceps and gastrocnemius, both ISIS 598768 and ISIS 598769 achieved equal or greater inhibition of DMPK at 50 mg/kg/wk than ISIS 445569 achieved at 100 or 200 mg/kg/wk. Thus, ISIS 598768 and ISIS 598769 have greater activity than ISIS 445569 at achieving dose-dependent inhibition of DMPK across multiple different muscle tissues.

In certain embodiments, the compounds disclosed herein are more tolerable than appropriate comparator compounds, such as ISIS 445569, when administered to CD-1 mice. In another example, as provided in Example 17 (described herein), ISIS 598769, ISIS 598768, and ISIS 486178 exhibited more favorable tolerability markers than ISIS 445569 when administered to CD-1 mice. ISIS 598769, ISIS 598768, and ISIS 486178 were administered subcutaneously twice a week for 6 weeks at 50 mg/kg/wk. ISIS 445569 was administered subcutaneously twice a week for 6 weeks at 100 mg/kg/wk. After treatment, ALT, AST, and BUN levels were lower in ISIS 486178 and ISIS 598768 treated mice than in ISIS 445569 treated mice. After treatment, ALT and AST levels were lower in ISIS 598769 treated mice than in ISIS 445569 treated mice. Therefore, ISIS 598769, ISIS 598768, and ISIS 486178 are more tolerable than the comparator compound, ISIS 445569 in CD-1 mice.

In certain embodiments, the compounds disclosed herein are more tolerable than appropriate comparator compounds, such as ISIS 445569, when administered to Sprague-Dawley rats. In another example, as provided in Example 18 (described herein), ISIS 598769, ISIS 598768, and ISIS 486178 exhibited more favorable tolerability markers than ISIS 445569 when administered to Sprague-Dawley rats. ISIS 598769, ISIS 598768, and ISIS 486178 were administered subcutaneously twice a week for 6 weeks at 50 mg/kg/wk. ISIS 445569 was administered subcutaneously twice a week for 6 weeks at 100 mg/kg/wk. After treatment, ALT and AST levels were lower in ISIS 486178, ISIS 598769, and ISIS 598768 treated mice than in ISIS 445569 treated mice. Therefore ISIS 598769, ISIS 598768, and ISIS 486178 are more tolerable than the comparator compound, ISIS 445569 in Sprague-Dawley rats.

In certain embodiments, the compounds disclosed herein exhibit more favorable tolerability markers in cynomolgous monkeys than appropriate comparator compounds, such as ISIS 445569. In another example, as provided in Example 19 (described herein), ISIS 598769, ISIS 598768, and ISIS 486178 exhibited more favorable tolerability markers in cynomolgous monkeys including Alanine aminotransferase (ALT), aspartate aminotransferase (AST), lactate dehydrogenase (LDH), and creatine kinase (CK) assessment. In certain embodiments, ALT and AST levels are used as indicators of hepatotoxicity. For example, in certain embodiments, elevated ALT and AST levels indicate trauma to liver cells. In certain embodiments, elevated CK levels are associated with damage to cells in muscle tissue. In certain embodiments, elevated LDH levels are associated with cellular tissue damage.

In certain embodiments, the compounds disclosed herein are more tolerable than appropriate comparator compounds, such as ISIS 445569, when administered to cynomolgous monkeys. As provided in Example 19, groups of cynomolgous monkeys were treated with 40 mg/kg/wk of ISIS 598769, ISIS 598768, ISIS 486178, and ISIS 445569. Treatment with ISIS 445569 resulted in elevated ALT and AST levels at 93 days into treatment. Treatment with ISIS 598768, and ISIS 486178 resulted in lower ALT and AST levels at 58 and 93 days into treatment compared to ISIS 445569. Treatment with ISIS 598769, resulted in lower AST levels at 58 and 93 days into treatment and lower ALT levels at 93 days of treatment compared to ISIS 445569. Furthermore, the ALT and AST levels of monkeys receiving doses of ISIS 598769, ISIS 598768, and ISIS 486178 were consistent with the ALT and AST levels of monkeys given saline. Treatment with ISIS 445569 resulted in elevated LDH levels compared to the LDH levels measured in animals given ISIS 598769, ISIS 598768, and ISIS 486178 at 93 days into treatment. Additionally, treatment with ISIS 445569 resulted in elevated CK levels compared to the CK levels measured in animals given ISIS 598769, ISIS 598768, and ISIS 486178 at 93 days into treatment. Therefore, ISIS 598769, ISIS 598768, and ISIS 486178 are more tolerable than the comparator compound, ISIS 445569.

As the data discussed above demonstrate, ISIS 598769, ISIS 598768, and ISIS 486178 possess a wider range of well-tolerated doses at which ISIS 598769, ISIS 598768, and ISIS 486178 are active compared to the comparator compound, ISIS 445569. Additionally, the totality of the data presented in the examples herein and discussed above demonstrate that each of ISIS 598769, ISIS 598768, and ISIS 486178 possess a number of safety and activity advantages over the comparator compound, ISIS 445569. In other words, each of ISIS 598769, ISIS 598768, and ISIS 486178 are likely to be safer and more active drugs in humans than ISIS 445569.

In certain embodiments, ISIS 445569 is likely to be a safer and more active drug in humans for reducing CUGexp DMPK mRNA and\or treating conditions or symptoms associated with having myotonic dystrophy type 1 than the other compounds disclosed in WO 2012/012443 and/or WO 2012/012467.

In certain embodiments, ISIS 512497 has a better safety profile in primates and CD-1 mice than ISIS 445569. In certain embodiments, ISIS 512497 achieves greater knockdown of human DMPK nucleic acid in multiple muscle tissues when administered at the same dose and at lower doses than ISIS 445569.

In certain embodiments, ISIS 486178 has a better safety profile in mice, rats, and primates than ISIS 445569. In certain embodiments, ISIS 486178 achieves greater knockdown of human DMPK nucleic acid in one or more muscle tissues when administered at the same dose and at lower doses than ISIS 445569.

In certain embodiments, ISIS 570808 achieves much greater knockdown of human DMPK nucleic acid at least five different muscle tissues when administered at the same dose and at lower dose than ISIS 445569.

In certain embodiments, ISIS 594292 achieves greater knockdown of human DMPK nucleic acid in one or more muscle tissues when administered at the same dose as ISIS 445569. In certain embodiments, ISIS 486178 has a better safety profile in primates than ISIS 445569.

In certain embodiments, ISIS 569473 achieves greater knockdown of human DMPK nucleic acid in one or more muscle tissues when administered at the same dose as ISIS 445569. In certain embodiments, ISIS 569473 has a better safety profile in primates than ISIS 445569.

In certain embodiments, ISIS 594300 achieves greater knockdown of human DMPK nucleic acid in one or more muscle tissues when administered at the same dose as ISIS 445569. In certain embodiments, ISIS 594300 has a better safety profile in primates than ISIS 445569.

In certain embodiments, ISIS 598777 achieves greater knockdown of human DMPK nucleic acid in one or more muscle tissues when administered at the same dose as ISIS 445569. In certain embodiments, ISIS 598777 has a better safety profile in primates than ISIS 445569.

In certain embodiments, ISIS 598768 achieves greater knockdown of human DMPK nucleic acid in one or more muscle tissues when administered at the same dose as ISIS 445569. In certain embodiments, ISIS 598768 has a better safety profile in primates than ISIS 445569.

In certain embodiments, ISIS 598769 achieves greater knockdown of human DMPK nucleic acid in one or more muscle tissues when administered at the same dose as ISIS 445569. In certain embodiments, ISIS 598769 has a better safety profile in primates than ISIS 445569.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either “RNA” or “DNA” as required, in reality, those sequences may be modified with any combination of chemical modifications. One of skill in the art will readily appreciate that such designation as “RNA” or “DNA” to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence “ATCGATCG” encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT${}^{me}$CGAUCG," wherein ${}^{me}$C indicates a cytosine base comprising a methyl group at the 5-position.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Design of Antisense Oligonucleotides Targeting Human Dystrophia Myotonica Protein Kinase (hDMPK)

A series of antisense oligonucleotides (ASOs) were designed to target hDMPK. The newly designed ASOs were prepared using standard oligonucleotide synthesis well known in the art and are described in Tables 1 and 2, below. Subscripts "s" indicate phosphorothioate internucleoside linkages; subscripts "k" indicate 6'-(S)—$CH_3$ bicyclic nucleosides (cEt); subscripts "e" indicate 2'-O-methoxyethyl (MOE) modified nucleosides; and subscripts "d" indicate β-D-2'-deoxyribonucleosides. "${}^{m}$C" indicates 5-methylcytosine nucleosides.

The antisense oligonucleotides are targeted to either SEQ ID NO: 1 (GENBANK Accession No. NM_001081560.1) and/or SEQ ID NO: 2 (the complement of GENBANK Accession No. NT_011109.15 truncated from nucleotides 18540696 to 18555106). "Start site" indicates the 5'-most nucleoside to which the gapmer is targeted in the human gene sequence. "Stop site" indicates the 3'-most nucleoside to which the gapmer is targeted human gene sequence.

TABLE 1

Design of antisense oligonucleotides targeting hDMPK and targeted to SEQ ID NO 2

| ISIS No. | Composition (5' to 3') | Motif | Length | Start Site | Stop Site | SEQ ID No. |
|---|---|---|---|---|---|---|
| 486178 | $A_{ks}{}^{m}C_{ks}A_{ks}A_{ds}T_{ds}A_{ds}A_{ds}A_{ds}T_{ds}A_{ds}{}^{m}C_{ds}{}^{m}C_{ds}G_{ds}A_{ks}G_{ks}G_{k}$ | kkk-10-kkk | 16 | 13836 | 13851 | 23 |
| 445569 | ${}^{m}C_{es}G_{es}G_{es}A_{es}G_{es}{}^{m}C_{ds}G_{ds}G_{ds}T_{ds}T_{ds}G_{ds}T_{ds}G_{ds}A_{ds}A_{ds}{}^{m}C_{es}T_{es}G_{es}G_{es}{}^{m}C_{e}$ | e5-d10-e5 | 20 | 13226 | 13245 | 24 |
| 512497 | $G_{es}{}^{m}C_{es}G_{es}{}^{m}C_{es}A_{es}{}^{m}C_{ds}{}^{m}C_{ds}T_{ds}T_{ds}{}^{m}C_{ds}{}^{m}C_{ds}{}^{m}C_{ds}G_{ds}A_{ds}A_{ds}T_{es}G_{es}T_{es}{}^{m}C_{es}{}^{m}C_{e}$ | e5-d10-e5 | 20 | 8608 | 8627 | 25 |
| 598768 | ${}^{m}C_{es}{}^{m}C_{es}{}^{m}C_{ks}G_{ks}A_{ds}A_{ds}T_{ds}G_{ds}T_{ds}{}^{m}C_{ds}{}^{m}C_{ds}G_{ds}A_{ks}{}^{m}C_{ks}A_{es}G_{e}$ | eekk-d8-kkee | 16 | 8603 | 8618 | 26 |
| 594300 | ${}^{m}C_{es}G_{es}G_{es}A_{ks}G_{ks}{}^{m}C_{ds}G_{ds}G_{ds}T_{ds}T_{ds}G_{ds}T_{ds}G_{ks}A_{ks}A_{es}{}^{m}C_{es}T_{e}$ | eeekk-d7-kkeee | 17 | 13229 | 13245 | 27 |
| 594292 | $A_{es}{}^{m}C_{es}A_{es}A_{ks}T_{ks}A_{ds}A_{ds}A_{ds}T_{ds}A_{ds}{}^{m}C_{ds}{}^{m}C_{ds}G_{ks}A_{ks}G_{es}G_{es}A_{e}$ | eeekk-d7-kkeee | 17 | 13835 | 13851 | 28 |
| 569473 | $G_{ks}A_{ks}{}^{m}C_{ks}A_{ds}A_{ds}T_{ds}{}^{m}C_{ds}T_{ds}{}^{m}C_{ds}{}^{m}C_{ds}G_{ds}{}^{m}C_{ds}{}^{m}C_{ds}A_{ks}G_{ks}G_{k}$ | kkk-d10-kkk | 16 | 5082 | 5097 | 29 |
| 598769 | $T_{es}{}^{m}C_{es}{}^{m}C_{ks}{}^{m}C_{ks}G_{ds}A_{ds}A_{ds}T_{ds}G_{ds}T_{ds}{}^{m}C_{ds}{}^{m}C_{ds}G_{ks}A_{ks}{}^{m}C_{es}A_{e}$ | eekk-d8-kkee | 16 | 8604 | 8619 | 30 |
| 570808 | $T_{ks}G_{ks}T_{ks}A_{ds}A_{ds}T_{ds}G_{ds}T_{ds}T_{ds}G_{ds}T_{ds}{}^{m}C_{ds}{}^{m}C_{ds}A_{ks}G_{ks}T_{k}$ | kkk-d10-kkk | 16 | 10201 | 10216 | 31 |
| 598777 | $G_{es}T_{es}G_{ks}T_{ks}A_{ds}A_{ds}T_{ds}G_{ds}T_{ds}T_{ds}G_{ds}T_{ds}{}^{m}C_{ks}{}^{m}C_{ks}A_{es}G_{e}$ | eekk-d8-kkee | 16 | 10202 | 10217 | 32 |

TABLE 2

Design of antisense oligonucleotides targeting hDMPK and targeted to SEQ ID NO 1

| ISIS No. | Composition (5' to 3') | Motif | Length | Start Site | Stop Site |
|---|---|---|---|---|---|
| 486178 | $A_{ks}{}^{m}C_{ks}A_{ks}A_{ds}T_{ds}A_{ds}A_{ds}A_{ds}T_{ds}A_{ds}{}^{m}C_{ds}{}^{m}C_{ds}G_{ds}A_{ks}G_{ks}G_{k}$ | kkk-10-kkk | 16 | 2773 | 2788 |
| 445569 | ${}^{m}C_{es}G_{es}G_{es}A_{es}G_{es}{}^{m}C_{ds}G_{ds}G_{ds}T_{ds}T_{ds}G_{ds}T_{ds}G_{ds}A_{ds}A_{ds}{}^{m}C_{es}T_{es}G_{es}G_{es}{}^{m}C_{e}$ | e5-d10-e5 | 20 | 2163 | 2182 |
| 512497 | $G_{es}{}^{m}C_{es}G_{es}{}^{m}C_{es}A_{es}{}^{m}C_{ds}{}^{m}C_{ds}T_{ds}T_{ds}{}^{m}C_{ds}{}^{m}C_{ds}{}^{m}C_{ds}G_{ds}A_{ds}A_{ds}T_{es}G_{es}T_{es}{}^{m}C_{es}{}^{m}C_{e}$ | e5-d10-e5 | 20 | 1348 | 1367 |
| 598768 | ${}^{m}C_{es}{}^{m}C_{es}{}^{m}C_{ks}G_{ks}A_{ds}A_{ds}T_{ds}G_{ds}T_{ds}{}^{m}C_{ds}{}^{m}C_{ds}G_{ds}A_{ks}{}^{m}C_{ks}A_{es}G_{e}$ | eekk-d8-kkee | 16 | 1343 | 1358 |
| 594300 | ${}^{m}C_{es}G_{es}G_{es}A_{ks}G_{ks}{}^{m}C_{ds}G_{ds}G_{ds}T_{ds}T_{ds}G_{ds}T_{ds}G_{ks}A_{ks}A_{es}{}^{m}C_{es}T_{e}$ | eeekk-d7-kkeee | 17 | 2166 | 2182 |
| 594292 | $A_{es}{}^{m}C_{es}A_{es}A_{ks}T_{ks}A_{ds}A_{ds}A_{ds}T_{ds}A_{ds}{}^{m}C_{ds}{}^{m}C_{ds}G_{ks}A_{ks}G_{es}G_{es}A_{e}$ | eeekk-d7-kkeee | 17 | 2772 | 2788 |
| 569473 | $G_{ks}A_{ks}{}^{m}C_{ks}A_{ds}A_{ds}T_{ds}{}^{m}C_{ds}T_{ds}{}^{m}C_{ds}{}^{m}C_{ds}G_{ds}{}^{m}C_{ds}{}^{m}C_{ds}A_{ks}G_{ks}G_{k}$ | kkk-d10-kkk | 16 | 730 | 745 |
| 598769 | $T_{es}{}^{m}C_{es}{}^{m}C_{ks}{}^{m}C_{ks}G_{ds}A_{ds}A_{ds}T_{ds}G_{ds}T_{ds}{}^{m}C_{ds}{}^{m}C_{ds}G_{ks}A_{ks}{}^{m}C_{es}A_{e}$ | eekk-d8-kkee | 16 | 1344 | 1359 |

Example 2: Antisense Inhibition of Human DMPK in Human Skeletal Muscle Cells (hSKMc)

Antisense oligonucleotides targeted to a human DMPK nucleic acid were tested for their effect on DMPK RNA transcript in vitro. Cultured hSKMc cells at a density of 20,000 cells per well were transfected using electroporation with 10,000 nM antisense oligonucleotide. After approximately 24 hours, RNA was isolated from the cells and DMPK transcript levels were measured by quantitative real-time PCR. DMPK RNA transcript levels were adjusted according to total RNA content, as measured by RIBOGREEN®. Results are presented as percent expression of DMPK, relative to untreated control cells.

The antisense oligonucleotides in Tables 3, 4, 5, and 6 are 5-10-5 gapmers, where the gap segment comprises ten 2'-deoxynucleosides and each wing segment comprises five 2'-MOE nucleosides. The internucleoside linkages throughout each gapmer are phosphorothioate (P═S) linkages. All cytsoine residues throughout each gapmer are 5-methylcytosines. ‘Target start site’ indicates the 5'-most nucleoside to which the antisense oligonucleotide is targeted in the human genomic gene sequence. ‘Target stop site’ indicates the 3'-most nucleoside to which the antisense oligonucleotide is targeted in the human genomic sequence. All the antisense oligonucleotides listed in Table 3, 4, or 5 target SEQ ID NO: 1 (GENBANK Accession No. NM_001081560.1). All the antisense oligonucleotides listed in Table 6 target SEQ ID NO: 2 (the complement of GENBANK Accession No. NT_011109.15 truncated from nucleotides 18540696 to 18555106).

Several of the antisense oligonucleotides in Tables 2, 3, 4, and 5 demonstrated significant inhibition of DMPK mRNA levels under the conditions specified above.

TABLE 3

Inhibition of human DMPK RNA transcript in hSKMc by 5-10-5 gapmers targeting SEQ ID NO: 1

| ISIS No. | Sequence | % Target Expression | Start Site on Seq ID: 1 | Stop Site on Seq ID: 1 | SEQ ID NO. |
|---|---|---|---|---|---|
| UTC | N/A | 100.0 | N/A | N/A | 33 |
| 444401 | TTGCACTTTGCGAACCAACG | 7.3 | 2490 | 2509 | 34 |
| 512326 | CGACACCTCGCCCCTCTTCA | 13.4 | 528 | 547 | 35 |
| 512327 | ACGACACCTCGCCCCTCTTC | 40.8 | 529 | 548 | 36 |
| 512328 | CACGACACCTCGCCCCTCTT | 27.8 | 530 | 549 | 37 |
| 512329 | GCACGACACCTCGCCCCTCT | 16.5 | 531 | 550 | 38 |
| 512330 | AGCACGACACCTCGCCCCTC | 17.9 | 532 | 551 | 39 |
| 512331 | AAGCACGACACCTCGCCCCT | 18.8 | 533 | 552 | 40 |
| 512332 | GAAGCACGACACCTCGCCCC | 23.3 | 534 | 553 | 41 |
| 512333 | GGAAGCACGACACCTCGCCC | 28.1 | 535 | 554 | 42 |
| 512334 | CGGAAGCACGACACCTCGCC | 16.3 | 536 | 555 | 43 |
| 512335 | ACGGAAGCACGACACCTCGC | 28.7 | 537 | 556 | 44 |
| 512336 | CACGGAAGCACGACACCTCG | 15.9 | 538 | 557 | 45 |

TABLE 3-continued

Inhibition of human DMPK RNA transcript in hSKMc by 5-10-5 gapmers targeting SEQ ID NO: 1

| ISIS No. | Sequence | % Target Expression | Start Site on Seq ID: 1 | Stop Site on Seq ID: 1 | SEQ ID NO. |
|---|---|---|---|---|---|
| 512337 | TCACGGAAGCACGACACCTC | 18.8 | 539 | 558 | 46 |
| 512338 | CTCACGGAAGCACGACACCT | 16.4 | 540 | 559 | 47 |
| 512339 | CCTCACGGAAGCACGACACC | 20.2 | 541 | 560 | 48 |
| 512340 | TCCTCACGGAAGCACGACAC | 19.3 | 542 | 561 | 49 |
| 512341 | CTCCTCACGGAAGCACGACA | 15.2 | 543 | 562 | 50 |
| 512342 | TCTCCTCACGGAAGCACGAC | 16.2 | 544 | 563 | 51 |
| 512343 | CTCTCCTCACGGAAGCACGA | 16.4 | 545 | 564 | 52 |
| 512344 | CCTCTCCTCACGGAAGCACG | 15.7 | 546 | 565 | 53 |
| 512345 | CCCTCTCCTCACGGAAGCAC | 14.7 | 547 | 566 | 54 |
| 512346 | TCCCTCTCCTCACGGAAGCA | 20.6 | 548 | 567 | 55 |
| 512347 | GTCCCTCTCCTCACGGAAGC | 32.6 | 549 | 568 | 56 |
| 512348 | CGTCCCTCTCCTCACGGAAG | 31.5 | 550 | 569 | 57 |
| 512349 | GGTCCCCATTCACCAACACG | 41.6 | 568 | 587 | 58 |
| 512350 | CGGTCCCCATTCACCAACAC | 31.6 | 569 | 588 | 59 |
| 512351 | CCGGTCCCCATTCACCAACA | 38.1 | 570 | 589 | 60 |
| 512352 | GCCGGTCCCCATTCACCAAC | 55.5 | 571 | 590 | 61 |
| 512353 | CGCCGGTCCCCATTCACCAA | 42.9 | 572 | 591 | 62 |
| 512354 | CCGCCGGTCCCCATTCACCA | 35.7 | 573 | 592 | 63 |
| 512355 | ACCGCCGGTCCCCATTCACC | 51.4 | 574 | 593 | 64 |
| 512356 | CACCGCCGGTCCCCATTCAC | 34.4 | 575 | 594 | 65 |
| 512357 | CCACCGCCGGTCCCCATTCA | 40.4 | 576 | 595 | 66 |
| 512358 | TCCACCGCCGGTCCCCATTC | 35.5 | 577 | 596 | 67 |
| 512359 | ATCCACCGCCGGTCCCCATT | 41.7 | 578 | 597 | 68 |
| 512360 | GATCCACCGCCGGTCCCCAT | 51.0 | 579 | 598 | 69 |
| 512361 | TGATCCACCGCCGGTCCCCA | 35.9 | 580 | 599 | 70 |
| 512362 | GTGATCCACCGCCGGTCCCC | 53.2 | 581 | 600 | 71 |
| 512363 | CGTGATCCACCGCCGGTCCC | 28.2 | 582 | 601 | 72 |
| 512364 | TTCTCATCCTGGAAGGCGAA | 34.6 | 611 | 630 | 73 |
| 512365 | GTTCTCATCCTGGAAGGCGA | 57.1 | 612 | 631 | 74 |
| 512366 | AGTTCTCATCCTGGAAGGCG | 72.1 | 613 | 632 | 75 |
| 512367 | GTAGTTCTCATCCTGGAAGG | 47.1 | 615 | 634 | 76 |
| 512368 | GGTAGTTCTCATCCTGGAAG | 56.0 | 616 | 635 | 77 |
| 512369 | AGGTAGTTCTCATCCTGGAA | 48.3 | 617 | 636 | 78 |
| 512370 | CAGGTAGTTCTCATCCTGGA | 20.2 | 618 | 637 | 79 |
| 512371 | TACAGGTAGTTCTCATCCTG | 44.0 | 620 | 639 | 80 |

TABLE 3-continued

Inhibition of human DMPK RNA transcript in hSKMc by 5-10-5 gapmers targeting SEQ ID NO: 1

| ISIS No. | Sequence | % Target Expres-sion | Start Site on Seq ID: 1 | Stop Site on Seq ID: 1 | SEQ ID NO. |
|---|---|---|---|---|---|
| 512372 | GTACAGGTAGTTCTCATCCT | 64.1 | 621 | 640 | 81 |
| 512373 | GGTACAGGTAGTTCTCATCC | 54.2 | 622 | 641 | 82 |
| 512374 | AGGTACAGGTAGTTCTCATC | 65.6 | 623 | 642 | 83 |
| 512375 | CCAGGTACAGGTAGTTCTCA | 45.7 | 625 | 644 | 84 |
| 512376 | ACCAGGTACAGGTAGTTCTC | 60.4 | 626 | 645 | 85 |
| 512377 | GACCAGGTACAGGTAGTTCT | 62.2 | 627 | 646 | 86 |
| 512378 | TGACCAGGTACAGGTAGTTC | 64.9 | 628 | 647 | 87 |
| 512379 | CATGACCAGGTACAGGTAGT | 39.2 | 630 | 649 | 88 |
| 512380 | CCATGACCAGGTACAGGTAG | 27.7 | 631 | 650 | 89 |
| 512381 | TCCATGACCAGGTACAGGTA | 21.6 | 632 | 651 | 90 |
| 512382 | CTCCATGACCAGGTACAGGT | 25.7 | 633 | 652 | 91 |
| 512383 | ACTCCATGACCAGGTACAGG | 28.6 | 634 | 653 | 92 |
| 512384 | TACTCCATGACCAGGTACAG | 23.7 | 635 | 654 | 93 |
| 512385 | ATACTCCATGACCAGGTACA | 20.8 | 636 | 655 | 94 |
| 512386 | AATACTCCATGACCAGGTAC | 22.0 | 637 | 656 | 95 |
| 512387 | TAATACTCCATGACCAGGTA | 14.7 | 638 | 657 | 96 |
| 512388 | CGTAATACTCCATGACCAGG | 10.4 | 640 | 659 | 97 |
| 512389 | AGCAGTGTCAGCAGGTCCCC | 15.0 | 665 | 684 | 98 |
| 512390 | CAGCAGTGTCAGCAGGTCCC | 13.0 | 666 | 685 | 99 |
| 512391 | TCAGCAGTGTCAGCAGGTCC | 22.3 | 667 | 686 | 100 |
| 512392 | CTCAGCAGTGTCAGCAGGTC | 16.4 | 668 | 687 | 101 |
| 512393 | GCTCAGCAGTGTCAGCAGGT | 22.2 | 669 | 688 | 102 |
| 512394 | TGCTCAGCAGTGTCAGCAGG | 26.2 | 670 | 689 | 103 |
| 512395 | TTGCTCAGCAGTGTCAGCAG | 27.4 | 671 | 690 | 104 |
| 512396 | CTTGCTCAGCAGTGTCAGCA | 15.7 | 672 | 691 | 105 |
| 512397 | ACTTGCTCAGCAGTGTCAGC | 43.5 | 673 | 692 | 106 |
| 512398 | AACTTGCTCAGCAGTGTCAG | 26.9 | 674 | 693 | 107 |
| 512399 | AAACTTGCTCAGCAGTGTCA | 20.0 | 675 | 694 | 108 |
| 512400 | CAAACTTGCTCAGCAGTGTC | 23.1 | 676 | 695 | 109 |
| 512401 | CCAAACTTGCTCAGCAGTGT | 20.5 | 677 | 696 | 110 |
| 512402 | CCCAAACTTGCTCAGCAGTG | 13.5 | 678 | 697 | 33 |

TABLE 4

Inhibition of human DMPK RNA transcript in hSKMc by 5-10-5 gapmers targeting SEQ ID NO: 1

| ISIS No. | Sequence | % Target Expres-sion | Start Site on Seq ID: 1 | Stop Site on Seq ID: 1 | SEQ ID NO. |
|---|---|---|---|---|---|
| UTC | N/A | 100 | N/A | N/A | |
| 444401 | TTGCACTTTGCGAACCAACG | 13.4 | 2490 | 2509 | 33 |
| 512480 | GTGAGCCCGTCCTCCACCAA | 29.8 | 1310 | 1329 | 111 |
| 512481 | AGTGAGCCCGTCCTCCACCA | 15.6 | 1311 | 1330 | 112 |
| 512482 | CAGTGAGCCCGTCCTCCACC | 10.7 | 1312 | 1331 | 113 |
| 512483 | GCAGTGAGCCCGTCCTCCAC | 33.3 | 1313 | 1332 | 114 |
| 512484 | GGCAGTGAGCCCGTCCTCCA | 9.6 | 1314 | 1333 | 115 |
| 512485 | TGGCAGTGAGCCCGTCCTCC | 8.8 | 1315 | 1334 | 116 |
| 512486 | CATGGCAGTGAGCCCGTCCT | 10.5 | 1317 | 1336 | 117 |
| 512487 | CCATGGCAGTGAGCCCGTCC | 10.1 | 1318 | 1337 | 118 |
| 512488 | TCCATGGCAGTGAGCCCGTC | 13.7 | 1319 | 1338 | 119 |
| 512489 | CTCCATGGCAGTGAGCCCGT | 16.9 | 1320 | 1339 | 120 |
| 512490 | TCTCCATGGCAGTGAGCCCG | 29.1 | 1321 | 1340 | 121 |
| 512491 | GTCTCCATGGCAGTGAGCCC | 41.3 | 1322 | 1341 | 122 |
| 512492 | CCTTCCCGAATGTCCGACAG | 8.8 | 1343 | 1362 | 123 |
| 512493 | ACCTTCCCGAATGTCCGACA | 12.1 | 1344 | 1363 | 124 |
| 512494 | CACCTTCCCGAATGTCCGAC | 6 | 1345 | 1364 | 125 |
| 512495 | GCACCTTCCCGAATGTCCGA | 8.5 | 1346 | 1365 | 126 |
| 512496 | CGCACCTTCCCGAATGTCCG | 5.6 | 1347 | 1366 | 127 |
| 512497 | GCGCACCTTCCCGAATGTCC | 7.7 | 1348 | 1367 | 25 |
| 512498 | GGCGCACCTTCCCGAATGTC | 15 | 1349 | 1368 | 128 |
| 512499 | ACAAAAGGCAGGTGGACCCC | 22.8 | 1373 | 1392 | 129 |
| 512500 | CACAAAAGGCAGGTGGACCC | 22 | 1374 | 1393 | 130 |
| 512501 | CCACAAAAGGCAGGTGGACC | 16.4 | 1375 | 1394 | 131 |
| 512502 | CCCACAAAAGGCAGGTGGAC | 15.8 | 1376 | 1395 | 132 |
| 512503 | GCCCACAAAAGGCAGGTGGA | 25.1 | 1377 | 1396 | 133 |
| 512504 | AGCCCACAAAAGGCAGGTGG | 24.7 | 1378 | 1397 | 134 |
| 512505 | TAGCCCACAAAAGGCAGGTG | 20.7 | 1379 | 1398 | 135 |
| 512506 | GTAGCCCACAAAAGGCAGGT | 20.7 | 1380 | 1399 | 136 |
| 512507 | AGTAGCCCACAAAAGGCAGG | 27.8 | 1381 | 1400 | 137 |
| 512508 | GAGTAGCCCACAAAAGGCAG | 43.9 | 1382 | 1401 | 138 |
| 512509 | GGAGTAGCCCACAAAAGGCA | 29.9 | 1383 | 1402 | 139 |
| 512510 | AGGAGTAGCCCACAAAAGGC | 31.9 | 1384 | 1403 | 140 |
| 512511 | TAGGAGTAGCCCACAAAAGG | 59.9 | 1385 | 1404 | 141 |
| 512512 | GTAGGAGTAGCCCACAAAAG | 40.1 | 1386 | 1405 | 142 |

TABLE 4-continued

Inhibition of human DMPK RNA transcript in hSKMc by 5-10-5 gapmers targeting SEQ ID NO: 1

| ISIS No. | Sequence | % Target Expres-sion | Start Site on Seq ID: 1 | Stop Site on Seq ID: 1 | SEQ ID NO. |
|---|---|---|---|---|---|
| 512513 | AGTAGGAGTAGCCCACAAAA | 48.1 | 1387 | 1406 | 143 |
| 512514 | GAGTAGGAGTAGCCCACAAA | 53.3 | 1388 | 1407 | 144 |
| 512515 | GGAGTAGGAGTAGCCCACAA | 24.7 | 1389 | 1408 | 145 |
| 512516 | AGGAGTAGGAGTAGCCCACA | 22.1 | 1390 | 1409 | 146 |
| 512517 | CAGGAGTAGGAGTAGCCCAC | 15.4 | 1391 | 1410 | 147 |
| 512518 | GCAGGAGTAGGAGTAGCCCA | 32.8 | 1392 | 1411 | 148 |
| 512519 | TGCAGGAGTAGGAGTAGCCC | 37.6 | 1393 | 1412 | 149 |
| 512520 | ATGCAGGAGTAGGAGTAGCC | 47.4 | 1394 | 1413 | 150 |
| 512521 | CATGCAGGAGTAGGAGTAGC | 67.2 | 1395 | 1414 | 151 |
| 512522 | CCATGCAGGAGTAGGAGTAG | 58.8 | 1396 | 1415 | 152 |
| 512523 | GCCATGCAGGAGTAGGAGTA | 42.4 | 1397 | 1416 | 153 |
| 512524 | GGCCATGCAGGAGTAGGAGT | 34.1 | 1398 | 1417 | 154 |
| 512525 | GGGCCATGCAGGAGTAGGAG | 44.5 | 1399 | 1418 | 155 |
| 512526 | AGGGCCATGCAGGAGTAGGA | 42 | 1400 | 1419 | 156 |
| 512527 | GAGGGCCATGCAGGAGTAGG | 46.3 | 1401 | 1420 | 157 |
| 512528 | CTGAGGGCCATGCAGGAGTA | 25.3 | 1403 | 1422 | 158 |
| 512529 | CCTGAGGGCCATGCAGGAGT | 28.1 | 1404 | 1423 | 159 |
| 512530 | CCCTGAGGGCCATGCAGGAG | 22.8 | 1405 | 1424 | 160 |
| 512531 | TCCCTGAGGGCCATGCAGGA | 25.7 | 1406 | 1425 | 161 |
| 512532 | GTCCCTGAGGGCCATGCAGG | 17 | 1407 | 1426 | 162 |
| 512533 | TGTCCCTGAGGGCCATGCAG | 18.9 | 1408 | 1427 | 163 |
| 512534 | CTGTCCCTGAGGGCCATGCA | 27.3 | 1409 | 1428 | 164 |
| 512535 | ACTGTCCCTGAGGGCCATGC | 16.5 | 1410 | 1429 | 165 |
| 512536 | CACTGTCCCTGAGGGCCATG | 26 | 1411 | 1430 | 166 |
| 512537 | TCACTGTCCCTGAGGGCCAT | 22.7 | 1412 | 1431 | 167 |
| 512538 | CTCACTGTCCCTGAGGGCCA | 20.2 | 1413 | 1432 | 168 |
| 512539 | CCTCACTGTCCCTGAGGGCC | 19.3 | 1414 | 1433 | 169 |
| 512540 | ACCTCACTGTCCCTGAGGGC | 31 | 1415 | 1434 | 170 |
| 512541 | GACCTCACTGTCCCTGAGGG | 51.4 | 1416 | 1435 | 171 |
| 512542 | GGACCTCACTGTCCCTGAGG | 28 | 1417 | 1436 | 172 |
| 512543 | GGGACCTCACTGTCCCTGAG | 42.6 | 1418 | 1437 | 173 |
| 512544 | CCTCCAGTTCCATGGGTGTG | 16.7 | 1444 | 1463 | 174 |
| 512545 | GCCTCCAGTTCCATGGGTGT | 21.9 | 1445 | 1464 | 175 |
| 512546 | GGCCTCCAGTTCCATGGGTG | 19 | 1446 | 1465 | 176 |
| 512547 | CGGCCTCCAGTTCCATGGGT | 14.9 | 1447 | 1466 | 177 |

TABLE 4-continued

Inhibition of human DMPK RNA transcript in hSKMc by 5-10-5 gapmers targeting SEQ ID NO: 1

| ISIS No. | Sequence | % Target Expres-sion | Start Site on Seq ID: 1 | Stop Site on Seq ID: 1 | SEQ ID NO. |
|---|---|---|---|---|---|
| 512548 | TCGGCCTCCAGTTCCATGGG | 23 | 1448 | 1467 | 178 |
| 512549 | CTCGGCCTCCAGTTCCATGG | 15.7 | 1449 | 1468 | 179 |
| 512550 | GCTCGGCCTCCAGTTCCATG | 16.2 | 1450 | 1469 | 180 |
| 512551 | TGCTCGGCCTCCAGTTCCAT | 17.7 | 1451 | 1470 | 181 |
| 512552 | CTGCTCGGCCTCCAGTTCCA | 18.4 | 1452 | 1471 | 182 |
| 512553 | GCTGCTCGGCCTCCAGTTCC | 22 | 1453 | 1472 | 183 |
| 512554 | AGCTGCTCGGCCTCCAGTTC | 32.4 | 1454 | 1473 | 184 |
| 512555 | CAGCTGCTCGGCCTCCAGTT | 15.7 | 1455 | 1474 | 185 |
| 512556 | GCAGCTGCTCGGCCTCCAGT | 16.3 | 1456 | 1475 | 186 |

TABLE 5

Inhibition of human DMPK RNA transcript in hSKMc by 5-10-5 gapmers targeting SEQ ID NO: 1

| ISIS No. | Sequence | % Target Expres-sion | Start Site on Seq ID: 1 | Stop Site on Seq ID: 1 | SEQ ID NO. |
|---|---|---|---|---|---|
| UTC | N/A | 100.0 | N/A | N/A | |
| 444401 | TTGCACTTTGCGAACCAACG | 7.0 | 2490 | 2509 | 33 |
| 512557 | AGCAGCTGCTCGGCCTCCAG | 25.2 | 1457 | 1476 | 187 |
| 512558 | AAGCAGCTGCTCGGCCTCCA | 16.1 | 1458 | 1477 | 188 |
| 512559 | CAAGCAGCTGCTCGGCCTCC | 21.9 | 1459 | 1478 | 189 |
| 512560 | TCAAGCAGCTGCTCGGCCTC | 24.8 | 1460 | 1479 | 190 |
| 512561 | CTCAAGCAGCTGCTCGGCCT | 19.8 | 1461 | 1480 | 191 |
| 512562 | GCTCAAGCAGCTGCTCGGCC | 11.6 | 1462 | 1481 | 192 |
| 512563 | GGCTCAAGCAGCTGCTCGGC | 19.8 | 1463 | 1482 | 193 |
| 512564 | TGGCTCAAGCAGCTGCTCGG | 31.9 | 1464 | 1483 | 194 |
| 512565 | GTGGCTCAAGCAGCTGCTCG | 27.5 | 1465 | 1484 | 195 |
| 512566 | TGTGGCTCAAGCAGCTGCTC | 35.4 | 1466 | 1485 | 196 |
| 512567 | GTGTGGCTCAAGCAGCTGCT | 24.8 | 1467 | 1486 | 197 |
| 512568 | CCACTTCAGCTGTTTCATCC | 43.1 | 1525 | 1544 | 198 |
| 512569 | TGCCACTTCAGCTGTTTCAT | 35.0 | 1527 | 1546 | 199 |
| 512570 | CTGCCACTTCAGCTGTTTCA | 27.8 | 1528 | 1547 | 200 |
| 512571 | ACTGCCACTTCAGCTGTTTC | 78.9 | 1529 | 1548 | 201 |
| 512572 | AACTGCCACTTCAGCTGTTT | 36.4 | 1530 | 1549 | 202 |
| 512573 | GAACTGCCACTTCAGCTGTT | 30.3 | 1531 | 1550 | 203 |

TABLE 5-continued

Inhibition of human DMPK RNA transcript in hSKMc by 5-10-5 gapmers targeting SEQ ID NO: 1

| ISIS No. | Sequence | % Target Expres-sion | Start Site on Seq ID: 1 | Stop Site on Seq ID: 1 | SEQ ID NO. |
|---|---|---|---|---|---|
| 512574 | GGAACTGCCACTTCAGCTGT | 66.7 | 1532 | 1551 | 204 |
| 512575 | TGGAACTGCCACTTCAGCTG | 22.6 | 1533 | 1552 | 205 |
| 512576 | CTGGAACTGCCACTTCAGCT | 22.9 | 1534 | 1553 | 206 |
| 512577 | GCTGGAACTGCCACTTCAGC | 59.5 | 1535 | 1554 | 207 |
| 512578 | CGCTGGAACTGCCACTTCAG | 24.9 | 1536 | 1555 | 208 |
| 512579 | CCGCTGGAACTGCCACTTCA | 42.5 | 1537 | 1556 | 209 |
| 512580 | GCCGCTGGAACTGCCACTTC | 20.0 | 1538 | 1557 | 210 |
| 512581 | AGCCGCTGGAACTGCCACTT | 19.4 | 1539 | 1558 | 211 |
| 512582 | CTCAGCCTCTGCCGCAGGGA | 22.1 | 1560 | 1579 | 212 |
| 512583 | CCTCAGCCTCTGCCGCAGGG | 33.7 | 1561 | 1580 | 213 |
| 512584 | GGCCTCAGCCTCTGCCGCAG | 24.6 | 1563 | 1582 | 214 |
| 512585 | CGGCCTCAGCCTCTGCCGCA | 55.1 | 1564 | 1583 | 215 |
| 512586 | TCGGCCTCAGCCTCTGCCGC | 60.8 | 1565 | 1584 | 216 |
| 512587 | CTCGGCCTCAGCCTCTGCCG | 31.8 | 1566 | 1585 | 217 |
| 512588 | CCTCGGCCTCAGCCTCTGCC | 16.4 | 1567 | 1586 | 218 |
| 512589 | ACCTCGGCCTCAGCCTCTGC | 31.1 | 1568 | 1587 | 219 |
| 512590 | CACCTCGGCCTCAGCCTCTG | 39.7 | 1569 | 1588 | 220 |
| 512591 | TCACCTCGGCCTCAGCCTCT | 24.8 | 1570 | 1589 | 221 |
| 512592 | GTCACCTCGGCCTCAGCCTC | 28.7 | 1571 | 1590 | 222 |
| 512593 | CGTCACCTCGGCCTCAGCCT | 20.3 | 1572 | 1591 | 223 |
| 512594 | AGCACCTCCTCCTCCAGGGC | 18.4 | 1610 | 1629 | 224 |
| 512595 | GAGCACCTCCTCCTCCAGGG | 19.9 | 1611 | 1630 | 225 |
| 512596 | TGAGCACCTCCTCCTCCAGG | 15.6 | 1612 | 1631 | 226 |
| 512597 | GTGAGCACCTCCTCCTCCAG | 22.3 | 1613 | 1632 | 227 |
| 512598 | GGTGAGCACCTCCTCCTCCA | 19.4 | 1614 | 1633 | 228 |
| 512599 | GGGTGAGCACCTCCTCCTCC | 17.3 | 1615 | 1634 | 229 |
| 512600 | CGGGTGAGCACCTCCTCCTC | 12.2 | 1616 | 1635 | 230 |
| 512601 | CCGGGTGAGCACCTCCTCCT | 15.9 | 1617 | 1636 | 231 |
| 512602 | GCCGGGTGAGCACCTCCTCC | 15.7 | 1618 | 1637 | 232 |
| 512603 | TGCCGGGTGAGCACCTCCTC | 15.1 | 1619 | 1638 | 233 |
| 512604 | CTGCCGGGTGAGCACCTCCT | 24.5 | 1620 | 1639 | 234 |
| 512605 | TCTGCCGGGTGAGCACCTCC | 33.8 | 1621 | 1640 | 235 |
| 512606 | GCTCTGCCGGGTGAGCACCT | 26.1 | 1623 | 1642 | 236 |
| 512607 | GGCTCTGCCGGGTGAGCACC | 50.4 | 1624 | 1643 | 237 |
| 512608 | AGGCTCTGCCGGGTGAGCAC | 42.9 | 1625 | 1644 | 238 |

TABLE 5-continued

Inhibition of human DMPK RNA transcript in hSKMc by 5-10-5 gapmers targeting SEQ ID NO: 1

| ISIS No. | Sequence | % Target Expres-sion | Start Site on Seq ID: 1 | Stop Site on Seq ID: 1 | SEQ ID NO. |
|---|---|---|---|---|---|
| 512609 | CAGGCTCTGCCGGGTGAGCA | 39.2 | 1626 | 1645 | 239 |
| 512610 | TCAGGCTCTGCCGGGTGAGC | 20.2 | 1627 | 1646 | 240 |
| 512611 | GCTCAGGCTCTGCCGGGTGA | 22.5 | 1629 | 1648 | 241 |
| 512612 | CGGCTCAGGCTCTGCCGGGT | 27.0 | 1631 | 1650 | 242 |
| 512613 | CCGGCTCAGGCTCTGCCGGG | 68.8 | 1632 | 1651 | 243 |
| 512614 | CCCGGCTCAGGCTCTGCCGG | 58.8 | 1633 | 1652 | 244 |
| 512615 | TCCCGGCTCAGGCTCTGCCG | 24.8 | 1634 | 1653 | 245 |
| 512616 | CTCCCGGCTCAGGCTCTGCC | 10.4 | 1635 | 1654 | 246 |
| 512617 | TCTCCCGGCTCAGGCTCTGC | 12.8 | 1636 | 1655 | 247 |
| 512618 | ATCTCCCGGCTCAGGCTCTG | 13.3 | 1637 | 1656 | 248 |
| 512619 | CATCTCCCGGCTCAGGCTCT | 7.7 | 1638 | 1657 | 249 |
| 512620 | CCATCTCCCGGCTCAGGCTC | 2.8 | 1639 | 1658 | 250 |
| 512621 | TCCATCTCCCGGCTCAGGCT | 2.6 | 1640 | 1659 | 251 |
| 512622 | CTCCATCTCCCGGCTCAGGC | 1.5 | 1641 | 1660 | 252 |
| 512623 | CCTCCATCTCCCGGCTCAGG | 1.4 | 1642 | 1661 | 253 |
| 512624 | GCCTCCATCTCCCGGCTCAG | 2.0 | 1643 | 1662 | 254 |
| 512625 | GGCCTCCATCTCCCGGCTCA | 8.3 | 1644 | 1663 | 255 |
| 512626 | TGGCCTCCATCTCCCGGCTC | 9.4 | 1645 | 1664 | 256 |
| 512627 | ATGGCCTCCATCTCCCGGCT | 6.3 | 1646 | 1665 | 257 |
| 512628 | GATGGCCTCCATCTCCCGGC | 2.7 | 1647 | 1666 | 258 |
| 512629 | GGATGGCCTCCATCTCCCGG | 1.3 | 1648 | 1667 | 259 |
| 512630 | CGGATGGCCTCCATCTCCCG | 1.5 | 1649 | 1668 | 260 |
| 512631 | GCGGATGGCCTCCATCTCCC | 2.4 | 1650 | 1669 | 261 |
| 512632 | TGCGGATGGCCTCCATCTCC | 2.2 | 1651 | 1670 | 262 |
| 512633 | GTTCCGAGCCTCTGCCTCGC | 29.2 | 1701 | 1720 | 263 |

TABLE 6

Inhibition of human DMPK RNA transcript in hSKMc by 5-10-5 gapmers targeting SEQ ID NO: 2

| ISIS No. | Sequence | % Target Expres-sion | Start Site on Seq ID: 2 | Stop Site on Seq ID: 2 | SEQ ID NO. |
|---|---|---|---|---|---|
| UTC | N/A | 100.0 | N/A | N/A | |
| 444401 | TTGCACTTTGCGAACCAACG | 7.0 | 13553 | 13572 | 33 |

TABLE 6-continued

Inhibition of human DMPK RNA transcript in hSKMc by 5-10-5 gapmers targeting SEQ ID NO: 2

| ISIS No. | Sequence | % Target Expres-sion | Start Site on Seq ID: 2 | Stop Site on Seq ID: 2 | SEQ ID NO. |
|---|---|---|---|---|---|
| 444436 | GTCGGAGGACGAGGTCAATA | 9.7 | 13748 | 13767 | 264 |
| 512634 | AGGGCCTCAGCCTGGCCGAA | 31.7 | 13452 | 13471 | 265 |
| 512635 | CAGGGCCTCAGCCTGGCCGA | 39.5 | 13453 | 13472 | 266 |
| 512636 | GTCAGGGCCTCAGCCTGGCC | 20.5 | 13455 | 13474 | 267 |
| 512637 | CGTCAGGGCCTCAGCCTGGC | 23.3 | 13456 | 13475 | 268 |
| 512638 | AGCAAATTTCCCGAGTAAGC | 14.7 | 13628 | 13647 | 269 |
| 512639 | AAGCAAATTTCCCGAGTAAG | 21.2 | 13629 | 13648 | 270 |
| 512640 | AAAAGCAAATTTCCCGAGTA | 23.0 | 13631 | 13650 | 271 |
| 512641 | CAAAAGCAAATTTCCCGAGT | 19.7 | 13632 | 13651 | 272 |
| 512642 | GCAAAAGCAAATTTCCCGAG | 26.6 | 13633 | 13652 | 273 |
| 512643 | GGCAAAAGCAAATTTCCCGA | 12.8 | 13634 | 13653 | 274 |
| 512644 | TGGCAAAAGCAAATTTCCCG | 12.2 | 13635 | 13654 | 275 |
| 512645 | TTTGGCAAAAGCAAATTTCC | 24.2 | 13637 | 13656 | 276 |
| 512646 | GTTTGGCAAAAGCAAATTTC | 25.5 | 13638 | 13657 | 277 |
| 512647 | GGGTTTGGCAAAAGCAAATT | 43.0 | 13640 | 13659 | 278 |
| 512648 | CGGGTTTGGCAAAAGCAAAT | 27.2 | 13641 | 13660 | 279 |
| 512649 | AAGCGGGTTTGGCAAAAGCA | 27.0 | 13644 | 13663 | 280 |
| 512650 | AATATCCAAACCGCCGAAGC | 45.7 | 13728 | 13747 | 281 |
| 512651 | AAATATCCAAACCGCCGAAG | 56.6 | 13729 | 13748 | 282 |
| 512652 | ATAAATATCCAAACCGCCGA | 39.0 | 13731 | 13750 | 283 |
| 512653 | AATAAATATCCAAACCGCCG | 34.7 | 13732 | 13751 | 284 |
| 512654 | TCAATAAATATCCAAACCGC | 34.7 | 13734 | 13753 | 285 |
| 512655 | GTCAATAAATATCCAAACCG | 19.1 | 13735 | 13754 | 286 |
| 512656 | GGTCAATAAATATCCAAACC | 24.3 | 13736 | 13755 | 287 |
| 512657 | AGGTCAATAAATATCCAAAC | 23.5 | 13737 | 13756 | 288 |
| 512658 | GAGGTCAATAAATATCCAAA | 24.2 | 13738 | 13757 | 289 |
| 512659 | ACGAGGTCAATAAATATCCA | 28.3 | 13740 | 13759 | 290 |
| 512660 | GACGAGGTCAATAAATATCC | 17.8 | 13741 | 13760 | 291 |
| 512661 | AGGACGAGGTCAATAAATAT | 45.7 | 13743 | 13762 | 292 |
| 512662 | GAGGACGAGGTCAATAAATA | 27.6 | 13744 | 13763 | 293 |
| 512663 | CGGAGGACGAGGTCAATAAA | 15.8 | 13746 | 13765 | 294 |
| 512664 | TCGGAGGACGAGGTCAATAA | 10.8 | 13747 | 13766 | 295 |
| 512665 | AGTCGGAGGACGAGGTCAAT | 15.4 | 13749 | 13768 | 296 |
| 512666 | GAGTCGGAGGACGAGGTCAA | 18.8 | 13750 | 13769 | 297 |
| 512667 | GCGAGTCGGAGGACGAGGTC | 26.0 | 13752 | 13771 | 298 |

TABLE 6-continued

Inhibition of human DMPK RNA transcript in hSKMc by 5-10-5 gapmers targeting SEQ ID NO: 2

| ISIS No. | Sequence | % Target Expres-sion | Start Site on Seq ID: 2 | Stop Site on Seq ID: 2 | SEQ ID NO. |
|---|---|---|---|---|---|
| 512668 | AGCGAGTCGGAGGACGAGGT | 21.7 | 13753 | 13772 | 299 |
| 512669 | CAGCGAGTCGGAGGACGAGG | 13.7 | 13754 | 13773 | 300 |
| 512670 | TCAGCGAGTCGGAGGACGAG | 16.5 | 13755 | 13774 | 301 |
| 512671 | GTCAGCGAGTCGGAGGACGA | 17.4 | 13756 | 13775 | 302 |
| 512672 | CTGTCAGCGAGTCGGAGGAC | 25.2 | 13758 | 13777 | 303 |
| 512673 | CCTGTCAGCGAGTCGGAGGA | 18.4 | 13759 | 13778 | 304 |
| 512674 | AGCCTGTCAGCGAGTCGGAG | 16.8 | 13761 | 13780 | 305 |
| 512675 | GTCTCAGTGCATCCAAAACG | 11.8 | 13807 | 13826 | 306 |
| 512676 | GGTCTCAGTGCATCCAAAAC | 17.7 | 13808 | 13827 | 307 |
| 512677 | GGGTCTCAGTGCATCCAAAA | 11.2 | 13809 | 13828 | 308 |
| 512678 | GGAGGGCCTTTTATTCGCGA | 17.8 | 13884 | 13903 | 309 |
| 512679 | TGGAGGGCCTTTTATTCGCG | 13.2 | 13885 | 13904 | 310 |
| 512680 | ATGGAGGGCCTTTTATTCGC | 19.3 | 13886 | 13905 | 311 |
| 512681 | GATGGAGGGCCTTTTATTCG | 30.5 | 13887 | 13906 | 312 |
| 512682 | AGATGGAGGGCCTTTTATTC | 50.8 | 13888 | 13907 | 313 |
| 512683 | CAGATGGAGGGCCTTTTATT | 46.1 | 13889 | 13908 | 314 |
| 512684 | GCAGATGGAGGGCCTTTTAT | 50.4 | 13890 | 13909 | 315 |
| 512685 | CCCTCAGGCTCTCTGCTTTA | 34.7 | 655 | 674 | 316 |
| 512686 | GCCCTCAGGCTCTCTGCTTT | 47.9 | 656 | 675 | 317 |
| 512687 | AGCCCTCAGGCTCTCTGCTT | 47.4 | 657 | 676 | 318 |
| 512688 | TAGCCCTCAGGCTCTCTGCT | 54.1 | 658 | 677 | 319 |
| 512689 | TTAGCCCTCAGGCTCTCTGC | 48.0 | 659 | 678 | 320 |
| 512690 | TTTAGCCCTCAGGCTCTCTG | 50.7 | 660 | 679 | 321 |
| 512691 | ATTTAGCCCTCAGGCTCTCT | 47.3 | 661 | 680 | 322 |
| 512692 | AATTTAGCCCTCAGGCTCTC | 44.8 | 662 | 681 | 323 |
| 512693 | AAATTTAGCCCTCAGGCTCT | 39.2 | 663 | 682 | 324 |
| 512694 | TAAATTTAGCCCTCAGGCTC | 48.0 | 664 | 683 | 325 |
| 512695 | TTAAATTTAGCCCTCAGGCT | 54.9 | 665 | 684 | 326 |
| 512696 | GTTAAATTTAGCCCTCAGGC | 48.1 | 666 | 685 | 327 |
| 512697 | AGTTAAATTTAGCCCTCAGG | 39.3 | 667 | 686 | 328 |
| 512698 | CAGTTAAATTTAGCCCTCAG | 47.5 | 668 | 687 | 329 |
| 512699 | ACAGTTAAATTTAGCCCTCA | 68.2 | 669 | 688 | 330 |
| 512700 | GACAGTTAAATTTAGCCCTC | 59.2 | 670 | 689 | 331 |
| 512701 | GGACAGTTAAATTTAGCCCT | 63.7 | 671 | 690 | 332 |
| 512702 | CGGACAGTTAAATTTAGCCC | 50.7 | 672 | 691 | 333 |

TABLE 6-continued

| Inhibition of human DMPK RNA transcript in hSKMc by 5-10-5 gapmers targeting SEQ ID NO: 2 | | | | | |
|---|---|---|---|---|---|
| ISIS No. | Sequence | % Target Expres-sion | Start Site on Seq ID: 2 | Stop Site on Seq ID: 2 | SEQ ID NO. |
| 512703 | TCGGACAGTTAAATTTAGCC | 39.6 | 673 | 692 | 334 |
| 512704 | CTCGGACAGTTAAATTTAGC | 36.5 | 674 | 693 | 335 |
| 512705 | ACTCGGACAGTTAAATTTAG | 59.1 | 675 | 694 | 336 |
| 512706 | GACTCGGACAGTTAAATTTA | 50.0 | 676 | 695 | 337 |
| 512707 | CGACTCGGACAGTTAAATTT | 63.0 | 677 | 696 | 338 |
| 512708 | CCGACTCGGACAGTTAAATT | 34.3 | 678 | 697 | 339 |
| 512709 | TCCGACTCGGACAGTTAAAT | 39.5 | 679 | 698 | 340 |

Example 3: Design of Antisense Oligonucleotides Targeting Human Dystrophia Myotonica Protein Kinase (hDMPK)

A series of antisense oligonucleotides (ASOs) were designed to target hDMPK. The newly designed ASOs were prepared using standard oligonucleotide synthesis well known in the art and are described in Table 7, below. Subscripts "s" indicate phosphorothioate internucleoside linkages; subscripts "k" indicate 6'-(S)—$CH_3$ bicyclic nucleosides (cEt); subscripts "e" indicate 2'-O-methoxyethyl (MOE) modified nucleosides; and subscripts "d" indicate β-D-2'-deoxyribonucleosides. "$^{m}C$" indicates 5-methylcytosine nucleosides.

The antisense oligonucleotides targeted to a human DMPK nucleic acid were tested for their effect on DMPK RNA transcript in vitro. Cultured HepG2 cells at a density of 20,000 cells per well were transfected using electroporation with 4,500 nM antisense oligonucleotide. After approximately 24 hours, RNA was isolated from the cells and DMPK transcript levels were measured by quantitative real-time PCR. DMPK RNA transcript levels were adjusted according to total RNA content, as measured by RIBOGREEN®. Results are presented as percent expression of DMPK, relative to untreated control cells.

'Target start site' indicates the 5'-most nucleoside to which the antisense oligonucleotide is targeted in the human genomic gene sequence. 'Target stop site' indicates the 3'-most nucleoside to which the antisense oligonucleotide is targeted in the human genomic sequence. All the antisense oligonucleotides listed in Table 7 target SEQ ID NO: 1 (GENBANK Accession No. NM_001081560.1).

Several of the antisense oligonucleotides demonstrated significant inhibition of DMPK mRNA levels under the conditions specified above.

TABLE 7

| Inhibition of human DMPK RNA transcript in HepG2 cells targeting SEQ ID NO: 1 | | | | | |
|---|---|---|---|---|---|
| ISIS No. | Sequence | % Target Expres-sion | Start Site on Seq ID: 1 | Stop Site on Seq ID: 1 | Seq ID No. |
| UTC | N/A | 100 | N/A | N/A | |
| 533424 | $T_{es}{}^{m}C_{es}T_{es}{}^{m}C_{ds}{}^{m}C_{ds}T_{ds}{}^{m}C_{ds}A_{ds}{}^{m}C_{ds}G_{ds}G_{ds}A_{ds}A_{ds}G_{ks}{}^{m}C_{ks}A_{k}$ | 34.4 | 548 | 563 | 341 |
| 533425 | ${}^{m}C_{es}T_{es}{}^{m}C_{es}T_{ds}{}^{m}C_{ds}{}^{m}C_{ds}T_{ds}{}^{m}C_{ds}A_{ds}{}^{m}C_{ds}G_{ds}G_{ds}A_{ds}A_{ks}G_{ks}{}^{m}C_{k}$ | 32.1 | 549 | 564 | 342 |
| 533426 | ${}^{m}C_{es}{}^{m}C_{es}T_{es}{}^{m}C_{ds}T_{ds}{}^{m}C_{ds}{}^{m}C_{ds}T_{ds}{}^{m}C_{ds}A_{ds}{}^{m}C_{ds}G_{ds}G_{ds}A_{ks}A_{ks}G_{k}$ | 52.1 | 550 | 565 | 343 |
| 533427 | $A_{es}A_{es}A_{es}{}^{m}C_{ds}T_{ds}T_{ds}G_{ds}{}^{m}C_{ds}T_{ds}{}^{m}C_{ds}A_{ds}G_{ds}{}^{m}C_{ds}A_{ks}G_{ks}T_{k}$ | 36.8 | 679 | 694 | 344 |
| 533428 | ${}^{m}C_{es}A_{es}A_{es}A_{ds}{}^{m}C_{ds}T_{ds}T_{ds}G_{ds}{}^{m}C_{ds}T_{ds}{}^{m}C_{ds}A_{ds}G_{ds}{}^{m}C_{ks}A_{ks}G_{k}$ | 59.9 | 680 | 695 | 345 |
| 533429 | ${}^{m}C_{es}{}^{m}C_{es}A_{es}A_{ds}A_{ds}{}^{m}C_{ds}T_{ds}T_{ds}G_{ds}{}^{m}C_{ds}T_{ds}{}^{m}C_{ds}A_{ds}G_{ks}{}^{m}C_{ks}A_{k}$ | 39.3 | 681 | 696 | 346 |
| 533430 | ${}^{m}C_{es}{}^{m}C_{es}{}^{m}C_{es}A_{ds}A_{ds}A_{ds}{}^{m}C_{ds}T_{ds}T_{ds}G_{ds}{}^{m}C_{ds}T_{ds}{}^{m}C_{ds}A_{ks}G_{ks}{}^{m}C_{k}$ | 37.6 | 682 | 697 | 347 |
| 533431 | ${}^{m}C_{es}{}^{m}C_{es}{}^{m}C_{es}{}^{m}C_{ds}A_{ds}A_{ds}A_{ds}{}^{m}C_{ds}T_{ds}T_{ds}G_{ds}{}^{m}C_{ds}T_{ds}{}^{m}C_{ks}A_{ks}G_{k}$ | 39.6 | 683 | 698 | 348 |
| 533432 | $T_{es}{}^{m}C_{es}{}^{m}C_{es}{}^{m}C_{ds}{}^{m}C_{ds}A_{ds}A_{ds}A_{ds}{}^{m}C_{ds}T_{ds}T_{ds}G_{ds}{}^{m}C_{ds}T_{ks}{}^{m}C_{ks}A_{k}$ | 52.1 | 684 | 699 | 349 |
| 533433 | $G_{es}T_{es}T_{es}T_{ds}G_{ds}A_{ds}T_{ds}G_{ds}T_{ds}{}^{m}C_{ds}{}^{m}C_{ds}{}^{m}C_{ds}T_{ds}G_{ks}T_{ks}G_{k}$ | 53.9 | 782 | 797 | 350 |
| 533434 | $G_{es}G_{es}T_{es}T_{ds}T_{ds}G_{ds}A_{ds}T_{ds}G_{ds}T_{ds}{}^{m}C_{ds}{}^{m}C_{ds}{}^{m}C_{ds}T_{ks}G_{ks}T_{k}$ | 38.1 | 783 | 798 | 351 |
| 533435 | $G_{es}G_{es}G_{es}T_{ds}T_{ds}T_{ds}G_{ds}A_{ds}T_{ds}G_{ds}T_{ds}{}^{m}C_{ds}{}^{m}C_{ds}{}^{m}C_{ks}T_{ks}G_{k}$ | 43.7 | 784 | 799 | 352 |
| 533436 | $A_{es}{}^{m}C_{es}A_{es}G_{ds}{}^{m}C_{ds}{}^{m}C_{ds}T_{ds}G_{ds}{}^{m}C_{ds}A_{ds}G_{ds}G_{ds}A_{ds}T_{ks}{}^{m}C_{ks}T_{k}$ | 29.5 | 927 | 942 | 353 |
| 533437 | ${}^{m}C_{es}A_{es}{}^{m}C_{es}A_{ds}G_{ds}{}^{m}C_{ds}{}^{m}C_{ds}T_{ds}G_{ds}{}^{m}C_{ds}A_{ds}G_{ds}G_{ds}A_{ks}T_{ks}{}^{m}C_{k}$ | 48.6 | 928 | 943 | 354 |
| 533438 | ${}^{m}C_{es}{}^{m}C_{es}A_{es}{}^{m}C_{ds}A_{ds}G_{ds}{}^{m}C_{ds}{}^{m}C_{ds}T_{ds}G_{ds}{}^{m}C_{ds}A_{ds}G_{ds}G_{ks}A_{ks}T_{k}$ | 46.9 | 929 | 944 | 355 |
| 533439 | ${}^{m}C_{es}{}^{m}C_{es}{}^{m}C_{es}A_{ds}{}^{m}C_{ds}A_{ds}G_{ds}{}^{m}C_{ds}{}^{m}C_{ds}T_{ds}G_{ds}{}^{m}C_{ds}A_{ds}G_{ks}G_{ks}A_{k}$ | 43.6 | 930 | 945 | 356 |

TABLE 7-continued

Inhibition of human DMPK RNA transcript in HepG2 cells targeting SEQ ID NO: 1

| ISIS No. | Sequence | % Target Expression | Start Site on Seq ID: 1 | Stop Site on Seq ID: 1 | Seq ID No. |
|---|---|---|---|---|---|
| 533440 | $G_{es}{}^{m}C_{es}{}^{m}C_{es}{}^{m}C_{ds}A_{ds}{}^{m}C_{ds}A_{ds}G_{ds}{}^{m}C_{ds}{}^{m}C_{ds}T_{ds}G_{ds}{}^{m}C_{ds}A_{ks}G_{ks}G_{k}$ | 26.9 | 931 | 946 | 357 |
| 533441 | ${}^{m}C_{es}G_{es}{}^{m}C_{es}{}^{m}C_{ds}{}^{m}C_{ds}A_{ds}{}^{m}C_{ds}A_{ds}G_{ds}{}^{m}C_{ds}{}^{m}C_{ds}T_{ds}G_{ds}{}^{m}C_{ks}A_{ks}G_{k}$ | 31.3 | 932 | 947 | 358 |
| 533442 | ${}^{m}C_{es}{}^{m}C_{es}G_{es}{}^{m}C_{ds}{}^{m}C_{ds}{}^{m}C_{ds}A_{ds}{}^{m}C_{ds}A_{ds}G_{ds}{}^{m}C_{ds}{}^{m}C_{ds}T_{ds}G_{ks}{}^{m}C_{ks}A_{k}$ | 20.5 | 933 | 948 | 359 |
| 533443 | $A_{es}{}^{m}C_{es}{}^{m}C_{es}G_{ds}{}^{m}C_{ds}{}^{m}C_{ds}{}^{m}C_{ds}A_{ds}{}^{m}C_{ds}A_{ds}G_{ds}{}^{m}C_{ds}{}^{m}C_{ds}T_{ks}G_{ks}{}^{m}C_{k}$ | 13.7 | 934 | 949 | 360 |
| 533444 | ${}^{m}C_{es}A_{es}{}^{m}C_{es}{}^{m}C_{ds}G_{ds}{}^{m}C_{ds}{}^{m}C_{ds}{}^{m}C_{ds}A_{ds}{}^{m}C_{ds}A_{ds}G_{ds}{}^{m}C_{ds}{}^{m}C_{ks}T_{ks}G_{k}$ | 29.4 | 935 | 950 | 361 |
| 533445 | ${}^{m}C_{es}{}^{m}C_{es}A_{es}{}^{m}C_{ds}{}^{m}C_{ds}G_{ds}{}^{m}C_{ds}{}^{m}C_{ds}{}^{m}C_{ds}A_{ds}{}^{m}C_{ds}A_{ds}G_{ds}{}^{m}C_{ks}{}^{m}C_{ks}T_{k}$ | 32 | 936 | 951 | 362 |
| 533446 | ${}^{m}C_{es}{}^{m}C_{es}{}^{m}C_{es}A_{ds}{}^{m}C_{ds}{}^{m}C_{ds}G_{ds}{}^{m}C_{ds}{}^{m}C_{ds}{}^{m}C_{ds}A_{ds}{}^{m}C_{ds}A_{ds}G_{ks}{}^{m}C_{ks}{}^{m}C_{k}$ | 8.3 | 937 | 952 | 363 |
| 533447 | $G_{es}{}^{m}C_{es}{}^{m}C_{es}{}^{m}C_{ds}A_{ds}{}^{m}C_{ds}{}^{m}C_{ds}G_{ds}{}^{m}C_{ds}{}^{m}C_{ds}{}^{m}C_{ds}A_{ds}{}^{m}C_{ds}A_{ks}G_{ks}{}^{m}C_{k}$ | 18.3 | 938 | 953 | 364 |
| 533448 | ${}^{m}C_{es}{}^{m}C_{es}A_{es}G_{ds}G_{ds}{}^{m}C_{ds}{}^{m}C_{ds}{}^{m}C_{ds}A_{ds}{}^{m}C_{ds}{}^{m}C_{ds}G_{ds}{}^{m}C_{ds}{}^{m}C_{ks}{}^{m}C_{ks}A_{k}$ | 19.4 | 942 | 957 | 365 |
| 533449 | ${}^{m}C_{es}{}^{m}C_{es}{}^{m}C_{es}A_{ds}G_{ds}G_{ds}{}^{m}C_{ds}{}^{m}C_{ds}{}^{m}C_{ds}A_{ds}{}^{m}C_{ds}{}^{m}C_{ds}G_{ds}{}^{m}C_{ks}{}^{m}C_{ks}{}^{m}C_{k}$ | 24.2 | 943 | 958 | 366 |
| 533450 | $T_{es}{}^{m}C_{es}{}^{m}C_{es}{}^{m}C_{ds}A_{ds}G_{ds}G_{ds}{}^{m}C_{ds}{}^{m}C_{ds}{}^{m}C_{ds}A_{ds}{}^{m}C_{ds}{}^{m}C_{ds}G_{ks}{}^{m}C_{ks}{}^{m}C_{k}$ | 39.2 | 944 | 959 | 367 |
| 533451 | $T_{es}G_{es}{}^{m}C_{es}{}^{m}C_{ds}T_{ds}G_{ds}T_{ds}{}^{m}C_{ds}{}^{m}C_{ds}{}^{m}C_{ds}A_{ds}G_{ds}G_{ds}{}^{m}C_{ks}{}^{m}C_{ks}{}^{m}C_{k}$ | 44.2 | 950 | 965 | 368 |
| 533452 | ${}^{m}C_{es}T_{es}G_{es}{}^{m}C_{ds}{}^{m}C_{ds}T_{ds}G_{ds}T_{ds}{}^{m}C_{ds}{}^{m}C_{ds}{}^{m}C_{ds}A_{ds}G_{ds}G_{ks}{}^{m}C_{ks}{}^{m}C_{k}$ | 55.6 | 951 | 966 | 369 |
| 533453 | $G_{es}{}^{m}C_{es}T_{es}G_{ds}{}^{m}C_{ds}{}^{m}C_{ds}T_{ds}G_{ds}T_{ds}{}^{m}C_{ds}{}^{m}C_{ds}{}^{m}C_{ds}A_{ds}G_{ks}G_{ks}{}^{m}C_{k}$ | 71.2 | 952 | 967 | 370 |
| 533454 | $G_{es}G_{es}T_{es}G_{ds}G_{ds}{}^{m}C_{ds}A_{ds}{}^{m}C_{ds}{}^{m}C_{ds}T_{ds}T_{ds}{}^{m}C_{ds}G_{ds}A_{ks}A_{ks}A_{k}$ | 39.6 | 1276 | 1291 | 371 |
| 533455 | ${}^{m}C_{es}G_{es}G_{es}T_{ds}G_{ds}G_{ds}{}^{m}C_{ds}A_{ds}{}^{m}C_{ds}{}^{m}C_{ds}T_{ds}T_{ds}{}^{m}C_{ds}G_{ks}A_{ks}A_{k}$ | 52.9 | 1277 | 1292 | 372 |
| 533456 | $T_{es}{}^{m}C_{es}G_{es}G_{ds}T_{ds}G_{ds}G_{ds}{}^{m}C_{ds}A_{ds}{}^{m}C_{ds}{}^{m}C_{ds}T_{ds}T_{ds}{}^{m}C_{ks}G_{ks}A_{k}$ | 27 | 1278 | 1293 | 373 |
| 533457 | $A_{es}G_{es}T_{es}G_{ds}A_{ds}G_{ds}{}^{m}C_{ds}{}^{m}C_{ds}{}^{m}C_{ds}G_{ds}T_{ds}{}^{m}C_{ds}{}^{m}C_{ds}T_{ks}{}^{m}C_{ks}{}^{m}C_{k}$ | 51.5 | 1315 | 1330 | 374 |
| 533458 | ${}^{m}C_{es}A_{es}G_{es}T_{ds}G_{ds}A_{ds}G_{ds}{}^{m}C_{ds}{}^{m}C_{ds}{}^{m}C_{ds}G_{ds}T_{ds}{}^{m}C_{ds}{}^{m}C_{ks}T_{ks}{}^{m}C_{k}$ | 55.1 | 1316 | 1331 | 375 |
| 533459 | $G_{es}{}^{m}C_{es}A_{es}G_{ds}T_{ds}G_{ds}A_{ds}G_{ds}{}^{m}C_{ds}{}^{m}C_{ds}{}^{m}C_{ds}G_{ds}T_{ds}{}^{m}C_{ks}{}^{m}C_{ks}T_{k}$ | 33.7 | 1317 | 1332 | 376 |
| 533460 | $T_{es}{}^{m}C_{es}{}^{m}C_{es}{}^{m}C_{ds}G_{ds}A_{ds}A_{ds}T_{ds}G_{ds}T_{ds}{}^{m}C_{ds}{}^{m}C_{ds}G_{ds}A_{ks}{}^{m}C_{ks}A_{k}$ | 28.7 | 1344 | 1359 | 377 |
| 533461 | $T_{es}T_{es}{}^{m}C_{es}{}^{m}C_{ds}{}^{m}C_{ds}G_{ds}A_{ds}A_{ds}T_{ds}G_{ds}T_{ds}{}^{m}C_{ds}{}^{m}C_{ds}G_{ks}A_{ks}{}^{m}C_{k}$ | 36.2 | 1345 | 1360 | 378 |
| 533462 | ${}^{m}C_{es}T_{es}T_{es}{}^{m}C_{ds}{}^{m}C_{ds}{}^{m}C_{ds}G_{ds}A_{ds}A_{ds}T_{ds}G_{ds}T_{ds}{}^{m}C_{ds}{}^{m}C_{ks}G_{ks}A_{k}$ | 23 | 1346 | 1361 | 379 |
| 533463 | ${}^{m}C_{es}{}^{m}C_{es}T_{es}T_{ds}{}^{m}C_{ds}{}^{m}C_{ds}{}^{m}C_{ds}G_{ds}A_{ds}A_{ds}T_{ds}G_{ds}T_{ds}{}^{m}C_{ks}{}^{m}C_{ks}G_{k}$ | 11.5 | 1347 | 1362 | 380 |
| 533464 | $A_{es}{}^{m}C_{es}{}^{m}C_{es}T_{ds}T_{ds}{}^{m}C_{ds}{}^{m}C_{ds}{}^{m}C_{ds}G_{ds}A_{ds}A_{ds}T_{ds}G_{ds}T_{ks}{}^{m}C_{ks}{}^{m}C_{k}$ | 19.9 | 1348 | 1363 | 381 |
| 533465 | ${}^{m}C_{es}A_{es}{}^{m}C_{es}{}^{m}C_{ds}T_{ds}T_{ds}{}^{m}C_{ds}{}^{m}C_{ds}{}^{m}C_{ds}G_{ds}A_{ds}A_{ds}T_{ds}G_{ks}T_{ks}{}^{m}C_{k}$ | 30.2 | 1349 | 1364 | 382 |
| 533466 | $G_{es}{}^{m}C_{es}A_{es}{}^{m}C_{ds}{}^{m}C_{ds}T_{ds}T_{ds}{}^{m}C_{ds}{}^{m}C_{ds}{}^{m}C_{ds}G_{ds}A_{ds}A_{ds}T_{ks}G_{ks}T_{k}$ | 30.2 | 1350 | 1365 | 383 |
| 533467 | ${}^{m}C_{es}G_{es}{}^{m}C_{es}A_{ds}{}^{m}C_{ds}{}^{m}C_{ds}T_{ds}T_{ds}{}^{m}C_{ds}{}^{m}C_{ds}{}^{m}C_{ds}G_{ds}A_{ds}A_{ks}T_{ks}G_{k}$ | 35.5 | 1351 | 1366 | 384 |
| 533468 | $A_{es}T_{es}{}^{m}C_{es}{}^{m}C_{ds}G_{ds}{}^{m}C_{ds}T_{ds}{}^{m}C_{ds}{}^{m}C_{ds}T_{ds}G_{ds}{}^{m}C_{ds}A_{ds}A_{ks}{}^{m}C_{ks}T_{k}$ | 47.4 | 1746 | 1761 | 385 |
| 533469 | ${}^{m}C_{es}A_{es}T_{es}{}^{m}C_{ds}{}^{m}C_{ds}G_{ds}{}^{m}C_{ds}T_{ds}{}^{m}C_{ds}{}^{m}C_{ds}T_{ds}G_{ds}{}^{m}C_{ds}A_{ks}A_{ks}{}^{m}C_{k}$ | 51.2 | 1747 | 1762 | 386 |
| 533470 | ${}^{m}C_{es}{}^{m}C_{es}A_{es}T_{ds}{}^{m}C_{ds}{}^{m}C_{ds}G_{ds}{}^{m}C_{ds}T_{ds}{}^{m}C_{ds}{}^{m}C_{ds}T_{ds}G_{ds}{}^{m}C_{ks}A_{ks}A_{k}$ | 35.5 | 1748 | 1763 | 387 |
| 533471 | $G_{es}{}^{m}C_{es}T_{es}{}^{m}C_{ds}{}^{m}C_{ds}{}^{m}C_{ds}T_{ds}{}^{m}C_{ds}T_{ds}G_{ds}{}^{m}C_{ds}{}^{m}C_{ds}T_{ds}G_{ks}{}^{m}C_{ks}A_{k}$ | 65.6 | 1770 | 1785 | 388 |
| 533472 | $A_{es}G_{es}G_{es}T_{ds}G_{ds}G_{ds}A_{ds}T_{ds}{}^{m}C_{ds}{}^{m}C_{ds}G_{ds}T_{ds}G_{ds}G_{ks}{}^{m}C_{ks}{}^{m}C_{k}$ | 51.8 | 1816 | 1831 | 389 |
| 533473 | $G_{es}G_{es}G_{es}A_{ds}A_{ds}G_{ds}G_{ds}T_{ds}G_{ds}G_{ds}A_{ds}T_{ds}{}^{m}C_{ds}{}^{m}C_{ks}G_{ks}T_{k}$ | 44.9 | 1820 | 1835 | 390 |
| 533474 | $A_{es}{}^{m}C_{es}A_{es}G_{ds}G_{ds}A_{ds}G_{ds}{}^{m}C_{ds}A_{ds}G_{ds}G_{ds}G_{ds}A_{ds}A_{ks}A_{ks}G_{k}$ | 80.8 | 1955 | 1970 | 391 |

TABLE 7-continued

Inhibition of human DMPK RNA transcript in HepG2 cells targeting SEQ ID NO: 1

| ISIS No. | Sequence | % Target Expres-sion | Start Site on Seq ID: 1 | Stop Site on Seq ID: 1 | Seq ID No. |
|---|---|---|---|---|---|
| 533475 | ${}^{m}C_{es}A_{es}G_{es}A_{ds}{}^{m}C_{ds}T_{ds}G_{ds}{}^{m}C_{ds}G_{ds}G_{ds}T_{ds}G_{ds}A_{ds}G_{ks}T_{ks}T_{k}$ | 95.5 | 2034 | 2049 | 392 |
| 533476 | $G_{es}G_{es}{}^{m}C_{es}T_{ds}{}^{m}C_{ds}{}^{m}C_{ds}T_{ds}G_{ds}G_{ds}G_{ds}{}^{m}C_{ds}G_{ds}G_{ds}{}^{m}C_{ks}G_{ks}{}^{m}C_{k}$ | 55.7 | 2050 | 2065 | 393 |
| 533477 | $G_{es}G_{es}{}^{m}C_{es}G_{ds}G_{ds}{}^{m}C_{ds}T_{ds}{}^{m}C_{ds}{}^{m}C_{ds}T_{ds}G_{ds}G_{ds}G_{ds}{}^{m}C_{ks}G_{ks}G_{k}$ | 45.8 | 2053 | 2068 | 394 |
| 533478 | ${}^{m}C_{es}G_{es}{}^{m}C_{es}G_{ds}G_{ds}G_{ds}{}^{m}C_{ds}G_{ds}G_{ds}{}^{m}C_{ds}T_{ds}{}^{m}C_{ds}{}^{m}C_{ds}T_{ks}G_{ks}G_{k}$ | 83.7 | 2057 | 2072 | 395 |
| 533479 | $G_{es}A_{es}G_{es}{}^{m}C_{ds}G_{ds}{}^{m}C_{ds}G_{ds}G_{ds}G_{ds}{}^{m}C_{ds}G_{ds}G_{ds}{}^{m}C_{ds}T_{ks}{}^{m}C_{ks}{}^{m}C_{k}$ | 79.8 | 2060 | 2075 | 396 |
| 533480 | $G_{es}G_{es}T_{es}T_{ds}{}^{m}C_{ds}A_{ds}G_{ds}G_{ds}G_{ds}A_{ds}G_{ds}{}^{m}C_{ds}G_{ds}{}^{m}C_{ks}G_{ks}G_{k}$ | 49.4 | 2068 | 2083 | 397 |
| 533481 | $A_{es}G_{es}T_{es}T_{ds}{}^{m}C_{ds}T_{ds}A_{ds}G_{ds}G_{ds}G_{ds}T_{ds}T_{ds}{}^{m}C_{ds}A_{ks}G_{ks}G_{k}$ | 37 | 2076 | 2091 | 398 |
| 533482 | ${}^{m}C_{es}A_{es}G_{es}T_{ds}T_{ds}{}^{m}C_{ds}T_{ds}A_{ds}G_{ds}G_{ds}G_{ds}T_{ds}T_{ds}{}^{m}C_{ks}A_{ks}G_{k}$ | 28.5 | 2077 | 2092 | 399 |
| 533483 | $A_{es}{}^{m}C_{es}A_{es}G_{ds}T_{ds}T_{ds}{}^{m}C_{ds}T_{ds}A_{ds}G_{ds}G_{ds}G_{ds}T_{ds}T_{ks}{}^{m}C_{ks}A_{k}$ | 42 | 2078 | 2093 | 400 |
| 533484 | $G_{es}A_{es}{}^{m}C_{es}A_{ds}G_{ds}T_{ds}T_{ds}{}^{m}C_{ds}T_{ds}A_{ds}G_{ds}G_{ds}G_{ds}T_{ks}T_{ks}{}^{m}C_{k}$ | 37.4 | 2079 | 2094 | 401 |
| 533485 | $A_{es}G_{es}A_{es}{}^{m}C_{ds}A_{ds}G_{ds}T_{ds}T_{ds}{}^{m}C_{ds}T_{ds}A_{ds}G_{ds}G_{ds}G_{ks}T_{ks}T_{k}$ | 66.5 | 2080 | 2095 | 402 |
| 533486 | $A_{es}A_{es}G_{es}A_{ds}{}^{m}C_{ds}A_{ds}G_{ds}T_{ds}T_{ds}{}^{m}C_{ds}T_{ds}A_{ds}G_{ds}G_{ks}G_{ks}T_{k}$ | 62.4 | 2081 | 2096 | 403 |
| 533487 | $G_{es}A_{es}A_{es}G_{ds}A_{ds}{}^{m}C_{ds}A_{ds}G_{ds}T_{ds}T_{ds}{}^{m}C_{ds}T_{ds}A_{ds}G_{ks}G_{ks}G_{k}$ | 56.9 | 2082 | 2097 | 404 |
| 533488 | ${}^{m}C_{es}G_{es}A_{es}A_{ds}G_{ds}A_{ds}{}^{m}C_{ds}A_{ds}G_{ds}T_{ds}T_{ds}{}^{m}C_{ds}T_{ds}A_{ks}G_{ks}G_{k}$ | 36.8 | 2083 | 2098 | 405 |
| 533489 | $T_{es}{}^{m}C_{es}G_{es}A_{ds}A_{ds}G_{ds}A_{ds}{}^{m}C_{ds}A_{ds}G_{ds}T_{ds}T_{ds}{}^{m}C_{ds}T_{ks}A_{ks}G_{k}$ | 49.6 | 2084 | 2099 | 406 |
| 533490 | $G_{es}T_{es}{}^{m}C_{es}G_{ds}A_{ds}A_{ds}G_{ds}A_{ds}{}^{m}C_{ds}A_{ds}G_{ds}T_{ds}T_{ds}{}^{m}C_{ks}T_{ks}A_{k}$ | 40.4 | 2085 | 2100 | 407 |
| 533491 | $A_{es}G_{es}T_{es}{}^{m}C_{ds}G_{ds}A_{ds}A_{ds}G_{ds}A_{ds}{}^{m}C_{ds}A_{ds}G_{ds}T_{ds}T_{ks}{}^{m}C_{ks}T_{k}$ | 37.4 | 2086 | 2101 | 408 |
| 533492 | $G_{es}A_{es}G_{es}T_{ds}{}^{m}C_{ds}G_{ds}A_{ds}A_{ds}G_{ds}A_{ds}{}^{m}C_{ds}A_{ds}G_{ds}T_{ks}T_{ks}{}^{m}C_{k}$ | 36.6 | 2087 | 2102 | 409 |
| 533493 | $G_{es}G_{es}A_{es}G_{ds}T_{ds}{}^{m}C_{ds}G_{ds}A_{ds}A_{ds}G_{ds}A_{ds}{}^{m}C_{ds}A_{ds}G_{ks}T_{ks}T_{k}$ | 33.2 | 2088 | 2103 | 410 |
| 533494 | ${}^{m}C_{es}G_{es}G_{es}A_{ds}G_{ds}T_{ds}{}^{m}C_{ds}G_{ds}A_{ds}A_{ds}G_{ds}A_{ds}{}^{m}C_{ds}A_{ks}G_{ks}T_{k}$ | 45.3 | 2089 | 2104 | 411 |
| 533495 | ${}^{m}C_{es}{}^{m}C_{es}G_{es}G_{ds}A_{ds}G_{ds}T_{ds}{}^{m}C_{ds}G_{ds}A_{ds}A_{ds}G_{ds}A_{ds}{}^{m}C_{ks}A_{ks}G_{k}$ | 45.9 | 2090 | 2105 | 412 |
| 533496 | ${}^{m}C_{es}{}^{m}C_{es}{}^{m}C_{es}G_{ds}G_{ds}A_{ds}G_{ds}T_{ds}{}^{m}C_{ds}G_{ds}A_{ds}A_{ds}G_{ds}A_{ks}{}^{m}C_{ks}A_{k}$ | 51.3 | 2091 | 2106 | 413 |
| 533497 | ${}^{m}C_{es}{}^{m}C_{es}{}^{m}C_{es}{}^{m}C_{ds}G_{ds}G_{ds}A_{ds}G_{ds}T_{ds}{}^{m}C_{ds}G_{ds}A_{ds}A_{ds}G_{ks}A_{ks}{}^{m}C_{k}$ | 49.2 | 2092 | 2107 | 414 |
| 533498 | $G_{es}{}^{m}C_{es}{}^{m}C_{es}{}^{m}C_{ds}{}^{m}C_{ds}G_{ds}G_{ds}A_{ds}G_{ds}T_{ds}{}^{m}C_{ds}G_{ds}A_{ds}A_{ks}G_{ks}A_{k}$ | 52.3 | 2093 | 2108 | 415 |
| 533499 | $G_{es}G_{es}{}^{m}C_{es}{}^{m}C_{ds}{}^{m}C_{ds}{}^{m}C_{ds}G_{ds}G_{ds}A_{ds}G_{ds}T_{ds}{}^{m}C_{ds}G_{ds}A_{ks}A_{ks}G_{k}$ | 54.9 | 2094 | 2109 | 416 |
| 533500 | $G_{es}G_{es}G_{es}{}^{m}C_{ds}{}^{m}C_{ds}{}^{m}C_{ds}{}^{m}C_{ds}G_{ds}G_{ds}A_{ds}G_{ds}T_{ds}{}^{m}C_{ds}G_{ks}A_{ks}A_{k}$ | 46.7 | 2095 | 2110 | 417 |
| 533809 | $A_{es}{}^{m}C_{es}A_{es}A_{ds}T_{ds}A_{ds}A_{ds}A_{ds}T_{ds}A_{ds}{}^{m}C_{ds}{}^{m}C_{ds}G_{ds}A_{ks}G_{ks}G_{k}$ | 51.4 | 2773 | 2788 | 418 |

Example 4: Design of Antisense Oligonucleotides Targeting Human Dystrophia Myotonica Protein Kinase (hDMPK)

Dose Response HepG2

A series of antisense oligonucleotides (ASOs) were designed to target hDMPK. The newly designed ASOs were prepared using standard oligonucleotide synthesis well known in the art and are described in Table 8, below. Subscripts "s" indicate phosphorothioate internucleoside linkages; subscripts "k" indicate 6'-(S)—$CH_3$ bicyclic nucleosides (cEt); subscripts "e" indicate 2'-O-methoxyethyl (MOE) modified nucleosides; and subscripts "d" indicate β-D-2'-deoxyribonucleosides. "${}^{m}C$" ~ indicates 5-methylcytosine nucleosides.

The antisense oligonucleotides are targeted to SEQ TD NO: 1 (GENBANK Accession No. NM_001081560.1). "Start site" indicates the 5'-most nucleoside to which the gapmer is targeted in the human gene sequence. "Stop site" indicates the 3'-most nucleoside to which the gapmer is targeted human gene sequence.

TABLE 8

Design of antisense oligonucleotides targeting hDMPK

| ISIS No. | Composition (5' to 3') | Start Site | Stop Site | SEQ ID NO |
|---|---|---|---|---|
| 533440 | $G_{es}{}^{m}C_{es}{}^{m}C_{es}{}^{m}C_{ds}A_{ds}{}^{m}C_{ds}A_{ds}Ga_{s}{}^{m}C_{ds}{}^{m}C_{ds}Ta_{s}Ga_{s}{}^{m}C_{ds}A_{ks}G_{ks}G_{k}$ | 931 | 946 | 357 |
| 533442 | ${}^{m}C_{es}{}^{m}C_{es}G_{es}{}^{m}C_{ds}{}^{m}C_{ds}{}^{m}C_{ds}A_{ds}{}^{m}C_{ds}A_{ds}G_{ds}{}^{m}C_{ds}{}^{m}C_{ds}Ta_{s}G_{ks}{}^{m}C_{ks}A_{k}$ | 933 | 948 | 359 |
| 533443 | $A_{es}{}^{m}C_{es}{}^{m}C_{es}Ga_{s}{}^{m}C_{ds}{}^{m}C_{ds}{}^{m}C_{ds}A_{ds}{}^{m}C_{ds}A_{ds}Ga_{s}{}^{m}C_{ds}{}^{m}C_{ds}T_{ks}G_{ks}{}^{m}C_{k}$ | 934 | 949 | 360 |
| 533446 | ${}^{m}C_{es}{}^{m}C_{es}{}^{m}C_{es}A_{ds}{}^{m}C_{ds}{}^{m}C_{ds}G_{ds}{}^{m}C_{ds}{}^{m}C_{ds}{}^{m}C_{ds}A_{ds}{}^{m}C_{ds}A_{ds}G_{ks}{}^{m}C_{ks}{}^{m}C_{k}$ | 937 | 952 | 363 |
| 533447 | $G_{es}{}^{m}C_{es}{}^{m}C_{es}{}^{m}C_{ds}A_{ds}{}^{m}C_{ds}{}^{m}C_{ds}G_{ds}{}^{m}C_{ds}{}^{m}C_{ds}{}^{m}C_{ds}A_{ds}{}^{m}C_{ds}A_{ks}G_{ks}{}^{m}C_{k}$ | 938 | 953 | 364 |
| 533448 | ${}^{m}C_{es}{}^{m}C_{es}A_{es}G_{ds}G_{ds}{}^{m}C_{ds}{}^{m}C_{ds}{}^{m}C_{ds}A_{ds}{}^{m}C_{ds}{}^{m}C_{ds}G_{ds}{}^{m}C_{ds}{}^{m}C_{ks}{}^{m}C_{ks}A_{k}$ | 942 | 957 | 365 |
| 533449 | ${}^{m}C_{es}{}^{m}C_{es}{}^{m}C_{es}A_{ds}G_{ds}G_{ds}{}^{m}C_{ds}{}^{m}C_{ds}{}^{m}C_{ds}A_{ds}{}^{m}C_{ds}{}^{m}C_{ds}G_{ds}{}^{m}C_{ks}{}^{m}C_{ks}{}^{m}C_{k}$ | 943 | 958 | 366 |
| 533462 | ${}^{m}C_{es}T_{es}T_{es}{}^{m}C_{ds}{}^{m}C_{ds}{}^{m}C_{ds}G_{ds}A_{ds}A_{ds}T_{ds}G_{ds}T_{ds}{}^{m}C_{ds}{}^{m}C_{ks}G_{ks}A_{k}$ | 1346 | 1361 | 379 |
| 533463 | ${}^{m}C_{es}{}^{m}C_{es}T_{es}T_{ds}{}^{m}C_{ds}{}^{m}C_{ds}{}^{m}C_{ds}G_{ds}A_{ds}A_{ds}T_{ds}G_{ds}T_{ds}{}^{m}C_{ks}{}^{m}C_{ks}G_{k}$ | 1347 | 1362 | 380 |
| 533464 | $A_{es}{}^{m}C_{es}{}^{m}C_{es}T_{ds}T_{ds}{}^{m}C_{ds}{}^{m}C_{ds}{}^{m}C_{ds}G_{ds}A_{ds}A_{ds}T_{ds}G_{ds}T_{ks}{}^{m}C_{ks}{}^{m}C_{k}$ | 1348 | 1363 | 381 |
| 533529 | ${}^{m}C_{es}G_{es}G_{es}T_{ds}T_{ds}G_{ds}T_{ds}G_{ds}A_{ds}A_{ds}{}^{m}C_{ds}T_{ds}G_{ds}G_{ks}{}^{m}C_{ks}A_{k}$ | 2162 | 2177 | 23 |
| 533530 | $A_{es}G_{es}{}^{m}C_{es}G_{ds}G_{ds}T_{ds}T_{ds}G_{ds}T_{ds}G_{ds}A_{ds}A_{ds}{}^{m}C_{ds}T_{ks}G_{ks}G_{k}$ | 2164 | 2179 | 419 |
| 533599 | $G_{es}{}^{m}C_{es}A_{es}{}^{m}C_{ds}T_{ds}T_{ds}T_{ds}G_{ds}{}^{m}C_{ds}G_{ds}A_{ds}A_{ds}{}^{m}C_{ds}{}^{m}C_{ks}A_{ks}A_{k}$ | 2492 | 2507 | 420 |
| 533600 | $T_{es}G_{es}{}^{m}C_{es}A_{ds}{}^{m}C_{ds}T_{ds}T_{ds}T_{ds}G_{ds}{}^{m}C_{ds}G_{ds}A_{ds}A_{ds}{}^{m}C_{ks}{}^{m}C_{ks}A_{k}$ | 2493 | 2508 | 421 |

Example 5: Dose Response HepG2

Antisense oligonucleotides targeted to a human DMPK nucleic acid were tested for their effect on human DMPK RNA transcript in vitro. Cultured HepG2 cells at a density of 20,000 cells 4 per well were transfected using electroporation with 625 nM, 1250 nM, 2500 nM, 5000 nM, and 10000.0 nM concentrations of each antisense oligonucleotide. After approximately 24 hours, RNA was isolated from the cells and DMPK RNA transcript levels were measured by quantitative real-time PCR using primer probe set RTS3164 (forward sequence AGCCTGAGCCGG-GAGATG, designated herein as SEQ ID NO: 20; reverse sequence GCGTAGTTGACTGGCGAAGTT, designated herein as SEQ ID NO: 21; probe sequence AGGC-CATCCGCACGGACAACCX, designated herein as SEQ ID NO: 22). Human DMPK RNA transcript levels were adjusted according to total RNA content, as measured by RIBOGREEN®. Results are presented in the table below as percent expression of human DMPK, relative to untreated control (UTC) cells. The tested antisense oligonucleotide sequences demonstrated dose-dependent inhibition of human DMPK mRNA levels under the conditions specified above.

TABLE 9

Inhibition of human DMPK RNA transcript in HepG2 cells targeting SEQ ID NO: 1

| ISIS No. | Dose (nM) | % Target Expression | Start Site on Seq ID: 1 | Stop Site on Seq ID: 1 |
|---|---|---|---|---|
| UTC | N/A | 100 | N/A | N/A |
| 486178 | 625.0 | 39.4 | 2773 | 2788 |
| 486178 | 1250.0 | 31.2 | 2773 | 2788 |
| 486178 | 2500.0 | 20.6 | 2773 | 2788 |
| 486178 | 5000.0 | 13 | 2773 | 2788 |

TABLE 9-continued

Inhibition of human DMPK RNA transcript in HepG2 cells targeting SEQ ID NO: 1

| ISIS No. | Dose (nM) | % Target Expression | Start Site on Seq ID: 1 | Stop Site on Seq ID: 1 |
|---|---|---|---|---|
| 486178 | 10000.0 | 11.5 | 2773 | 2788 |
| 533440 | 625.0 | 55.4 | 931 | 946 |
| 533440 | 1250.0 | 40.4 | 931 | 946 |
| 533440 | 2500.0 | 25.4 | 931 | 946 |
| 533440 | 5000.0 | 22.6 | 931 | 946 |
| 533440 | 10000.0 | 10.3 | 931 | 946 |
| 533442 | 625.0 | 55.2 | 933 | 948 |
| 533442 | 1250.0 | 33.1 | 933 | 948 |
| 533442 | 2500.0 | 29 | 933 | 948 |
| 533442 | 5000.0 | 16.9 | 933 | 948 |
| 533442 | 10000.0 | 7.2 | 933 | 948 |
| 533443 | 625.0 | 44.8 | 934 | 949 |
| 533443 | 1250.0 | 29.4 | 934 | 949 |
| 533443 | 2500.0 | 19.9 | 934 | 949 |
| 533443 | 5000.0 | 10.8 | 934 | 949 |
| 533443 | 10000.0 | 7 | 934 | 949 |
| 533446 | 625.0 | 50.9 | 937 | 952 |
| 533446 | 1250.0 | 35.5 | 937 | 952 |
| 533446 | 2500.0 | 30.4 | 937 | 952 |
| 533446 | 5000.0 | 14.6 | 937 | 952 |
| 533446 | 10000.0 | 14 | 937 | 952 |
| 533447 | 625.0 | 53.3 | 938 | 953 |
| 533447 | 1250.0 | 31.7 | 938 | 953 |
| 533447 | 2500.0 | 16.8 | 938 | 953 |
| 533447 | 5000.0 | 11.7 | 938 | 953 |
| 533447 | 10000.0 | 4.4 | 938 | 953 |
| 533448 | 625.0 | 58.8 | 942 | 957 |
| 533448 | 1250.0 | 36.9 | 942 | 957 |
| 533448 | 2500.0 | 24.8 | 942 | 957 |
| 533448 | 5000.0 | 11.5 | 942 | 957 |
| 533448 | 10000.0 | 10.1 | 942 | 957 |
| 533449 | 625.0 | 61.1 | 943 | 958 |
| 533449 | 1250.0 | 42.8 | 943 | 958 |
| 533449 | 2500.0 | 30.4 | 943 | 958 |
| 533449 | 5000.0 | 20.2 | 943 | 958 |
| 533449 | 10000.0 | 10.1 | 943 | 958 |

TABLE 9-continued

Inhibition of human DMPK RNA transcript in HepG2 cells targeting SEQ ID NO: 1

| ISIS No. | Dose (nM) | % Target Expression | Start Site on Seq ID: 1 | Stop Site on Seq ID: 1 |
|---|---|---|---|---|
| 533462 | 625.0 | 50.7 | 1346 | 1361 |
| 533462 | 1250.0 | 32.3 | 1346 | 1361 |
| 533462 | 2500.0 | 29.2 | 1346 | 1361 |
| 533462 | 5000.0 | 12.5 | 1346 | 1361 |
| 533462 | 10000.0 | 5.8 | 1346 | 1361 |
| 533463 | 625.0 | 39.1 | 1347 | 1362 |
| 533463 | 1250.0 | 23.7 | 1347 | 1362 |
| 533463 | 2500.0 | 12.6 | 1347 | 1362 |
| 533463 | 5000.0 | 9.3 | 1347 | 1362 |
| 533463 | 10000.0 | 3.2 | 1347 | 1362 |
| 533464 | 625.0 | 48.8 | 1348 | 1363 |
| 533464 | 1250.0 | 36.4 | 1348 | 1363 |
| 533464 | 2500.0 | 24.5 | 1348 | 1363 |
| 533464 | 5000.0 | 11.7 | 1348 | 1363 |
| 533464 | 10000.0 | 5 | 1348 | 1363 |
| 533529 | 625.0 | 35.8 | 2162 | 2177 |
| 533529 | 1250.0 | 26.4 | 2162 | 2177 |
| 533529 | 2500.0 | 18.3 | 2162 | 2177 |
| 533529 | 5000.0 | 14.8 | 2162 | 2177 |
| 533529 | 10000.0 | 14.7 | 2162 | 2177 |
| 533530 | 625.0 | 47.4 | 2164 | 2179 |
| 533530 | 1250.0 | 22.1 | 2164 | 2179 |
| 533530 | 2500.0 | 21.5 | 2164 | 2179 |
| 533530 | 5000.0 | 14.4 | 2164 | 2179 |
| 533530 | 10000.0 | 8 | 2164 | 2179 |
| 533599 | 625.0 | 31.3 | 2492 | 2507 |
| 533599 | 1250.0 | 21.9 | 2492 | 2507 |
| 533599 | 2500.0 | 13.1 | 2492 | 2507 |
| 533599 | 5000.0 | 8.8 | 2492 | 2507 |
| 533599 | 10000.0 | 7.3 | 2492 | 2507 |
| 533600 | 625.0 | 33.8 | 2493 | 2508 |
| 533600 | 1250.0 | 20.9 | 2493 | 2508 |
| 533600 | 2500.0 | 16.5 | 2493 | 2508 |
| 533600 | 5000.0 | 10.4 | 2493 | 2508 |
| 533600 | 10000.0 | 12.1 | 2493 | 2508 |

Example 6: Design of Antisense Oligonucleotides Targeting Human Dystrophia Myotonica Protein Kinase (hDMPK)

A series of antisense oligonucleotides (ASOs) were designed to target hDMPK. The newly designed ASOs were prepared using standard oligonucleotide synthesis well known in the art and are described in Table 10, below. Subscripts "s" indicate phosphorothioate internucleoside linkages; subscripts "k" indicate 6'-(S)—$CH_3$ bicyclic nucleosides (cEt); subscripts "e" indicate 2'-O-methoxyethyl (MOE) modified nucleosides; and subscripts "d" indicate β-D-2'-deoxyribonucleosides. C indicates 5-methylcytosine nucleosides.

The antisense oligonucleotides are targeted to SEQ ID NO: 2 (the complement of GENBANK Accession No. NT_011109.15 truncated from nucleotides 18540696 to 18555106). "Start site" indicates the 5'-most nucleoside to which the gapmer is targeted in the human gene sequence. "Stop site" indicates the 3'-most nucleoside to which the gapmer is targeted human gene sequence.

TABLE 10

Design of antisense oligonucleotides targeting hDMPK

| ISIS No. | Sequence | Start Site on Seq ID: 2 | Stop Site on Seq ID: 2 | Seq ID No. |
|---|---|---|---|---|
| UTC | N/A | N/A | N/A | |
| 486178 | $A_{ks}{}^{m}C_{ks}A_{ks}A_{ds}T_{ds}A_{ds}A_{ds}A_{ds}T_{ds}A_{ds}{}^{m}C_{ds}{}^{m}C_{ds}G_{ds}A_{ks}G_{ks}G_{k}$ | 13836 | 13851 | 23 |
| 533597 | $A_{es}{}^{m}C_{es}T_{es}T_{ds}T_{ds}G_{ds}{}^{m}C_{ds}G_{ds}A_{ds}A_{ds}{}^{m}C_{ds}{}^{m}C_{ds}A_{ds}A_{ks}{}^{m}C_{ks}G_{k}$ | 13553 | 13568 | 422 |
| 533603 | $A_{es}A_{es}A_{es}G_{ds}{}^{m}C_{ds}T_{ds}T_{ds}T_{ds}G_{ds}{}^{m}C_{ds}A_{ds}{}^{m}C_{ds}T_{ds}T_{ks}T_{ks}G_{k}$ | 13563 | 13578 | 423 |
| 533617 | $T_{es}{}^{m}C_{es}{}^{m}C_{es}{}^{m}C_{ds}G_{ds}A_{ds}G_{ds}T_{ds}A_{ds}A_{ds}G_{ds}{}^{m}C_{ds}A_{ds}G_{ks}G_{ks}{}^{m}C_{k}$ | 13624 | 13639 | 424 |
| 533649 | $G_{es}{}^{m}C_{es}A_{es}G_{ds}{}^{m}C_{ds}G_{ds}{}^{m}C_{ds}A_{ds}A_{ds}G_{ds}T_{ds}G_{ds}A_{ds}G_{ks}G_{ks}A_{k}$ | 13686 | 13701 | 425 |
| 533694 | $G_{es}T_{es}{}^{m}C_{es}A_{ds}G_{ds}{}^{m}C_{ds}G_{ds}A_{ds}G_{ds}T_{ds}{}^{m}C_{ds}G_{ds}G_{ds}A_{ks}G_{ks}G_{k}$ | 13760 | 13775 | 426 |
| 533697 | ${}^{m}C_{es}{}^{m}C_{es}T_{es}G_{ds}T_{ds}{}^{m}C_{ds}A_{ds}G_{ds}{}^{m}C_{ds}G_{ds}A_{ds}G_{ds}T_{ds}{}^{m}C_{ks}G_{ks}G_{k}$ | 13763 | 13778 | 427 |
| 533698 | $G_{es}{}^{m}C_{es}{}^{m}C_{es}T_{ds}G_{ds}T_{ds}{}^{m}C_{ds}A_{ds}G_{ds}{}^{m}C_{ds}G_{ds}A_{ds}G_{ds}T_{ks}{}^{m}C_{ks}G_{k}$ | 13764 | 13779 | 428 |
| 533699 | $A_{es}G_{es}{}^{m}C_{es}{}^{m}C_{ds}T_{ds}G_{ds}T_{ds}{}^{m}C_{ds}A_{ds}G_{ds}{}^{m}C_{ds}G_{ds}A_{ds}G_{ks}T_{ks}{}^{m}C_{k}$ | 13765 | 13780 | 429 |
| 533711 | $G_{es}G_{es}G_{es}T_{ds}{}^{m}C_{ds}T_{ds}{}^{m}C_{ds}A_{ds}G_{ds}T_{ds}G_{ds}{}^{m}C_{ds}A_{ds}T_{ks}{}^{m}C_{ks}{}^{m}C_{k}$ | 13813 | 13828 | 430 |
| 533721 | $A_{es}G_{es}G_{es}T_{ds}T_{ds}T_{ds}T_{ds}T_{ds}{}^{m}C_{ds}{}^{m}C_{ds}A_{ds}G_{ds}A_{ds}G_{ks}G_{ks}{}^{m}C_{k}$ | 2580 | 2595 | 431 |
| 533722 | $A_{es}A_{es}G_{es}G_{ds}T_{ds}T_{ds}T_{ds}T_{ds}T_{ds}{}^{m}C_{ds}{}^{m}C_{ds}A_{ds}G_{ds}A_{ks}G_{ks}G_{k}$ | 2581 | 2596 | 432 |
| 533751 | $G_{es}G_{es}T_{es}{}^{m}C_{ds}A_{ds}{}^{m}C_{ds}T_{ds}G_{ds}{}^{m}C_{ds}T_{ds}G_{ds}G_{ds}G_{ds}T_{ks}{}^{m}C_{ks}{}^{m}C_{k}$ | 6446 | 6461 | 433 |
| 533786 | $G_{es}T_{es}G_{es}G_{ds}T_{ds}T_{ds}T_{ds}{}^{m}C_{ds}T_{ds}G_{ds}T_{ds}{}^{m}C_{ds}T_{ds}G_{ks}{}^{m}C_{ks}T_{k}$ | 11099 | 11114 | 434 |
| 533787 | ${}^{m}C_{es}G_{es}T_{es}G_{ds}G_{ds}T_{ds}T_{ds}T_{ds}{}^{m}C_{ds}T_{ds}G_{ds}T_{ds}{}^{m}C_{ds}T_{ks}G_{ks}{}^{m}C_{k}$ | 11100 | 11115 | 435 |

Example 7: Dose Response for ASOs Targeted to a Human DMPK RNA Transcript in HepG2 Cells Antisense oligonucleotides targeted to a human DMPK nucleic acid were tested for their effect on human DMPK RNA transcript in vitro. Cultured HepG2 cells at a density of 20,000 cells per well were transfected using electroporation with 625 nM, 1250 nM, 2500 nM, 5000 nM, and 10000.0 nM concentrations of each antisense oligonucleotide. After approximately 24 hours, RNA was isolated from the cells and DMPK RNA transcript levels were measured by quantitative real-time PCR using primer probe set RTS3164 (forward sequence AGCCTGAGCCGGGAGATG, designated herein as SEQ ID NO: 20; reverse sequence GCGTAGTTGACTGGCGAAGTT, designated herein as SEQ ID NO: 21; probe sequence AGGCCATCCGCACGGACAACCX, designated herein as SEQ ID NO: 22). Human DMPK RNA transcript levels were adjusted according to total RNA content, as measured by RIBOGREEN®. Results are presented as percent expression of human DMPK, relative to untreated control (UTC) cells and are shown in the table below. The tested antisense oligonucleotide sequences demonstrated dose-dependent inhibition of human DMPK mRNA levels under the conditions specified above.

TABLE 11

Inhibition of human DMPK RNA transcript in HepG2 cells targeting SEQ ID NO: 1

| ISIS No. | Dose (nM) | % Target Expression | Start Site on Seq ID: 2 | Stop Site on Seq ID: 2 |
|---|---|---|---|---|
| UTC | NA | 100 | N/A | N/A |
| 486178 | 625.000 | 39.4 | 13836 | 13851 |
| 486178 | 1250.000 | 27.3 | 13836 | 13851 |
| 486178 | 2500.000 | 14 | 13836 | 13851 |
| 486178 | 5000.000 | 16.3 | 13836 | 13851 |
| 486178 | 10000.000 | 8.3 | 13836 | 13851 |
| 533597 | 625.000 | 42.4 | 13553 | 13568 |
| 533597 | 1250.000 | 30.3 | 13553 | 13568 |
| 533597 | 2500.000 | 15.3 | 13553 | 13568 |
| 533597 | 5000.000 | 10 | 13553 | 13568 |
| 533597 | 10000.000 | 10.6 | 13553 | 13568 |
| 533603 | 625.000 | 48.2 | 13563 | 13578 |
| 533603 | 1250.000 | 31.1 | 13563 | 13578 |
| 533603 | 2500.000 | 22.4 | 13563 | 13578 |
| 533603 | 5000.000 | 15.6 | 13563 | 13578 |
| 533603 | 10000.000 | 9.9 | 13563 | 13578 |
| 533617 | 625.000 | 38.4 | 13624 | 13639 |
| 533617 | 1250.000 | 26.3 | 13624 | 13639 |
| 533617 | 2500.000 | 21.6 | 13624 | 13639 |
| 533617 | 5000.000 | 15.8 | 13624 | 13639 |
| 533617 | 10000.000 | 14.6 | 13624 | 13639 |
| 533649 | 625.000 | 52.2 | 13686 | 13701 |
| 533649 | 1250.000 | 27.8 | 13686 | 13701 |
| 533649 | 2500.000 | 24.6 | 13686 | 13701 |
| 533649 | 5000.000 | 20.5 | 13686 | 13701 |
| 533649 | 10000.000 | 14.5 | 13686 | 13701 |
| 533694 | 625.000 | 53.3 | 13760 | 13775 |
| 533694 | 1250.000 | 29.4 | 13760 | 13775 |
| 533694 | 2500.000 | 23.6 | 13760 | 13775 |
| 533694 | 5000.000 | 18.7 | 13760 | 13775 |
| 533694 | 10000.000 | 13.5 | 13760 | 13775 |
| 533697 | 625.000 | 30.6 | 13763 | 13778 |
| 533697 | 1250.000 | 14.9 | 13763 | 13778 |
| 533697 | 2500.000 | 13.8 | 13763 | 13778 |
| 533697 | 5000.000 | 9.7 | 13763 | 13778 |
| 533697 | 10000.000 | 7.1 | 13763 | 13778 |
| 533698 | 625.000 | 23.4 | 13764 | 13779 |
| 533698 | 1250.000 | 15.5 | 13764 | 13779 |
| 533698 | 2500.000 | 13.8 | 13764 | 13779 |
| 533698 | 5000.000 | 12.4 | 13764 | 13779 |
| 533698 | 10000.000 | 10.2 | 13764 | 13779 |
| 533699 | 625.000 | 38.2 | 13765 | 13780 |
| 533699 | 1250.000 | 26.9 | 13765 | 13780 |

TABLE 11-continued

Inhibition of human DMPK RNA transcript in HepG2 cells targeting SEQ ID NO: 1

| ISIS No. | Dose (nM) | % Target Expression | Start Site on Seq ID: 2 | Stop Site on Seq ID: 2 |
|---|---|---|---|---|
| 533699 | 2500.000 | 17.6 | 13765 | 13780 |
| 533699 | 5000.000 | 12.9 | 13765 | 13780 |
| 533699 | 10000.000 | 9.3 | 13765 | 13780 |
| 533711 | 625.000 | 35.1 | 13813 | 13828 |
| 533711 | 1250.000 | 34.6 | 13813 | 13828 |
| 533711 | 2500.000 | 22.4 | 13813 | 13828 |
| 533711 | 5000.000 | 22 | 13813 | 13828 |
| 533711 | 10000.000 | 13 | 13813 | 13828 |
| 533721 | 625.000 | 36.3 | 2580 | 2595 |
| 533721 | 1250.000 | 29.8 | 2580 | 2595 |
| 533721 | 2500.000 | 23.2 | 2580 | 2595 |
| 533721 | 5000.000 | 17.8 | 2580 | 2595 |
| 533721 | 10000.000 | 17.2 | 2580 | 2595 |
| 533722 | 625.000 | 48.5 | 2581 | 2596 |
| 533722 | 1250.000 | 28.6 | 2581 | 2596 |
| 533722 | 2500.000 | 21.9 | 2581 | 2596 |
| 533722 | 5000.000 | 28.1 | 2581 | 2596 |
| 533722 | 10000.000 | 13.8 | 2581 | 2596 |
| 533751 | 625.000 | 37.7 | 6446 | 6461 |
| 533751 | 1250.000 | 21.6 | 6446 | 6461 |
| 533751 | 2500.000 | 12.6 | 6446 | 6461 |
| 533751 | 5000.000 | 9.7 | 6446 | 6461 |
| 533751 | 10000.000 | 8.5 | 6446 | 6461 |
| 533786 | 625.000 | 53.6 | 11099 | 11114 |
| 533786 | 1250.000 | 26.6 | 11099 | 11114 |
| 533786 | 2500.000 | 14.7 | 11099 | 11114 |
| 533786 | 5000.000 | 9.6 | 11099 | 11114 |
| 533786 | 10000.000 | 5.5 | 11099 | 11114 |
| 533787 | 625.000 | 43.8 | 11100 | 11115 |
| 533787 | 1250.000 | 27.7 | 11100 | 11115 |
| 533787 | 2500.000 | 16.3 | 11100 | 11115 |
| 533787 | 5000.000 | 7 | 11100 | 11115 |
| 533787 | 10000.000 | 4.5 | 11100 | 11115 |

Example 8: ASOs Designed to Target a Human DMPK RNA Transcript

A series of antisense oligonucleotides (ASOs) were designed to target hDMPK. The newly designed ASOs were prepared using standard oligonucleotide synthesis well known in the art and are described in Table 12, below. Subscripts "s" indicate phosphorothioate internucleoside linkages; subscripts "k" indicate 6'-(S)—$CH_3$ bicyclic nucleosides (cEt); subscripts "e" indicate 2'-O-methoxyethyl (MOE) modified nucleosides; and subscripts "d" indicate 3-D-2'-deoxyribonucleosides. "$^m$C" indicates 5-methylcytosine nucleosides.

The antisense oligonucleotides targeted to a human DMPK nucleic acid were tested for their effect on DMPK RNA transcript in vitro. Cultured hSKMC cells at a density of 20,000 cells per well were transfected using electroporation with 800 nM antisense oligonucleotide. After approximately 24 hours, RNA was isolated from the cells and DMPK transcript levels were measured by quantitative real-time PCR. DMPK RNA transcript levels were adjusted according to total RNA content, as measured by RIBOGREEN®. Results are presented as percent expression of DMPK, relative to untreated control cells.

'Target start site' indicates the 5'-most nucleoside to which the antisense oligonucleotide is targeted in the human genomic gene sequence. 'Target stop site' indicates the 3'-most nucleoside to which the antisense oligonucleotide is targeted in the human genomic sequence. All the antisense oligonucleotides listed in Table 12 target SEQ ID NO: 1 (GENBANK Accession No. NM_001081560.1).

Several of the antisense oligonucleotides demonstrated significant inhibition of DMPK mRNA levels under the conditions specified above.

TABLE 12

Inhibition of human DMPK RNA transcript in HepG2 cells using ASOs targeting SEQ ID NO: 1

| ISIS No. | Sequence | % Target Expression | Start Site on Seq ID: 1 | Stop Site on Seq ID: 1 | Seq ID No. |
|---|---|---|---|---|---|
| UTC | N/A | 100 | N/A | N/A | |
| 444401 | $T_{es}T_{es}G_{es}{}^{m}C_{es}A_{es}{}^{m}C_{ds}T_{ds}T_{ds}T_{ds}G_{ds}{}^{m}C_{ds}G_{ds}A_{ds}A_{ds}{}^{m}C_{ds}{}^{m}C_{es}A_{es}A_{es}{}^{m}C_{es}G_{e}$ | 25.2 | 2490 | 2509 | 33 |
| 444436 | $G_{es}T_{es}{}^{m}C_{es}G_{es}G_{es}A_{ds}G_{ds}G_{ds}A_{ds}{}^{m}C_{ds}G_{ds}A_{ds}G_{ds}G_{ds}T_{ds}{}^{m}C_{es}A_{es}A_{es}T_{es}A_{e}$ | 30.8 | 2685 | 2704 | 264 |
| 486072 | $A_{ks}A_{ks}G_{ks}A_{ds}{}^{m}C_{ds}A_{ds}G_{ds}T_{ds}T_{ds}{}^{m}C_{ds}T_{ds}A_{ds}G_{ds}G_{ks}G_{ks}T_{k}$ | 36.8 | 2081 | 2096 | 403 |
| 486073 | ${}^{m}C_{ks}G_{ks}A_{ks}A_{ds}G_{ds}A_{ds}{}^{m}C_{ds}A_{ds}G_{ds}T_{ds}T_{ds}{}^{m}C_{ds}T_{ds}A_{ks}G_{ks}G_{k}$ | 22.4 | 2083 | 2098 | 405 |
| 486075 | $G_{ks}T_{ks}{}^{m}C_{ks}G_{ds}A_{ds}A_{ds}G_{ds}A_{ds}{}^{m}C_{ds}A_{ds}G_{ds}T_{ds}T_{ds}{}^{m}C_{ks}T_{ks}A_{k}$ | 41.3 | 2085 | 2100 | 407 |
| 486076 | $A_{ks}G_{ks}T_{ks}{}^{m}C_{ds}G_{ds}A_{ds}A_{ds}G_{ds}A_{ds}{}^{m}C_{ds}A_{ds}G_{ds}T_{ds}T_{ks}{}^{m}C_{ks}T_{k}$ | 22.4 | 2086 | 2101 | 408 |
| 486077 | $G_{ks}A_{ks}G_{ks}T_{ds}{}^{m}C_{ds}G_{ds}A_{ds}A_{ds}G_{ds}A_{ds}{}^{m}C_{ds}A_{ds}G_{ds}T_{ks}T_{ks}{}^{m}C_{k}$ | 35.2 | 2087 | 2102 | 409 |
| 486078 | ${}^{m}C_{ks}G_{ks}G_{ks}A_{ds}G_{ds}T_{ds}{}^{m}C_{ds}G_{ds}A_{ds}A_{ds}G_{ds}A_{ds}{}^{m}C_{ds}A_{ks}G_{ks}T_{k}$ | 12.4 | 2089 | 2104 | 411 |
| 486079 | ${}^{m}C_{ks}{}^{m}C_{ks}{}^{m}C_{ks}G_{ds}G_{ds}A_{ds}G_{ds}T_{ds}{}^{m}C_{ds}G_{ds}A_{ds}A_{ds}G_{ds}A_{ks}{}^{m}C_{ks}A_{k}$ | 36.5 | 2091 | 2106 | 413 |
| 486080 | ${}^{m}C_{ks}{}^{m}C_{ks}{}^{m}C_{ks}{}^{m}C_{ds}G_{ds}G_{ds}A_{ds}G_{ds}T_{ds}{}^{m}C_{ds}G_{ds}A_{ds}A_{ds}G_{ks}A_{ks}{}^{m}C_{k}$ | 19.9 | 2092 | 2107 | 414 |
| 486085 | $G_{ks}A_{ks}A_{ks}{}^{m}C_{ds}T_{ds}G_{ds}G_{ds}{}^{m}C_{ds}A_{ds}G_{ds}G_{ds}{}^{m}C_{ds}G_{ds}G_{ks}T_{ks}G_{k}$ | 30.1 | 2155 | 2170 | 436 |
| 486086 | $T_{ks}G_{ks}T_{ks}G_{ds}A_{ds}A_{ds}{}^{m}C_{ds}T_{ds}G_{ds}G_{ds}{}^{m}C_{ds}A_{ds}G_{ds}G_{ks}{}^{m}C_{ks}G_{k}$ | 17.2 | 2158 | 2173 | 437 |
| 486087 | $G_{ks}G_{ks}T_{ks}T_{ds}G_{ds}T_{ds}G_{ds}A_{ds}A_{ds}{}^{m}C_{ds}T_{ds}G_{ds}G_{ds}{}^{m}C_{ks}A_{ks}G_{k}$ | 11.5 | 2161 | 2176 | 438 |
| 486088 | $G_{ks}A_{ks}G_{ks}{}^{m}C_{ds}G_{ds}G_{ds}T_{ds}T_{ds}G_{ds}T_{ds}G_{ds}A_{ds}A_{ds}{}^{m}C_{ks}T_{ks}G_{k}$ | 21.7 | 2165 | 2180 | 439 |
| 486094 | $A_{ks}{}^{m}C_{ks}T_{ks}G_{ds}G_{ds}A_{ds}G_{ds}{}^{m}C_{ds}T_{ds}G_{ds}G_{ds}G_{ds}{}^{m}C_{ds}G_{ks}G_{ks}A_{k}$ | 30.2 | 2193 | 2208 | 440 |
| 486096 | $A_{ks}G_{ks}G_{ks}A_{ds}{}^{m}C_{ds}T_{ds}G_{ds}G_{ds}A_{ds}G_{ds}{}^{m}C_{ds}T_{ds}G_{ds}G_{ks}G_{ks}{}^{m}C_{k}$ | 43.5 | 2196 | 2211 | 441 |
| 486097 | $T_{ks}{}^{m}C_{ks}A_{ks}{}^{m}C_{ds}A_{ds}G_{ds}G_{ds}A_{ds}{}^{m}C_{ds}T_{ds}G_{ds}G_{ds}A_{ds}G_{ks}{}^{m}C_{ks}T_{k}$ | 54.5 | 2200 | 2215 | 442 |
| 486098 | $A_{ks}T_{ks}{}^{m}C_{ks}A_{ds}{}^{m}C_{ds}A_{ds}G_{ds}G_{ds}A_{ds}{}^{m}C_{ds}T_{ds}G_{ds}G_{ds}A_{ks}G_{ks}{}^{m}C_{k}$ | 77.3 | 2201 | 2216 | 443 |
| 486099 | $G_{ks}G_{ks}A_{ks}T_{ds}{}^{m}C_{ds}A_{ds}{}^{m}C_{ds}A_{ds}G_{ds}G_{ds}A_{ds}{}^{m}C_{ds}T_{ds}G_{ks}G_{ks}A_{k}$ | 24.8 | 2203 | 2218 | 444 |
| 486101 | ${}^{m}C_{ks}A_{ks}G_{ks}{}^{m}C_{ds}{}^{m}C_{ds}T_{ds}G_{ds}G_{ds}{}^{m}C_{ds}{}^{m}C_{ds}G_{ds}A_{ds}A_{ds}A_{ks}G_{ks}A_{k}$ | 31.6 | 2386 | 2401 | 445 |
| 486102 | ${}^{m}C_{ks}T_{ks}{}^{m}C_{ks}A_{ds}G_{ds}{}^{m}C_{ds}{}^{m}C_{ds}T_{ds}G_{ds}G_{ds}{}^{m}C_{ds}{}^{m}C_{ds}G_{ds}A_{ks}A_{ks}A_{k}$ | 35.1 | 2388 | 2403 | 446 |
| 486104 | $G_{ks}T_{ks}{}^{m}C_{ks}A_{ds}G_{ds}G_{ds}G_{ds}{}^{m}C_{ds}{}^{m}C_{ds}T_{ds}{}^{m}C_{ds}A_{ds}G_{ds}{}^{m}C_{ks}{}^{m}C_{ks}T_{k}$ | 26.9 | 2396 | 2411 | 447 |
| 486105 | ${}^{m}C_{ks}G_{ks}T_{ks}{}^{m}C_{ds}A_{ds}G_{ds}G_{ds}G_{ds}{}^{m}C_{ds}{}^{m}C_{ds}T_{ds}{}^{m}C_{ds}A_{ds}G_{ks}{}^{m}C_{ks}{}^{m}C_{k}$ | 48.4 | 2397 | 2412 | 448 |
| 486110 | $T_{ks}T_{ks}T_{ks}G_{ds}{}^{m}C_{ds}A_{ds}{}^{m}C_{ds}T_{ds}T_{ds}T_{ds}G_{ds}{}^{m}C_{ds}G_{ds}A_{ks}A_{ks}{}^{m}C_{k}$ | 31.6 | 2495 | 2510 | 449 |
| 486111 | $G_{ks}A_{ks}A_{ks}A_{ds}G_{ds}{}^{m}C_{ds}T_{ds}T_{ds}T_{ds}G_{ds}{}^{m}C_{ds}A_{ds}{}^{m}C_{ds}T_{ks}T_{ks}T_{k}$ | 31.9 | 2501 | 2516 | 450 |
| 486112 | $A_{ks}A_{ks}T_{ks}T_{ds}T_{ds}{}^{m}C_{ds}{}^{m}C_{ds}{}^{m}C_{ds}G_{ds}A_{ds}G_{ds}T_{ds}A_{ds}A_{ks}G_{ks}{}^{m}C_{k}$ | 47.4 | 2565 | 2580 | 451 |
| 486115 | $G_{ks}{}^{m}C_{ks}A_{ks}A_{ds}A_{ds}T_{ds}T_{ds}T_{ds}{}^{m}C_{ds}{}^{m}C_{ds}{}^{m}C_{ds}G_{ds}A_{ds}G_{ks}T_{ks}A_{k}$ | 20.8 | 2568 | 2583 | 452 |
| 486116 | $A_{ks}G_{ks}{}^{m}C_{ks}A_{ds}A_{ds}A_{ds}T_{ds}T_{ds}T_{ds}{}^{m}C_{ds}{}^{m}C_{ds}{}^{m}C_{ds}G_{ds}A_{ks}G_{ks}T_{k}$ | 23.9 | 2569 | 2584 | 453 |
| 486117 | $A_{ks}A_{ks}G_{ks}{}^{m}C_{ds}A_{ds}A_{ds}A_{ds}T_{ds}T_{ds}T_{ds}{}^{m}C_{ds}{}^{m}C_{ds}{}^{m}C_{ds}G_{ks}A_{ks}G_{k}$ | 22 | 2570 | 2585 | 454 |
| 486118 | $A_{ks}A_{ks}A_{ks}G_{ds}{}^{m}C_{ds}A_{ds}A_{ds}A_{ds}T_{ds}T_{ds}T_{ds}{}^{m}C_{ds}{}^{m}C_{ds}{}^{m}C_{ks}G_{ks}A_{k}$ | 26.7 | 2571 | 2586 | 455 |
| 486119 | $A_{ks}A_{ks}A_{ks}A_{ds}G_{ds}{}^{m}C_{ds}A_{ds}A_{ds}A_{ds}T_{ds}T_{ds}T_{ds}{}^{m}C_{ds}{}^{m}C_{ks}{}^{m}C_{ks}G_{k}$ | 33.5 | 2572 | 2587 | 456 |
| 486120 | $G_{ks}{}^{m}C_{ks}A_{ks}A_{ds}A_{ds}A_{ds}G_{ds}{}^{m}C_{ds}A_{ds}A_{ds}A_{ds}T_{ds}T_{ds}T_{ks}{}^{m}C_{ks}{}^{m}C_{k}$ | 51.4 | 2574 | 2589 | 457 |
| 486121 | $G_{ks}G_{ks}{}^{m}C_{ks}A_{ds}A_{ds}A_{ds}A_{ds}G_{ds}{}^{m}C_{ds}A_{ds}A_{ds}A_{ds}T_{ds}T_{ks}T_{ks}{}^{m}C_{k}$ | 60.8 | 2575 | 2590 | 458 |
| 486123 | $T_{ks}T_{ks}G_{ks}G_{ds}{}^{m}C_{ds}A_{ds}A_{ds}A_{ds}A_{ds}G_{ds}{}^{m}C_{ds}A_{ds}A_{ds}A_{ks}T_{ks}T_{k}$ | 39.8 | 2577 | 2592 | 459 |
| 486125 | $G_{ks}T_{ks}T_{ks}T_{ds}G_{ds}G_{ds}{}^{m}C_{ds}A_{ds}A_{ds}A_{ds}A_{ds}G_{ds}{}^{m}C_{ds}A_{ks}A_{ks}A_{k}$ | 32.7 | 2579 | 2594 | 460 |
| 486126 | $G_{ks}G_{ks}T_{ks}T_{ds}T_{ds}G_{ds}G_{ds}{}^{m}C_{ds}A_{ds}A_{ds}A_{ds}A_{ds}G_{ds}{}^{m}C_{ks}A_{ks}A_{k}$ | 19.2 | 2580 | 2595 | 461 |

TABLE 12-continued

Inhibition of human DMPK RNA transcript in HepG2 cells using ASOs targeting SEQ ID NO: 1

| ISIS No. | Sequence | % Target Expression | Start Site on Seq ID: 1 | Stop Site on Seq ID: 1 | Seq ID No. |
|---|---|---|---|---|---|
| 486127 | $G_{ks}G_{ks}G_{ks}T_{ds}T_{ds}T_{ds}G_{ds}G_{ds}{}^{m}C_{ds}A_{ds}A_{ds}A_{ds}A_{ds}G_{ks}{}^{m}C_{ks}A_{k}$ | 36.1 | 2581 | 2596 | 462 |
| 486128 | $G_{ks}{}^{m}C_{ks}G_{ks}G_{ds}G_{ds}T_{ds}T_{ds}T_{ds}G_{ds}G_{ds}{}^{m}C_{ds}A_{ds}A_{ds}A_{ks}A_{ks}G_{k}$ | 39.1 | 2583 | 2598 | 463 |
| 486129 | $A_{ks}G_{ks}{}^{m}C_{ks}G_{ds}G_{ds}G_{ds}T_{ds}T_{ds}T_{ds}G_{ds}G_{ds}{}^{m}C_{ds}A_{ds}A_{ks}A_{ks}A_{k}$ | 31.4 | 2584 | 2599 | 464 |
| 486130 | $A_{ks}A_{ks}G_{ks}{}^{m}C_{ds}G_{ds}G_{ds}G_{ds}T_{ds}T_{ds}T_{ds}G_{ds}G_{ds}{}^{m}C_{ds}A_{ks}A_{ks}A_{k}$ | 35.7 | 2585 | 2600 | 465 |
| 486133 | ${}^{m}C_{ks}T_{ks}{}^{m}C_{ks}{}^{m}C_{ds}G_{ds}A_{ds}G_{ds}A_{ds}G_{ds}{}^{m}C_{ds}A_{ds}G_{ds}{}^{m}C_{ds}G_{ks}{}^{m}C_{ks}A_{k}$ | 45.9 | 2631 | 2646 | 466 |
| 486134 | $G_{ks}{}^{m}C_{ks}T_{ks}{}^{m}C_{ds}{}^{m}C_{ds}G_{ds}A_{ds}G_{ds}A_{ds}G_{ds}{}^{m}C_{ds}A_{ds}G_{ds}{}^{m}C_{ks}G_{ks}{}^{m}C_{k}$ | 29.5 | 2632 | 2647 | 467 |
| 486135 | $G_{ks}G_{ks}{}^{m}C_{ks}T_{ds}{}^{m}C_{ds}{}^{m}C_{ds}G_{ds}A_{ds}G_{ds}A_{ds}G_{ds}{}^{m}C_{ds}A_{ds}G_{ks}{}^{m}C_{ks}G_{k}$ | 51.4 | 2633 | 2648 | 468 |
| 486142 | $T_{ks}A_{ks}A_{ks}A_{ds}T_{ds}A_{ds}T_{ds}{}^{m}C_{ds}{}^{m}C_{ds}A_{ds}A_{ds}A_{ds}{}^{m}C_{ds}{}^{m}C_{ks}G_{ks}{}^{m}C_{k}$ | 64.4 | 2671 | 2686 | 469 |
| 486147 | $G_{ks}T_{ks}{}^{m}C_{ks}A_{ds}A_{ds}T_{ds}A_{ds}A_{ds}A_{ds}T_{ds}A_{ds}T_{ds}{}^{m}C_{ds}{}^{m}C_{ks}A_{ks}A_{k}$ | 16.1 | 2676 | 2691 | 470 |
| 486148 | $A_{ks}G_{ks}G_{ks}T_{ds}{}^{m}C_{ds}A_{ds}A_{ds}T_{ds}A_{ds}A_{ds}A_{ds}T_{ds}A_{ds}T_{ks}{}^{m}C_{ks}{}^{m}C_{k}$ | 18.3 | 2678 | 2693 | 471 |
| 486149 | ${}^{m}C_{ks}G_{ks}A_{ks}G_{ds}G_{ds}T_{ds}{}^{m}C_{ds}A_{ds}A_{ds}T_{ds}A_{ds}A_{ds}A_{ds}T_{ks}A_{ks}T_{k}$ | 37.9 | 2680 | 2695 | 472 |
| 486150 | $A_{ks}{}^{m}C_{ks}G_{ks}A_{ds}G_{ds}G_{ds}T_{ds}{}^{m}C_{ds}A_{ds}A_{ds}T_{ds}A_{ds}A_{ds}A_{ks}T_{ks}A_{k}$ | 45.3 | 2681 | 2696 | 473 |
| 486151 | $G_{ks}A_{ks}{}^{m}C_{ks}G_{ds}A_{ds}G_{ds}G_{ds}T_{ds}{}^{m}C_{ds}A_{ds}A_{ds}T_{ds}A_{ds}A_{ks}A_{ks}T_{k}$ | 52.2 | 2682 | 2697 | 474 |
| 486152 | $G_{ks}G_{ks}A_{ks}{}^{m}C_{ds}G_{ds}A_{ds}G_{ds}G_{ds}T_{ds}{}^{m}C_{ds}A_{ds}A_{ds}T_{ds}A_{ks}A_{ks}A_{k}$ | 19.8 | 2683 | 2698 | 475 |
| 486153 | $A_{ks}G_{ks}G_{ks}A_{ds}{}^{m}C_{ds}G_{ds}A_{ds}G_{ds}G_{ds}T_{ds}{}^{m}C_{ds}A_{ds}A_{ds}T_{ks}A_{ks}A_{k}$ | 19.9 | 2684 | 2699 | 476 |
| 486154 | $G_{ks}A_{ks}G_{ks}G_{ds}A_{ds}{}^{m}C_{ds}G_{ds}A_{ds}G_{ds}G_{ds}T_{ds}{}^{m}C_{ds}A_{ds}A_{ks}T_{ks}A_{k}$ | 19.6 | 2685 | 2700 | 477 |
| 486155 | $G_{ks}G_{ks}A_{ks}G_{ds}G_{ds}A_{ds}{}^{m}C_{ds}G_{ds}A_{ds}G_{ds}G_{ds}T_{ds}{}^{m}C_{ds}A_{ks}A_{ks}T_{k}$ | 38.3 | 2686 | 2701 | 478 |
| 486156 | ${}^{m}C_{ks}G_{ks}G_{ks}A_{ds}G_{ds}G_{ds}A_{ds}{}^{m}C_{ds}G_{ds}A_{ds}G_{ds}G_{ds}T_{ds}{}^{m}C_{ks}A_{ks}A_{k}$ | 14.1 | 2687 | 2702 | 479 |
| 486157 | $T_{ks}{}^{m}C_{ks}G_{ks}G_{ds}A_{ds}G_{ds}G_{ds}A_{ds}{}^{m}C_{ds}G_{ds}A_{ds}G_{ds}G_{ds}T_{ks}{}^{m}C_{ks}A_{k}$ | 23.2 | 2688 | 2703 | 480 |
| 486158 | $G_{ks}T_{ks}{}^{m}C_{ks}G_{ds}G_{ds}A_{ds}G_{ds}G_{ds}A_{ds}{}^{m}C_{ds}G_{ds}A_{ds}G_{ds}G_{ks}T_{ks}{}^{m}C_{k}$ | 34.5 | 2689 | 2704 | 481 |
| 486159 | $A_{ks}G_{ks}T_{ks}{}^{m}C_{ds}G_{ds}G_{ds}A_{ds}G_{ds}G_{ds}A_{ds}{}^{m}C_{ds}G_{ds}A_{ds}G_{ks}G_{ks}T_{k}$ | 23.7 | 2690 | 2705 | 482 |
| 486160 | $G_{ks}A_{ks}G_{ks}T_{ds}{}^{m}C_{ds}G_{ds}G_{ds}A_{ds}G_{ds}G_{ds}A_{ds}{}^{m}C_{ds}G_{ds}A_{ks}G_{ks}G_{k}$ | 14.3 | 2691 | 2706 | 483 |
| 486161 | ${}^{m}C_{ks}G_{ks}A_{ks}G_{ds}T_{ds}{}^{m}C_{ds}G_{ds}G_{ds}A_{ds}G_{ds}G_{ds}A_{ds}{}^{m}C_{ds}G_{ks}A_{ks}G_{k}$ | 29 | 2692 | 2707 | 484 |
| 486162 | $A_{ks}G_{ks}{}^{m}C_{ks}G_{ds}A_{ds}G_{ds}T_{ds}{}^{m}C_{ds}G_{ds}G_{ds}A_{ds}G_{ds}G_{ds}A_{ks}{}^{m}C_{ks}G_{k}$ | 20.6 | 2694 | 2709 | 485 |
| 486163 | ${}^{m}C_{ks}A_{ks}G_{ks}{}^{m}C_{ds}G_{ds}A_{ds}G_{ds}T_{ds}{}^{m}C_{ds}G_{ds}G_{ds}A_{ds}G_{ds}G_{ks}A_{ks}{}^{m}C_{k}$ | 29 | 2695 | 2710 | 486 |
| 486164 | $T_{ks}{}^{m}C_{ks}A_{ks}G_{ds}{}^{m}C_{ds}G_{ds}A_{ds}G_{ds}T_{ds}{}^{m}C_{ds}G_{ds}G_{ds}A_{ds}G_{ks}G_{ks}A_{k}$ | 17 | 2696 | 2711 | 487 |
| 486165 | $G_{ks}T_{ks}{}^{m}C_{ks}A_{ds}G_{ds}{}^{m}C_{ds}G_{ds}A_{ds}G_{ds}T_{ds}{}^{m}C_{ds}G_{ds}G_{ds}A_{ks}G_{ks}G_{k}$ | 14.2 | 2697 | 2712 | 426 |
| 486166 | $T_{ks}G_{ks}T_{ks}{}^{m}C_{ds}A_{ds}G_{ds}{}^{m}C_{ds}G_{ds}A_{ds}G_{ds}T_{ds}{}^{m}C_{ds}G_{ds}G_{ks}A_{ks}G_{k}$ | 25.1 | 2698 | 2713 | 488 |
| 486167 | ${}^{m}C_{ks}T_{ks}G_{ks}T_{ds}{}^{m}C_{ds}A_{ds}G_{ds}{}^{m}C_{ds}G_{ds}A_{ds}G_{ds}T_{ds}{}^{m}C_{ds}G_{ks}G_{ks}A_{k}$ | 15 | 2699 | 2714 | 489 |
| 486168 | ${}^{m}C_{ks}{}^{m}C_{ks}T_{ks}G_{ds}T_{ds}{}^{m}C_{ds}A_{ds}G_{ds}{}^{m}C_{ds}G_{ds}A_{ds}G_{ds}T_{ds}{}^{m}C_{ks}G_{ks}G_{k}$ | 12.4 | 2700 | 2715 | 427 |
| 486169 | $G_{ks}{}^{m}C_{ks}{}^{m}C_{ks}T_{ds}G_{ds}T_{ds}{}^{m}C_{ds}A_{ds}G_{ds}{}^{m}C_{ds}G_{ds}A_{ds}G_{ds}T_{ks}{}^{m}C_{ks}G_{k}$ | 24.5 | 2701 | 2716 | 428 |
| 486170 | $A_{ks}G_{ks}{}^{m}C_{ks}{}^{m}C_{ds}T_{ds}G_{ds}T_{ds}{}^{m}C_{ds}A_{ds}G_{ds}{}^{m}C_{ds}G_{ds}A_{ds}G_{ks}T_{ks}{}^{m}C_{k}$ | 16.3 | 2702 | 2717 | 429 |
| 486171 | ${}^{m}C_{ks}A_{ks}G_{ks}T_{ds}G_{ds}{}^{m}C_{ds}A_{ds}T_{ds}{}^{m}C_{ds}{}^{m}C_{ds}A_{ds}A_{ds}A_{ds}A_{ks}{}^{m}C_{ks}G_{k}$ | 31.8 | 2744 | 2759 | 490 |
| 486172 | $T_{ks}{}^{m}C_{ks}A_{ks}G_{ds}T_{ds}G_{ds}{}^{m}C_{ds}A_{ds}T_{ds}{}^{m}C_{ds}{}^{m}C_{ds}A_{ds}A_{ds}A_{ks}A_{ks}{}^{m}C_{k}$ | 23.1 | 2745 | 2760 | 491 |
| 486173 | ${}^{m}C_{ks}T_{ks}{}^{m}C_{ks}A_{ds}G_{ds}T_{ds}G_{ds}{}^{m}C_{ds}A_{ds}T_{ds}{}^{m}C_{ds}{}^{m}C_{ds}A_{ds}A_{ks}A_{ks}A_{k}$ | 23 | 2746 | 2761 | 492 |
| 486174 | $T_{ks}{}^{m}C_{ks}T_{ks}{}^{m}C_{ds}A_{ds}G_{ds}T_{ds}G_{ds}{}^{m}C_{ds}A_{ds}T_{ds}{}^{m}C_{ds}{}^{m}C_{ds}A_{ks}A_{ks}A_{k}$ | 50.9 | 2747 | 2762 | 493 |

TABLE 12-continued

Inhibition of human DMPK RNA transcript in HepG2 cells using ASOs targeting SEQ ID NO: 1

| ISIS No. | Sequence | % Target Expression | Start Site on Seq ID: 1 | Stop Site on Seq ID: 1 | Seq ID No. |
|---|---|---|---|---|---|
| 486175 | $G_{ks}T_{ks}{}^mC_{ks}T_{ds}{}^mC_{ds}A_{ds}G_{ds}T_{ds}G_{ds}{}^mC_{ds}A_{ds}T_{ds}{}^mC_{ds}{}^mC_{ks}A_{ks}A_k$ | 17.2 | 2748 | 2763 | 494 |
| 486176 | $G_{ks}G_{ks}G_{ks}T_{ds}{}^mC_{ds}T_{ds}{}^mC_{ds}A_{ds}G_{ds}T_{ds}G_{ds}{}^mC_{ds}A_{ds}T_{ks}{}^mC_{ks}{}^mC_k$ | 37.6 | 2750 | 2765 | 430 |
| 486177 | ${}^mC_{ks}A_{ks}A_{ks}T_{ds}A_{ds}A_{ds}A_{ds}T_{ds}A_{ds}{}^mC_{ds}{}^mC_{ds}G_{ds}A_{ds}G_{ks}G_{ks}A_k$ | 40 | 2772 | 2787 | 495 |
| 486178 | $A_{ks}{}^mC_{ks}A_{ks}A_{ds}T_{ds}A_{ds}A_{ds}A_{ds}T_{ds}A_{ds}{}^mC_{ds}{}^mC_{ds}G_{ds}A_{ks}G_{ks}G_k$ | 11.3 | 2773 | 2788 | 23 |
| 486179 | $A_{ks}G_{ks}A_{ks}{}^mC_{ds}A_{ds}A_{ds}T_{ds}A_{ds}A_{ds}A_{ds}T_{ds}A_{ds}{}^mC_{ds}{}^mC_{ks}G_{ks}A_k$ | 13.5 | 2775 | 2790 | 496 |
| 486180 | ${}^mC_{ks}A_{ks}G_{ks}A_{ds}{}^mC_{ds}A_{ds}A_{ds}T_{ds}A_{ds}A_{ds}A_{ds}T_{ds}A_{ds}{}^mC_{ks}{}^mC_{ks}G_k$ | 18.6 | 2776 | 2791 | 497 |

Example 9: ASOs Designed to Target a Human DMPK RNA Transcript

A series of antisense oligonucleotides (ASOs) were designed to target hDMPK. The newly designed ASOs were prepared using standard oligonucleotide synthesis well known in the art and are described in Table 13 to 18, below. Subscripts "s" indicate phosphorothioate internucleoside linkages; subscripts "k" indicate 6'-(S)—$CH_3$ bicyclic nucleosides (cEt); subscripts "e" indicate 2'-methoxyethyl (MOE) modified nucleosides; and subscripts "d" indicate β-D-2'-deoxyribonucleosides. "${}^mC$" indicates 5-methylcytosine nucleosides.

The antisense oligonucleotides targeted to a human DMPK nucleic acid were tested for their effect on DMPK RNA transcript in vitro. Cultured HepG2 cells at a density of 20,000 cells per well were transfected using electroporation with 4,500 nM antisense oligonucleotide. After approximately 24 hours, RNA was isolated from the cells and DMPK transcript levels were measured by quantitative real-time PCR. DMPK RNA transcript levels were adjusted according to total RNA content, as measured by RIBOGREEN®. Results are presented as percent expression of DMPK, relative to untreated control cells, with "% Target Expression" representing the percent expression of DMPK relative to untreated control cells All the antisense oligonucleotides listed in Table 13 target SEQ TD NO: 1 (GENBANK Accession No. NM_001081560.1). All the antisense oligonucleotides listed in Table 14 to 18 target SEQ ID NO: 2 (the complement of GENBANK Accession No. NT_011109.15 truncated from nucleotides 18540696 to 18555106). 'Target start site' indicates the 5'-most nucleoside to which the antisense oligonucleotide is targeted in the human genomic gene sequence. 'Target stop site' indicates the 3'-most nucleoside to which the antisense oligonucleotide is targeted in the human genomic sequence.

TABLE 13

Inhibition of human DMPK RNA transcript in HepG2 cells targeting SEQ ID NO: 1

| ISIS No. | Sequence | % Target Expression | Start Site on Seq ID: 1 | Stop Site on Seq ID: 1 | Seq ID No. |
|---|---|---|---|---|---|
| UTC | N/A | 100 | N/A | N/A | |
| 445569 | ${}^mC_{es}G_{es}G_{es}A_{es}G_{es}{}^mC_{ds}G_{ds}G_{ds}T_{ds}T_{ds}G_{ds}T_{ds}G_{ds}A_{ds}A_{ds}{}^mC_{es}T_{es}G_{es}G_{es}{}^mC_e$ | 36.7 | 2163 | 2182 | 24 |
| 486178 | $A_{ks}{}^mC_{ks}A_{ks}A_{ds}T_{ds}A_{ds}A_{ds}A_{ds}T_{ds}A_{ds}{}^mC_{ds}{}^mC_{ds}G_{ds}A_{ks}G_{ks}G_k$ | 21.3 | 2773 | 2788 | 23 |
| 569403 | ${}^mC_{ks}A_{ks}{}^mC_{ks}G_{ds}G_{ds}A_{ds}A_{ds}G_{ds}{}^mC_{ds}A_{ds}{}^mC_{ds}G_{ds}A_{ds}{}^mC_{ks}A_{ks}{}^mC_k$ | 18.8 | 542 | 557 | 498 |
| 569404 | $T_{ks}{}^mC_{ks}A_{ks}{}^mC_{ds}G_{ds}G_{ds}A_{ds}A_{ds}G_{ds}{}^mC_{ds}A_{ds}{}^mC_{ds}G_{ds}A_{ks}{}^mC_{ks}A_k$ | 25.2 | 543 | 558 | 499 |
| 569405 | ${}^mC_{ks}T_{ks}{}^mC_{ks}A_{ds}{}^mC_{ds}G_{ds}G_{ds}A_{ds}A_{ds}G_{ds}{}^mC_{ds}A_{ds}{}^mC_{ds}G_{ks}A_{ks}{}^mC_k$ | 21.2 | 544 | 559 | 500 |
| 569406 | ${}^mC_{ks}{}^mC_{ks}T_{ks}{}^mC_{ds}T_{ds}{}^mC_{ds}{}^mC_{ds}T_{ds}{}^mC_{ds}A_{ds}{}^mC_{ds}G_{ds}G_{ds}A_{ks}A_{ks}G_k$ | 27.9 | 550 | 565 | 343 |
| 569407 | $G_{ks}T_{ks}{}^mC_{ks}{}^mC_{ds}{}^mC_{ds}T_{ds}{}^mC_{ds}T_{ds}{}^mC_{ds}{}^mC_{ds}T_{ds}{}^mC_{ds}A_{ds}{}^mC_{ks}G_{ks}G_k$ | 30.9 | 553 | 568 | 501 |
| 569408 | ${}^mC_{ks}G_{ks}T_{ks}{}^mC_{ds}{}^mC_{ds}{}^mC_{ds}T_{ds}{}^mC_{ds}T_{ds}{}^mC_{ds}{}^mC_{ds}T_{ds}{}^mC_{ds}A_{ks}{}^mC_{ks}G_k$ | 32.8 | 554 | 569 | 502 |
| 569409 | ${}^mC_{ks}{}^mC_{ks}{}^mC_{ks}A_{ds}T_{ds}T_{ds}{}^mC_{ds}A_{ds}{}^mC_{ds}{}^mC_{ds}A_{ds}A_{ds}{}^mC_{ds}A_{ks}{}^mC_{ks}G_k$ | 33 | 568 | 583 | 503 |
| 569410 | ${}^mC_{ks}{}^mC_{ks}{}^mC_{ks}{}^mC_{ds}A_{ds}T_{ds}T_{ds}{}^mC_{ds}A_{ds}{}^mC_{ds}{}^mC_{ds}A_{ds}A_{ds}{}^mC_{ks}A_{ks}{}^mC_k$ | 42.1 | 569 | 584 | 504 |
| 569411 | $T_{ks}{}^mC_{ks}{}^mC_{ks}{}^mC_{ds}{}^mC_{ds}A_{ds}T_{ds}T_{ds}{}^mC_{ds}A_{ds}{}^mC_{ds}{}^mC_{ds}A_{ds}A_{ks}{}^mC_{ks}A_k$ | 68.6 | 570 | 585 | 505 |
| 569412 | $G_{ks}T_{ks}{}^mC_{ks}{}^mC_{ds}{}^mC_{ds}{}^mC_{ds}A_{ds}T_{ds}T_{ds}{}^mC_{ds}A_{ds}{}^mC_{ds}{}^mC_{ds}A_{ks}A_{ks}{}^mC_k$ | 60.7 | 571 | 586 | 506 |

TABLE 13-continued

Inhibition of human DMPK RNA transcript in HepG2 cells targeting SEQ ID NO: 1

| ISIS No. | Sequence | % Target Expression | Start Site on Seq ID: 1 | Stop Site on Seq ID: 1 | Seq ID No. |
|---|---|---|---|---|---|
| 569413 | $G_{ks}G_{ks}T_{ks}{}^{m}C_{ds}{}^{m}C_{ds}{}^{m}C_{ds}{}^{m}C_{ds}A_{ds}T_{ds}T_{ds}{}^{m}C_{ds}A_{ds}{}^{m}C_{ds}{}^{m}C_{ks}A_{ks}A_{k}$ | 65.1 | 572 | 587 | 507 |
| 569414 | ${}^{m}C_{ks}G_{ks}G_{ks}T_{ds}{}^{m}C_{ds}{}^{m}C_{ds}{}^{m}C_{ds}{}^{m}C_{ds}A_{ds}T_{ds}T_{ds}{}^{m}C_{ds}A_{ds}{}^{m}C_{ks}{}^{m}C_{ks}A_{k}$ | 54.4 | 573 | 588 | 508 |
| 569415 | ${}^{m}C_{ks}{}^{m}C_{ks}G_{ks}G_{ds}T_{ds}{}^{m}C_{ds}{}^{m}C_{ds}{}^{m}C_{ds}{}^{m}C_{ds}A_{ds}T_{ds}T_{ds}{}^{m}C_{ds}A_{ks}{}^{m}C_{ks}{}^{m}C_{k}$ | 51.3 | 574 | 589 | 509 |
| 569416 | $G_{ks}{}^{m}C_{ks}{}^{m}C_{ks}G_{ds}G_{ds}T_{ds}{}^{m}C_{ds}{}^{m}C_{ds}{}^{m}C_{ds}{}^{m}C_{ds}A_{ds}T_{ds}T_{ds}{}^{m}C_{ks}A_{ks}{}^{m}C_{k}$ | 57.9 | 575 | 590 | 510 |
| 569417 | ${}^{m}C_{ks}G_{ks}{}^{m}C_{ks}{}^{m}C_{ds}G_{ds}G_{ds}T_{ds}{}^{m}C_{ds}{}^{m}C_{ds}{}^{m}C_{ds}{}^{m}C_{ds}A_{ds}T_{ds}T_{ks}{}^{m}C_{ks}A_{k}$ | 43.2 | 576 | 591 | 511 |
| 569418 | ${}^{m}C_{ks}{}^{m}C_{ks}G_{ks}{}^{m}C_{ds}{}^{m}C_{ds}G_{ds}G_{ds}T_{ds}{}^{m}C_{ds}{}^{m}C_{ds}{}^{m}C_{ds}{}^{m}C_{ds}A_{ds}T_{ks}T_{ks}{}^{m}C_{k}$ | 79.3 | 577 | 592 | 512 |
| 569419 | $A_{ks}{}^{m}C_{ks}{}^{m}C_{ks}G_{ds}{}^{m}C_{ds}{}^{m}C_{ds}G_{ds}G_{ds}T_{ds}{}^{m}C_{ds}{}^{m}C_{ds}{}^{m}C_{ds}{}^{m}C_{ds}A_{ks}T_{ks}T_{k}$ | 36 | 578 | 593 | 513 |
| 569420 | ${}^{m}C_{ks}A_{ks}{}^{m}C_{ks}{}^{m}C_{ds}G_{ds}{}^{m}C_{ds}{}^{m}C_{ds}G_{ds}G_{ds}T_{ds}{}^{m}C_{ds}{}^{m}C_{ds}{}^{m}C_{ds}{}^{m}C_{ks}A_{ks}T_{k}$ | 36.2 | 579 | 594 | 514 |
| 569421 | ${}^{m}C_{ks}{}^{m}C_{ks}A_{ks}{}^{m}C_{ds}{}^{m}C_{ds}G_{ds}{}^{m}C_{ds}{}^{m}C_{ds}G_{ds}G_{ds}T_{ds}{}^{m}C_{ds}{}^{m}C_{ds}{}^{m}C_{ks}{}^{m}C_{ks}A_{k}$ | 34.7 | 580 | 595 | 515 |
| 569422 | $T_{ks}{}^{m}C_{ks}{}^{m}C_{ks}A_{ds}{}^{m}C_{ds}{}^{m}C_{ds}G_{ds}{}^{m}C_{ds}{}^{m}C_{ds}G_{ds}G_{ds}T_{ds}{}^{m}C_{ds}{}^{m}C_{ks}{}^{m}C_{ks}{}^{m}C_{k}$ | 40 | 581 | 596 | 516 |
| 569423 | $A_{ks}T_{ks}{}^{m}C_{ks}{}^{m}C_{ds}A_{ds}{}^{m}C_{ds}{}^{m}C_{ds}G_{ds}{}^{m}C_{ds}{}^{m}C_{ds}G_{ds}G_{ds}T_{ds}{}^{m}C_{ks}{}^{m}C_{ks}{}^{m}C_{k}$ | 31.6 | 582 | 597 | 517 |
| 569424 | $G_{ks}A_{ks}T_{ks}{}^{m}C_{ds}{}^{m}C_{ds}A_{ds}{}^{m}C_{ds}{}^{m}C_{ds}G_{ds}{}^{m}C_{ds}{}^{m}C_{ds}G_{ds}G_{ds}T_{ks}{}^{m}C_{ks}{}^{m}C_{k}$ | 56 | 583 | 598 | 518 |
| 569425 | $T_{ks}G_{ks}A_{ks}T_{ds}{}^{m}C_{ds}{}^{m}C_{ds}A_{ds}{}^{m}C_{ds}{}^{m}C_{ds}G_{ds}{}^{m}C_{ds}{}^{m}C_{ds}G_{ds}G_{ks}T_{ks}{}^{m}C_{k}$ | 53.9 | 584 | 599 | 519 |
| 569426 | $G_{ks}T_{ks}G_{ks}A_{ds}T_{ds}{}^{m}C_{ds}{}^{m}C_{ds}A_{ds}{}^{m}C_{ds}{}^{m}C_{ds}G_{ds}{}^{m}C_{ds}{}^{m}C_{ds}G_{ks}G_{ks}T_{k}$ | 54.1 | 585 | 600 | 520 |
| 569427 | ${}^{m}C_{ks}G_{ks}T_{ks}G_{ds}A_{ds}T_{ds}{}^{m}C_{ds}{}^{m}C_{ds}A_{ds}{}^{m}C_{ds}{}^{m}C_{ds}G_{ds}{}^{m}C_{ds}{}^{m}C_{ks}G_{ks}G_{k}$ | 34.8 | 586 | 601 | 521 |
| 569428 | ${}^{m}C_{ks}A_{ks}T_{ks}{}^{m}C_{ds}{}^{m}C_{ds}T_{ds}G_{ds}G_{ds}A_{ds}A_{ds}G_{ds}G_{ds}{}^{m}C_{ds}G_{ks}A_{ks}A_{k}$ | 71 | 611 | 626 | 522 |
| 569429 | $T_{ks}{}^{m}C_{ks}A_{ks}T_{ds}{}^{m}C_{ds}{}^{m}C_{ds}T_{ds}G_{ds}G_{ds}A_{ds}A_{ds}G_{ds}G_{ds}{}^{m}C_{ks}G_{ks}A_{k}$ | 51.1 | 612 | 627 | 523 |
| 569430 | $A_{ks}G_{ks}T_{ks}T_{ds}{}^{m}C_{ds}T_{ds}{}^{m}C_{ds}A_{ds}T_{ds}{}^{m}C_{ds}{}^{m}C_{ds}T_{ds}G_{ds}G_{ks}A_{ks}A_{k}$ | 69.2 | 617 | 632 | 524 |
| 569431 | $T_{ks}A_{ks}G_{ks}T_{ds}T_{ds}{}^{m}C_{ds}T_{ds}{}^{m}C_{ds}A_{ds}T_{ds}{}^{m}C_{ds}{}^{m}C_{ds}T_{ds}G_{ks}G_{ks}A_{k}$ | 48.6 | 618 | 633 | 525 |
| 569432 | $G_{ks}T_{ks}A_{ks}G_{ds}T_{ds}T_{ds}{}^{m}C_{ds}T_{ds}{}^{m}C_{ds}A_{ds}T_{ds}{}^{m}C_{ds}{}^{m}C_{ds}T_{ks}G_{ks}G_{k}$ | 29.6 | 619 | 634 | 526 |
| 569433 | ${}^{m}C_{ks}A_{ks}G_{ks}G_{ds}T_{ds}A_{ds}{}^{m}C_{ds}A_{ds}G_{ds}G_{ds}T_{ds}A_{ds}G_{ds}T_{ks}T_{ks}{}^{m}C_{k}$ | 36.5 | 628 | 643 | 527 |
| 569434 | ${}^{m}C_{ks}{}^{m}C_{ks}A_{ks}G_{ds}G_{ds}T_{ds}A_{ds}{}^{m}C_{ds}A_{ds}G_{ds}G_{ds}T_{ds}A_{ds}G_{ks}T_{ks}T_{k}$ | 51 | 629 | 644 | 528 |
| 569435 | $G_{ks}A_{ks}{}^{m}C_{ks}{}^{m}C_{ds}A_{ds}G_{ds}G_{ds}T_{ds}A_{ds}{}^{m}C_{ds}A_{ds}G_{ds}G_{ds}T_{ks}A_{ks}G_{k}$ | 49.9 | 631 | 646 | 529 |
| 569436 | ${}^{m}C_{ks}T_{ks}{}^{m}C_{ks}{}^{m}C_{ds}A_{ds}T_{ds}G_{ds}A_{ds}{}^{m}C_{ds}{}^{m}C_{ds}A_{ds}G_{ds}G_{ds}T_{ks}A_{ks}{}^{m}C_{k}$ | 41 | 637 | 652 | 530 |
| 569437 | $A_{ks}{}^{m}C_{ks}T_{ks}{}^{m}C_{ds}{}^{m}C_{ds}A_{ds}T_{ds}G_{ds}A_{ds}{}^{m}C_{ds}{}^{m}C_{ds}A_{ds}G_{ds}G_{ks}T_{ks}A_{k}$ | 32.9 | 638 | 653 | 531 |
| 569438 | $T_{ks}A_{ks}{}^{m}C_{ks}T_{ds}{}^{m}C_{ds}{}^{m}C_{ds}A_{ds}T_{ds}G_{ds}A_{ds}{}^{m}C_{ds}{}^{m}C_{ds}A_{ds}G_{ks}G_{ks}T_{k}$ | 25.7 | 639 | 654 | 532 |
| 569439 | $A_{ks}T_{ks}A_{ks}{}^{m}C_{ds}T_{ds}{}^{m}C_{ds}{}^{m}C_{ds}A_{ds}T_{ds}G_{ds}A_{ds}{}^{m}C_{ds}{}^{m}C_{ds}A_{ks}G_{ks}G_{k}$ | 9.4 | 640 | 655 | 533 |
| 569440 | $A_{ks}A_{ks}T_{ks}A_{ds}{}^{m}C_{ds}T_{ds}{}^{m}C_{ds}{}^{m}C_{ds}A_{ds}T_{ds}G_{ds}A_{ds}{}^{m}C_{ds}{}^{m}C_{ks}A_{ks}G_{k}$ | 21.2 | 641 | 656 | 534 |
| 569441 | $T_{ks}A_{ks}A_{ks}T_{ds}A_{ds}{}^{m}C_{ds}T_{ds}{}^{m}C_{ds}{}^{m}C_{ds}A_{ds}T_{ds}G_{ds}A_{ds}{}^{m}C_{ks}{}^{m}C_{ks}A_{k}$ | 30.8 | 642 | 657 | 535 |
| 569442 | $G_{ks}T_{ks}A_{ks}A_{ds}T_{ds}A_{ds}{}^{m}C_{ds}T_{ds}{}^{m}C_{ds}{}^{m}C_{ds}A_{ds}T_{ds}G_{ds}A_{ks}{}^{m}C_{ks}{}^{m}C_{k}$ | 29.8 | 643 | 658 | 536 |
| 569443 | ${}^{m}C_{ks}G_{ks}T_{ks}A_{ds}A_{ds}T_{ds}A_{ds}{}^{m}C_{ds}T_{ds}{}^{m}C_{ds}{}^{m}C_{ds}A_{ds}T_{ds}G_{ks}A_{ks}{}^{m}C_{k}$ | 25.3 | 644 | 659 | 537 |
| 569444 | ${}^{m}C_{ks}T_{ks}T_{ks}G_{ds}{}^{m}C_{ds}T_{ds}{}^{m}C_{ds}A_{ds}G_{ds}{}^{m}C_{ds}A_{ds}G_{ds}T_{ds}G_{ks}T_{ks}{}^{m}C_{k}$ | 19.3 | 676 | 691 | 538 |
| 569445 | $A_{ks}{}^{m}C_{ks}T_{ks}T_{ds}G_{ds}{}^{m}C_{ds}T_{ds}{}^{m}C_{ds}A_{ds}G_{ds}{}^{m}C_{ds}A_{ds}G_{ds}T_{ks}G_{ks}T_{k}$ | 35 | 677 | 692 | 539 |
| 569446 | $A_{ks}A_{ks}{}^{m}C_{ks}T_{ds}T_{ds}G_{ds}{}^{m}C_{ds}T_{ds}{}^{m}C_{ds}A_{ds}G_{ds}{}^{m}C_{ds}A_{ds}G_{ks}T_{ks}G_{k}$ | 30 | 678 | 693 | 540 |
| 569447 | $A_{ks}A_{ks}A_{ks}{}^{m}C_{ds}T_{ds}T_{ds}G_{ds}{}^{m}C_{ds}T_{ds}{}^{m}C_{ds}A_{ds}G_{ds}{}^{m}C_{ds}A_{ks}G_{ks}T_{k}$ | 32.2 | 679 | 694 | 344 |
| 569448 | ${}^{m}C_{ks}{}^{m}C_{ks}A_{ks}A_{ds}A_{ds}{}^{m}C_{ds}T_{ds}T_{ds}G_{ds}{}^{m}C_{ds}T_{ds}{}^{m}C_{ds}A_{ds}G_{ks}{}^{m}C_{ks}A_{k}$ | 30.1 | 681 | 696 | 346 |

TABLE 13-continued

Inhibition of human DMPK RNA transcript in HepG2 cells targeting SEQ ID NO: 1

| ISIS No. | Sequence | % Target Expression | Start Site on Seq ID: 1 | Stop Site on Seq ID: 1 | Seq ID No. |
|---|---|---|---|---|---|
| 569449 | $^mC_{ks}{}^mC_{ks}{}^mC_{ks}A_{ds}A_{ds}A_{ds}{}^mC_{ds}T_{ds}T_{ds}G_{ds}{}^mC_{ds}T_{ds}{}^mC_{ds}A_{ks}G_{ks}{}^mC_k$ | 18.4 | 682 | 697 | 347 |
| 569450 | $^mC_{ks}{}^mC_{ks}{}^mC_{ks}{}^mC_{ds}A_{ds}A_{ds}A_{ds}{}^mC_{ds}T_{ds}T_{ds}G_{ds}{}^mC_{ds}T_{ds}{}^mC_{ks}A_{ks}G_k$ | 44.8 | 683 | 698 | 348 |
| 569451 | $G_{ks}{}^mC_{ks}T_{ks}{}^mC_{ds}{}^mC_{ds}{}^mC_{ds}{}^mC_{ds}A_{ds}A_{ds}A_{ds}{}^mC_{ds}T_{ds}T_{ds}G_{ks}{}^mC_{ks}T_k$ | 47 | 686 | 701 | 541 |
| 569452 | $^mC_{ks}G_{ks}{}^mC_{ks}T_{ds}{}^mC_{ds}{}^mC_{ds}{}^mC_{ds}{}^mC_{ds}{}^mC_{ds}A_{ds}A_{ds}A_{ds}{}^mC_{ds}T_{ds}T_{ks}G_{ks}{}^mC_k$ | 35.4 | 687 | 702 | 542 |
| 569453 | $^mC_{ks}{}^mC_{ks}G_{ks}{}^mC_{ds}T_{ds}{}^mC_{ds}{}^mC_{ds}{}^mC_{ds}{}^mC_{ds}A_{ds}A_{ds}A_{ds}{}^mC_{ds}T_{ks}T_{ks}G_k$ | 46.6 | 688 | 703 | 543 |
| 569454 | $T_{ks}{}^mC_{ks}{}^mC_{ks}G_{ds}{}^mC_{ds}T_{ds}{}^mC_{ds}{}^mC_{ds}{}^mC_{ds}{}^mC_{ds}A_{ds}A_{ds}A_{ds}{}^mC_{ks}T_{ks}T_k$ | 29.4 | 689 | 704 | 544 |
| 569455 | $A_{ks}T_{ks}{}^mC_{ks}{}^mC_{ds}G_{ds}{}^mC_{ds}T_{ds}{}^mC_{ds}{}^mC_{ds}{}^mC_{ds}{}^mC_{ds}A_{ds}A_{ds}A_{ks}{}^mC_{ks}T_k$ | 36.9 | 690 | 705 | 545 |
| 569456 | $A_{ks}A_{ks}T_{ks}{}^mC_{ds}{}^mC_{ds}G_{ds}{}^mC_{ds}T_{ds}{}^mC_{ds}{}^mC_{ds}{}^mC_{ds}{}^mC_{ds}A_{ds}A_{ks}A_{ks}{}^mC_k$ | 32.9 | 691 | 706 | 546 |
| 569457 | $G_{ks}A_{ks}A_{ks}T_{ds}{}^mC_{ds}{}^mC_{ds}G_{ds}{}^mC_{ds}T_{ds}{}^mC_{ds}{}^mC_{ds}{}^mC_{ds}{}^mC_{ds}A_{ks}A_{ks}A_k$ | 41.7 | 692 | 707 | 547 |
| 569458 | $G_{ks}G_{ks}A_{ks}A_{ds}T_{ds}{}^mC_{ds}{}^mC_{ds}G_{ds}{}^mC_{ds}T_{ds}{}^mC_{ds}{}^mC_{ds}{}^mC_{ds}{}^mC_{ks}A_{ks}A_k$ | 36.4 | 693 | 708 | 548 |
| 569459 | $^mC_{ks}G_{ks}G_{ks}A_{ds}A_{ds}T_{ds}{}^mC_{ds}{}^mC_{ds}G_{ds}{}^mC_{ds}T_{ds}{}^mC_{ds}{}^mC_{ds}{}^mC_{ks}{}^mC_{ks}A_k$ | 30 | 694 | 709 | 549 |
| 569460 | $^mC_{ks}{}^mC_{ks}G_{ks}G_{ds}A_{ds}A_{ds}T_{ds}{}^mC_{ds}{}^mC_{ds}G_{ds}{}^mC_{ds}T_{ds}{}^mC_{ds}{}^mC_{ks}{}^mC_{ks}{}^mC_k$ | 26.5 | 695 | 710 | 550 |
| 569461 | $G_{ks}{}^mC_{ks}{}^mC_{ks}G_{ds}G_{ds}A_{ds}A_{ds}T_{ds}{}^mC_{ds}{}^mC_{ds}G_{ds}{}^mC_{ds}T_{ds}{}^mC_{ks}{}^mC_{ks}{}^mC_k$ | 36.5 | 696 | 711 | 551 |
| 569462 | $A_{ks}G_{ks}A_{ks}A_{ds}G_{ds}{}^mC_{ds}G_{ds}{}^mC_{ds}G_{ds}{}^mC_{ds}{}^mC_{ds}A_{ds}T_{ds}{}^mC_{ks}T_{ks}{}^mC_k$ | 26 | 713 | 728 | 552 |
| 569463 | $T_{ks}A_{ks}G_{ks}A_{ds}A_{ds}G_{ds}{}^mC_{ds}G_{ds}{}^mC_{ds}G_{ds}{}^mC_{ds}{}^mC_{ds}A_{ds}T_{ks}{}^mC_{ks}T_k$ | 40.3 | 714 | 729 | 553 |
| 569464 | $G_{ks}T_{ks}A_{ks}G_{ds}A_{ds}A_{ds}G_{ds}{}^mC_{ds}G_{ds}{}^mC_{ds}G_{ds}{}^mC_{ds}{}^mC_{ds}A_{ks}T_{ks}{}^mC_k$ | 28.9 | 715 | 730 | 554 |
| 569465 | $G_{ks}G_{ks}T_{ks}A_{ds}G_{ds}A_{ds}A_{ds}G_{ds}{}^mC_{ds}G_{ds}{}^mC_{ds}G_{ds}{}^mC_{ds}{}^mC_{ks}A_{ks}T_k$ | 35.7 | 716 | 731 | 555 |
| 569466 | $A_{ks}G_{ks}G_{ks}T_{ds}A_{ds}G_{ds}A_{ds}A_{ds}G_{ds}{}^mC_{ds}G_{ds}{}^mC_{ds}G_{ds}{}^mC_{ks}{}^mC_{ks}A_k$ | 31.1 | 717 | 732 | 556 |
| 569467 | $^mC_{ks}A_{ks}G_{ks}G_{ds}T_{ds}A_{ds}G_{ds}A_{ds}A_{ds}G_{ds}{}^mC_{ds}G_{ds}{}^mC_{ds}G_{ks}{}^mC_{ks}{}^mC_k$ | 14.8 | 718 | 733 | 557 |
| 569468 | $^mC_{ks}{}^mC_{ks}A_{ks}G_{ds}G_{ds}T_{ds}A_{ds}G_{ds}A_{ds}A_{ds}G_{ds}{}^mC_{ds}G_{ds}{}^mC_{ks}G_{ks}{}^mC_k$ | 32.1 | 719 | 734 | 558 |
| 569469 | $G_{ks}{}^mC_{ks}{}^mC_{ks}A_{ds}G_{ds}G_{ds}T_{ds}A_{ds}G_{ds}A_{ds}A_{ds}G_{ds}{}^mC_{ds}G_{ks}{}^mC_{ks}G_k$ | 54.5 | 720 | 735 | 559 |
| 569470 | $^mC_{ks}G_{ks}{}^mC_{ks}{}^mC_{ds}A_{ds}G_{ds}G_{ds}T_{ds}A_{ds}G_{ds}A_{ds}A_{ds}G_{ds}{}^mC_{ks}G_{ks}{}^mC_k$ | 50.5 | 721 | 736 | 560 |
| 569471 | $^mC_{ks}{}^mC_{ks}G_{ks}{}^mC_{ds}{}^mC_{ds}A_{ds}G_{ds}G_{ds}T_{ds}A_{ds}G_{ds}A_{ds}A_{ds}G_{ks}{}^mC_{ks}G_k$ | 56.6 | 722 | 737 | 561 |
| 569472 | $T_{ks}{}^mC_{ks}{}^mC_{ks}G_{ds}{}^mC_{ds}{}^mC_{ds}A_{ds}G_{ds}G_{ds}T_{ds}A_{ds}G_{ds}A_{ds}A_{ks}G_{ks}{}^mC_k$ | 44.1 | 723 | 738 | 562 |
| 569473 | $G_{ks}A_{ks}{}^mC_{ks}A_{ds}A_{ds}A_{ds}T_{ds}{}^mC_{ds}T_{ds}{}^mC_{ds}{}^mC_{ds}G_{ds}{}^mC_{ds}A_{ks}G_{ks}G_k$ | 14.2 | 730 | 745 | 29 |
| 569474 | $T_{ks}G_{ks}A_{ks}{}^mC_{ds}A_{ds}A_{ds}A_{ds}T_{ds}{}^mC_{ds}T_{ds}{}^mC_{ds}{}^mC_{ds}G_{ds}{}^mC_{ds}{}^mC_{ks}A_{ks}G_k$ | 25.9 | 731 | 746 | 563 |
| 569475 | $A_{ks}T_{ks}G_{ks}A_{ds}{}^mC_{ds}A_{ds}A_{ds}T_{ds}{}^mC_{ds}T_{ds}{}^mC_{ds}{}^mC_{ds}G_{ds}{}^mC_{ks}{}^mC_{ks}A_k$ | 28.7 | 732 | 747 | 564 |
| 569476 | $^mC_{ks}A_{ks}T_{ks}G_{ds}A_{ds}{}^mC_{ds}A_{ds}A_{ds}T_{ds}{}^mC_{ds}T_{ds}{}^mC_{ds}{}^mC_{ds}G_{ks}{}^mC_{ks}{}^mC_k$ | 27.4 | 733 | 748 | 565 |
| 569477 | $^mC_{ks}{}^mC_{ks}A_{ks}T_{ds}G_{ds}A_{ds}{}^mC_{ds}A_{ds}A_{ds}T_{ds}{}^mC_{ds}T_{ds}{}^mC_{ds}{}^mC_{ks}G_{ks}{}^mC_k$ | 52.4 | 734 | 749 | 566 |
| 569478 | $G_{ks}{}^mC_{ks}{}^mC_{ks}A_{ds}T_{ds}G_{ds}A_{ds}{}^mC_{ds}A_{ds}A_{ds}T_{ds}{}^mC_{ds}T_{ds}{}^mC_{ks}{}^mC_{ks}G_k$ | 50.5 | 735 | 750 | 567 |
| 569479 | $G_{ks}G_{ks}{}^mC_{ks}{}^mC_{ds}A_{ds}T_{ds}G_{ds}A_{ds}{}^mC_{ds}A_{ds}A_{ds}T_{ds}{}^mC_{ds}T_{ks}{}^mC_{ks}{}^mC_k$ | 48.4 | 736 | 751 | 568 |

TABLE 14

Inhibition of human DMPK RNA transcript in HepG2 cells targeting SEQ ID NO: 2

| ISIS No. | Sequence | % Target Expression | Start Site on Seq ID: 2 | Stop Site on Seq ID: 2 | Seq ID No. |
|---|---|---|---|---|---|
| UTC | N/A | 100 | N/A | N/A | |
| 445569 | ${}^{m}C_{es}G_{es}G_{es}A_{es}G_{es}{}^{m}C_{ds}G_{ds}G_{ds}T_{ds}T_{ds}G_{ds}T_{ds}G_{ds}A_{ds}A_{ds}{}^{m}C_{es}T_{es}G_{es}G_{es}{}^{m}C_{e}$ | 31.4 | 13226 | 13245 | 24 |
| 486178 | $A_{ks}{}^{m}C_{ks}A_{ks}A_{ds}T_{ds}A_{ds}A_{ds}A_{ds}T_{ds}A_{ds}{}^{m}C_{ds}{}^{m}C_{ds}G_{ds}A_{ks}G_{ks}G_{k}$ | 25.3 | 13836 | 13851 | 23 |
| 570801 | ${}^{m}C_{ks}{}^{m}C_{ks}A_{ks}A_{ds}{}^{m}C_{ds}T_{ds}G_{ds}T_{ds}T_{ds}{}^{m}C_{ds}T_{ds}{}^{m}C_{ds}T_{ds}T_{ks}A_{ks}G_{k}$ | 22.7 | 10165 | 10180 | 569 |
| 570802 | $A_{ks}A_{ks}{}^{m}C_{ks}{}^{m}C_{ds}A_{ds}A_{ds}{}^{m}C_{ds}T_{ds}G_{ds}T_{ds}T_{ds}{}^{m}C_{ds}T_{ds}{}^{m}C_{ks}T_{ks}T_{k}$ | 22.6 | 10167 | 10182 | 570 |
| 570803 | ${}^{m}C_{ks}{}^{m}C_{ks}A_{ks}G_{ds}T_{ds}A_{ds}A_{ds}T_{ds}A_{ds}A_{ds}A_{ds}A_{ds}G_{ds}{}^{m}C_{ks}T_{ks}G_{k}$ | 37.4 | 10190 | 10205 | 571 |
| 570804 | $G_{ks}T_{ks}{}^{m}C_{ks}{}^{m}C_{ds}A_{ds}G_{ds}T_{ds}A_{ds}A_{ds}T_{ds}A_{ds}A_{ds}A_{ds}A_{ks}G_{ks}{}^{m}C_{k}$ | 24.9 | 10192 | 10207 | 572 |
| 570805 | $G_{ks}T_{ks}T_{ks}G_{ds}T_{ds}{}^{m}C_{ds}{}^{m}C_{ds}A_{ds}G_{ds}T_{ds}A_{ds}A_{ds}T_{ds}A_{ks}A_{ks}A_{k}$ | 23.8 | 10195 | 10210 | 573 |
| 570806 | $A_{ks}T_{ks}G_{ks}T_{ds}T_{ds}G_{ds}T_{ds}{}^{m}C_{ds}{}^{m}C_{ds}A_{ds}G_{ds}T_{ds}A_{ds}A_{ks}T_{ks}A_{k}$ | 21.9 | 10197 | 10212 | 574 |
| 570807 | $T_{ks}A_{ks}A_{ks}T_{ds}G_{ds}T_{ds}T_{ds}G_{ds}T_{ds}{}^{m}C_{ds}{}^{m}C_{ds}A_{ds}G_{ds}T_{ks}A_{ks}A_{k}$ | 20 | 10199 | 10214 | 575 |
| 570808 | $T_{ks}G_{ks}T_{ks}A_{ds}A_{ds}T_{ds}G_{ds}T_{ds}T_{ds}G_{ds}T_{ds}{}^{m}C_{ds}{}^{m}C_{ds}A_{ks}G_{ks}T_{k}$ | 11.5 | 10201 | 10216 | 31 |
| 570809 | $T_{ks}T_{ks}{}^{m}C_{ks}A_{ds}A_{ds}T_{ds}{}^{m}C_{ds}{}^{m}C_{ds}T_{ds}G_{ds}A_{ds}{}^{m}C_{ds}{}^{m}C_{ds}{}^{m}C_{ks}A_{ks}{}^{m}C_{k}$ | 34.7 | 10279 | 10294 | 576 |
| 570810 | $G_{ks}G_{ks}T_{ks}T_{ds}{}^{m}C_{ds}A_{ds}A_{ds}T_{ds}{}^{m}C_{ds}{}^{m}C_{ds}T_{ds}G_{ds}A_{ds}{}^{m}C_{ks}{}^{m}C_{ks}{}^{m}C_{k}$ | 76.4 | 10281 | 10296 | 577 |
| 570811 | $T_{ks}G_{ks}G_{ks}G_{ds}T_{ds}T_{ds}{}^{m}C_{ds}A_{ds}A_{ds}T_{ds}{}^{m}C_{ds}{}^{m}C_{ds}T_{ds}G_{ks}A_{ks}{}^{m}C_{k}$ | 72.4 | 10283 | 10298 | 578 |
| 570812 | $G_{ks}A_{ks}T_{ks}G_{ds}G_{ds}G_{ds}T_{ds}T_{ds}{}^{m}C_{ds}A_{ds}A_{ds}T_{ds}{}^{m}C_{ds}{}^{m}C_{ks}T_{ks}G_{k}$ | 49 | 10285 | 10300 | 579 |
| 570813 | $A_{ks}G_{ks}G_{ks}A_{ds}T_{ds}G_{ds}G_{ds}G_{ds}T_{ds}T_{ds}{}^{m}C_{ds}A_{ds}A_{ds}T_{ks}{}^{m}C_{ks}{}^{m}C_{k}$ | 80.8 | 10287 | 10302 | 580 |
| 570814 | $A_{ks}G_{ks}A_{ks}G_{ds}G_{ds}A_{ds}T_{ds}G_{ds}G_{ds}G_{ds}T_{ds}T_{ds}{}^{m}C_{ds}A_{ks}A_{ks}T_{k}$ | 43.3 | 10289 | 10304 | 581 |
| 570815 | $A_{ks}T_{ks}A_{ks}G_{ds}A_{ds}G_{ds}G_{ds}A_{ds}T_{ds}G_{ds}G_{ds}G_{ds}T_{ds}T_{ks}{}^{m}C_{ks}A_{k}$ | 63.2 | 10291 | 10306 | 582 |
| 570816 | ${}^{m}C_{ks}{}^{m}C_{ks}{}^{m}C_{ks}T_{ds}{}^{m}C_{ds}{}^{m}C_{ds}T_{ds}G_{ds}T_{ds}G_{ds}G_{ds}G_{ds}A_{ds}A_{ks}{}^{m}C_{ks}A_{k}$ | 38.8 | 10349 | 10364 | 583 |
| 570817 | $G_{ks}T_{ks}{}^{m}C_{ks}{}^{m}C_{ds}{}^{m}C_{ds}T_{ds}{}^{m}C_{ds}{}^{m}C_{ds}T_{ds}G_{ds}T_{ds}G_{ds}G_{ds}G_{ks}A_{ks}A_{k}$ | 91 | 10351 | 10366 | 584 |
| 570818 | ${}^{m}C_{ks}A_{ks}G_{ks}T_{ds}{}^{m}C_{ds}{}^{m}C_{ds}{}^{m}C_{ds}T_{ds}{}^{m}C_{ds}{}^{m}C_{ds}T_{ds}G_{ds}T_{ds}G_{ks}G_{ks}G_{k}$ | 64.8 | 10353 | 10368 | 585 |
| 570819 | $A_{ks}G_{ks}{}^{m}C_{ks}A_{ds}G_{ds}T_{ds}{}^{m}C_{ds}{}^{m}C_{ds}{}^{m}C_{ds}T_{ds}{}^{m}C_{ds}{}^{m}C_{ds}T_{ds}G_{ks}T_{ks}G_{k}$ | 28.5 | 10355 | 10370 | 586 |
| 570820 | $A_{ks}{}^{m}C_{ks}T_{ks}{}^{m}C_{ds}A_{ds}G_{ds}{}^{m}C_{ds}T_{ds}G_{ds}T_{ds}G_{ds}G_{ds}G_{ds}A_{ks}A_{ks}G_{k}$ | 62.9 | 10417 | 10432 | 587 |
| 570821 | ${}^{m}C_{ks}{}^{m}C_{ks}{}^{m}C_{ks}A_{ds}{}^{m}C_{ds}T_{ds}{}^{m}C_{ds}A_{ds}G_{ds}{}^{m}C_{ds}T_{ds}G_{ds}T_{ds}G_{ks}G_{ks}G_{k}$ | 79.9 | 10420 | 10435 | 588 |
| 570822 | $A_{ks}{}^{m}C_{ks}{}^{m}C_{ks}{}^{m}C_{ds}{}^{m}C_{ds}A_{ds}{}^{m}C_{ds}T_{ds}{}^{m}C_{ds}A_{ds}G_{ds}{}^{m}C_{ds}T_{ds}G_{ks}T_{ks}G_{k}$ | 47.5 | 10422 | 10437 | 589 |
| 570823 | $A_{ks}{}^{m}C_{ks}A_{ks}{}^{m}C_{ds}{}^{m}C_{ds}{}^{m}C_{ds}{}^{m}C_{ds}A_{ds}{}^{m}C_{ds}T_{ds}{}^{m}C_{ds}A_{ds}G_{ds}{}^{m}C_{ks}T_{ks}G_{k}$ | 78.1 | 10424 | 10439 | 590 |
| 570824 | $G_{ks}{}^{m}C_{ks}A_{ks}{}^{m}C_{ds}A_{ds}{}^{m}C_{ds}{}^{m}C_{ds}{}^{m}C_{ds}{}^{m}C_{ds}A_{ds}{}^{m}C_{ds}T_{ds}{}^{m}C_{ds}A_{ks}G_{ks}{}^{m}C_{k}$ | 82.5 | 10426 | 10441 | 591 |
| 570825 | $T_{ks}{}^{m}C_{ks}A_{ks}G_{ds}{}^{m}C_{ds}A_{ds}{}^{m}C_{ds}A_{ds}{}^{m}C_{ds}{}^{m}C_{ds}{}^{m}C_{ds}{}^{m}C_{ds}A_{ds}{}^{m}C_{ks}T_{ks}{}^{m}C_{k}$ | 52.6 | 10429 | 10444 | 592 |
| 570826 | $G_{ks}T_{ks}G_{ks}G_{ds}T_{ds}{}^{m}C_{ds}{}^{m}C_{ds}T_{ds}A_{ds}A_{ds}G_{ds}A_{ds}{}^{m}C_{ds}T_{ks}G_{ks}G_{k}$ | 30.9 | 10474 | 10489 | 593 |
| 570827 | $G_{ks}A_{ks}T_{ks}G_{ds}T_{ds}G_{ds}G_{ds}T_{ds}{}^{m}C_{ds}{}^{m}C_{ds}T_{ds}A_{ds}A_{ds}G_{ks}A_{ks}{}^{m}C_{k}$ | 25.5 | 10477 | 10492 | 594 |
| 570828 | ${}^{m}C_{ks}A_{ks}G_{ks}A_{ds}T_{ds}G_{ds}T_{ds}G_{ds}G_{ds}T_{ds}{}^{m}C_{ds}{}^{m}C_{ds}T_{ds}A_{ks}A_{ks}G_{k}$ | 18.6 | 10479 | 10494 | 595 |
| 570829 | ${}^{m}C_{ks}{}^{m}C_{ks}T_{ks}{}^{m}C_{ds}{}^{m}C_{ds}A_{ds}{}^{m}C_{ds}A_{ds}G_{ds}A_{ds}T_{ds}G_{ds}T_{ds}G_{ks}G_{ks}T_{k}$ | 44.5 | 10485 | 10500 | 596 |
| 570830 | ${}^{m}C_{ks}A_{ks}{}^{m}C_{ks}{}^{m}C_{ds}T_{ds}{}^{m}C_{ds}{}^{m}C_{ds}A_{ds}{}^{m}C_{ds}A_{ds}G_{ds}A_{ds}T_{ds}G_{ks}T_{ks}G_{k}$ | 67.4 | 10487 | 10502 | 597 |
| 570831 | $G_{ks}G_{ks}{}^{m}C_{ks}{}^{m}C_{ds}A_{ds}{}^{m}C_{ds}{}^{m}C_{ds}T_{ds}{}^{m}C_{ds}{}^{m}C_{ds}A_{ds}{}^{m}C_{ds}A_{ds}G_{ks}A_{ks}T_{k}$ | 56.3 | 10490 | 10505 | 598 |
| 570832 | $T_{ks}G_{ks}{}^{m}C_{ks}T_{ds}T_{ds}G_{ds}G_{ds}{}^{m}C_{ds}T_{ds}{}^{m}C_{ds}T_{ds}G_{ds}G_{ds}{}^{m}C_{ks}{}^{m}C_{ks}A_{k}$ | 42.4 | 10501 | 10516 | 599 |
| 570833 | $A_{ks}{}^{m}C_{ks}T_{ks}G_{ds}{}^{m}C_{ds}T_{ds}T_{ds}G_{ds}G_{ds}{}^{m}C_{ds}T_{ds}{}^{m}C_{ds}T_{ds}G_{ks}G_{ks}{}^{m}C_{k}$ | 16 | 10503 | 10518 | 600 |
| 570834 | $A_{ks}G_{ks}A_{ks}{}^{m}C_{ds}T_{ds}G_{ds}{}^{m}C_{ds}T_{ds}T_{ds}G_{ds}G_{ds}{}^{m}C_{ds}T_{ds}{}^{m}C_{ks}T_{ks}G_{k}$ | 47.5 | 10505 | 10520 | 601 |

TABLE 14-continued

Inhibition of human DMPK RNA transcript in HepG2 cells targeting SEQ ID NO: 2

| ISIS No. | Sequence | % Target Expression | Start Site on Seq ID: 2 | Stop Site on Seq ID: 2 | Seq ID No. |
|---|---|---|---|---|---|
| 570835 | $G_{ks}G_{ks}A_{ks}G_{ds}A_{ds}{}^{m}C_{ds}T_{ds}G_{ds}{}^{m}C_{ds}T_{ds}T_{ds}G_{ds}G_{ds}{}^{m}C_{ks}T_{ks}{}^{m}C_{k}$ | 37.2 | 10507 | 10522 | 602 |
| 570836 | $T_{ks}G_{ks}{}^{m}C_{ks}A_{ds}G_{ds}A_{ds}{}^{m}C_{ds}{}^{m}C_{ds}{}^{m}C_{ds}{}^{m}C_{ds}T_{ds}{}^{m}C_{ds}T_{ds}T_{ks}{}^{m}C_{ks}T_{k}$ | 63.1 | 10556 | 10571 | 603 |
| 570837 | ${}^{m}C_{ks}T_{ks}{}^{m}C_{ks}{}^{m}C_{ds}T_{ds}{}^{m}C_{ds}{}^{m}C_{ds}{}^{m}C_{ds}T_{ds}T_{ds}G_{ds}A_{ds}{}^{m}C_{ds}A_{ks}T_{ks}G_{k}$ | 60.7 | 10579 | 10594 | 604 |
| 570838 | ${}^{m}C_{ks}{}^{m}C_{ks}A_{ks}G_{ds}A_{ds}{}^{m}C_{ds}{}^{m}C_{ds}{}^{m}C_{ds}{}^{m}C_{ds}{}^{m}C_{ds}A_{ds}T_{ds}G_{ds}T_{ks}T_{ks}{}^{m}C_{k}$ | 42.9 | 10609 | 10624 | 605 |
| 570839 | $G_{ks}T_{ks}{}^{m}C_{ks}{}^{m}C_{ds}A_{ds}G_{ds}A_{ds}{}^{m}C_{ds}{}^{m}C_{ds}{}^{m}C_{ds}{}^{m}C_{ds}{}^{m}C_{ds}A_{ds}T_{ks}G_{ks}T_{k}$ | 64.3 | 10611 | 10626 | 606 |
| 570840 | $G_{ks}G_{ks}G_{ks}T_{ds}{}^{m}C_{ds}{}^{m}C_{ds}A_{ds}G_{ds}A_{ds}{}^{m}C_{ds}{}^{m}C_{ds}{}^{m}C_{ds}{}^{m}C_{ds}{}^{m}C_{ks}A_{ks}T_{k}$ | 68.5 | 10613 | 10628 | 607 |
| 570841 | $A_{ks}{}^{m}C_{ks}{}^{m}C_{ks}T_{ds}T_{ds}{}^{m}C_{ds}T_{ds}G_{ds}{}^{m}C_{ds}A_{ds}G_{ds}G_{ds}G_{ds}A_{ks}{}^{m}C_{ks}T_{k}$ | 14.9 | 10631 | 10646 | 608 |
| 570842 | $T_{ks}A_{ks}A_{ks}A_{ds}{}^{m}C_{ds}{}^{m}C_{ds}T_{ds}T_{ds}{}^{m}C_{ds}T_{ds}G_{ds}{}^{m}C_{ds}A_{ds}G_{ks}G_{ks}G_{k}$ | 51.7 | 10634 | 10649 | 609 |
| 570843 | $G_{ks}A_{ks}A_{ks}A_{ds}A_{ds}G_{ds}{}^{m}C_{ds}{}^{m}C_{ds}{}^{m}C_{ds}T_{ds}G_{ds}{}^{m}C_{ds}{}^{m}C_{ds}{}^{m}C_{ks}{}^{m}C_{ks}T_{k}$ | 46.3 | 10684 | 10699 | 610 |
| 570844 | $T_{ks}A_{ks}G_{ks}G_{ds}A_{ds}A_{ds}A_{ds}A_{ds}G_{ds}{}^{m}C_{ds}{}^{m}C_{ds}{}^{m}C_{ds}T_{ds}G_{ks}{}^{m}C_{ks}{}^{m}C_{k}$ | 52.3 | 10687 | 10702 | 611 |
| 570845 | ${}^{m}C_{ks}T_{ks}T_{ks}A_{ds}G_{ds}G_{ds}A_{ds}A_{ds}A_{ds}A_{ds}G_{ds}{}^{m}C_{ds}{}^{m}C_{ds}{}^{m}C_{ks}T_{ks}G_{k}$ | 53.8 | 10689 | 10704 | 612 |
| 570846 | $T_{ks}G_{ks}{}^{m}C_{ks}T_{ds}T_{ds}A_{ds}G_{ds}G_{ds}A_{ds}A_{ds}A_{ds}A_{ds}G_{ds}{}^{m}C_{ks}{}^{m}C_{ks}{}^{m}C_{k}$ | 47.8 | 10691 | 10706 | 613 |
| 570847 | $T_{ks}{}^{m}C_{ks}T_{ks}G_{ds}{}^{m}C_{ds}T_{ds}T_{ds}A_{ds}G_{ds}G_{ds}A_{ds}A_{ds}A_{ds}A_{ks}G_{ks}{}^{m}C_{k}$ | 43.9 | 10693 | 10708 | 614 |
| 570848 | ${}^{m}C_{ks}T_{ks}{}^{m}C_{ks}{}^{m}C_{ds}T_{ds}{}^{m}C_{ds}T_{ds}G_{ds}{}^{m}C_{ds}T_{ds}T_{ds}A_{ds}G_{ds}G_{ks}A_{ks}A_{k}$ | 67.9 | 10697 | 10712 | 615 |
| 570849 | ${}^{m}C_{ks}{}^{m}C_{ks}{}^{m}C_{ks}T_{ds}{}^{m}C_{ds}{}^{m}C_{ds}T_{ds}{}^{m}C_{ds}T_{ds}G_{ds}{}^{m}C_{ds}T_{ds}T_{ds}A_{ks}G_{ks}G_{k}$ | 50.8 | 10699 | 10714 | 616 |
| 570850 | ${}^{m}C_{ks}T_{ks}G_{ks}A_{ds}T_{ds}T_{ds}T_{ds}G_{ds}A_{ds}G_{ds}G_{ds}A_{ds}A_{ds}G_{ks}G_{ks}G_{k}$ | 41.1 | 10759 | 10774 | 617 |
| 570851 | $T_{ks}{}^{m}C_{ks}{}^{m}C_{ks}T_{ds}G_{ds}A_{ds}T_{ds}T_{ds}T_{ds}G_{ds}A_{ds}G_{ds}G_{ds}A_{ks}A_{ks}G_{k}$ | 87.4 | 10761 | 10776 | 618 |
| 570852 | ${}^{m}C_{ks}{}^{m}C_{ks}T_{ks}{}^{m}C_{ds}{}^{m}C_{ds}T_{ds}G_{ds}A_{ds}T_{ds}T_{ds}T_{ds}G_{ds}A_{ds}G_{ks}G_{ks}A_{k}$ | 75.8 | 10763 | 10778 | 619 |
| 570853 | $G_{ks}A_{ks}{}^{m}C_{ks}{}^{m}C_{ds}T_{ds}{}^{m}C_{ds}{}^{m}C_{ds}T_{ds}G_{ds}A_{ds}T_{ds}T_{ds}T_{ds}G_{ks}A_{ks}G_{k}$ | 87.4 | 10765 | 10780 | 620 |
| 570854 | $A_{ks}A_{ks}G_{ks}A_{ds}{}^{m}C_{ds}{}^{m}C_{ds}T_{ds}{}^{m}C_{ds}{}^{m}C_{ds}T_{ds}G_{ds}A_{ds}T_{ds}T_{ks}T_{ks}G_{k}$ | 60.3 | 10767 | 10782 | 621 |
| 570855 | ${}^{m}C_{ks}{}^{m}C_{ks}A_{ks}A_{ds}G_{ds}A_{ds}{}^{m}C_{ds}{}^{m}C_{ds}T_{ds}{}^{m}C_{ds}{}^{m}C_{ds}T_{ds}G_{ds}A_{ks}T_{ks}T_{k}$ | 61.4 | 10769 | 10784 | 622 |
| 570856 | ${}^{m}C_{ks}T_{ks}G_{ks}{}^{m}C_{ds}T_{ds}T_{ds}{}^{m}C_{ds}{}^{m}C_{ds}A_{ds}A_{ds}G_{ds}A_{ds}{}^{m}C_{ds}{}^{m}C_{ks}T_{ks}{}^{m}C_{k}$ | 40.4 | 10775 | 10790 | 623 |
| 570857 | $A_{ks}G_{ks}{}^{m}C_{ks}T_{ds}G_{ds}{}^{m}C_{ds}T_{ds}T_{ds}{}^{m}C_{ds}{}^{m}C_{ds}A_{ds}A_{ds}G_{ds}A_{ks}{}^{m}C_{ks}{}^{m}C_{k}$ | 48.5 | 10777 | 10792 | 624 |
| 570858 | $G_{ks}{}^{m}C_{ks}A_{ks}G_{ds}{}^{m}C_{ds}T_{ds}G_{ds}{}^{m}C_{ds}T_{ds}T_{ds}{}^{m}C_{ds}{}^{m}C_{ds}A_{ds}A_{ks}G_{ks}A_{k}$ | 87.7 | 10779 | 10794 | 625 |
| 570859 | ${}^{m}C_{ks}T_{ks}G_{ks}G_{ds}T_{ds}G_{ds}G_{ds}A_{ds}G_{ds}A_{ds}A_{ds}{}^{m}C_{ds}{}^{m}C_{ds}A_{ks}G_{ks}A_{k}$ | 92.6 | 10816 | 10831 | 626 |
| 570860 | ${}^{m}C_{ks}T_{ks}{}^{m}C_{ks}T_{ds}G_{ds}G_{ds}T_{ds}G_{ds}G_{ds}A_{ds}G_{ds}A_{ds}A_{ds}{}^{m}C_{ks}{}^{m}C_{ks}A_{k}$ | 86.6 | 10818 | 10833 | 627 |
| 570861 | $T_{ks}T_{ks}{}^{m}C_{ks}T_{ds}{}^{m}C_{ds}T_{ds}G_{ds}G_{ds}T_{ds}G_{ds}G_{ds}A_{ds}G_{ds}A_{ks}A_{ks}{}^{m}C_{k}$ | 82.6 | 10820 | 10835 | 628 |
| 570862 | $G_{ks}A_{ks}T_{ks}T_{ds}{}^{m}C_{ds}T_{ds}{}^{m}C_{ds}T_{ds}G_{ds}G_{ds}T_{ds}G_{ds}G_{ds}A_{ks}G_{ks}A_{k}$ | 76.1 | 10822 | 10837 | 629 |
| 570863 | $A_{ks}{}^{m}C_{ks}T_{ks}T_{ds}A_{ds}{}^{m}C_{ds}T_{ds}G_{ds}T_{ds}T_{ds}T_{ds}{}^{m}C_{ds}A_{ds}T_{ks}{}^{m}C_{ks}{}^{m}C_{k}$ | 80.6 | 10981 | 10996 | 630 |
| 570864 | ${}^{m}C_{ks}G_{ks}G_{ks}A_{ds}{}^{m}C_{ds}{}^{m}C_{ds}{}^{m}C_{ds}{}^{m}C_{ds}{}^{m}C_{ds}T_{ds}{}^{m}C_{ds}{}^{m}C_{ds}{}^{m}C_{ds}{}^{m}C_{ks}T_{ks}{}^{m}C_{k}$ | 58.7 | 11002 | 11017 | 631 |
| 570865 | $G_{ks}A_{ks}{}^{m}C_{ks}G_{ds}G_{ds}A_{ds}{}^{m}C_{ds}{}^{m}C_{ds}{}^{m}C_{ds}{}^{m}C_{ds}{}^{m}C_{ds}T_{ds}{}^{m}C_{ds}{}^{m}C_{ks}{}^{m}C_{ks}{}^{m}C_{k}$ | 61.5 | 11004 | 11019 | 632 |
| 570866 | ${}^{m}C_{ks}T_{ks}G_{ks}A_{ds}{}^{m}C_{ds}G_{ds}G_{ds}A_{ds}{}^{m}C_{ds}{}^{m}C_{ds}{}^{m}C_{ds}{}^{m}C_{ds}{}^{m}C_{ds}T_{ks}{}^{m}C_{ks}{}^{m}C_{k}$ | 47.6 | 11006 | 11021 | 633 |
| 570867 | ${}^{m}C_{ks}{}^{m}C_{ks}{}^{m}C_{ks}T_{ds}G_{ds}A_{ds}{}^{m}C_{ds}G_{ds}G_{ds}A_{ds}{}^{m}C_{ds}{}^{m}C_{ds}{}^{m}C_{ds}{}^{m}C_{ks}{}^{m}C_{ks}T_{k}$ | 69.5 | 11008 | 11023 | 634 |
| 570868 | $A_{ks}A_{ks}G_{ks}{}^{m}C_{ds}{}^{m}C_{ds}{}^{m}C_{ds}T_{ds}{}^{m}C_{ds}A_{ds}{}^{m}C_{ds}{}^{m}C_{ds}T_{ds}T_{ds}T_{ks}T_{ks}{}^{m}C_{k}$ | 54 | 11036 | 11051 | 635 |
| 570869 | $G_{ks}G_{ks}A_{ks}A_{ds}G_{ds}{}^{m}C_{ds}{}^{m}C_{ds}{}^{m}C_{ds}T_{ds}{}^{m}C_{ds}A_{ds}{}^{m}C_{ds}{}^{m}C_{ds}T_{ks}T_{ks}T_{k}$ | 37.5 | 11038 | 11053 | 636 |
| 570870 | ${}^{m}C_{ks}G_{ks}G_{ks}G_{ds}A_{ds}A_{ds}G_{ds}{}^{m}C_{ds}{}^{m}C_{ds}{}^{m}C_{ds}T_{ds}{}^{m}C_{ds}A_{ds}{}^{m}C_{ks}{}^{m}C_{ks}T_{k}$ | 70.7 | 11040 | 11055 | 637 |

TABLE 14-continued

Inhibition of human DMPK RNA transcript in HepG2 cells targeting SEQ ID NO: 2

| ISIS No. | Sequence | % Target Expression | Start Site on Seq ID: 2 | Stop Site on Seq ID: 2 | Seq ID No. |
|---|---|---|---|---|---|
| 570871 | ${}^{m}C_{ks}{}^{m}C_{ks}{}^{m}C_{ks}G_{ds}G_{ds}G_{ds}A_{ds}A_{ds}G_{ds}{}^{m}C_{ds}{}^{m}C_{ds}{}^{m}C_{ds}T_{ds}{}^{m}C_{ks}A_{ks}{}^{m}C_{k}$ | 71.2 | 11042 | 11057 | 638 |
| 570872 | ${}^{m}C_{ks}A_{ks}{}^{m}C_{ks}{}^{m}C_{ds}{}^{m}C_{ds}G_{ds}G_{ds}G_{ds}A_{ds}A_{ds}G_{ds}{}^{m}C_{ds}{}^{m}C_{ds}{}^{m}C_{ks}T_{ks}{}^{m}C_{k}$ | 51.6 | 11044 | 11059 | 639 |
| 570873 | $G_{ks}{}^{m}C_{ks}{}^{m}C_{ks}A_{ds}{}^{m}C_{ds}{}^{m}C_{ds}{}^{m}C_{ds}G_{ds}G_{ds}G_{ds}A_{ds}A_{ds}G_{ds}{}^{m}C_{ks}{}^{m}C_{ks}{}^{m}C_{k}$ | 45.8 | 11046 | 11061 | 640 |
| 570874 | $A_{ks}{}^{m}C_{ks}G_{ks}{}^{m}C_{ds}{}^{m}C_{ds}A_{ds}{}^{m}C_{ds}{}^{m}C_{ds}{}^{m}C_{ds}G_{ds}G_{ds}G_{ds}A_{ds}A_{ks}G_{ks}{}^{m}C_{k}$ | 31.8 | 11048 | 11063 | 641 |
| 570875 | ${}^{m}C_{ks}T_{ks}G_{ks}T_{ds}T_{ds}{}^{m}C_{ds}A_{ds}G_{ds}G_{ds}A_{ds}A_{ds}G_{ds}T_{ds}{}^{m}C_{ks}{}^{m}C_{ks}{}^{m}C_{k}$ | 14.3 | 11082 | 11097 | 642 |
| 570876 | $T_{ks}T_{ks}{}^{m}C_{ks}T_{ds}G_{ds}T_{ds}T_{ds}{}^{m}C_{ds}A_{ds}G_{ds}G_{ds}A_{ds}A_{ds}G_{ks}T_{ks}{}^{m}C_{k}$ | 18 | 11084 | 11099 | 643 |
| 570877 | $G_{ks}{}^{m}C_{ks}T_{ks}T_{ds}{}^{m}C_{ds}T_{ds}G_{ds}T_{ds}T_{ds}{}^{m}C_{ds}A_{ds}G_{ds}G_{ds}A_{ks}A_{ks}G_{k}$ | 44 | 11086 | 11101 | 644 |

TABLE 15

Inhibition of human DMPK RNA transcript in HepG2 cells targeting SEQ ID NO: 2

| ISIS No. | Sequence | % Target Expression | Start Site on Seq ID: 2 | Stop Site on Seq ID: 2 | Seq ID No. |
|---|---|---|---|---|---|
| UTC | N/A | 100 | N/A | N/A | |
| 445569 | ${}^{m}C_{es}G_{es}G_{es}A_{es}G_{es}{}^{m}C_{ds}G_{ds}G_{ds}T_{ds}T_{ds}G_{ds}T_{ds}G_{ds}A_{ds}A_{ds}{}^{m}C_{es}T_{es}G_{es}G_{es}{}^{m}C_{e}$ | 55 | 13226 | 13245 | 24 |
| 486178 | $A_{ks}{}^{m}C_{ks}A_{ks}A_{ds}T_{ds}A_{ds}A_{ds}A_{ds}T_{ds}A_{ds}{}^{m}C_{ds}{}^{m}C_{ds}G_{ds}A_{ks}G_{ks}G_{k}$ | 33.9 | 13836 | 13851 | 23 |
| 570647 | $G_{ks}{}^{m}C_{ks}T_{ks}T_{ds}G_{ds}G_{ds}G_{ds}{}^{m}C_{ds}{}^{m}C_{ds}{}^{m}C_{ds}A_{ds}{}^{m}C_{ds}{}^{m}C_{ds}{}^{m}C_{ks}{}^{m}C_{ks}T_{k}$ | 80.3 | 5718 | 5733 | 645 |
| 570648 | $A_{ks}G_{ks}G_{ks}{}^{m}C_{ds}T_{ds}T_{ds}G_{ds}G_{ds}G_{ds}{}^{m}C_{ds}{}^{m}C_{ds}{}^{m}C_{ds}A_{ds}{}^{m}C_{ks}{}^{m}C_{ks}{}^{m}C_{k}$ | 92.3 | 5720 | 5735 | 646 |
| 570649 | ${}^{m}C_{ks}G_{ks}A_{ks}G_{ds}G_{ds}{}^{m}C_{ds}T_{ds}T_{ds}G_{ds}G_{ds}G_{ds}{}^{m}C_{ds}{}^{m}C_{ds}{}^{m}C_{ks}A_{ks}{}^{m}C_{k}$ | 100.7 | 5722 | 5737 | 647 |
| 570650 | $A_{ks}G_{ks}{}^{m}C_{ks}G_{ds}A_{ds}G_{ds}G_{ds}{}^{m}C_{ds}T_{ds}T_{ds}G_{ds}G_{ds}G_{ds}{}^{m}C_{ks}{}^{m}C_{ks}{}^{m}C_{k}$ | 75.8 | 5724 | 5739 | 648 |
| 570651 | $A_{ks}G_{ks}A_{ks}G_{ds}{}^{m}C_{ds}G_{ds}A_{ds}G_{ds}G_{ds}{}^{m}C_{ds}T_{ds}T_{ds}G_{ds}G_{ks}G_{ks}{}^{m}C_{k}$ | 99.8 | 5726 | 5741 | 649 |
| 570652 | $G_{ks}{}^{m}C_{ks}A_{ks}G_{ds}A_{ds}G_{ds}{}^{m}C_{ds}G_{ds}A_{ds}G_{ds}G_{ds}{}^{m}C_{ds}T_{ds}T_{ks}G_{ks}G_{k}$ | 135.4 | 5728 | 5743 | 650 |
| 570653 | $G_{ks}A_{ks}G_{ks}{}^{m}C_{ds}A_{ds}G_{ds}A_{ds}G_{ds}{}^{m}C_{ds}G_{ds}A_{ds}G_{ds}G_{ds}{}^{m}C_{ks}T_{ks}T_{k}$ | 111.5 | 5730 | 5745 | 651 |
| 570654 | $A_{ks}A_{ks}A_{ks}G_{ds}G_{ds}A_{ds}G_{ds}{}^{m}C_{ds}A_{ds}G_{ds}A_{ds}G_{ds}{}^{m}C_{ds}G_{ks}A_{ks}G_{k}$ | 87.5 | 5734 | 5749 | 652 |
| 570655 | ${}^{m}C_{ks}A_{ks}A_{ks}A_{ds}A_{ds}G_{ds}G_{ds}A_{ds}G_{ds}{}^{m}C_{ds}A_{ds}G_{ds}A_{ds}G_{ks}{}^{m}C_{ks}G_{k}$ | 94.5 | 5736 | 5751 | 653 |
| 570656 | $T_{ks}G_{ks}G_{ks}A_{ds}{}^{m}C_{ds}{}^{m}C_{ds}A_{ds}A_{ds}A_{ds}A_{ds}G_{ds}G_{ds}A_{ds}G_{ks}{}^{m}C_{ks}A_{k}$ | 75.4 | 5741 | 5756 | 654 |
| 570657 | ${}^{m}C_{ks}{}^{m}C_{ks}T_{ks}G_{ds}G_{ds}A_{ds}{}^{m}C_{ds}{}^{m}C_{ds}A_{ds}A_{ds}A_{ds}A_{ds}G_{ds}G_{ks}A_{ks}G_{k}$ | 87.3 | 5743 | 5758 | 655 |
| 570658 | ${}^{m}C_{ks}A_{ks}{}^{m}C_{ks}{}^{m}C_{ds}T_{ds}G_{ds}G_{ds}A_{ds}{}^{m}C_{ds}{}^{m}C_{ds}A_{ds}A_{ds}A_{ds}A_{ks}G_{ks}G_{k}$ | 93.2 | 5745 | 5760 | 656 |
| 570659 | ${}^{m}C_{ks}G_{ks}{}^{m}C_{ks}A_{ds}{}^{m}C_{ds}{}^{m}C_{ds}T_{ds}G_{ds}G_{ds}A_{ds}{}^{m}C_{ds}{}^{m}C_{ds}A_{ds}A_{ks}A_{ks}A_{k}$ | 70 | 5747 | 5762 | 657 |
| 570660 | $G_{ks}A_{ks}{}^{m}C_{ks}{}^{m}C_{ds}G_{ds}{}^{m}C_{ds}A_{ds}{}^{m}C_{ds}{}^{m}C_{ds}T_{ds}G_{ds}G_{ds}A_{ds}{}^{m}C_{ks}{}^{m}C_{ks}A_{k}$ | 46.4 | 5750 | 5765 | 658 |
| 570661 | $A_{ks}{}^{m}C_{ks}{}^{m}C_{ks}T_{ds}T_{ds}G_{ds}T_{ds}A_{ds}G_{ds}T_{ds}G_{ds}G_{ds}A_{ds}{}^{m}C_{ks}G_{ks}A_{k}$ | 44 | 5951 | 5966 | 659 |
| 570662 | $T_{ks}{}^{m}C_{ks}A_{ks}{}^{m}C_{ds}{}^{m}C_{ds}T_{ds}T_{ds}G_{ds}T_{ds}A_{ds}G_{ds}T_{ds}G_{ds}G_{ks}A_{ks}{}^{m}C_{k}$ | 76.8 | 5953 | 5968 | 660 |
| 570663 | $G_{ks}{}^{m}C_{ks}T_{ks}{}^{m}C_{ds}A_{ds}{}^{m}C_{ds}{}^{m}C_{ds}T_{ds}T_{ds}G_{ds}T_{ds}A_{ds}G_{ds}T_{ks}G_{ks}G_{k}$ | 69.5 | 5955 | 5970 | 661 |
| 570664 | $G_{ks}G_{ks}A_{ks}G_{ds}A_{ds}G_{ds}G_{ds}A_{ds}G_{ds}G_{ds}{}^{m}C_{ds}G_{ds}A_{ds}T_{ks}A_{ks}G_{k}$ | 88.2 | 6015 | 6030 | 662 |
| 570665 | $A_{ks}G_{ks}G_{ks}G_{ds}A_{ds}G_{ds}A_{ds}G_{ds}G_{ds}A_{ds}G_{ds}G_{ds}{}^{m}C_{ds}G_{ks}A_{ks}T_{k}$ | 96.9 | 6017 | 6032 | 663 |
| 570666 | ${}^{m}C_{ks}T_{ks}{}^{m}C_{ks}{}^{m}C_{ds}T_{ds}G_{ds}{}^{m}C_{ds}T_{ds}{}^{m}C_{ds}A_{ds}G_{ds}A_{ds}G_{ds}G_{ks}G_{ks}A_{k}$ | 74.7 | 6028 | 6043 | 664 |
| 570667 | $G_{ks}T_{ks}G_{ks}{}^{m}C_{ds}T_{ds}{}^{m}C_{ds}{}^{m}C_{ds}T_{ds}G_{ds}{}^{m}C_{ds}T_{ds}{}^{m}C_{ds}A_{ds}G_{ks}A_{ks}G_{k}$ | 77.5 | 6031 | 6046 | 665 |

TABLE 15-continued

Inhibition of human DMPK RNA transcript in HepG2 cells targeting SEQ ID NO: 2

| ISIS No. | Sequence | % Target Expression | Start Site on Seq ID: 2 | Stop Site on Seq ID: 2 | Seq ID No. |
|---|---|---|---|---|---|
| 570668 | $A_{ks}G_{ks}G_{ks}T_{ds}G_{ds}{}^{m}C_{ds}T_{ds}{}^{m}C_{ds}{}^{m}C_{ds}T_{ds}G_{ds}{}^{m}C_{ds}T_{ds}{}^{m}C_{ks}A_{ks}G_{k}$ | 76.7 | 6033 | 6048 | 666 |
| 570669 | $A_{ks}G_{ks}A_{ks}G_{ds}G_{ds}T_{ds}G_{ds}{}^{m}C_{ds}T_{ds}{}^{m}C_{ds}{}^{m}C_{ds}T_{ds}G_{ds}{}^{m}C_{ks}T_{ks}{}^{m}C_{k}$ | 43.3 | 6035 | 6050 | 667 |
| 570670 | $A_{ks}G_{ks}A_{ks}G_{ds}A_{ds}G_{ds}G_{ds}T_{ds}G_{ds}{}^{m}C_{ds}T_{ds}{}^{m}C_{ds}{}^{m}C_{ds}T_{ks}G_{ks}{}^{m}C_{k}$ | 27.1 | 6037 | 6052 | 668 |
| 570671 | $A_{ks}{}^{m}C_{ks}{}^{m}C_{ks}{}^{m}C_{ds}{}^{m}C_{ds}G_{ds}{}^{m}C_{ds}{}^{m}C_{ds}{}^{m}C_{ds}{}^{m}C_{ds}{}^{m}C_{ds}G_{ds}{}^{m}C_{ds}T_{ks}{}^{m}C_{ks}A_{k}$ | 42.6 | 6291 | 6306 | 669 |
| 570672 | ${}^{m}C_{ks}T_{ks}A_{ks}{}^{m}C_{ds}{}^{m}C_{ds}{}^{m}C_{ds}{}^{m}C_{ds}G_{ds}{}^{m}C_{ds}{}^{m}C_{ds}{}^{m}C_{ds}{}^{m}C_{ds}{}^{m}C_{ds}G_{ks}{}^{m}C_{ks}T_{k}$ | 44.9 | 6293 | 6308 | 670 |
| 570673 | $A_{ks}{}^{m}C_{ks}{}^{m}C_{ks}T_{ds}A_{ds}{}^{m}C_{ds}{}^{m}C_{ds}{}^{m}C_{ds}{}^{m}C_{ds}G_{ds}{}^{m}C_{ds}{}^{m}C_{ds}{}^{m}C_{ds}{}^{m}C_{ks}{}^{m}C_{ks}G_{k}$ | 36.6 | 6295 | 6310 | 671 |
| 570674 | $G_{ks}T_{ks}A_{ks}{}^{m}C_{ds}{}^{m}C_{ds}T_{ds}A_{ds}{}^{m}C_{ds}{}^{m}C_{ds}{}^{m}C_{ds}{}^{m}C_{ds}G_{ds}{}^{m}C_{ds}{}^{m}C_{ks}{}^{m}C_{ks}{}^{m}C_{k}$ | 52 | 6297 | 6312 | 672 |
| 570675 | $A_{ks}G_{ks}G_{ks}T_{ds}A_{ds}{}^{m}C_{ds}{}^{m}C_{ds}T_{ds}A_{ds}{}^{m}C_{ds}{}^{m}C_{ds}{}^{m}C_{ds}{}^{m}C_{ds}G_{ks}{}^{m}C_{ks}{}^{m}C_{k}$ | 56.4 | 6299 | 6314 | 673 |
| 570676 | $G_{ks}G_{ks}G_{ks}A_{ds}G_{ds}G_{ds}T_{ds}T_{ds}{}^{m}C_{ds}{}^{m}C_{ds}{}^{m}C_{ds}G_{ds}{}^{m}C_{ds}A_{ks}G_{ks}{}^{m}C_{k}$ | 51.4 | 6329 | 6344 | 674 |
| 570677 | $G_{ks}T_{ks}{}^{m}C_{ks}{}^{m}C_{ds}T_{ds}T_{ds}A_{ds}{}^{m}C_{ds}T_{ds}{}^{m}C_{ds}{}^{m}C_{ds}A_{ds}A_{ds}{}^{m}C_{ks}T_{ks}T_{k}$ | 28 | 6360 | 6375 | 675 |
| 570678 | ${}^{m}C_{ks}T_{ks}G_{ks}T_{ds}{}^{m}C_{ds}{}^{m}C_{ds}T_{ds}T_{ds}A_{ds}{}^{m}C_{ds}T_{ds}{}^{m}C_{ds}{}^{m}C_{ds}A_{ks}A_{ks}{}^{m}C_{k}$ | 33.6 | 6362 | 6377 | 676 |
| 570679 | ${}^{m}C_{ks}A_{ks}{}^{m}C_{ks}T_{ds}G_{ds}T_{ds}{}^{m}C_{ds}{}^{m}C_{ds}T_{ds}T_{ds}A_{ds}{}^{m}C_{ds}T_{ds}{}^{m}C_{ks}{}^{m}C_{ks}A_{k}$ | 7.9 | 6364 | 6379 | 677 |
| 570680 | $G_{ks}G_{ks}{}^{m}C_{ks}A_{ds}{}^{m}C_{ds}T_{ds}G_{ds}T_{ds}{}^{m}C_{ds}{}^{m}C_{ds}T_{ds}T_{ds}A_{ds}{}^{m}C_{ks}T_{ks}{}^{m}C_{k}$ | 20.2 | 6366 | 6381 | 678 |
| 570681 | $T_{ks}A_{ks}G_{ks}G_{ds}{}^{m}C_{ds}A_{ds}{}^{m}C_{ds}T_{ds}G_{ds}T_{ds}{}^{m}C_{ds}{}^{m}C_{ds}T_{ds}T_{ks}A_{ks}{}^{m}C_{k}$ | 38.3 | 6368 | 6383 | 679 |
| 570682 | $G_{ks}G_{ks}T_{k}A_{ds}G_{ds}G_{ds}{}^{m}C_{ds}A_{ds}{}^{m}C_{ds}T_{ds}G_{ds}T_{ds}{}^{m}C_{ds}{}^{m}C_{ks}T_{ks}T_{k}$ | 13.9 | 6370 | 6385 | 680 |
| 570683 | $G_{ks}T_{ks}{}^{m}C_{ks}A_{ds}{}^{m}C_{ds}T_{ds}G_{ds}{}^{m}C_{ds}T_{ds}G_{ds}G_{ds}G_{ds}T_{ds}{}^{m}C_{ks}{}^{m}C_{ks}T_{k}$ | 29 | 6445 | 6460 | 681 |
| 570684 | $G_{ks}G_{ks}T_{ks}{}^{m}C_{ds}A_{ds}{}^{m}C_{ds}T_{ds}G_{ds}{}^{m}C_{ds}T_{ds}G_{ds}G_{ds}G_{ds}T_{ks}{}^{m}C_{ks}{}^{m}C_{k}$ | 21.3 | 6446 | 6461 | 43 |
| 570685 | $A_{ks}G_{ks}G_{ks}T_{ds}{}^{m}C_{ds}A_{ds}{}^{m}C_{ds}T_{ds}G_{ds}{}^{m}C_{ds}T_{ds}G_{ds}G_{ds}G_{ks}T_{ks}{}^{m}C_{k}$ | 16.9 | 6447 | 6462 | 682 |
| 570686 | $'T_{ks}T_{ks}A_{ks}G_{ds}G_{ds}T_{ds}{}^{m}C_{ds}A_{ds}{}^{m}C_{ds}T_{ds}G_{ds}{}^{m}C_{ds}T_{ds}G_{ks}G_{ks}G_{k}$ | 19.6 | 6449 | 6464 | 683 |
| 570687 | $G_{ks}T_{ks}{}^{m}C_{ks}T_{ds}A_{ds}G_{ds}G_{ds}T_{ds}{}^{m}C_{ds}A_{ds}{}^{m}C_{ds}T_{ds}G_{ds}{}^{m}C_{ks}T_{ks}G_{k}$ | 15.7 | 6451 | 6466 | 684 |
| 570688 | $A_{ks}A_{ks}G_{ks}T_{ds}{}^{m}C_{ds}T_{ds}A_{ds}G_{ds}G_{ds}T_{ds}{}^{m}C_{ds}A_{ds}{}^{m}C_{ds}T_{ks}G_{ks}{}^{m}C_{k}$ | 16.6 | 6453 | 6468 | 685 |
| 570689 | $G_{ks}{}^{m}C_{ks}A_{ks}{}^{m}C_{ds}T_{ds}{}^{m}C_{ds}{}^{m}C_{ds}A_{ds}T_{ds}T_{ds}G_{ds}T_{ds}{}^{m}C_{ds}T_{ks}{}^{m}C_{ks}A_{k}$ | 13.2 | 6530 | 6545 | 686 |
| 570690 | ${}^{m}C_{ks}T_{ks}G_{ks}{}^{m}C_{ds}A_{ds}{}^{m}C_{ds}T_{ds}{}^{m}C_{ds}{}^{m}C_{ds}A_{ds}T_{ds}T_{ds}G_{ds}T_{k}s{}^{m}C_{ks}T_{k}$ | 50.1 | 6532 | 6547 | 687 |
| 570691 | ${}^{m}C_{ks}{}^{m}C_{ks}{}^{m}C_{ks}T_{ds}G_{ds}{}^{m}C_{ds}A_{ds}{}^{m}C_{ds}T_{ds}{}^{m}C_{ds}{}^{m}C_{ds}A_{ds}T_{ds}T_{ks}G_{ks}T_{k}$ | 48.4 | 6534 | 6549 | 688 |
| 570692 | ${}^{m}C_{ks}{}^{m}C_{ks}{}^{m}C_{ks}{}^{m}C_{ds}{}^{m}C_{ds}T_{ds}G_{ds}{}^{m}C_{ds}A_{ds}{}^{m}C_{ds}T_{ds}{}^{m}C_{ds}{}^{m}C_{ds}A_{ks}T_{ks}T_{k}$ | 74 | 6536 | 6551 | 689 |
| 570693 | ${}^{m}C_{ks}T_{ks}T_{ks}G_{ds}{}^{m}C_{ds}T_{ds}G_{ds}A_{ds}G_{ds}T_{ds}{}^{m}C_{ds}A_{ds}G_{ds}G_{ks}A_{ks}G_{k}$ | 25.3 | 6559 | 6574 | 690 |
| 570694 | $T_{ks}{}^{m}C_{ks}{}^{m}C_{ks}T_{ds}T_{ds}G_{ds}{}^{m}C_{ds}T_{ds}G_{ds}A_{ds}G_{ds}T_{ds}{}^{m}C_{ds}A_{ks}G_{ks}G_{k}$ | 39.5 | 6561 | 6576 | 691 |
| 570695 | ${}^{m}C_{ks}T_{ks}T_{ks}{}^{m}C_{ds}{}^{m}C_{ds}T_{ds}T_{ds}G_{ds}{}^{m}C_{ds}T_{ds}G_{ds}A_{ds}G_{ds}T_{ks}{}^{m}C_{ks}A_{k}$ | 22.9 | 6563 | 6578 | 692 |
| 570696 | $A_{ks}{}^{m}C_{ks}{}^{m}C_{ks}T_{ds}T_{ds}{}^{m}C_{ds}{}^{m}C_{ds}T_{ds}T_{ds}G_{ds}{}^{m}C_{ds}T_{ds}G_{ds}A_{ks}G_{ks}T_{k}$ | 52.5 | 6565 | 6580 | 693 |
| 570697 | $G_{ks}G_{ks}A_{ks}{}^{m}C_{ds}{}^{m}C_{ds}T_{ds}T_{ds}{}^{m}C_{ds}{}^{m}C_{ds}T_{ds}T_{ds}G_{ds}{}^{m}C_{ds}T_{ks}G_{ks}A_{k}$ | 37.6 | 6567 | 6582 | 694 |
| 570698 | ${}^{m}C_{ks}A_{ks}G_{ks}G_{ds}A_{ds}{}^{m}C_{ds}{}^{m}C_{ds}T_{ds}T_{ds}{}^{m}C_{ds}{}^{m}C_{ds}T_{ds}T_{ds}G_{ks}{}^{m}C_{ks}T_{k}$ | 44.2 | 6569 | 6584 | 695 |
| 570699 | $A_{ks}G_{ks}{}^{m}C_{ks}{}^{m}C_{ds}{}^{m}C_{ds}T_{ds}{}^{m}C_{ds}{}^{m}C_{ds}A_{ds}G_{ds}G_{ds}A_{ds}{}^{m}C_{ds}{}^{m}C_{ks}T_{ks}T_{k}$ | 26.6 | 6576 | 6591 | 696 |
| 570700 | $T_{ks}A_{ks}G_{ks}{}^{m}C_{ds}T_{ds}{}^{m}C_{ds}{}^{m}C_{ds}{}^{m}C_{ds}{}^{m}C_{ds}A_{ds}{}^{m}C_{ds}T_{ds}{}^{m}C_{ds}{}^{m}C_{ks}A_{ks}G_{k}$ | 33.6 | 6594 | 6609 | 697 |
| 570701 | $G_{ks}A_{ks}T_{ks}A_{ds}G_{ds}{}^{m}C_{ds}T_{ds}{}^{m}C_{ds}{}^{m}C_{ds}{}^{m}C_{ds}{}^{m}C_{ds}A_{ds}{}^{m}C_{ds}T_{ks}{}^{m}C_{ks}{}^{m}C_{k}$ | 20.4 | 6596 | 6611 | 698 |
| 570702 | ${}^{m}C_{ks}A_{ks}G_{ks}A_{ds}T_{ds}A_{ds}G_{ds}{}^{m}C_{ds}T_{ds}{}^{m}C_{ds}{}^{m}C_{ds}{}^{m}C_{ds}{}^{m}C_{ds}A_{ks}{}^{m}C_{ks}T_{k}$ | 33.8 | 6598 | 6613 | 699 |
| 570703 | ${}^{m}C_{ks}T_{ks}{}^{m}C_{ks}A_{ds}G_{ds}A_{ds}T_{ds}A_{ds}G_{ds}{}^{m}C_{ds}T_{ds}{}^{m}C_{ds}{}^{m}C_{ds}{}^{m}C_{ks}{}^{m}C_{ks}A_{k}$ | 25.8 | 6600 | 6615 | 700 |

TABLE 15-continued

Inhibition of human DMPK RNA transcript in HepG2 cells targeting SEQ ID NO: 2

| ISIS No. | Sequence | % Target Expression | Start Site on Seq ID: 2 | Stop Site on Seq ID: 2 | Seq ID No. |
|---|---|---|---|---|---|
| 570704 | $A_{ks}G_{ks}{}^{m}C_{ks}T_{ds}{}^{m}C_{ds}A_{ds}G_{ds}A_{ds}T_{ds}A_{ds}G_{ds}{}^{m}C_{ds}T_{ds}{}^{m}C_{ks}{}^{m}C_{ks}{}^{m}C_{k}$ | 29.1 | 6602 | 6617 | 701 |
| 570705 | $T_{ks}{}^{m}C_{ks}A_{ks}G_{ds}{}^{m}C_{ds}T_{ds}{}^{m}C_{ds}A_{ds}G_{ds}A_{ds}T_{ds}A_{ds}G_{ds}{}^{m}C_{ks}T_{ks}{}^{m}C_{k}$ | 47.4 | 6604 | 6619 | 702 |
| 570706 | $T_{ks}{}^{m}C_{ks}T_{ks}{}^{m}C_{ds}A_{ds}G_{ds}{}^{m}C_{ds}T_{ds}{}^{m}C_{ds}A_{ds}G_{ds}A_{ds}T_{ds}A_{ks}G_{ks}{}^{m}C_{k}$ | 33.4 | 6606 | 6621 | 703 |
| 570707 | $G_{ks}A_{ks}G_{ks}T_{ds}{}^{m}C_{ds}{}^{m}C_{ds}T_{ds}{}^{m}C_{ds}T_{ds}{}^{m}C_{ds}{}^{m}C_{ds}T_{ds}G_{ds}{}^{m}C_{ks}T_{ks}T_{k}$ | 49 | 6636 | 6651 | 704 |
| 570708 | $G_{ks}G_{ks}A_{ks}G_{ds}G_{ds}A_{ds}G_{ds}T_{ds}{}^{m}C_{ds}{}^{m}C_{ds}T_{ds}{}^{m}C_{ds}T_{ds}{}^{m}C_{ks}{}^{m}C_{ks}T_{k}$ | 79.2 | 6640 | 6655 | 705 |
| 570709 | $G_{ks}A_{ks}G_{ks}G_{ds}A_{ds}G_{ds}G_{ds}A_{ds}G_{ds}T_{ds}{}^{m}C_{ds}{}^{m}C_{ds}T_{ds}{}^{m}C_{ks}T_{ks}{}^{m}C_{k}$ | 63.3 | 6642 | 6657 | 706 |
| 570710 | ${}^{m}C_{ks}A_{ks}A_{ks}A_{ds}A_{ds}G_{ds}G_{ds}G_{ds}{}^{m}C_{ds}A_{ds}{}^{m}C_{ds}{}^{m}C_{ds}{}^{m}C_{ds}A_{ks}G_{ks}A_{k}$ | 38.8 | 6713 | 6728 | 707 |
| 570711 | $A_{ks}G_{ks}{}^{m}C_{ks}A_{ds}A_{ds}A_{ds}A_{ds}G_{ds}G_{ds}G_{ds}{}^{m}C_{ds}A_{ds}{}^{m}C_{ds}{}^{m}C_{ks}{}^{m}C_{ks}A_{k}$ | 13.7 | 6715 | 6730 | 708 |
| 570712 | $G_{ks}G_{ks}A_{ks}T_{ds}{}^{m}C_{ds}{}^{m}C_{ds}{}^{m}C_{ds}{}^{m}C_{ds}A_{ds}G_{ds}T_{ds}A_{ds}T_{ds}T_{ks}G_{ks}T_{k}$ | 45.8 | 6733 | 6748 | 709 |
| 570713 | ${}^{m}C_{ks}T_{ks}G_{ks}G_{ds}A_{ds}T_{ds}{}^{m}C_{ds}{}^{m}C_{ds}{}^{m}C_{ds}{}^{m}C_{ds}A_{ds}G_{ds}T_{ds}A_{ks}T_{ks}T_{k}$ | 45.6 | 6735 | 6750 | 710 |
| 570714 | $T_{ks}G_{ks}{}^{m}C_{ks}T_{ds}G_{ds}G_{ds}A_{ds}T_{ds}{}^{m}C_{ds}{}^{m}C_{ds}{}^{m}C_{ds}{}^{m}C_{ds}A_{ds}G_{ks}T_{ks}A_{k}$ | 43.6 | 6737 | 6752 | 711 |
| 570715 | $A_{ks}T_{ks}T_{ks}{}^{m}C_{ds}T_{ds}{}^{m}C_{ds}T_{ds}A_{ds}G_{ds}A_{ds}{}^{m}C_{ds}T_{ds}G_{ds}{}^{m}C_{ks}A_{ks}A_{k}$ | 18.3 | 6789 | 6804 | 712 |
| 570716 | $T_{ks}A_{ks}A_{ks}T_{ds}T_{ds}{}^{m}C_{ds}T_{ds}{}^{m}C_{ds}T_{ds}A_{ds}G_{ds}A_{ds}{}^{m}C_{ds}T_{ks}G_{ks}{}^{m}C_{k}$ | 15.1 | 6791 | 6806 | 713 |
| 570717 | $T_{ks}{}^{m}C_{ks}T_{ks}A_{ds}A_{ds}T_{ds}T_{ds}{}^{m}C_{ds}T_{ds}{}^{m}C_{ds}T_{ds}A_{ds}G_{ds}A_{ks}{}^{m}C_{ks}T_{k}$ | 49.9 | 6793 | 6808 | 714 |
| 570718 | $T_{ks}{}^{m}C_{ks}T_{ks}{}^{m}C_{ds}T_{ds}A_{ds}A_{ds}T_{ds}T_{ds}{}^{m}C_{ds}T_{ds}{}^{m}C_{ds}T_{ds}A_{ks}G_{ks}A_{k}$ | 77.6 | 6795 | 6810 | 715 |
| 570719 | ${}^{m}C_{ks}T_{ks}{}^{m}C_{ks}{}^{m}C_{ds}A_{ds}T_{ds}A_{ds}A_{ds}T_{ds}T_{ds}{}^{m}C_{ds}T_{ds}{}^{m}C_{ds}T_{ks}A_{ks}A_{k}$ | 42 | 6804 | 6819 | 716 |
| 570720 | $A_{ks}{}^{m}C_{ks}T_{ks}{}^{m}C_{ds}T_{ds}{}^{m}C_{ds}{}^{m}C_{ds}A_{ds}T_{ds}A_{ds}A_{ds}T_{ds}T_{ds}{}^{m}C_{ks}T_{ks}{}^{m}C_{k}$ | 28.5 | 6807 | 6822 | 717 |
| 570721 | $A_{ks}{}^{m}C_{ks}A_{ks}{}^{m}C_{ds}T_{ds}{}^{m}C_{ds}T_{ds}{}^{m}C_{ds}{}^{m}C_{ds}A_{ds}T_{ds}A_{ds}A_{ds}T_{ks}T_{ks}{}^{m}C_{k}$ | 27.4 | 6809 | 6824 | 718 |
| 570722 | ${}^{m}C_{ks}{}^{m}C_{ks}A_{ks}{}^{m}C_{ds}A_{ds}{}^{m}C_{ds}T_{ds}{}^{m}C_{ds}T_{ds}{}^{m}C_{ds}{}^{m}C_{ds}A_{ds}T_{ds}A_{ks}A_{ks}T_{k}$ | 35.4 | 6811 | 6826 | 719 |
| 570723 | $T_{ks}G_{ks}{}^{m}C_{ks}{}^{m}C_{ds}A_{ds}{}^{m}C_{ds}A_{ds}{}^{m}C_{ds}T_{ds}{}^{m}C_{ds}T_{ds}{}^{m}C_{ds}{}^{m}C_{ds}A_{ks}T_{ks}A_{k}$ | 45 | 6813 | 6828 | 720 |

TABLE 16

Inhibition of human DMPK RNA transcript in HepG2 cells targeting SEQ ID NO: 2

| ISIS No. | Sequence | % Target Expression | Start Site on Seq ID: 2 | Stop Site on Seq ID: 2 | Seq ID No. |
|---|---|---|---|---|---|
| UTC | N/A | 100 | N/A | N/A | |
| 445569 | ${}^{m}C_{es}G_{es}G_{es}A_{es}G_{es}{}^{m}C_{ds}G_{ds}G_{ds}T_{ds}T_{ds}G_{ds}T_{ds}G_{ds}A_{ds}A_{ds}{}^{m}C_{es}T_{es}G_{es}G_{es}{}^{m}C_{e}$ | 33.9 | 13226 | 13245 | 24 |
| 486178 | $A_{ks}{}^{m}C_{ks}A_{ks}A_{ds}T_{ds}A_{ds}A_{ds}A_{ds}T_{ds}A_{ds}{}^{m}C_{ds}{}^{m}C_{ds}G_{ds}A_{ks}G_{ks}G_{k}$ | 21.5 | 13836 | 13851 | 23 |
| 570339 | ${}^{m}C_{ks}{}^{m}C_{ks}{}^{m}C_{ks}A_{ds}T_{ds}G_{ds}{}^{m}C_{ds}{}^{m}C_{ds}{}^{m}C_{ds}A_{ds}T_{ds}{}^{m}C_{ds}{}^{m}C_{ds}T_{ks}G_{ks}{}^{m}C_{k}$ | 56.2 | 1534 | 1549 | 721 |
| 570340 | $G_{ks}G_{ks}A_{ks}{}^{m}C_{ds}A_{ds}G_{ds}A_{ds}G_{ds}A_{ds}A_{ds}A_{ds}T_{ds}G_{ds}T_{ks}T_{ks}G_{k}$ | 46.7 | 1597 | 1612 | 722 |
| 570341 | $G_{ks}G_{ks}{}^{m}C_{ks}A_{ds}T_{ds}A_{ds}G_{ds}G_{ds}A_{ds}{}^{m}C_{ds}A_{ds}G_{ds}A_{ds}G_{ks}A_{ks}A_{k}$ | 35.6 | 1603 | 1618 | 723 |
| 570342 | $G_{ks}T_{ks}G_{ks}G_{ds}{}^{m}C_{ds}A_{ds}T_{ds}A_{ds}G_{ds}G_{ds}A_{ds}{}^{m}C_{ds}A_{ds}G_{ks}A_{ks}G_{k}$ | 34.8 | 1605 | 1620 | 724 |
| 570343 | $T_{ks}G_{ks}G_{ks}T_{ds}G_{ds}G_{ds}{}^{m}C_{ds}A_{ds}T_{ds}A_{ds}G_{ds}G_{ds}A_{ds}{}^{m}C_{ks}A_{ks}G_{k}$ | 60.3 | 1607 | 1622 | 725 |
| 570344 | ${}^{m}C_{ks}T_{ks}T_{ks}A_{ds}{}^{m}C_{ds}T_{ds}{}^{m}C_{ds}T_{ds}G_{ds}{}^{m}C_{ds}{}^{m}C_{ds}{}^{m}C_{ds}{}^{m}C_{ds}T_{ks}{}^{m}C_{ks}{}^{m}C_{k}$ | 49.6 | 1627 | 1642 | 726 |
| 570345 | $A_{ks}{}^{m}C_{ks}{}^{m}C_{ks}T_{ds}T_{ds}A_{ds}{}^{m}C_{ds}T_{ds}{}^{m}C_{ds}T_{ds}G_{ds}{}^{m}C_{ds}{}^{m}C_{ds}{}^{m}C_{ks}{}^{m}C_{ks}T_{k}$ | 48.6 | 1629 | 1644 | 727 |
| 570346 | $T_{ks}G_{ks}A_{ks}{}^{m}C_{ds}{}^{m}C_{ds}T_{ds}T_{ds}A_{ds}{}^{m}C_{ds}T_{ds}{}^{m}C_{ds}T_{ds}G_{ds}{}^{m}C_{ks}{}^{m}C_{ks}{}^{m}C_{k}$ | 36.8 | 1631 | 1646 | 728 |

TABLE 16-continued

Inhibition of human DMPK RNA transcript in HepG2 cells targeting SEQ ID NO: 2

| ISIS No. | Sequence | % Target Expression | Start Site on Seq ID: 2 | Stop Site on Seq ID: 2 | Seq ID No. |
|---|---|---|---|---|---|
| 570347 | $G_{ks}{}^{m}C_{ks}T_{ks}G_{ds}A_{ds}{}^{m}C_{ds}{}^{m}C_{ds}T_{ds}T_{ds}A_{ds}{}^{m}C_{ds}T_{ds}{}^{m}C_{ds}T_{ks}G_{ks}{}^{m}C_{k}$ | 53.5 | 1633 | 1648 | 729 |
| 570348 | ${}^{m}C_{ks}T_{ks}G_{ks}{}^{m}C_{ds}T_{ds}G_{ds}A_{ds}{}^{m}C_{ds}{}^{m}C_{ds}T_{ds}T_{ds}A_{ds}{}^{m}C_{ds}T_{ks}{}^{m}C_{ks}T_{k}$ | 59 | 1635 | 1650 | 730 |
| 570349 | ${}^{m}C_{ks}T_{ks}{}^{m}C_{ks}T_{ds}G_{ds}{}^{m}C_{ds}T_{ds}G_{ds}A_{ds}{}^{m}C_{ds}{}^{m}C_{ds}T_{ds}T_{ds}A_{ks}{}^{m}C_{ks}T_{k}$ | 70.8 | 1637 | 1652 | 731 |
| 570350 | $G_{ks}{}^{m}C_{ks}{}^{m}C_{ks}T_{ds}{}^{m}C_{ds}T_{ds}G_{ds}{}^{m}C_{ds}T_{ds}G_{ds}A_{ds}{}^{m}C_{ds}{}^{m}C_{ds}T_{ks}T_{ks}A_{k}$ | 54 | 1639 | 1654 | 732 |
| 570351 | ${}^{m}C_{ks}{}^{m}C_{ks}A_{ks}T_{ds}G_{ds}G_{ds}{}^{m}C_{ds}T_{ds}{}^{m}C_{ds}T_{ds}G_{ds}A_{ds}G_{ds}T_{ks}{}^{m}C_{ks}A_{k}$ | 52.6 | 1666 | 1681 | 733 |
| 570352 | $A_{ks}G_{ks}{}^{m}C_{ks}{}^{m}C_{ds}A_{ds}T_{ds}G_{ds}G_{ds}{}^{m}C_{ds}T_{ds}{}^{m}C_{ds}T_{ds}G_{ds}A_{ks}G_{ks}T_{k}$ | 60.7 | 1668 | 1683 | 734 |
| 570353 | $T_{ks}A_{ks}A_{ks}G_{ds}{}^{m}C_{ds}{}^{m}C_{ds}A_{ds}T_{ds}G_{ds}G_{ds}{}^{m}C_{ds}T_{ds}{}^{m}C_{ds}T_{ks}G_{ks}A_{k}$ | 82.3 | 1670 | 1685 | 735 |
| 570354 | $T_{ks}A_{ks}G_{ks}{}^{m}C_{ds}{}^{m}C_{ds}T_{ds}G_{ds}{}^{m}C_{ds}T_{ds}G_{ds}T_{ds}G_{ds}A_{ds}{}^{m}C_{ks}T_{ks}{}^{m}C_{k}$ | 40.8 | 1687 | 1702 | 736 |
| 570355 | $A_{ks}T_{ks}G_{ks}G_{ds}G_{ds}A_{ds}G_{ds}G_{ds}{}^{m}C_{ds}T_{ds}G_{ds}T_{ds}T_{ds}G_{ks}G_{ks}{}^{m}C_{k}$ | 90.7 | 1707 | 1722 | 737 |
| 570356 | ${}^{m}C_{ks}{}^{m}C_{ks}A_{ks}T_{ds}G_{ds}G_{ds}G_{ds}A_{ds}G_{ds}G_{ds}{}^{m}C_{ds}T_{ds}G_{ds}T_{ks}T_{ks}G_{k}$ | 73.9 | 1709 | 1724 | 738 |
| 570357 | $G_{ks}G_{ks}{}^{m}C_{ks}{}^{m}C_{ds}A_{ds}T_{ds}G_{ds}G_{ds}G_{ds}A_{ds}G_{ds}G_{ds}{}^{m}C_{ds}T_{ks}G_{ks}T_{k}$ | 94.9 | 1711 | 1726 | 739 |
| 570358 | $G_{ks}T_{ks}G_{ks}{}^{m}C_{ds}A_{ds}G_{ds}A_{ds}G_{ds}A_{ds}G_{ds}G_{ds}{}^{m}C_{ds}{}^{m}C_{ds}A_{ks}T_{ks}G_{k}$ | 73.5 | 1720 | 1735 | 740 |
| 570359 | $G_{ks}A_{ks}G_{ks}{}^{m}C_{ds}T_{ds}{}^{m}C_{ds}{}^{m}C_{ds}{}^{m}C_{ds}A_{ds}G_{ds}{}^{m}C_{ds}A_{ds}T_{ds}G_{ks}A_{ks}{}^{m}C_{k}$ | 70.2 | 1759 | 1774 | 741 |
| 570360 | $A_{ks}G_{ks}G_{ks}G_{ds}A_{ds}G_{ds}{}^{m}C_{ds}T_{ds}{}^{m}C_{ds}{}^{m}C_{ds}{}^{m}C_{ds}A_{ds}G_{ds}{}^{m}C_{ks}A_{ks}T_{k}$ | 56.1 | 1762 | 1777 | 742 |
| 570361 | $G_{ks}{}^{m}C_{ks}{}^{m}C_{ks}A_{ds}T_{ds}A_{ds}G_{ds}A_{ds}G_{ds}{}^{m}C_{ds}{}^{m}C_{ds}{}^{m}C_{ds}A_{ds}{}^{m}C_{ks}T_{ks}T_{k}$ | 54.9 | 1799 | 1814 | 743 |
| 570362 | $G_{ks}G_{ks}G_{ks}{}^{m}C_{ds}{}^{m}C_{ds}A_{ds}T_{ds}A_{ds}G_{ds}A_{ds}G_{ds}{}^{m}C_{ds}{}^{m}C_{ds}{}^{m}C_{ks}A_{ks}{}^{m}C_{k}$ | 78.1 | 1801 | 1816 | 744 |
| 570363 | $A_{ks}T_{ks}G_{ks}{}^{m}C_{ds}T_{ds}G_{ds}G_{ds}{}^{m}C_{ds}{}^{m}C_{ds}{}^{m}C_{ds}T_{ds}{}^{m}C_{ds}{}^{m}C_{ds}T_{ks}G_{ks}G_{k}$ | 76.2 | 1848 | 1863 | 745 |
| 570364 | $A_{ks}G_{ks}{}^{m}C_{ks}T_{ds}G_{ds}{}^{m}C_{ds}{}^{m}C_{ds}{}^{m}C_{ds}{}^{m}C_{ds}A_{ds}T_{ds}G_{ds}{}^{m}C_{ds}T_{ks}G_{ks}G_{k}$ | 92.6 | 1857 | 1872 | 746 |
| 570365 | ${}^{m}C_{ks}G_{ks}{}^{m}C_{ks}{}^{m}C_{ds}{}^{m}C_{ds}{}^{m}C_{ds}T_{ds}G_{ds}G_{ds}{}^{m}C_{ds}A_{ds}G_{ds}{}^{m}C_{ds}T_{ks}G_{ks}{}^{m}C_{k}$ | 73.6 | 1867 | 1882 | 747 |
| 570366 | $T_{ks}G_{ks}{}^{m}C_{ks}G_{ds}{}^{m}C_{ds}{}^{m}C_{ds}{}^{m}C_{ds}{}^{m}C_{ds}T_{ds}G_{ds}G_{ds}{}^{m}C_{ds}A_{ds}G_{ks}{}^{m}C_{ks}T_{k}$ | 76.6 | 1869 | 1884 | 748 |
| 570367 | $G_{ks}{}^{m}C_{ks}T_{ks}G_{ds}{}^{m}C_{ds}G_{ds}{}^{m}C_{ds}{}^{m}C_{ds}{}^{m}C_{ds}{}^{m}C_{ds}T_{ds}G_{ds}G_{ds}{}^{m}C_{ks}A_{ks}G_{k}$ | 79.1 | 1871 | 1886 | 749 |
| 570368 | ${}^{m}C_{ks}G_{ks}G_{ks}{}^{m}C_{ds}T_{ds}G_{ds}{}^{m}C_{ds}G_{ds}{}^{m}C_{ds}{}^{m}C_{ds}{}^{m}C_{ds}{}^{m}C_{ds}T_{ds}G_{ks}G_{ks}{}^{m}C_{k}$ | 82.9 | 1873 | 1888 | 750 |
| 570369 | $G_{ks}T_{ks}{}^{m}C_{ks}G_{ds}G_{ds}{}^{m}C_{ds}T_{ds}G_{ds}{}^{m}C_{ds}G_{ds}{}^{m}C_{ds}{}^{m}C_{ds}{}^{m}C_{ds}{}^{m}C_{ks}T_{ksk}$ | 47.5 | 1875 | 1890 | 751 |
| 570370 | ${}^{m}C_{ks}T_{ks}G_{ks}T_{ds}{}^{m}C_{ds}G_{ds}G_{ds}{}^{m}C_{ds}T_{ds}G_{ds}{}^{m}C_{ds}G_{ds}{}^{m}C_{ds}{}^{m}C_{ks}{}^{m}C_{ks}{}^{m}C_{k}$ | 79.6 | 1877 | 1892 | 752 |
| 570371 | $G_{ks}{}^{m}C_{ks}{}^{m}C_{ks}T_{ds}G_{ds}T_{ds}{}^{m}C_{ds}G_{ds}G_{ds}{}^{m}C_{ds}T_{ds}G_{ds}{}^{m}C_{ds}G_{ks}{}^{m}C_{ks}{}^{m}C_{k}$ | 58.4 | 1879 | 1894 | 753 |
| 570372 | ${}^{m}C_{ks}T_{ks}G_{ks}{}^{m}C_{ds}{}^{m}C_{ds}T_{ds}G_{ds}T_{ds}{}^{m}C_{ds}G_{ds}G_{ds}{}^{m}C_{ds}T_{ds}G_{ks}{}^{m}C_{ks}G_{k}$ | 49.9 | 1881 | 1896 | 754 |
| 570373 | $A_{ks}{}^{m}C_{ks}{}^{m}C_{ks}T_{ds}G_{ds}{}^{m}C_{ds}{}^{m}C_{ds}T_{ds}G_{ds}T_{ds}{}^{m}C_{ds}G_{ds}G_{ds}{}^{m}C_{ks}T_{ks}G_{k}$ | 27.4 | 1883 | 1898 | 755 |
| 570374 | $A_{ks}{}^{m}C_{ks}A_{ks}{}^{m}C_{ds}{}^{m}C_{ds}T_{ds}G_{ds}{}^{m}C_{ds}{}^{m}C_{ds}T_{ds}G_{ds}T_{ds}{}^{m}C_{ds}G_{ks}G_{ks}{}^{m}C_{k}$ | 54.3 | 1885 | 1900 | 756 |
| 570375 | $G_{ks}A_{ks}A_{ks}{}^{m}C_{ds}A_{ds}{}^{m}C_{ds}{}^{m}C_{ds}T_{ds}G_{ds}{}^{m}C_{ds}{}^{m}C_{ds}T_{ds}G_{ds}T_{ks}{}^{m}C_{ks}G_{k}$ | 50.5 | 1887 | 1902 | 757 |
| 570376 | ${}^{m}C_{ks}{}^{m}C_{ks}G_{ks}A_{ds}A_{ds}{}^{m}C_{ds}A_{ds}{}^{m}C_{ds}{}^{m}C_{ds}T_{ds}G_{ds}{}^{m}C_{ds}{}^{m}C_{ds}T_{ks}G_{ks}T_{k}$ | 57.7 | 1889 | 1904 | 758 |
| 570377 | ${}^{m}C_{ks}G_{ks}{}^{m}C_{ks}{}^{m}C_{ds}G_{ds}A_{ds}A_{ds}{}^{m}C_{ds}A_{ds}{}^{m}C_{ds}{}^{m}C_{ds}T_{ds}G_{ds}{}^{m}C_{ks}{}^{m}C_{ks}T_{k}$ | 69.3 | 1891 | 1906 | 759 |
| 570378 | ${}^{m}C_{ks}{}^{m}C_{ks}T_{ks}G_{ds}G_{ds}G_{ds}{}^{m}C_{ds}A_{ds}{}^{m}C_{ds}{}^{m}C_{ds}T_{ds}G_{ds}T_{ds}T_{ks}G_{ks}G_{k}$ | 188.2 | 1925 | 1940 | 760 |
| 570379 | $G_{ks}T_{ks}G_{ks}{}^{m}C_{ds}{}^{m}C_{ds}T_{ds}G_{ds}G_{ds}G_{ds}{}^{m}C_{ds}A_{ds}{}^{m}C_{ds}{}^{m}C_{ds}T_{ks}G_{ks}T_{k}$ | 111.5 | 1928 | 1943 | 761 |
| 570380 | ${}^{m}C_{ks}G_{ks}{}^{m}C_{ks}{}^{m}C_{ds}{}^{m}C_{ds}T_{ds}{}^{m}C_{ds}{}^{m}C_{ds}{}^{m}C_{ds}A_{ds}G_{ds}T_{ds}G_{ds}{}^{m}C_{ks}{}^{m}C_{ks}T_{k}$ | 78 | 1938 | 1953 | 762 |
| 570381 | $A_{ks}{}^{m}C_{ks}{}^{m}C_{ks}G_{ds}{}^{m}C_{ds}{}^{m}C_{ds}{}^{m}C_{ds}T_{ds}{}^{m}C_{ds}{}^{m}C_{ds}{}^{m}C_{ds}A_{ds}G_{ds}T_{ks}G_{ks}{}^{m}C_{k}$ | 74.9 | 1940 | 1955 | 763 |
| 570382 | $T_{ks}{}^{m}C_{ks}A_{ks}{}^{m}C_{ds}{}^{m}C_{ds}G_{ds}{}^{m}C_{ds}{}^{m}C_{ds}{}^{m}C_{ds}T_{ds}{}^{m}C_{ds}{}^{m}C_{ds}{}^{m}C_{ds}A_{ds}G_{ks}T_{k}$ | 71.6 | 1942 | 1957 | 764 |

TABLE 16-continued

Inhibition of human DMPK RNA transcript in HepG2 cells targeting SEQ ID NO: 2

| ISIS No. | Sequence | % Target Expression | Start Site on Seq ID: 2 | Stop Site on Seq ID: 2 | Seq ID No. |
|---|---|---|---|---|---|
| 570383 | $A_{ks}G_{ks}T_{ks}{}^{m}C_{ds}A_{ds}{}^{m}C_{ds}{}^{m}C_{ds}G_{ds}{}^{m}C_{ds}{}^{m}C_{ds}{}^{m}C_{ds}T_{ds}{}^{m}C_{ds}{}^{m}C_{ks}{}^{m}C_{ks}A_{k}$ | 62.1 | 1944 | 1959 | 765 |
| 570384 | $T_{ks}G_{ks}A_{ks}G_{ds}T_{ds}{}^{m}C_{ds}A_{ds}{}^{m}C_{ds}{}^{m}C_{ds}G_{ds}{}^{m}C_{ds}{}^{m}C_{ds}{}^{m}C_{ds}T_{ks}{}^{m}C_{ks}{}^{m}C_{k}$ | 65.6 | 1946 | 1961 | 766 |
| 570385 | ${}^{m}C_{ks}G_{ks}T_{ks}G_{ds}A_{ds}G_{ds}T_{ds}{}^{m}C_{ds}A_{ds}{}^{m}C_{ds}{}^{m}C_{ds}G_{ds}{}^{m}C_{ds}{}^{m}C_{ks}{}^{m}C_{ks}T_{k}$ | 37.3 | 1948 | 1963 | 767 |
| 570386 | ${}^{m}C_{ks}A_{ks}A_{ks}A_{ds}G_{ds}{}^{m}C_{ds}T_{ds}G_{ds}G_{ds}T_{ds}T_{ds}{}^{m}C_{ds}T_{ds}{}^{m}C_{ks}{}^{m}C_{ks}{}^{m}C_{k}$ | 30.5 | 1974 | 1989 | 768 |
| 570387 | $T_{ks}$Gis${}^{m}C_{ks}A_{ds}A_{ds}A_{ds}G_{ds}{}^{m}C_{ds}T_{ds}G_{ds}G_{ds}T_{ds}T_{ds}{}^{m}C_{ks}T_{ks}{}^{m}C_{k}$ | 35.8 | 1976 | 1991 | 769 |
| 570388 | $T_{ks}{}^{m}C_{ks}T_{ks}G_{ds}{}^{m}C_{ds}A_{ds}A_{ds}A_{ds}G_{ds}{}^{m}C_{ds}T_{ds}G_{ds}G_{ds}T_{ks}T_{ks}{}^{m}C_{k}$ | 30.1 | 1978 | 1993 | 770 |
| 570389 | $T_{ks}G_{ks}T_{ks}{}^{m}C_{ds}T_{ds}G_{ds}{}^{m}C_{ds}A_{ds}A_{ds}A_{ds}G_{ds}{}^{m}C_{ds}T_{ds}G_{ks}G_{ks}T_{k}$ | 50.1 | 1980 | 1995 | 771 |
| 570390 | ${}^{m}C_{ks}{}^{m}C_{ks}T_{ks}G_{ds}T_{ds}{}^{m}C_{ds}T_{ds}G_{ds}{}^{m}C_{ds}A_{ds}A_{ds}A_{ds}G_{ds}{}^{m}C_{ks}T_{ks}G_{k}$ | 36 | 1982 | 1997 | 772 |
| 570391 | ${}^{m}C_{ks}G_{ks}{}^{m}C_{ks}{}^{m}C_{ds}T_{ds}G_{ds}T_{ds}{}^{m}C_{ds}T_{ds}G_{ds}{}^{m}C_{ds}A_{ds}A_{ds}A_{ks}G_{ks}{}^{m}C_{k}$ | 31.1 | 1984 | 1999 | 773 |
| 570392 | $T_{ks}T_{ks}G_{ks}T_{ds}{}^{m}C_{ds}{}^{m}C_{ds}{}^{m}C_{ds}T_{ds}{}^{m}C_{ds}{}^{m}C_{ds}T_{ds}G_{ds}G_{ds}A_{ks}T_{ks}{}^{m}C_{k}$ | 62.9 | 2022 | 2037 | 774 |
| 570393 | $A_{ks}G_{ks}T_{ks}T_{ds}G_{ds}T_{ds}{}^{m}C_{ds}{}^{m}C_{ds}{}^{m}C_{ds}T_{ds}{}^{m}C_{ds}{}^{m}C_{ds}T_{ds}G_{ks}G_{ks}A_{k}$ | 57.1 | 2024 | 2039 | 775 |
| 570394 | $A_{ks}A_{ks}A_{ks}G_{ds}T_{ds}T_{ds}G_{ds}T_{ds}{}^{m}C_{ds}{}^{m}C_{ds}{}^{m}C_{ds}T_{ds}{}^{m}C_{ds}{}^{m}C_{ks}T_{ks}G_{k}$ | 56.2 | 2026 | 2041 | 776 |
| 570395 | ${}^{m}C_{ks}{}^{m}C_{ks}A_{ks}A_{ds}A_{ds}G_{ds}T_{ds}T_{ds}G_{ds}T_{ds}{}^{m}C_{ds}{}^{m}C_{ds}{}^{m}C_{ds}T_{ks}{}^{m}C_{ks}{}^{m}C_{k}$ | 48.9 | 2028 | 2043 | 777 |
| 570396 | $A_{ks}{}^{m}C_{ks}{}^{m}C_{ks}{}^{m}C_{ds}A_{ds}A_{ds}A_{ds}G_{ds}T_{ds}T_{ds}G_{ds}T_{ds}{}^{m}C_{ds}{}^{m}C_{ks}{}^{m}C_{ks}T_{k}$ | 59.9 | 2030 | 2045 | 778 |
| 570397 | $G_{ks}A_{ks}A_{ks}{}^{m}C_{ds}{}^{m}C_{ds}{}^{m}C_{ds}A_{ds}A_{ds}A_{ds}G_{ds}T_{ds}T_{ds}G_{ds}T_{ks}{}^{m}C_{ks}{}^{m}C_{k}$ | 47.9 | 2032 | 2047 | 779 |
| 570398 | $G_{ks}A_{ks}A_{ks}G_{ds}A_{ds}A_{ds}{}^{m}C_{ds}{}^{m}C_{ds}{}^{m}C_{ds}A_{ds}A_{ds}A_{ds}G_{ds}T_{ks}T_{ks}G_{k}$ | 60 | 2035 | 2050 | 780 |
| 570399 | ${}^{m}C_{ks}{}^{m}C_{ks}A_{ks}G_{ds}A_{ds}A_{ds}G_{ds}A_{ds}A_{ds}{}^{m}C_{ds}{}^{m}C_{ds}{}^{m}C_{ds}A_{ds}A_{ks}A_{ks}G_{k}$ | 51.2 | 2038 | 2053 | 781 |
| 570400 | ${}^{m}C_{ks}A_{ks}{}^{m}C_{ks}{}^{m}C_{ds}{}^{m}C_{ds}A_{ds}G_{ds}A_{ds}A_{ds}G_{ds}A_{ds}A_{ds}{}^{m}C_{ds}{}^{m}C_{ks}{}^{m}C_{ks}A_{k}$ | 51.1 | 2041 | 2056 | 782 |
| 570401 | $G_{ks}{}^{m}C_{ks}A_{ks}G_{ds}A_{ds}A_{ds}{}^{m}C_{ds}{}^{m}C_{ds}T_{ds}A_{ds}{}^{m}C_{ds}A_{ds}A_{ds}A_{ks}A_{ks}G_{k}$ | 44.9 | 2066 | 2081 | 783 |
| 570402 | $G_{ks}T_{ks}G_{ks}{}^{m}C_{ds}A_{ds}G_{ds}A_{ds}A_{ds}{}^{m}C_{ds}{}^{m}C_{ds}T_{ds}A_{ds}{}^{m}C_{ds}A_{ks}A_{ks}A_{k}$ | 53 | 2068 | 2083 | 784 |
| 570403 | $G_{ks}G_{ks}G_{ks}T_{ds}G_{ds}{}^{m}C_{ds}A_{ds}G_{ds}A_{ds}A_{ds}{}^{m}C_{ds}{}^{m}C_{ds}T_{ds}A_{ks}{}^{m}C_{ks}A_{k}$ | 51.5 | 2070 | 2085 | 785 |
| 570404 | $G_{ks}T_{ks}G_{ks}G_{ds}G_{ds}T_{ds}G_{ds}{}^{m}C_{ds}A_{ds}G_{ds}A_{ds}A_{ds}{}^{m}C_{ds}{}^{m}C_{ks}T_{ks}A_{k}$ | 57.4 | 2072 | 2087 | 786 |
| 570405 | ${}^{m}C_{ks}{}^{m}C_{ks}A_{ks}{}^{m}C_{ds}A_{ds}{}^{m}C_{ds}G_{ds}G_{ds}{}^{m}C_{ds}T_{ds}{}^{m}C_{ds}A_{ds}T_{ds}A_{ks}G_{ks}G_{k}$ | 54.3 | 2116 | 2131 | 787 |
| 570406 | $A_{ks}{}^{m}C_{ks}{}^{m}C_{ks}{}^{m}C_{ds}A_{ds}{}^{m}C_{ds}A_{ds}{}^{m}C_{ds}G_{ds}G_{ds}{}^{m}C_{ds}T_{ds}{}^{m}C_{ds}A_{ks}T_{ks}A_{k}$ | 43.6 | 2118 | 2133 | 788 |
| 570407 | $T_{ks}G_{ks}A_{ks}{}^{m}C_{ds}{}^{m}C_{ds}{}^{m}C_{ds}A_{ds}{}^{m}C_{ds}A_{ds}{}^{m}C_{ds}G_{ds}G_{ds}{}^{m}C_{ds}T_{ks}{}^{m}C_{ks}A_{k}$ | 44 | 2120 | 2135 | 789 |
| 570408 | $G_{ks}{}^{m}C_{ks}T_{ks}G_{ds}A_{ds}{}^{m}C_{ds}{}^{m}C_{ds}{}^{m}C_{ds}A_{ds}{}^{m}C_{ds}A_{ds}{}^{m}C_{ds}G_{ds}G_{ks}{}^{m}C_{ks}T_{k}$ | 56.5 | 2122 | 2137 | 790 |
| 570409 | $T_{ks}G_{ks}G_{ks}{}^{m}C_{ds}T_{ds}G_{ds}A_{ds}{}^{m}C_{ds}{}^{m}C_{ds}{}^{m}C_{ds}A_{ds}{}^{m}C_{ds}A_{ds}{}^{m}C_{ks}G_{ks}G_{k}$ | 54.8 | 2124 | 2139 | 791 |
| 570410 | $G_{ks}G_{ks}T_{ks}G_{ds}G_{ds}{}^{m}C_{ds}T_{ds}G_{ds}A_{ds}{}^{m}C_{ds}{}^{m}C_{ds}{}^{m}C_{ds}A_{ds}{}^{m}C_{ks}A_{ks}{}^{m}C_{k}$ | 46.8 | 2126 | 2141 | 792 |
| 570411 | $A_{ks}T_{ks}G_{ks}G_{ds}T_{ds}G_{ds}G_{ds}{}^{m}C_{ds}T_{ds}G_{ds}A_{ds}{}^{m}C_{ds}{}^{m}C_{ds}{}^{m}C_{ks}A_{ks}{}^{m}C_{k}$ | 73.8 | 2128 | 2143 | 793 |
| 570412 | $G_{ks}A_{ks}A_{ks}T_{ds}G_{ds}G_{ds}T_{ds}G_{ds}G_{ds}{}^{m}C_{ds}T_{ds}G_{ds}A_{ds}{}^{m}C_{ks}{}^{m}C_{ks}{}^{m}C_{k}$ | 43.5 | 2130 | 2145 | 794 |
| 570413 | ${}^{m}C_{ks}T_{ks}A_{ks}A_{ds}A_{ds}G_{ds}G_{ds}A_{ds}{}^{m}C_{ds}G_{ds}{}^{m}C_{ds}A_{ds}G_{ds}G_{ks}G_{ks}A_{k}$ | 54.4 | 2159 | 2174 | 795 |
| 570414 | $A_{ks}A_{ks}{}^{m}C_{ks}T_{ds}A_{ds}A_{ds}A_{ds}G_{ds}G_{ds}A_{ds}{}^{m}C_{ds}G_{ds}{}^{m}C_{ds}A_{ks}G_{ks}G_{k}$ | 49.1 | 2161 | 2176 | 796 |
| 570415 | $G_{ks}A_{ks}G_{ks}A_{ds}A_{ds}{}^{m}C_{ds}T_{ds}A_{ds}A_{ds}A_{ds}G_{ds}G_{ds}A_{ds}{}^{m}C_{ks}G_{ks}{}^{m}C_{k}$ | 35.4 | 2164 | 2179 | 797 |

TABLE 17

| Inhibition of human DMPK RNA transcript in HepG2 cells targeting SEQ ID NO: 2 | | | | | |
|---|---|---|---|---|---|
| ISIS No. | Sequence | % Target Expression | Start Site on Seq ID: 2 | Stop Site on Seq ID: 2 | Seq ID No. |
| UTC | N/A | 100 | N/A | N/A | |
| 445569 | ${}^{m}C_{es}G_{es}G_{es}A_{es}G_{es}{}^{m}C_{ds}G_{ds}G_{ds}T_{ds}T_{ds}G_{ds}T_{ds}G_{ds}A_{ds}A_{ds}{}^{m}C_{es}T_{es}G_{es}G_{es}{}^{m}C_{e}$ | 41.4 | 13226 | 13245 | 24 |
| 486178 | $A_{ks}{}^{m}C_{ks}A_{ks}A_{ds}T_{ds}A_{ds}A_{ds}A_{ds}T_{ds}A_{ds}{}^{m}C_{ds}{}^{m}C_{ds}G_{ds}A_{ks}G_{ks}G_{k}$ | 24 | 13836 | 13851 | 23 |
| 570493 | $A_{ks}T_{ks}T_{ks}G_{ds}G_{ds}T_{ds}{}^{m}C_{ds}{}^{m}C_{ds}{}^{m}C_{ds}A_{ds}A_{ds}G_{ds}{}^{m}C_{ds}{}^{m}C_{ks}{}^{m}C_{ks}{}^{m}C_{k}$ | 112.1 | 3973 | 3988 | 798 |
| 570494 | ${}^{m}C_{ks}{}^{m}C_{ks}A_{ks}T_{ds}T_{ds}G_{ds}G_{ds}T_{ds}{}^{m}C_{ds}{}^{m}C_{ds}{}^{m}C_{ds}A_{ds}A_{ds}G_{ks}{}^{m}C_{ks}{}^{m}C_{k}$ | 91.3 | 3975 | 3990 | 799 |
| 570495 | $G_{ks}{}^{m}C_{ks}{}^{m}C_{ks}{}^{m}C_{ds}A_{ds}T_{ds}T_{ds}G_{ds}G_{ds}T_{ds}{}^{m}C_{ds}{}^{m}C_{ds}{}^{m}C_{ds}A_{ks}A_{ks}G_{k}$ | 103.4 | 3977 | 3992 | 800 |
| 570496 | $A_{ks}{}^{m}C_{ks}G_{ks}{}^{m}C_{ds}{}^{m}C_{ds}{}^{m}C_{ds}A_{ds}T_{ds}T_{ds}G_{ds}G_{ds}T_{ds}{}^{m}C_{ds}{}^{m}C_{ks}{}^{m}C_{ks}A_{k}$ | 67.8 | 3979 | 3994 | 801 |
| 570497 | ${}^{m}C_{ks}{}^{m}C_{ks}A_{ks}{}^{m}C_{ds}G_{ds}{}^{m}C_{ds}{}^{m}C_{ds}{}^{m}C_{ds}A_{ds}T_{ds}T_{ds}G_{ds}G_{ds}T_{ks}{}^{m}C_{ks}{}^{m}C_{k}$ | 77.3 | 3981 | 3996 | 802 |
| 570498 | ${}^{m}C_{ks}A_{ks}{}^{m}C_{ks}{}^{m}C_{ds}A_{ds}{}^{m}C_{ds}G_{ds}{}^{m}C_{ds}{}^{m}C_{ds}{}^{m}C_{ds}A_{ds}T_{ds}T_{ds}G_{ks}G_{ks}T_{k}$ | 98.3 | 3983 | 3998 | 803 |
| 570499 | $A_{ks}G_{ks}A_{ks}{}^{m}C_{ds}{}^{m}C_{ds}{}^{m}C_{ds}A_{ds}A_{ds}{}^{m}C_{ds}T_{ds}{}^{m}C_{ds}{}^{m}C_{ds}A_{ds}{}^{m}C_{ks}{}^{m}C_{ks}{}^{m}C_{k}$ | 63.7 | 4036 | 4051 | 804 |
| 570500 | $T_{ks}{}^{m}C_{ks}A_{ks}{}^{m}C_{ds}{}^{m}C_{ds}T_{ds}{}^{m}C_{ds}G_{ds}{}^{m}C_{ds}{}^{m}C_{ds}{}^{m}C_{ds}{}^{m}C_{ds}T_{ds}{}^{m}C_{ks}T_{ks}T_{k}$ | 43 | 4181 | 4196 | 805 |
| 570501 | ${}^{m}C_{ks}{}^{m}C_{ks}T_{ks}{}^{m}C_{ds}A_{ds}{}^{m}C_{ds}{}^{m}C_{ds}T_{ds}{}^{m}C_{ds}G_{ds}{}^{m}C_{ds}{}^{m}C_{ds}{}^{m}C_{ds}{}^{m}C_{ks}T_{ks}{}^{m}C_{k}$ | 38.1 | 4183 | 4198 | 806 |
| 570502 | $A_{ks}G_{ks}{}^{m}C_{ks}{}^{m}C_{ds}{}^{m}C_{ds}{}^{m}C_{ds}T_{ds}{}^{m}C_{ds}A_{ds}{}^{m}C_{ds}{}^{m}C_{ds}T_{ds}{}^{m}C_{ds}G_{ks}{}^{m}C_{ks}{}^{m}C_{k}$ | 85.4 | 4187 | 4202 | 807 |
| 570503 | ${}^{m}C_{ks}T_{ks}{}^{m}C_{ks}A_{ds}A_{ds}A_{ds}G_{ds}{}^{m}C_{ds}{}^{m}C_{ds}{}^{m}C_{ds}{}^{m}C_{ds}{}^{m}C_{ds}{}^{m}C_{ds}A_{ks}{}^{m}C_{ks}G_{k}$ | 115.8 | 4210 | 4225 | 808 |
| 570504 | $A_{ks}T_{ks}{}^{m}C_{ks}{}^{m}C_{ds}T_{ds}{}^{m}C_{ds}A_{ds}A_{ds}A_{ds}G_{ds}{}^{m}C_{ds}{}^{m}C_{ds}{}^{m}C_{ds}{}^{m}C_{ks}{}^{m}C_{ks}{}^{m}C_{k}$ | 114.5 | 4213 | 4228 | 809 |
| 570505 | $G_{ks}G_{ks}A_{ks}T_{ds}{}^{m}C_{ds}{}^{m}C_{ds}T_{ds}{}^{m}C_{ds}A_{ds}A_{ds}A_{ds}G_{ds}{}^{m}C_{ds}{}^{m}C_{ks}{}^{m}C_{ks}{}^{m}C_{k}$ | 88.1 | 4215 | 4230 | 810 |
| 570506 | $G_{ks}{}^{m}C_{ks}G_{ks}G_{ds}A_{ds}T_{ds}{}^{m}C_{ds}{}^{m}C_{ds}T_{ds}{}^{m}C_{ds}A_{ds}A_{ds}A_{ds}G_{ks}{}^{m}C_{ks}{}^{m}C_{k}$ | 93.1 | 4217 | 4232 | 811 |
| 570507 | $G_{ks}{}^{m}C_{ks}G_{ks}{}^{m}C_{ds}G_{ds}G_{ds}A_{ds}T_{ds}{}^{m}C_{ds}{}^{m}C_{ds}T_{ds}{}^{m}C_{ds}A_{ds}A_{ks}A_{ks}G_{k}$ | 102.9 | 4219 | 4234 | 812 |
| 570508 | $G_{ks}G_{ks}G_{ks}{}^{m}C_{ds}G_{ds}{}^{m}C_{ds}G_{ds}G_{ds}A_{ds}T_{ds}{}^{m}C_{ds}{}^{m}C_{ds}T_{ds}{}^{m}C_{ks}A_{ks}A_{k}$ | 78.5 | 4221 | 4236 | 813 |
| 570509 | $G_{ks}A_{ks}G_{ks}{}^{m}C_{ds}T_{ds}G_{ds}{}^{m}C_{ds}A_{ds}G_{ds}{}^{m}C_{ds}{}^{m}C_{ds}G_{ds}G_{ds}A_{ks}G_{ks}A_{k}$ | 192.2 | 4239 | 4254 | 814 |
| 570510 | $A_{ks}G_{ks}G_{ks}A_{ds}G_{ds}{}^{m}C_{ds}T_{ds}G_{ds}{}^{m}C_{ds}A_{ds}G_{ds}{}^{m}C_{ds}{}^{m}C_{ds}G_{ks}G_{ks}A_{k}$ | 219.8 | 4241 | 4256 | 815 |
| 570511 | ${}^{m}C_{ks}G_{ks}G_{ks}A_{ds}G_{ds}G_{ds}A_{ds}G_{ds}{}^{m}C_{ds}T_{ds}G_{ds}{}^{m}C_{ds}A_{ds}G_{ks}{}^{m}C_{ks}{}^{m}C_{k}$ | 128.6 | 4244 | 4259 | 816 |
| 570512 | $A_{ks}{}^{m}C_{ks}{}^{m}C_{ks}{}^{m}C_{ds}G_{ds}G_{ds}A_{ds}G_{ds}G_{ds}A_{ds}G_{ds}{}^{m}C_{ds}T_{ds}G_{ks}{}^{m}C_{ks}A_{k}$ | 89.9 | 4247 | 4262 | 817 |
| 570513 | $G_{ks}{}^{m}C_{ks}A_{ks}{}^{m}C_{ds}{}^{m}C_{ds}{}^{m}C_{ds}G_{ds}G_{ds}A_{ds}G_{ds}G_{ds}A_{ds}G_{ds}{}^{m}C_{ks}T_{ks}G_{k}$ | 96.1 | 4249 | 4264 | 818 |
| 570514 | $G_{ks}G_{ks}G_{ks}{}^{m}C_{ds}A_{ds}{}^{m}C_{ds}{}^{m}C_{ds}{}^{m}C_{ds}G_{ds}G_{ds}A_{ds}G_{ds}G_{ds}A_{ks}G_{ks}{}^{m}C_{k}$ | 67.8 | 4251 | 4266 | 819 |
| 570515 | ${}^{m}C_{ks}A_{ks}G_{ks}G_{ds}G_{ds}{}^{m}C_{ds}A_{ds}{}^{m}C_{ds}{}^{m}C_{ds}{}^{m}C_{ds}G_{ds}G_{ds}A_{ds}G_{ks}G_{ks}A_{k}$ | 64.2 | 4253 | 4268 | 820 |
| 570516 | $T_{ks}G_{ks}{}^{m}C_{ks}A_{ds}G_{ds}G_{ds}G_{ds}{}^{m}C_{ds}A_{ds}{}^{m}C_{ds}{}^{m}C_{ds}{}^{m}C_{ds}G_{ds}G_{ks}A_{ks}G_{k}$ | 62.2 | 4255 | 4270 | 821 |
| 570517 | ${}^{m}C_{ks}{}^{m}C_{ks}T_{ks}G_{ds}{}^{m}C_{ds}A_{ds}G_{ds}G_{ds}G_{ds}{}^{m}C_{ds}A_{ds}{}^{m}C_{ds}{}^{m}C_{ds}{}^{m}C_{ks}G_{ks}G_{k}$ | 77.7 | 4257 | 4272 | 822 |
| 570518 | ${}^{m}C_{ks}G_{ks}A_{ks}{}^{m}C_{ds}A_{ds}{}^{m}C_{ds}{}^{m}C_{ds}T_{ds}G_{ds}{}^{m}C_{ds}A_{ds}G_{ds}G_{ds}G_{ks}{}^{m}C_{ks}A_{k}$ | 79 | 4262 | 4277 | 823 |
| 570519 | ${}^{m}C_{ks}A_{ks}{}^{m}C_{ks}G_{ds}A_{ds}{}^{m}C_{ds}A_{ds}{}^{m}C_{ds}{}^{m}C_{ds}T_{ds}G_{ds}{}^{m}C_{ds}A_{ds}G_{ks}G_{ks}G_{k}$ | 68.5 | 4264 | 4279 | 824 |
| 570520 | $A_{ks}G_{ks}{}^{m}C_{ks}A_{ds}{}^{m}C_{ds}G_{ds}A_{ds}{}^{m}C_{ds}A_{ds}{}^{m}C_{ds}{}^{m}C_{ds}T_{ds}G_{ds}{}^{m}C_{ks}A_{ks}G_{k}$ | 39.8 | 4266 | 4281 | 825 |
| 570521 | $G_{ks}A_{ks}A_{ks}G_{ds}{}^{m}C_{ds}A_{ds}{}^{m}C_{ds}G_{ds}A_{ds}{}^{m}C_{ds}A_{ds}{}^{m}C_{ds}{}^{m}C_{ds}T_{ks}G_{ks}{}^{m}C_{k}$ | 32.4 | 4268 | 4283 | 826 |
| 570522 | ${}^{m}C_{ks}{}^{m}C_{ks}A_{ks}G_{ds}G_{ds}T_{ds}A_{ds}G_{ds}T_{ds}T_{ds}{}^{m}C_{ds}T_{ds}{}^{m}C_{ds}A_{ks}T_{ks}{}^{m}C_{k}$ | 41 | 4353 | 4368 | 827 |
| 570523 | ${}^{m}C_{ks}A_{ks}{}^{m}C_{ks}{}^{m}C_{ds}A_{ds}G_{ds}G_{ds}T_{ds}A_{ds}G_{ds}T_{ds}T_{ds}{}^{m}C_{ds}T_{ks}{}^{m}C_{ks}A_{k}$ | 71.9 | 4355 | 4370 | 828 |
| 570524 | ${}^{m}C_{ks}T_{ks}{}^{m}C_{ks}A_{ds}{}^{m}C_{ds}{}^{m}C_{ds}A_{ds}G_{ds}G_{ds}T_{ds}A_{ds}G_{ds}T_{ds}T_{ks}{}^{m}C_{ks}T_{k}$ | 105.9 | 4357 | 4372 | 829 |
| 570525 | $A_{ks}G_{ks}{}^{m}C_{ks}T_{ds}{}^{m}C_{ds}A_{ds}{}^{m}C_{ds}{}^{m}C_{ds}A_{ds}G_{ds}G_{ds}T_{ds}A_{ds}G_{ks}T_{ks}T_{k}$ | 99.3 | 4359 | 4374 | 830 |
| 570526 | $G_{ks}G_{ks}A_{ks}G_{ds}{}^{m}C_{ds}T_{ds}{}^{m}C_{ds}A_{ds}{}^{m}C_{ds}{}^{m}C_{ds}A_{ds}G_{ds}G_{ds}T_{ks}A_{ks}G_{k}$ | 85.2 | 4361 | 4376 | 831 |

TABLE 17-continued

| Inhibition of human DMPK RNA transcript in HepG2 cells targeting SEQ ID NO: 2 | | | | | |
|---|---|---|---|---|---|
| ISIS No. | Sequence | % Target Expression | Start Site on Seq ID: 2 | Stop Site on Seq ID: 2 | Seq ID No. |
| 570527 | ${}^{m}C_{ks}{}^{m}C_{ks}G_{ks}G_{ds}A_{ds}G_{ds}{}^{m}C_{ds}T_{ds}{}^{m}C_{ds}A_{ds}{}^{m}C_{ds}{}^{m}C_{ds}A_{ds}G_{ks}G_{ks}T_{k}$ | 82.5 | 4363 | 4378 | 832 |
| 570528 | $G_{ks}{}^{m}C_{ks}{}^{m}C_{ks}{}^{m}C_{ds}G_{ds}G_{ds}A_{ds}G_{ds}{}^{m}C_{ds}T_{ds}{}^{m}C_{ds}A_{ds}{}^{m}C_{ds}{}^{m}C_{ks}A_{ks}G_{k}$ | 60.5 | 4365 | 4380 | 833 |
| 570529 | $T_{ks}A_{ks}G_{ks}A_{ds}G_{ds}{}^{m}C_{ds}T_{ds}T_{ds}{}^{m}C_{ds}{}^{m}C_{ds}T_{ds}{}^{m}C_{ds}T_{ds}{}^{m}C_{ks}{}^{m}C_{ks}{}^{m}C_{k}$ | 35.4 | 4435 | 4450 | 834 |
| 570530 | ${}^{m}C_{ks}{}^{m}C_{ks}T_{ks}A_{ds}G_{ds}A_{ds}G_{ds}{}^{m}C_{ds}T_{ds}T_{ds}{}^{m}C_{ds}{}^{m}C_{ds}T_{ds}{}^{m}C_{ks}T_{ks}{}^{m}C_{k}$ | 29.4 | 4437 | 4452 | 835 |
| 570531 | $A_{ks}T_{ks}{}^{m}C_{ks}{}^{m}C_{ds}T_{ds}A_{ds}G_{ds}A_{ds}G_{ds}{}^{m}C_{ds}T_{ds}T_{ds}{}^{m}C_{ds}{}^{m}C_{ks}T_{ks}{}^{m}C_{k}$ | 30.4 | 4439 | 4454 | 836 |
| 570532 | ${}^{m}C_{ks}A_{ks}A_{ks}T_{ds}{}^{m}C_{ds}{}^{m}C_{ds}T_{ds}A_{ds}G_{ds}A_{ds}G_{ds}{}^{m}C_{ds}T_{ds}T_{ks}{}^{m}C_{ks}{}^{m}C_{k}$ | 30.3 | 4441 | 4456 | 837 |
| 570533 | ${}^{m}C_{ks}{}^{m}C_{ks}{}^{m}C_{ks}A_{ds}A_{ds}T_{ds}{}^{m}C_{ds}{}^{m}C_{ds}T_{ds}A_{ds}G_{ds}A_{ds}G_{ds}{}^{m}C_{ks}T_{ks}T_{k}$ | 54.1 | 4443 | 4458 | 838 |
| 570534 | ${}^{m}C_{ks}{}^{m}C_{ks}{}^{m}C_{ks}{}^{m}C_{ds}{}^{m}C_{ds}A_{ds}A_{ds}T_{ds}{}^{m}C_{ds}{}^{m}C_{ds}T_{ds}A_{ds}G_{ds}A_{ks}G_{ks}{}^{m}C_{k}$ | 60.1 | 4445 | 4460 | 839 |
| 570535 | ${}^{m}C_{ks}A_{ks}{}^{m}C_{ks}{}^{m}C_{ds}{}^{m}C_{ds}{}^{m}C_{ds}{}^{m}C_{ds}A_{ds}A_{ds}T_{ds}{}^{m}C_{ds}{}^{m}C_{ds}T_{ds}A_{ks}G_{ks}A_{k}$ | 68.5 | 4447 | 4462 | 840 |
| 570536 | $A_{ks}G_{ks}{}^{m}C_{ks}A_{ds}{}^{m}C_{ds}{}^{m}C_{ds}{}^{m}C_{ds}{}^{m}C_{ds}{}^{m}C_{ds}A_{ds}A_{ds}T_{ds}{}^{m}C_{ds}{}^{m}C_{ks}T_{ks}A_{k}$ | 37.5 | 4449 | 4464 | 841 |
| 570537 | $G_{ks}{}^{m}C_{ks}A_{ks}G_{ds}{}^{m}C_{ds}A_{ds}{}^{m}C_{ds}{}^{m}C_{ds}{}^{m}C_{ds}{}^{m}C_{ds}{}^{m}C_{ds}A_{ds}A_{ds}T_{ks}{}^{m}C_{ks}{}^{m}C_{k}$ | 50.9 | 4451 | 4466 | 842 |
| 570538 | $G_{ks}G_{ks}G_{ks}{}^{m}C_{ds}A_{ds}G_{ds}{}^{m}C_{ds}A_{ds}{}^{m}C_{ds}{}^{m}C_{ds}{}^{m}C_{ds}{}^{m}C_{ds}{}^{m}C_{ds}A_{ks}A_{ks}T_{k}$ | 67.7 | 4453 | 4468 | 843 |
| 570539 | $T_{ks}G_{ks}A_{ks}{}^{m}C_{ds}A_{ds}{}^{m}C_{ds}A_{ds}{}^{m}C_{ds}{}^{m}C_{ds}{}^{m}C_{ds}T_{ds}{}^{m}C_{ds}T_{ds}T_{ks}A_{ks}{}^{m}C_{k}$ | 55.9 | 4498 | 4513 | 844 |
| 570540 | ${}^{m}C_{ks}{}^{m}C_{ks}T_{ks}G_{ds}A_{ds}{}^{m}C_{ds}A_{ds}{}^{m}C_{ds}A_{ds}{}^{m}C_{ds}{}^{m}C_{ds}{}^{m}C_{ds}T_{ds}{}^{m}C_{ks}T_{ks}T_{k}$ | 45.1 | 4500 | 4515 | 845 |
| 570541 | ${}^{m}C_{ks}A_{ks}{}^{m}C_{ks}{}^{m}C_{ds}T_{ds}G_{ds}A_{ds}{}^{m}C_{ds}A_{ds}{}^{m}C_{ds}A_{ds}{}^{m}C_{ds}{}^{m}C_{ds}{}^{m}C_{ks}T_{ks}{}^{m}C_{k}$ | 30.9 | 4502 | 4517 | 846 |
| 570542 | $T_{ks}{}^{m}C_{ks}{}^{m}C_{ks}A_{ds}{}^{m}C_{ds}{}^{m}C_{ds}T_{ds}G_{ds}A_{ds}{}^{m}C_{ds}A_{ds}{}^{m}C_{ds}A_{ds}{}^{m}C_{ks}{}^{m}C_{ks}{}^{m}C_{k}$ | 35 | 4504 | 4519 | 847 |
| 570543 | ${}^{m}C_{ks}A_{ks}T_{ks}{}^{m}C_{ds}{}^{m}C_{ds}A_{ds}{}^{m}C_{ds}{}^{m}C_{ds}T_{ds}G_{ds}A_{ds}{}^{m}C_{ds}A_{ds}{}^{m}C_{ks}A_{ks}{}^{m}C_{k}$ | 48 | 4506 | 4521 | 848 |
| 570544 | ${}^{m}C_{ks}T_{ks}{}^{m}C_{ks}A_{ds}T_{ds}{}^{m}C_{ds}{}^{m}C_{ds}A_{ds}{}^{m}C_{ds}{}^{m}C_{ds}T_{ds}G_{ds}A_{ds}{}^{m}C_{ks}A_{ks}{}^{m}C_{k}$ | 37.1 | 4508 | 4523 | 849 |
| 570545 | ${}^{m}C_{ks}{}^{m}C_{ks}{}^{m}C_{ks}T_{ds}{}^{m}C_{ds}A_{ds}T_{ds}{}^{m}C_{ds}{}^{m}C_{ds}A_{ds}{}^{m}C_{ds}{}^{m}C_{ds}T_{ds}G_{ks}A_{ks}{}^{m}C_{k}$ | 46 | 4510 | 4525 | 850 |
| 570546 | $G_{ks}{}^{m}C_{ks}{}^{m}C_{ks}{}^{m}C_{ds}{}^{m}C_{ds}T_{ds}{}^{m}C_{ds}A_{ds}T_{ds}{}^{m}C_{ds}{}^{m}C_{ds}A_{ds}{}^{m}C_{ds}{}^{m}C_{ks}T_{ks}G_{k}$ | 79.2 | 4512 | 4527 | 851 |
| 570547 | $A_{ks}G_{ks}G_{ks}{}^{m}C_{ds}{}^{m}C_{ds}{}^{m}C_{ds}{}^{m}C_{ds}T_{ds}{}^{m}C_{ds}A_{ds}T_{ds}{}^{m}C_{ds}{}^{m}C_{ds}A_{ks}{}^{m}C_{ks}{}^{m}C_{k}$ | 40.7 | 4514 | 4529 | 852 |
| 570548 | $G_{ks}A_{ks}A_{ks}G_{ds}G_{ds}{}^{m}C_{ds}{}^{m}C_{ds}{}^{m}C_{ds}{}^{m}C_{ds}T_{ds}{}^{m}C_{ds}A_{ds}T_{ds}{}^{m}C_{ks}{}^{m}C_{ks}A_{k}$ | 35.9 | 4516 | 4531 | 853 |
| 570549 | $A_{ks}G_{ks}G_{ks}T_{ds}A_{ds}A_{ds}G_{ds}A_{ds}G_{ds}A_{ds}{}^{m}C_{ds}{}^{m}C_{ds}{}^{m}C_{ds}{}^{m}C_{ks}{}^{m}C_{ks}{}^{m}C_{k}$ | 18.8 | 4613 | 4628 | 854 |
| 570550 | ${}^{m}C_{ks}{}^{m}C_{ks}A_{ks}G_{ds}G_{ds}T_{ds}A_{ds}A_{ds}G_{ds}A_{ds}G_{ds}A_{ds}{}^{m}C_{ds}{}^{m}C_{ks}{}^{m}C_{ks}{}^{m}C_{k}$ | 16.2 | 4615 | 4630 | 855 |
| 570551 | $T_{ks}T_{ks}{}^{m}C_{ks}{}^{m}C_{ds}A_{ds}G_{ds}G_{ds}T_{ds}A_{ds}A_{ds}G_{ds}A_{ds}G_{ds}A_{ks}{}^{m}C_{ks}{}^{m}C_{k}$ | 38.9 | 4617 | 4632 | 856 |
| 570552 | ${}^{m}C_{ks}{}^{m}C_{ks}A_{ks}T_{ds}T_{ds}{}^{m}C_{ds}{}^{m}C_{ds}A_{ds}G_{ds}G_{ds}T_{ds}A_{ds}A_{ds}G_{ks}A_{ks}G_{k}$ | 28.6 | 4620 | 4635 | 857 |
| 570553 | $T_{ks}{}^{m}C_{ks}{}^{m}C_{ks}{}^{m}C_{ds}A_{ds}T_{ds}T_{ds}{}^{m}C_{ds}{}^{m}C_{ds}A_{ds}G_{ds}G_{ds}T_{ds}A_{ks}A_{ks}G_{k}$ | 42.6 | 4622 | 4637 | 858 |
| 570554 | $T_{ks}A_{ks}T_{ks}{}^{m}C_{ds}{}^{m}C_{ds}{}^{m}C_{ds}A_{ds}T_{ds}T_{ds}{}^{m}C_{ds}{}^{m}C_{ds}A_{ds}G_{ds}G_{ks}T_{ks}A_{k}$ | 31.8 | 4624 | 4639 | 859 |
| 570555 | ${}^{m}C_{ks}{}^{m}C_{ks}T_{ks}A_{ds}T_{ds}{}^{m}C_{ds}{}^{m}C_{ds}{}^{m}C_{ds}A_{ds}T_{ds}T_{ds}{}^{m}C_{ds}{}^{m}C_{ds}A_{ks}G_{ks}G_{k}$ | 62 | 4626 | 4641 | 860 |
| 570556 | $G_{ks}A_{ks}{}^{m}C_{ks}{}^{m}C_{ds}T_{ds}A_{ds}T_{ds}{}^{m}C_{ds}{}^{m}C_{ds}{}^{m}C_{ds}A_{ds}T_{ds}T_{ds}{}^{m}C_{ks}{}^{m}C_{ks}A_{k}$ | 20 | 4628 | 4643 | 861 |
| 570557 | $A_{ks}A_{ks}G_{ks}A_{ds}{}^{m}C_{ds}{}^{m}C_{ds}T_{ds}A_{ds}T_{ds}{}^{m}C_{ds}{}^{m}C_{ds}{}^{m}C_{ds}A_{ds}T_{ks}T_{ks}{}^{m}C_{k}$ | 29.8 | 4630 | 4645 | 862 |
| 570558 | $T_{ks}G_{ks}A_{ks}A_{ds}G_{ds}A_{ds}{}^{m}C_{ds}{}^{m}C_{ds}T_{ds}A_{ds}T_{ds}{}^{m}C_{ds}{}^{m}C_{ds}{}^{m}C_{ks}A_{ks}T_{k}$ | 45.5 | 4632 | 4647 | 863 |
| 570559 | $T_{ks}G_{ks}G_{ks}{}^{m}C_{ds}{}^{m}C_{ds}{}^{m}C_{ds}{}^{m}C_{ds}G_{ds}T_{ds}T_{ds}A_{ds}G_{ds}A_{ds}A_{ks}T_{ks}T_{k}$ | 72.7 | 4650 | 4665 | 864 |
| 570560 | $A_{ks}G_{ks}T_{ks}G_{ds}G_{ds}{}^{m}C_{ds}{}^{m}C_{ds}{}^{m}C_{ds}{}^{m}C_{ds}G_{ds}T_{ds}T_{ds}A_{ds}G_{ks}A_{ks}A_{k}$ | 33.7 | 4652 | 4667 | 865 |
| 570561 | $G_{ks}{}^{m}C_{ks}A_{ks}G_{ds}T_{ds}G_{ds}G_{ds}{}^{m}C_{ds}{}^{m}C_{ds}{}^{m}C_{ds}{}^{m}C_{ds}G_{ds}T_{ds}T_{ks}A_{ks}G_{k}$ | 17.5 | 4654 | 4669 | 866 |
| 570562 | $A_{ks}G_{ks}G_{ks}{}^{m}C_{ds}A_{ds}G_{ds}T_{ds}G_{ds}G_{ds}{}^{m}C_{ds}{}^{m}C_{ds}{}^{m}C_{ds}{}^{m}C_{ds}G_{ks}T_{ks}T_{k}$ | 27.9 | 4656 | 4671 | 867 |

TABLE 17-continued

Inhibition of human DMPK RNA transcript in HepG2 cells targeting SEQ ID NO: 2

| ISIS No. | Sequence | % Target Expression | Start Site on Seq ID: 2 | Stop Site on Seq ID: 2 | Seq ID No. |
|---|---|---|---|---|---|
| 570563 | ${}^{m}C_{ks}T_{ks}A_{ks}G_{ds}G_{ds}{}^{m}C_{ds}A_{ds}G_{ds}T_{ds}G_{ds}G_{ds}{}^{m}C_{ds}{}^{m}C_{ds}{}^{m}C_{ks}{}^{m}C_{ks}G_{k}$ | 31.3 | 4658 | 4673 | 868 |
| 570564 | ${}^{m}C_{ks}{}^{m}C_{ks}{}^{m}C_{ks}T_{ds}A_{ds}G_{ds}G_{ds}{}^{m}C_{ds}A_{ds}G_{ds}T_{ds}G_{ds}G_{ds}{}^{m}C_{ks}{}^{m}C_{ks}{}^{m}C_{k}$ | 23.8 | 4660 | 4675 | 869 |
| 570565 | $A_{ks}G_{ks}G_{ks}T_{ds}{}^{m}C_{ds}{}^{m}C_{ds}{}^{m}C_{ds}A_{ds}G_{ds}A_{ds}{}^{m}C_{ds}A_{ds}{}^{m}C_{ds}T_{ks}{}^{m}C_{ks}{}^{m}C_{k}$ | 17.2 | 4678 | 4693 | 870 |
| 570566 | $A_{ks}T_{ks}A_{ks}G_{ds}G_{ds}T_{ds}{}^{m}C_{ds}{}^{m}C_{ds}{}^{m}C_{ds}A_{ds}G_{ds}A_{ds}{}^{m}C_{ds}A_{ks}{}^{m}C_{ks}T_{k}$ | 33.1 | 4680 | 4695 | 871 |
| 570567 | $G_{ks}A_{ks}A_{ks}T_{ds}A_{ds}G_{ds}G_{ds}T_{ds}{}^{m}C_{ds}{}^{m}C_{ds}{}^{m}C_{ds}A_{ds}G_{ds}A_{ks}{}^{m}C_{ks}A_{k}$ | 51.8 | 4682 | 4697 | 872 |
| 570568 | $G_{ks}A_{ks}G_{ks}A_{ds}A_{ds}T_{ds}A_{ds}G_{ds}G_{ds}T_{ds}{}^{m}C_{ds}{}^{m}C_{ds}{}^{m}C_{ds}A_{ks}G_{ks}A_{k}$ | 20.3 | 4684 | 4699 | 873 |
| 570569 | ${}^{m}C_{ks}A_{ks}G_{ks}A_{ds}G_{ds}A_{ds}A_{ds}T_{ds}A_{ds}G_{ds}G_{ds}T_{ds}{}^{m}C_{ds}{}^{m}C_{ks}{}^{m}C_{ks}A_{k}$ | 19 | 4686 | 4701 | 874 |

TABLE 18

Inhibition of human DMPK RNA transcript in HepG2 cells targeting SEQ ID NO: 2

| ISIS No. | Sequence | % Target Expression | Start Site on Seq ID: 2 | Stop Site on Seq ID: 2 | Seq ID No. |
|---|---|---|---|---|---|
| UTC | N/A | 100 | N/A | N/A | |
| 445569 | ${}^{m}C_{es}G_{es}G_{es}A_{es}G_{es}{}^{m}C_{ds}G_{ds}G_{ds}T_{ds}T_{ds}G_{ds}T_{ds}G_{ds}A_{ds}A_{ds}{}^{m}C_{es}T_{es}G_{es}G_{es}{}^{m}C_{e}$ | 33.8 | 13226 | 13245 | 24 |
| 486178 | $A_{ks}{}^{m}C_{ks}A_{ks}A_{ds}T_{ds}A_{ds}A_{ds}A_{ds}T_{ds}A_{ds}{}^{m}C_{ds}{}^{m}C_{ds}G_{ds}A_{ks}G_{ks}G_{k}$ | 24.4 | 13836 | 13851 | 23 |
| 570647 | $G_{ks}{}^{m}C_{ks}T_{ks}T_{ds}G_{ds}G_{ds}G_{ds}{}^{m}C_{ds}{}^{m}C_{ds}{}^{m}C_{ds}A_{ds}{}^{m}C_{ds}{}^{m}C_{ds}{}^{m}C_{ks}{}^{m}C_{ks}T_{k}$ | 60.6 | 5718 | 5733 | 645 |
| 570648 | $A_{ks}G_{ks}G_{ks}{}^{m}C_{ds}T_{ds}T_{ds}G_{ds}G_{ds}G_{ds}{}^{m}C_{ds}{}^{m}C_{ds}{}^{m}C_{ds}A_{ds}{}^{m}C_{ks}{}^{m}C_{ks}{}^{m}C_{k}$ | 82 | 5720 | 5735 | 646 |
| 570649 | ${}^{m}C_{ks}G_{ks}A_{ks}G_{ds}G_{ds}{}^{m}C_{ds}T_{ds}T_{ds}G_{ds}G_{ds}G_{ds}{}^{m}C_{ds}{}^{m}C_{ds}{}^{m}C_{ks}A_{ks}{}^{m}C_{k}$ | 133.4 | 5722 | 5737 | 647 |
| 570650 | $A_{ks}G_{ks}{}^{m}C_{ks}G_{ds}A_{ds}G_{ds}G_{ds}{}^{m}C_{ds}T_{ds}T_{ds}G_{ds}G_{ds}G_{ds}{}^{m}C_{ks}{}^{m}C_{ks}{}^{m}C_{k}$ | 54.1 | 5724 | 5739 | 648 |
| 570651 | $A_{ks}G_{ks}A_{ks}G_{ds}{}^{m}C_{ds}G_{ds}A_{ds}G_{ds}G_{ds}{}^{m}C_{ds}T_{ds}T_{ds}G_{ds}G_{ks}G_{ks}{}^{m}C_{k}$ | 88.5 | 5726 | 5741 | 649 |
| 570652 | $G_{ks}{}^{m}C_{ks}A_{ks}G_{ds}A_{ds}G_{ds}{}^{m}C_{ds}G_{ds}A_{ds}G_{ds}G_{ds}{}^{m}C_{ds}T_{ds}T_{ks}G_{ks}G_{k}$ | 162.9 | 5728 | 5743 | 650 |
| 570653 | $G_{ks}A_{ks}G_{ks}{}^{m}C_{ds}A_{ds}G_{ds}A_{ds}G_{ds}{}^{m}C_{ds}G_{ds}A_{ds}G_{ds}G_{ds}{}^{m}C_{ks}T_{ks}T_{k}$ | 130 | 5730 | 5745 | 651 |
| 570654 | $A_{ks}A_{ks}A_{ks}G_{ds}G_{ds}A_{ds}G_{ds}{}^{m}C_{ds}A_{ds}G_{ds}A_{ds}G_{ds}{}^{m}C_{ds}G_{ks}A_{ks}G_{k}$ | 66.5 | 5734 | 5749 | 652 |
| 570655 | ${}^{m}C_{ks}A_{ks}A_{ks}A_{ds}A_{ds}G_{ds}G_{ds}A_{ds}G_{ds}{}^{m}C_{ds}A_{ds}G_{ds}A_{ds}G_{ks}{}^{m}C_{ks}G_{k}$ | 79 | 5736 | 5751 | 653 |
| 570656 | $T_{ks}G_{ks}G_{ks}A_{ds}{}^{m}C_{ds}{}^{m}C_{ds}A_{ds}A_{ds}A_{ds}A_{ds}G_{ds}G_{ds}A_{ds}G_{ks}{}^{m}C_{ks}A_{k}$ | 57.4 | 5741 | 5756 | 654 |
| 570657 | ${}^{m}C_{ks}{}^{m}C_{ks}T_{ks}G_{ds}G_{ds}A_{ds}{}^{m}C_{ds}{}^{m}C_{ds}A_{ds}A_{ds}A_{ds}A_{ds}G_{ds}G_{ks}A_{ks}G_{k}$ | 129.2 | 5743 | 5758 | 655 |
| 570658 | ${}^{m}C_{ks}A_{ks}{}^{m}C_{ks}{}^{m}C_{ds}T_{ds}G_{ds}G_{ds}A_{ds}{}^{m}C_{ds}{}^{m}C_{ds}A_{ds}A_{ds}A_{ds}A_{ks}G_{ks}G_{k}$ | 66.3 | 5745 | 5760 | 656 |
| 570659 | ${}^{m}C_{ks}G_{ks}{}^{m}C_{ks}A_{ds}{}^{m}C_{ds}{}^{m}C_{ds}T_{ds}G_{ds}G_{ds}A_{ds}{}^{m}C_{ds}{}^{m}C_{ds}A_{ds}A_{ks}A_{ks}A_{k}$ | 58.7 | 5747 | 5762 | 657 |
| 570660 | $G_{ks}A_{ks}{}^{m}C_{ks}{}^{m}C_{ds}G_{ds}{}^{m}C_{ds}A_{ds}{}^{m}C_{ds}{}^{m}C_{ds}T_{ds}G_{ds}G_{ds}A_{ds}{}^{m}C_{ks}{}^{m}C_{ks}A_{k}$ | 55.4 | 5750 | 5765 | 658 |
| 570661 | $A_{ks}{}^{m}C_{ks}{}^{m}C_{ks}T_{ds}T_{ds}G_{ds}T_{ds}A_{ds}G_{ds}T_{ds}G_{ds}G_{ds}A_{ds}{}^{m}C_{ks}G_{ks}A_{k}$ | 45.4 | 5951 | 5966 | 659 |
| 570662 | $T_{ks}{}^{m}C_{ks}A_{ks}{}^{m}C_{ds}{}^{m}C_{ds}T_{ds}T_{ds}G_{ds}T_{ds}A_{ds}G_{ds}T_{ds}G_{ds}G_{ks}A_{ks}{}^{m}C_{k}$ | 63.5 | 5953 | 5968 | 660 |
| 570663 | $G_{ks}{}^{m}C_{ks}T_{ks}{}^{m}C_{ds}A_{ds}{}^{m}C_{ds}{}^{m}C_{ds}T_{ds}T_{ds}G_{ds}T_{ds}A_{ds}G_{ds}T_{ks}G_{ks}G_{k}$ | 56.6 | 5955 | 5970 | 661 |
| 570664 | $G_{ks}G_{ks}A_{ks}G_{ds}A_{ds}G_{ds}G_{ds}A_{ds}G_{ds}G_{ds}{}^{m}C_{ds}G_{ds}A_{ds}T_{ks}A_{ks}G_{k}$ | 125.6 | 6015 | 6030 | 662 |
| 570665 | $A_{ks}G_{ks}G_{ks}G_{ds}A_{ds}G_{ds}A_{ds}G_{ds}G_{ds}A_{ds}G_{ds}G_{ds}{}^{m}C_{ds}G_{ks}A_{ks}T_{k}$ | 64.2 | 6017 | 6032 | 663 |
| 570666 | ${}^{m}C_{ks}T_{ks}{}^{m}C_{ks}{}^{m}C_{ds}T_{ds}G_{ds}{}^{m}C_{ds}T_{ds}{}^{m}C_{ds}A_{ds}G_{ds}A_{ds}G_{ds}G_{ks}G_{ks}A_{k}$ | 59 | 6028 | 6043 | 664 |
| 570667 | $G_{ks}T_{ks}G_{ks}{}^{m}C_{ds}T_{ds}{}^{m}C_{ds}{}^{m}C_{ds}T_{ds}G_{ds}{}^{m}C_{ds}T_{ds}{}^{m}C_{ds}A_{ds}G_{ks}A_{ks}G_{k}$ | 82.3 | 6031 | 6046 | 665 |

TABLE 18-continued

Inhibition of human DMPK RNA transcript in HepG2 cells targeting SEQ ID NO: 2

| ISIS No. | Sequence | % Target Expression | Start Site on Seq ID: 2 | Stop Site on Seq ID: 2 | Seq ID No. |
|---|---|---|---|---|---|
| 570668 | $A_{ks}G_{ks}G_{ks}T_{ds}G_{ds}{}^{m}C_{ds}T_{ds}{}^{m}C_{ds}{}^{m}C_{ds}T_{ds}G_{ds}{}^{m}C_{ds}T_{ds}{}^{m}C_{ks}A_{ks}G_{k}$ | 96.2 | 6033 | 6048 | 666 |
| 570669 | $A_{ks}G_{ks}A_{ks}G_{ds}G_{ds}T_{ds}G_{ds}{}^{m}C_{ds}T_{ds}{}^{m}C_{ds}{}^{m}C_{ds}T_{ds}G_{ds}{}^{m}C_{ks}T_{ks}{}^{m}C_{k}$ | 26.2 | 6035 | 6050 | 667 |
| 570670 | $A_{ks}G_{ks}A_{ks}G_{ds}A_{ds}G_{ds}G_{ds}T_{ds}G_{ds}{}^{m}C_{ds}T_{ds}{}^{m}C_{ds}{}^{m}C_{ds}T_{ks}G_{ks}{}^{m}C_{k}$ | 18.2 | 6037 | 6052 | 668 |
| 570671 | $A_{ks}{}^{m}C_{ks}{}^{m}C_{ks}{}^{m}C_{ds}{}^{m}C_{ds}G_{ds}{}^{m}C_{ds}{}^{m}C_{ds}{}^{m}C_{ds}{}^{m}C_{ds}{}^{m}C_{ds}G_{ds}{}^{m}C_{ds}T_{ks}{}^{m}C_{ks}A_{k}$ | 29.2 | 6291 | 6306 | 669 |
| 570672 | ${}^{m}C_{ks}T_{ks}A_{ks}{}^{m}C_{ds}{}^{m}C_{ds}{}^{m}C_{ds}{}^{m}C_{ds}G_{ds}{}^{m}C_{ds}{}^{m}C_{ds}{}^{m}C_{ds}{}^{m}C_{ds}{}^{m}C_{ds}G_{ks}{}^{m}C_{ks}T_{k}$ | 50.3 | 6293 | 6308 | 670 |
| 570673 | $A_{ks}{}^{m}C_{ks}{}^{m}C_{ks}T_{ds}A_{ds}{}^{m}C_{ds}{}^{m}C_{ds}{}^{m}C_{ds}{}^{m}C_{ds}G_{ds}{}^{m}C_{ds}{}^{m}C_{ds}{}^{m}C_{ds}{}^{m}C_{ks}{}^{m}C_{ks}G_{k}$ | 26.8 | 6295 | 6310 | 671 |
| 570674 | $G_{ks}T_{ks}A_{ks}{}^{m}C_{ds}{}^{m}C_{ds}T_{ds}A_{ds}{}^{m}C_{ds}{}^{m}C_{ds}{}^{m}C_{ds}{}^{m}C_{ds}G_{ds}{}^{m}C_{ds}{}^{m}C_{ks}{}^{m}C_{ks}{}^{m}C_{k}$ | 40.8 | 6297 | 6312 | 672 |
| 570675 | $A_{ks}G_{ks}G_{ks}T_{ds}A_{ds}{}^{m}C_{ds}{}^{m}C_{ds}T_{ds}A_{ds}{}^{m}C_{ds}{}^{m}C_{ds}{}^{m}C_{ds}{}^{m}C_{ds}G_{ks}{}^{m}C_{ks}{}^{m}C_{k}$ | 56.1 | 6299 | 6314 | 673 |
| 570676 | $G_{ks}G_{ks}G_{ks}A_{ds}G_{ds}G_{ds}T_{ds}T_{ds}{}^{m}C_{ds}{}^{m}C_{ds}{}^{m}C_{ds}G_{ds}{}^{m}C_{ds}A_{ks}G_{ks}{}^{m}C_{k}$ | 95 | 6329 | 6344 | 674 |
| 570677 | $G_{ks}T_{ks}{}^{m}C_{ks}{}^{m}C_{ds}T_{ds}T_{ds}A_{ds}{}^{m}C_{ds}T_{ds}{}^{m}C_{ds}{}^{m}C_{ds}A_{ds}A_{ds}{}^{m}C_{ks}T_{ks}T_{k}$ | 23 | 6360 | 6375 | 675 |
| 570678 | ${}^{m}C_{ks}T_{ks}G_{ks}T_{ds}{}^{m}C_{ds}{}^{m}C_{ds}T_{ds}T_{ds}A_{ds}{}^{m}C_{ds}T_{ds}{}^{m}C_{ds}{}^{m}C_{ds}A_{ks}A_{ks}{}^{m}C_{k}$ | 23.4 | 6362 | 6377 | 676 |
| 570679 | ${}^{m}C_{ks}A_{ks}{}^{m}C_{ks}T_{ds}G_{ds}T_{ds}{}^{m}C_{ds}{}^{m}C_{ds}T_{ds}T_{ds}A_{ds}{}^{m}C_{ds}T_{ds}{}^{m}C_{ks}{}^{m}C_{ks}A_{k}$ | 7.4 | 6364 | 6379 | 677 |
| 570680 | $G_{ks}G_{ks}{}^{m}C_{ks}A_{ds}{}^{m}C_{ds}T_{ds}G_{ds}T_{ds}{}^{m}C_{ds}{}^{m}C_{ds}T_{ds}T_{ds}A_{ds}{}^{m}C_{ks}T_{ks}{}^{m}C_{k}$ | 20.6 | 6366 | 6381 | 678 |
| 570681 | $T_{ks}A_{ks}G_{ks}G_{ds}{}^{m}C_{ds}A_{ds}{}^{m}C_{ds}T_{ds}G_{ds}T_{ds}{}^{m}C_{ds}{}^{m}C_{ds}T_{ds}T_{ks}A_{ks}{}^{m}C_{k}$ | 29 | 6368 | 6383 | 679 |
| 570682 | $G_{ks}G_{ks}T_{ks}A_{ds}G_{ds}G_{ds}{}^{m}C_{ds}A_{ds}{}^{m}C_{ds}T_{ds}G_{ds}T_{ds}{}^{m}C_{ds}{}^{m}C_{ks}T_{ks}T_{k}$ | 10.5 | 6370 | 6385 | 680 |
| 570683 | $G_{ks}T_{ks}{}^{m}C_{ks}A_{ds}{}^{m}C_{ds}T_{ds}G_{ds}{}^{m}C_{ds}T_{ds}G_{ds}G_{ds}G_{ds}T_{ds}{}^{m}C_{ks}{}^{m}C_{ks}T_{k}$ | 23 | 6445 | 6460 | 681 |
| 570684 | $G_{ks}G_{ks}T_{ks}{}^{m}C_{ds}A_{ds}{}^{m}C_{ds}T_{ds}G_{ds}{}^{m}C_{ds}T_{ds}G_{ds}G_{ds}G_{ds}T_{ks}{}^{m}C_{ks}{}^{m}C_{k}$ | 22.5 | 6446 | 6461 | 433 |
| 570685 | $A_{ks}G_{ks}G_{ks}T_{ds}{}^{m}C_{ds}A_{ds}{}^{m}C_{ds}T_{ds}G_{ds}{}^{m}C_{ds}T_{ds}G_{ds}G_{ds}G_{ks}T_{ks}{}^{m}C_{k}$ | 10.2 | 6447 | 6462 | 682 |
| 570686 | ${}^{m}T_{ks}T_{ks}A_{ks}G_{ds}G_{ds}T_{ds}{}^{m}C_{ds}A_{ds}{}^{m}C_{ds}T_{ds}G_{ds}{}^{m}C_{ds}T_{ds}G_{ks}G_{ks}G_{k}$ | 11.1 | 6449 | 6464 | 683 |
| 570687 | $G_{ks}T_{ks}{}^{m}C_{ks}T_{ds}A_{ds}G_{ds}G_{ds}T_{ds}{}^{m}C_{ds}A_{ds}{}^{m}C_{ds}T_{ds}G_{ds}{}^{m}C_{ks}T_{ks}G_{k}$ | 11.7 | 6451 | 6466 | 684 |
| 570688 | $A_{ks}A_{ks}G_{ks}T_{ds}{}^{m}C_{ds}T_{ds}A_{ds}G_{ds}G_{ds}T_{ds}{}^{m}C_{ds}A_{ds}{}^{m}C_{ds}T_{ks}G_{ks}{}^{m}C_{k}$ | 14.6 | 6453 | 6468 | 685 |
| 570689 | $G_{ks}{}^{m}C_{ks}A_{ks}{}^{m}C_{ds}T_{ds}{}^{m}C_{ds}{}^{m}C_{ds}A_{ds}T_{ds}T_{ds}G_{ds}T_{ds}{}^{m}C_{ds}T_{ks}{}^{m}C_{ks}A_{k}$ | 10.1 | 6530 | 6545 | 686 |
| 570690 | ${}^{m}C_{ks}T_{ks}G_{ks}{}^{m}C_{ds}A_{ds}{}^{m}C_{ds}T_{ds}{}^{m}C_{ds}{}^{m}C_{ds}A_{ds}T_{ds}T_{ds}G_{ds}T_{ks}{}^{m}C_{ks}T_{k}$ | 35.4 | 6532 | 6547 | 687 |
| 570691 | ${}^{m}C_{ks}{}^{m}C_{ks}{}^{m}C_{ks}T_{ds}G_{ds}{}^{m}C_{ds}A_{ds}{}^{m}C_{ds}T_{ds}{}^{m}C_{ds}{}^{m}C_{ds}A_{ds}T_{ds}T_{ks}G_{ks}T_{k}$ | 33.6 | 6534 | 6549 | 688 |
| 570692 | ${}^{m}C_{ks}{}^{m}C_{ks}{}^{m}C_{ks}{}^{m}C_{ds}{}^{m}C_{ds}T_{ds}G_{ds}{}^{m}C_{ds}A_{ds}{}^{m}C_{ds}T_{ds}{}^{m}C_{ds}{}^{m}C_{ds}A_{ks}T_{ks}T_{k}$ | 77.3 | 6536 | 6551 | 689 |
| 570693 | ${}^{m}C_{ks}T_{ks}T_{ks}G_{ds}{}^{m}C_{ds}T_{ds}G_{ds}A_{ds}G_{ds}T_{ds}{}^{m}C_{ds}A_{ds}G_{ds}G_{ks}A_{ks}G_{k}$ | 18.9 | 6559 | 6574 | 690 |
| 570694 | $T_{ks}{}^{m}C_{ks}{}^{m}C_{ks}T_{ds}T_{ds}G_{ds}{}^{m}C_{ds}T_{ds}G_{ds}A_{ds}G_{ds}T_{ds}{}^{m}C_{ds}A_{ks}G_{ks}G_{k}$ | 30.9 | 6561 | 6576 | 691 |
| 570695 | ${}^{m}C_{ks}T_{ks}T_{ks}{}^{m}C_{ds}{}^{m}C_{ds}T_{ds}T_{ds}G_{ds}{}^{m}C_{ds}T_{ds}G_{ds}A_{ds}G_{ds}T_{ks}{}^{m}C_{ks}A_{k}$ | 21 | 6563 | 6578 | 692 |
| 570696 | $A_{ks}{}^{m}C_{ks}{}^{m}C_{ks}T_{ds}T_{ds}{}^{m}C_{ds}{}^{m}C_{ds}T_{ds}T_{ds}G_{ds}{}^{m}C_{ds}T_{ds}G_{ds}A_{ks}G_{ks}T_{k}$ | 50.3 | 6565 | 6580 | 693 |
| 570697 | $G_{ks}G_{ks}A_{ks}{}^{m}C_{ds}{}^{m}C_{ds}T_{ds}T_{ds}{}^{m}C_{ds}{}^{m}C_{ds}T_{ds}T_{ds}G_{ds}{}^{m}C_{ds}T_{ks}G_{ks}A_{k}$ | 28.3 | 6567 | 6582 | 694 |
| 570698 | ${}^{m}C_{ks}A_{ks}G_{ks}G_{ds}A_{ds}{}^{m}C_{ds}{}^{m}C_{ds}T_{ds}T_{ds}{}^{m}C_{ds}{}^{m}C_{ds}T_{ds}T_{ds}G_{ks}{}^{m}C_{ks}T_{k}$ | 47.6 | 6569 | 6584 | 695 |
| 570699 | $A_{ks}G_{ks}{}^{m}C_{ks}{}^{m}C_{ds}{}^{m}C_{ds}T_{ds}{}^{m}C_{ds}{}^{m}C_{ds}A_{ds}G_{ds}G_{ds}A_{ds}{}^{m}C_{ds}{}^{m}C_{ks}T_{ks}T_{k}$ | 17.9 | 6576 | 6591 | 696 |
| 570700 | $T_{ks}A_{ks}G_{ks}{}^{m}C_{ds}T_{ds}{}^{m}C_{ds}{}^{m}C_{ds}{}^{m}C_{ds}{}^{m}C_{ds}A_{ds}{}^{m}C_{ds}T_{ds}{}^{m}C_{ds}{}^{m}C_{ks}A_{ks}G_{k}$ | 24.1 | 6594 | 6609 | 697 |
| 570701 | $G_{ks}A_{ks}T_{ks}A_{ds}G_{ds}{}^{m}C_{ds}T_{ds}{}^{m}C_{ds}{}^{m}C_{ds}{}^{m}C_{ds}{}^{m}C_{ds}A_{ds}{}^{m}C_{ds}T_{ks}{}^{m}C_{ks}{}^{m}C_{k}$ | 12.9 | 6596 | 6611 | 698 |
| 570702 | ${}^{m}C_{ks}A_{ks}G_{ks}A_{ds}T_{ds}A_{ds}G_{ds}{}^{m}C_{ds}T_{ds}{}^{m}C_{ds}{}^{m}C_{ds}{}^{m}C_{ds}{}^{m}C_{ds}A_{ks}{}^{m}C_{ks}T_{k}$ | 24 | 6598 | 6613 | 699 |
| 570703 | ${}^{m}C_{ks}T_{ks}{}^{m}C_{ks}A_{ds}G_{ds}A_{ds}T_{ds}A_{ds}G_{ds}{}^{m}C_{ds}T_{ds}{}^{m}C_{ds}{}^{m}C_{ds}{}^{m}C_{ks}{}^{m}C_{ks}A_{k}$ | 22.3 | 6600 | 6615 | 700 |

TABLE 18-continued

Inhibition of human DMPK RNA transcript in HepG2 cells targeting SEQ ID NO: 2

| ISIS No. | Sequence | % Target Expression | Start Site on Seq ID: 2 | Stop Site on Seq ID: 2 | Seq ID No. |
|---|---|---|---|---|---|
| 570704 | $A_{ks}G_{ks}{}^{m}C_{ks}T_{ds}{}^{m}C_{ds}A_{ds}G_{ds}A_{ds}T_{ds}A_{ds}G_{ds}{}^{m}C_{ds}T_{ds}{}^{m}C_{ks}{}^{m}C_{ks}{}^{m}C_{k}$ | 31.8 | 6602 | 6617 | 701 |
| 570705 | $T_{ks}{}^{m}C_{ks}A_{ks}G_{ds}{}^{m}C_{ds}T_{ds}{}^{m}C_{ds}A_{ds}G_{ds}A_{ds}T_{ds}A_{ds}G_{ds}{}^{m}C_{ks}T_{ks}{}^{m}C_{k}$ | 33.9 | 6604 | 6619 | 702 |
| 570706 | $T_{ks}{}^{m}C_{ks}T_{ks}{}^{m}C_{ds}A_{ds}G_{ds}{}^{m}C_{ds}T_{ds}{}^{m}C_{ds}A_{ds}G_{ds}A_{ds}T_{ds}A_{ks}G_{ks}{}^{m}C_{k}$ | 28.1 | 6606 | 6621 | 703 |
| 570707 | $G_{ks}A_{ks}G_{ks}T_{ds}{}^{m}C_{ds}{}^{m}C_{ds}T_{ds}{}^{m}C_{ds}T_{ds}{}^{m}C_{ds}{}^{m}C_{ds}T_{ds}G_{ds}{}^{m}C_{ks}T_{ks}T_{k}$ | 37.2 | 6636 | 6651 | 704 |
| 570708 | $G_{ks}G_{ks}A_{ks}G_{ds}G_{ds}A_{ds}G_{ds}T_{ds}{}^{m}C_{ds}{}^{m}C_{ds}T_{ds}{}^{m}C_{ds}T_{ds}{}^{m}C_{ks}{}^{m}C_{ks}T_{k}$ | 66.3 | 6640 | 6655 | 705 |
| 570709 | $G_{ks}A_{ks}G_{ks}G_{ds}A_{ds}G_{ds}G_{ds}A_{ds}G_{ds}T_{ds}{}^{m}C_{ds}{}^{m}C_{ds}T_{ds}{}^{m}C_{ks}T_{ks}{}^{m}C_{k}$ | 52.7 | 6642 | 6657 | 706 |
| 570710 | ${}^{m}C_{ks}A_{ks}A_{ks}A_{ds}A_{ds}G_{ds}G_{ds}G_{ds}{}^{m}C_{ds}A_{ds}{}^{m}C_{ds}{}^{m}C_{ds}{}^{m}C_{ds}A_{ks}G_{ks}A_{k}$ | 31.8 | 6713 | 6728 | 707 |
| 570711 | $A_{ks}G_{ks}{}^{m}C_{ks}A_{ds}A_{ds}A_{ds}A_{ds}G_{ds}G_{ds}G_{ds}{}^{m}C_{ds}A_{ds}{}^{m}C_{ds}{}^{m}C_{ks}{}^{m}C_{ks}A_{k}$ | 12.3 | 6715 | 6730 | 708 |
| 570712 | $G_{ks}G_{ks}A_{ks}T_{ds}{}^{m}C_{ds}{}^{m}C_{ds}{}^{m}C_{ds}{}^{m}C_{ds}A_{ds}G_{ds}T_{ds}A_{ds}T_{ds}T_{ks}G_{ks}T_{k}$ | 37.1 | 6733 | 6748 | 709 |
| 570713 | ${}^{m}C_{ks}T_{ks}G_{ks}G_{ds}A_{ds}T_{ds}{}^{m}C_{ds}{}^{m}C_{ds}{}^{m}C_{ds}{}^{m}C_{ds}A_{ds}G_{ds}T_{ds}A_{ks}T_{ks}T_{k}$ | 42.4 | 6735 | 6750 | 710 |
| 570714 | $T_{ks}G_{ks}{}^{m}C_{ks}T_{ds}G_{ds}G_{ds}A_{ds}T_{ds}{}^{m}C_{ds}{}^{m}C_{ds}{}^{m}C_{ds}{}^{m}C_{ds}A_{ds}G_{ks}T_{ks}A_{k}$ | 31.4 | 6737 | 6752 | 711 |
| 570715 | $A_{ks}T_{ks}T_{ks}{}^{m}C_{ds}T_{ds}{}^{m}C_{ds}T_{ds}A_{ds}G_{ds}A_{ds}{}^{m}C_{ds}T_{ds}G_{ds}{}^{m}C_{ks}A_{ks}A_{k}$ | 12.1 | 6789 | 6804 | 712 |
| 570716 | $T_{ks}A_{ks}A_{ks}T_{ds}T_{ds}{}^{m}C_{ds}T_{ds}{}^{m}C_{ds}T_{ds}A_{ds}G_{ds}A_{ds}{}^{m}C_{ds}T_{ks}G_{ks}{}^{m}C_{k}$ | 9 | 6791 | 6806 | 713 |
| 570717 | $T_{ks}{}^{m}C_{ks}T_{ks}A_{ds}A_{ds}T_{ds}T_{ds}{}^{m}C_{ds}T_{ds}{}^{m}C_{ds}T_{ds}A_{ds}G_{ds}A_{ks}{}^{m}C_{ks}T_{k}$ | 32.1 | 6793 | 6808 | 714 |
| 570718 | $T_{ks}{}^{m}C_{ks}T_{ks}{}^{m}C_{ds}T_{ds}A_{ds}A_{ds}T_{ds}T_{ds}{}^{m}C_{ds}T_{ds}{}^{m}C_{ds}T_{ds}A_{ks}G_{ks}A_{k}$ | 71.4 | 6795 | 6810 | 715 |
| 570719 | ${}^{m}C_{ks}T_{ks}{}^{m}C_{ks}{}^{m}C_{ds}A_{ds}T_{ds}A_{ds}A_{ds}T_{ds}T_{ds}{}^{m}C_{ds}T_{ds}{}^{m}C_{ds}T_{ks}A_{ks}A_{k}$ | 36.9 | 6804 | 6819 | 716 |
| 570720 | $A_{ks}{}^{m}C_{ks}T_{ks}{}^{m}C_{ds}T_{ds}{}^{m}C_{ds}{}^{m}C_{ds}A_{ds}T_{ds}A_{ds}A_{ds}T_{ds}T_{ds}{}^{m}C_{ks}T_{ks}{}^{m}C_{k}$ | 17.1 | 6807 | 6822 | 717 |
| 570721 | $A_{ks}{}^{m}C_{ks}A_{ks}{}^{m}C_{ds}T_{ds}{}^{m}C_{ds}T_{ds}{}^{m}C_{ds}{}^{m}C_{ds}A_{ds}T_{ds}A_{ds}A_{ds}T_{ks}T_{ks}{}^{m}C_{k}$ | 23.7 | 6809 | 6824 | 718 |
| 570722 | ${}^{m}C_{ks}{}^{m}C_{ks}A_{ks}{}^{m}C_{ds}A_{ds}{}^{m}C_{ds}T_{ds}{}^{m}C_{ds}T_{ds}{}^{m}C_{ds}{}^{m}C_{ds}A_{ds}T_{ds}A_{ks}A_{ks}T_{k}$ | 34.4 | 6811 | 6826 | 719 |
| 570723 | $T_{ks}G_{ks}{}^{m}C_{ks}{}^{m}C_{ds}A_{ds}{}^{m}C_{ds}A_{ds}{}^{m}C_{ds}T_{ds}{}^{m}C_{ds}T_{ds}{}^{m}C_{ds}{}^{m}C_{ds}A_{ks}T_{ks}A_{k}$ | 38.7 | 6813 | 6828 | 720 |

Example 10: Dose Response Studies with Antisense Oligonucleotides Targeting Human Dystrophia Myotonica-Protein Kinase (DMPK) in HepG2 Cells Antisense oligonucleotides targeted to a human DMPK nucleic acid were tested for their effect on human DMPK RNA transcript in vitro. Cultured HepG2 cells at a density of 20,000 cells per well were transfected using electroporation with 61.7 nM, 185.2 nM, 555.6 nM, 1666.7 nM, 5000.0 nM, and 15000.0 nM concentrations of each antisense oligonucleotide. After approximately 24 hours, RNA was isolated from the cells and DMPK RNA transcript levels were measured by quantitative real-time PCR using primer probe set RTS3164 (forward sequence AGCCTGAGCCGGGAGATG, designated herein as SEQ ID NO: 20; reverse sequence GCGTAGTTGACTGGCGAAGTT, designated herein as SEQ ID NO: 21; probe sequence AGGCCATCCGCACGGACAACCX, designated herein as SEQ ID NO: 22). Human DMPK RNA transcript levels were adjusted according to total RNA content, as measured by RIBOGREEN®. Results are presented as percent expression of human DMPK, relative to untreated control (UTC) cells. For example, if the UTC is 100 and a dose of 5000 nM of ISIS No. 445569 yields a % Expression of human DMPK of 35 then the 5000 nM dose of ISIS reduced expression of human DMPK by 65% relative to the UTC. The half maximal inhibitory concentration ($IC_{50}$) of each oligonucleotide is presented in the table below and was calculated by plotting the concentrations of oligonucleotides used versus the percent inhibition of human DMPK mRNA expression achieved at each concentration, and noting the concentration of oligonucleotide at which 50% inhibition of human DMPK mRNA expression was achieved compared to the control. The results are presented in Table 19.

The tested antisense oligonucleotide sequences demonstrated dose-dependent inhibition of human DMPK mRNA levels under the conditions specified above.

TABLE 19

Dose response studies for with antisense oligonucleotides targeting hDMPK in HepG2 Cells

| ISIS No. | Dose (nM) | % Expression of human DMPK | $IC_{50}$ |
|---|---|---|---|
| UTC | ND | 100 | ND |
| 445569 | 61.7 | 115.3 | 2.3 |
| | 185.2 | 87.9 | |
| | 555.6 | 69.0 | |
| | 1666.7 | 57.2 | |
| | 5000.0 | 35.0 | |
| | 15000.0 | 22.6 | |

TABLE 19-continued

Dose response studies for with antisense oligonucleotides targeting hDMPK in HepG2 Cells

| ISIS No. | Dose (nM) | % Expression of human DMPK | $IC_{50}$ |
|---|---|---|---|
| 512497 | 61.7 | 108.6 | 2 |
| | 185.2 | 98.4 | |
| | 555.6 | 77.9 | |
| | 1666.7 | 57.2 | |
| | 5000.0 | 28.0 | |
| | 15000.0 | 12.8 | |
| 486178 | 61.7 | 88.2 | 0.7 |
| | 185.2 | 67.1 | |
| | 555.6 | 49.4 | |
| | 1666.7 | 32.8 | |
| | 5000.0 | 26.7 | |
| | 15000.0 | 11.8 | |
| 569473 | 61.7 | 107.9 | 0.6 |
| | 185.2 | 66.5 | |
| | 555.6 | 33.6 | |
| | 1666.7 | 23.5 | |
| | 5000.0 | 12.8 | |
| | 15000.0 | 9.2 | |
| 570808 | 61.7 | 77.2 | 0.2 |
| | 185.2 | 52.7 | |
| | 555.6 | 20.6 | |
| | 1666.7 | 8.1 | |
| | 5000.0 | 7.2 | |
| | 15000.0 | 5.4 | |
| 594292 | 61.7 | 96.2 | 5.5 |
| | 185.2 | 99.6 | |
| | 555.6 | 80.0 | |
| | 1666.7 | 59.0 | |
| | 5000.0 | 45.5 | |
| | 15000.0 | 42.8 | |
| 594300 | 61.7 | 101.7 | >15 |
| | 185.2 | 104.3 | |
| | 555.6 | 101.6 | |
| | 1666.7 | 93.6 | |
| | 5000.0 | 74.9 | |
| | 15000.0 | 66.8 | |
| 598768 | 61.7 | 95.5 | 1.2 |
| | 185.2 | 83.6 | |
| | 555.6 | 70.6 | |
| | 1666.7 | 40.7 | |
| | 5000.0 | 22.2 | |
| | 15000.0 | 7.3 | |
| 598769 | 61.7 | 103.9 | 1.9 |
| | 185.2 | 105.3 | |
| | 555.6 | 76.1 | |
| | 1666.7 | 50.4 | |
| | 5000.0 | 29.8 | |
| | 15000.0 | 12.1 | |
| 598777 | 61.7 | 96.4 | 0.9 |
| | 185.2 | 69.4 | |
| | 555.6 | 41.8 | |
| | 1666.7 | 42.8 | |
| | 5000.0 | 16.4 | |
| | 15000.0 | 27.1 | |

Example 11: Dose Response Studies with Antisense Oligonucleotides Targeting Human Dystrophia Myotonica-Protein Kinase (hDMPK) in Steinert DM1 Myoblast Cells Antisense oligonucleotides targeted to a human DMPK nucleic acid were tested for their effect on human DMPK RNA transcript in vitro. Cultured Steinert DM1 myoblast cells at a density of 20,000 cells per well were transfected using electroporation with 61.7 nM, 185.2 nM, 555.6 nM, 1666.7 nM, 5000.0 nM, and 15000.0 nM concentrations of each antisense oligonucleotide. After approximately 24 hours, RNA was isolated from the cells and DMPK RNA transcript levels were measured by quantitative real-time PCR using primer probe set RTS3164 described above. Human DMPK RNA transcript levels were adjusted according to total RNA content, as measured by RIBOGREEN®. Results are presented as percent (%) expression of human DMPK, relative to untreated control (UTC) cells. The half maximal inhibitory concentration ($IC_{50}$) of each oligonucleotide is presented in the table below and was calculated by plotting the concentrations of oligonucleotides used versus the percent inhibition of human DMPK mRNA expression achieved at each concentration, and noting the concentration of oligonucleotide at which 5000 inhibition of human DMPK mRNA expression was achieved compared to the control. The results are presented in Table 20.

The tested antisense oligonucleotide sequences demonstrated dose-dependent inhibition of human DMPK mRNA levels under the conditions specified above.

TABLE 20

Dose response studies for with antisense oligonucleotides targeting hDMPK in Steinert DM1 Cells

| ISIS No. | Dose (nM) | % Expression of human DMPK | $IC_{50}$ |
|---|---|---|---|
| UTC | ND | 100 | ND |
| 445569 | 61.7 | 58.3 | 0.4 |
| | 185.2 | 56.7 | |
| | 555.6 | 58.5 | |
| | 1666.7 | 40.9 | |
| | 5000.0 | 26.0 | |
| | 15000.0 | 23.5 | |
| 512497 | 61.7 | 78.1 | 5.1 |
| | 185.2 | 77.5 | |
| | 555.6 | 98.8 | |
| | 1666.7 | 71.2 | |
| | 5000.0 | 51.3 | |
| | 15000.0 | 22.8 | |
| 486178 | 61.7 | 78.0 | 0.5 |
| | 185.2 | 61.3 | |
| | 555.6 | 43.3 | |
| | 1666.7 | 27.4 | |
| | 5000.0 | 24.6 | |
| | 15000.0 | 16.9 | |
| 569473 | 61.7 | 83.3 | 0.6 |
| | 185.2 | 54.8 | |
| | 555.6 | 64.5 | |
| | 1666.7 | 26.1 | |
| | 5000.0 | 19.4 | |
| | 15000.0 | 15.4 | |
| 570808 | 61.7 | 103.6 | 0.9 |
| | 185.2 | 77.8 | |
| | 555.6 | 46.7 | |
| | 1666.7 | 25.2 | |
| | 5000.0 | 20.8 | |
| | 15000.0 | 19.3 | |
| 594292 | 61.7 | 100.1 | 5.6 |
| | 185.2 | 109.7 | |
| | 555.6 | 72.6 | |
| | 1666.7 | 66.2 | |
| | 5000.0 | 39.5 | |
| | 15000.0 | 45.7 | |
| 594300 | 61.7 | 96.2 | 5.6 |
| | 185.2 | 87.1 | |
| | 555.6 | 70.3 | |
| | 1666.7 | 66.4 | |
| | 5000.0 | 58.1 | |
| | 15000.0 | 33.2 | |
| 598768 | 61.7 | 77.0 | 0.7 |
| | 185.2 | 62.9 | |
| | 555.6 | 62.0 | |
| | 1666.7 | 35.6 | |
| | 5000.0 | 24.5 | |
| | 15000.0 | 21.0 | |
| 598769 | 61.7 | 70.3 | 0.4 |
| | 185.2 | 49.2 | |
| | 555.6 | 55.3 | |
| | 1666.7 | 33.2 | |

TABLE 20-continued

Dose response studies for with antisense oligonucleotides targeting hDMPK in Steinert DM1 Cells

| ISIS No. | Dose (nM) | % Expression of human DMPK | $IC_{50}$ |
|---|---|---|---|
| | 5000.0 | 27.1 | |
| | 15000.0 | 13.4 | |
| 598777 | 61.7 | 87.7 | 1 |
| | 185.2 | 61.7 | |
| | 555.6 | 57.3 | |
| | 1666.7 | 37.9 | |
| | 5000.0 | 30.0 | |
| | 15000.0 | 29.7 | |

Example 12: Dose Response Studies with Antisense Oligonucleotides Targeting Rhesus Monkey Dystrophia Myotonica-Protein Kinase (DMPK) in Cynomolgus Monkey Primary Hepatocytes Antisense oligonucleotides targeted to a rhesus monkey DMPK nucleic acid were tested for their effect on rhesus monkey DMPK RNA transcript in vitro. Cultured cynomolgus monkey primary hepatocytes cells at a density of 20,000 cells per well were transfected using electroporation with 61.7 nM, 185.2 nM, 555.6 nM, 1666.7 nM, 5000.0 nM, and 15000.0 nM concentrations of each antisense oligonucleotide. After approximately 24 hours, RNA was isolated from the cells and DMPK RNA transcript levels were measured by quantitative real-time PCR using primer probe set RTS3164 described above. Rhesus monkey DMPK RNA transcript levels were adjusted according to total RNA content, as measured by RIBOGREEN®. Results are presented as percent (%) expression of rhesus monkey DMPK, relative to untreated control (UTC) cells. The half maximal inhibitory concentration ($IC_{50}$) of each oligonucleotide is presented in the table below and was calculated by plotting the concentrations of oligonucleotides used versus the percent inhibition of rhesus monkey DMPK mRNA expression achieved at each concentration, and noting the concentration of oligonucleotide at which 50% inhibition of rhesus monkey DMPK mRNA expression was achieved compared to the control.

The tested antisense oligonucleotide sequences demonstrated dose-dependent inhibition of rhesus monkey DMPK mRNA levels under the conditions specified above.

TABLE 21

Dose response studies for with antisense oligonucleotides targeting rhesus monkey DMPK in cynomolgus monkey primary hepatocytes

| ISIS No. | Dose (nM) | % Expression of human DMPK | $IC_{50}$ |
|---|---|---|---|
| UTC | ND | 100 | ND |
| 445569 | 61.7 | 79.7 | 1.4 |
| | 185.2 | 41.1 | |
| | 555.6 | 58.1 | |
| | 1666.7 | 33.5 | |
| | 5000.0 | 46.9 | |
| | 15000.0 | 50.0 | |
| 512497 | 61.7 | 123.4 | 1.5 |
| | 185.2 | 63.7 | |
| | 555.6 | 44.8 | |
| | 1666.7 | 34.1 | |
| | 5000.0 | 51.2 | |
| | 15000.0 | 23.5 | |
| 486178 | 61.7 | 51.1 | <.06 |
| | 185.2 | 30.6 | |
| | 555.6 | 22.0 | |
| | 1666.7 | 23.5 | |
| | 5000.0 | 9.8 | |
| | 15000.0 | 19.2 | |
| 569473 | 61.7 | 82.1 | .2 |
| | 185.2 | 39.4 | |
| | 555.6 | 17.7 | |
| | 1666.7 | 28.5 | |
| | 5000.0 | 20.0 | |
| | 15000.0 | 15.6 | |
| 570808 | 61.7 | 74.6 | 0.1 |
| | 185.2 | 27.6 | |
| | 555.6 | 16.4 | |
| | 1666.7 | 25.6 | |
| | 5000.0 | 8.8 | |
| | 15000.0 | 21.9 | |
| 594292 | 61.7 | 93.0 | >15 |
| | 185.2 | 82.1 | |
| | 555.6 | 106.0 | |
| | 1666.7 | 91.1 | |
| | 5000.0 | 62.2 | |
| | 15000.0 | 70.4 | |
| 594300 | 61.7 | 105.5 | >15 |
| | 185.2 | 91.8 | |
| | 555.6 | 114.9 | |
| | 1666.7 | 65.7 | |
| | 5000.0 | 110.2 | |
| | 15000.0 | 118.8 | |
| 598768 | 61.7 | 70.3 | 0.4 |
| | 185.2 | 57.8 | |
| | 555.6 | 58.5 | |
| | 1666.7 | 16.5 | |
| | 5000.0 | 24.0 | |
| | 15000.0 | 13.4 | |
| 598769 | 61.7 | 76.5 | 1.1 |
| | 185.2 | 65.1 | |
| | 555.6 | 64.0 | |
| | 1666.7 | 34.4 | |
| | 5000.0 | 60.9 | |
| | 15000.0 | 8.6 | |
| 598777 | 61.7 | 161.4 | 2.1 |
| | 185.2 | 51.7 | |
| | 555.6 | 47.5 | |
| | 1666.7 | 34.6 | |
| | 5000.0 | 27.8 | |
| | 15000.0 | 52.9 | |

Example 13: In Vivo Antisense Inhibition of hDMPK in DMSXL Transgenic Mice

To test the effect of antisense inhibition for the treatment of myotonic dystrophy type 1 (DM1), an appropriate mouse model was required. The transgenic mouse model, DMSXL carrying the hDMPK gene with large expansions of over 1000 CTG repeats was generated (Huguet et al., *PLOS Genetics,* 2012, 8(11), e1003034-e1003043). These DMSXL mice express the mutant hDMPK allele and display muscle weakness phenotype similar to that seen in DM1 patients.

ISIS 486178 from Table 1 was selected and tested for antisense inhibition of hDMPK transcript in vivo. ISIS 445569 was included in the study for comparison.

Treatment

DMSXL mice were maintained on a 12-hour light/dark cycle and fed ad libitum normal Purina mouse chow. Animals were acclimated for at least 7 days in the research facility before initiation of the experiment. Antisense oligonucleotides (ASOs) were prepared in PBS and sterilized by filtering through a 0.2 micron filter. ASOs were dissolved in 0.9% PBS for injection.

DMSXL mice received subcutaneous injections of ISIS 445569 at 50 mg/kg or ISIS 486178 at 25 mg/kg twice per week for 4 weeks. The control group received subcutaneous injections of PBS twice weekly for 4 weeks. Each treatment group consisted of 4 animals.

Inhibition of hDMPK mRNA Levels

Twenty four hours after the final dose, the mice were sacrificed and tissues were collected. mRNA was isolated for real-time PCR analysis of hDMPK and normalized to 18s RNA. Human primer probe set RTS3164 was used to measure mRNA levels. The results are expressed as the average percent of hDMPK mRNA levels for each treatment group, relative to PBS control.

Human primer probe set RTS3164 (forward sequence AGCCTGAGCCGGGAGATG, designated herein as SEQ ID NO: 20; reverse sequence GCGTAGTTG ACTGGCGAAGTT, designated herein as SEQ ID NO: 21; probe sequence AGGCCATCCGCACGGACAACCX, designated herein as SEQ ID NO: 22).

As presented in Table 22 below, treatment with antisense oligonucleotides reduced hDMPK transcript expression. The results indicate that treatment with ISIS 445569 and 486178 resulted in reduction of hDMPK mRNA levels in DMSXL mice.

TABLE 22

Effect of antisense oligonucleotides on hDMPK inhibition in DMSXL mice

| ISIS No. | Dosage (mg/kg) | Tissue Type | hDMPK mRNA levels (% PBS) | Motif/ Length |
|---|---|---|---|---|
| PBS | 0 | | | |
| 486178 | 25 | Tibialis Anterior | 70.7 | kkk-d10-kkk (16 mer) |
| | | Soleus | 67.3 | |
| | | Quadriceps | 73.9 | |
| | | Latissiumus grand dorsi | 71.0 | |
| | | Triceps | 67.1 | |
| | | Diaphragm | 68.9 | |
| | | Heart | 30.8 | |
| | | Brain | 11.8 | |
| 445569 | 50 | Tibialis Anterior | 38.4 | e5-d10-e5 (20 mer) |
| | | Soleus | 47.5 | |
| | | Quadriceps | 41.3 | |
| | | Latissiumus grand dorsi | 35.7 | |
| | | Triceps | 30.5 | |
| | | Diaphragm | 44.7 | |
| | | Heart | 7.6 | |
| | | Brain | 13.1 | |

Example 14: Effect of ASO Treatment on Muscle Strength in DMSXL Mice Targeting hDMPK Griptest Mice were assessed for grip strength performance in wild-type (WT) and DMSXL forelimb using a commercial grip strength dynamometer as described in the literature ((Huguet et al., *PLOS Genetics,* 2012, 8(11), e1003034-e1003043).

DMSXL mice received subcutaneous injections of ISIS 486178 at 25 mg/kg or ISIS 445569 at 50 mg/kg twice per week for 4 weeks. The control DMSXL group received subcutaneous injections of PBS twice weekly for 4 weeks. Each treatment group consisted of 4 animals. The forelimb force for each treatment group and WT was measured at day 0, 30, and 60 using the griptest. The grip strength performance was determined by measuring the force difference between day 60 and day 0. Results are presented as the average forelimb force from each group.

As illustrated in Table 23, below, treatment with ASOs targeting hDMPK improved muscle strength in DMSXL mice compared to untreated control. ISIS 486178, an ASO with cEt modifications, demonstrated substantial improvement in the forelimb strength (+3.4) compared to ISIS 445569 with MOE modifications (+0.38).

TABLE 23

Effect of ASO treatment on muscle strength in DMSXL mice targeting hDMPK

| Treatment group | Forelimb force (g) | | | |
|---|---|---|---|---|
| | Day 0 | Day 30 | Day 60 | Δ = Day 60 − Day 0 |
| Untreated control | 72.2 | 70.2 | 67.5 | −4.6 |
| ASO 486178 | 62.3 | 65.7 | 65.6 | +3.4 |
| ASO 445569 | 64.3 | 68 | 64.7 | +0.38 |
| Wild type (WT) | 75.2 | 76.5 | 78.4 | +3.2 |

Example 15: Effect of ASO Treatment on Muscle Fiber Distribution in DMSXL Mice Targeting hDMPK The muscle fiber distribution in DMSXL mice targeting hDMPK in the presence and absence of ISIS 445569 and 486178 was also assessed. Both ASOs were previously described in Table 1, above.

DMSXL mice received subcutaneous injections of ISIS 486178 at 25 mg/kg or ISIS 445569 at 50 mg/kg twice per week for 4 weeks. The control DMSXL group received subcutaneous injections of PBS twice weekly for 4 weeks. Each treatment group consisted of 4 animals. The muscle fiber distribution was assessed and the results are presented Table 44, below.

As illustrated, treatment with ASOs targeting hDMPK decreased the distribution of DM1 Associated Type 2c muscle fiber in the tibialis anterior (TA) of DMSXL mice compared to untreated control. The results demonstrated that normal pattern of fiber distribution in the skeletal muscles can be restored with ASO treatment. ISIS 445569 demonstrated an improvement in the muscle fiber distribution as compared to the untreated control; however ISIS 486178, an ASO with cEt modifications, demonstrated muscle fiber distribution that was more consistent with the muscle fiber distribution found in the wild-type mice.

TABLE 24

Effect of ASO treatment on muscle fiber distribution in DMSXL mice targeting hDMPK

| Treatment group | Fiber Type Distribution in TA muscle | | |
|---|---|---|---|
| | Fiber 1 | Fiber 2a | Fiber 2c |
| Untreated control | 4% | 25% | 5.90% |
| ASO 486178 | 3.10% | 15% | 0.70% |
| ASO 445569 | 4% | 21% | 2% |
| Wild type (WT) | 3.30% | 15% | 0.00% |

Example 16: Dose-Dependent Antisense Inhibition of hDMPK in DMSXL Transgenic Mice The newly designed ASOs from Table 1, above, were further evaluated in a dose-response study for antisense inhibition of hDMPK transcript in vivo. ISIS 445569 was included in the study for comparison.

Treatment

DMSXL mice were maintained on a 12-hour light/dark cycle and fed ad libitum normal Purina mouse chow. Animals were acclimated for at least 7 days in the research facility before initiation of the experiment. Antisense oligonucleotides (ASOs) were prepared in PBS and sterilized by filtering through a 0.2 micron filter. ASOs were dissolved in 0.9% PBS for injection.

DMSXL mice received subcutaneous injections of PBS or ASOs from Table 1, above, targeting hDMPK. The ASO was dosed twice per week for 4 weeks at the indicated doses in Table 25, below. The control group received subcutaneous injections of PBS twice weekly for 4 weeks. Each treatment group consisted of 4 animals.

Inhibition of hDMPK mRNA Levels

Forty eight hours after the final dose, the mice were sacrificed and tissue from the tibialis anterior muscles, quadriceps muscles (left), gastrocnlemius muscles, heart and diaphragm was isolated. mRNA was isolated for real-time PCR analysis of hDMPK and normalized to RIBOGREEN®. Human primer probe set RTS3164 was used to measure mRNA levels. The results summarized in Table 25, below, were independently generated from various dose-response studies. The results are presented as the average percent of hDMPK mRNA expression levels for each treatment group, relative to PBS control.

As presented, treatment with antisense oligonucleotides reduced hDMPK transcript expression in a dose-dependent manner.

TABLE 25

Dose-dependent inhibition of hDMPK mRNA levels in DMSXL mice

| ISIS | mg/ | hDMPK mRNA levels (% PBS) | | | | |
|---|---|---|---|---|---|---|
| No. | kg/wk | TA | Quad (Left) | Gastroc | Heart | Diaphragm |
| PBS | 0 | 100 | 100 | 100 | 100 | 100 |
| 445569 | 50 | 54.7 | 80.3 | 97.1 | 55.4 | 21.7 |
| | 100 | 28.3 | 42.1 | 71.3 | 48.9 | 19.7 |
| | 200 | 22.2 | 33.9 | 45.2 | 34.2 | 10.0 |
| 512497 | 50 | 23.8 | 48.9 | 52.9 | 44.4 | 35.0 |
| | 100 | 9.7 | 28.7 | 24.8 | 43.8 | 24.2 |
| | 200 | 11.4 | 22.4 | 16.4 | 42.0 | 15.2 |
| 486178 | 25 | 59.1 | 56.1 | 63.1 | 75.3 | 39.1 |
| | 50 | 33.8 | 61.9 | 58.7 | 59.2 | 32.5 |
| | 100 | 36.6 | 65.8 | 51.6 | 47.3 | 26.2 |
| 570808 | 25 | 26.3 | 41.1 | 39.8 | 44.9 | 17.3 |
| | 50 | 12.2 | 13.0 | 36.3 | 18.4 | 8.1 |
| | 100 | 6.1 | 5.4 | 7.9 | 10.2 | 3.0 |
| 594292 | 25 | 48.8 | 32.2 | 68.8 | 70.6 | 72.7 |
| | 50 | 32.0 | 30.4 | 41.1 | 85.1 | 48.3 |
| | 100 | 31.6 | 39.6 | 53.3 | 63.9 | 40.2 |
| 598768 | 25 | 16.9 | 27.1 | 27.5 | 56.3 | 26.9 |
| | 50 | 10.2 | 33.6 | 24.1 | 30.8 | 20.2 |
| | 100 | 6.8 | 22.0 | 25.5 | 22.6 | 13.1 |
| 598769 | 25 | 21.6 | 50.8 | 48.1 | 61.0 | 30.3 |
| | 50 | 12.7 | 25.1 | 42.3 | 36.4 | 16.7 |
| | 100 | 12.8 | 18.4 | 33.2 | 32.0 | 20.2 |
| 569473 | 25 | 42.0 | 21.8 | 48.9 | 51.8 | 34.8 |
| | 50 | 41.6 | 16.2 | 47.6 | 55.6 | 23.6 |
| | 100 | 31.9 | 19.2 | 31.9 | 35.6 | 20.5 |

TABLE 25-continued

Dose-dependent inhibition of hDMPK mRNA levels in DMSXL mice

| ISIS | mg/ | hDMPK mRNA levels (% PBS) | | | | |
|---|---|---|---|---|---|---|
| No. | kg/wk | TA | Quad (Left) | Gastroc | Heart | Diaphragm |
| 594300 | 25 | 114.5 | 56.7 | 96.2 | 91.0 | 62.6 |
| | 50 | 44.3 | 22.3 | 52.8 | 69.3 | 54.7 |
| | 100 | 73.0 | 22.6 | 56.6 | 78.3 | 44.5 |
| 598777 | 25 | 49.4 | 28.8 | 76.1 | 97.1 | 58.7 |
| | 50 | 44.8 | 13.6 | 36.5 | 87.4 | 40.8 |
| | 100 | 31.8 | 10.1 | 22.5 | 86.8 | 33.6 |

TA = Tibialis Anterior;
Quad = Quadriceps;
Gastroc = Gastrocnemius

Example 17: Six Week In Vivo Tolerability Study in CD-1 Mice

The newly designed ASOs from Table 1, above, were further evaluated in a 6 week study to assess plasma chemistry, body/organ weights and histology. Groups of CD-1 mice were administered 100 mg/kg/wk of ISIS 445569 or ISIS 512497. Further groups of CD-1 mice were administered 50 mg/kg/wk of ISIS 486178, ISIS 570808, ISIS 594292, ISIS 598768, ISIS 598769, ISIS 569473, ISIS 594300, and ISIS 598777. After six weeks and two days after each group of mice received the last dose, the mice were sacrificed and tissues were collected for analysis. For each group of mice, analysis to measure alanine transaminase levels, aspartate aminotransferase levels, blood urea nitrogen (BUN) levels, albumin levels, total bilirubin, and creatine levels was measured. Additionally, organ weights were also measured, the results of which are presented in the tables below.

TABLE 26

Plasma Chemistry in CD-1 mice

| ISIS No. | ALT (U/L) | AST (U/L) | BUN (mg/dL) | Albumin (g/dL) | T. Bil (mg/dL) | Creatinine (mg/dL) |
|---|---|---|---|---|---|---|
| PBS | 31.75 | 60.75 | 32.73 | 2.99 | 0.23 | 0.16 |
| 486178 | 65.00 | 103.00 | 27.18 | 2.90 | 0.19 | 0.13 |
| 445569 | 162.75 | 195.25 | 29.70 | 3.38 | 0.26 | 0.14 |
| 570808 | 313.50 | 332.50 | 32.40 | 2.81 | 0.28 | 0.15 |
| 594292 | 58.75 | 133.00 | 28.15 | 2.94 | 0.21 | 0.13 |
| 598768 | 45.50 | 92.00 | 26.85 | 2.90 | 0.21 | 0.11 |
| 598769 | 69.25 | 94.25 | 32.73 | 2.89 | 0.18 | 0.13 |
| 512497 | 101.25 | 144.50 | 26.90 | 2.90 | 0.19 | 0.12 |
| 569473 | 75.75 | 137.00 | 28.98 | 3.05 | 0.26 | 0.13 |
| 594300 | 46.00 | 76.75 | 24.70 | 2.94 | 0.18 | 0.11 |
| 598777 | 186.50 | 224.25 | 24.68 | 2.97 | 0.30 | 0.11 |

TABLE 27

Body & Organ Weights in CD-1 mice

| ISIS No. | *Kidney % BW | *Liver % BW | *Spleen % BW |
|---|---|---|---|
| PBS | 1.00 | 1.00 | 1.00 |
| 486178 | 1.05 | 1.05 | 1.03 |
| 445569 | 1.07 | 1.09 | 1.23 |
| 570808 | 0.94 | 1.27 | 1.43 |
| 594292 | 1.03 | 1.03 | 1.16 |
| 598768 | 1.14 | 1.08 | 0.97 |
| 598769 | 0.97 | 1.05 | 1.04 |
| 512497 | 0.99 | 1.17 | 1.38 |
| 569473 | 1.02 | 1.01 | 1.09 |

TABLE 27-continued

Body & Organ Weights in CD-1 mice

| ISIS No. | *Kidney % BW | *Liver % BW | *Spleen % BW |
|---|---|---|---|
| 594300 | 1.14 | 1.07 | 1.02 |
| 598777 | 1.05 | 1.20 | 1.01 |

*Fold change over Saline control group

Example 18: Six Week In Vivo Tolerability Study in Sprague-Dawley Rats

The newly designed ASOs from Table 1, above, were further evaluated in a 6 week study to assess plasma chemistry, body/organ weights and histology. Groups of Sprague-Dawley rats were administered 100 mpk/wk of ISIS 445569 or ISIS 512497. Further groups of Groups of Sprague-Dawley rats were administered 50 mpk/wk of ISIS 486178, ISIS 570808, ISIS 594292, ISIS 598768, ISIS 598769, ISIS 569473, ISIS 594300, and ISIS 598777. After six weeks and two days after each group of mice received the last dose, the mice were sacrificed and tissues were collected for analysis. For each group of mice, analysis to measure alanine transaminase levels, aspartate aminotransferase levels, blood urea nitrogen (BUN) levels, albumin levels, total bilirubin, creatine levels, and urinary creatine levels was measured. Additionally, organ weights were also measured, the results of which are presented in the tables below.

Example 19: Thirteen (13) Week In Vivo Study in Cynomolgus Monkeys

Groups of 4 cynomolgus male monkeys were administered 40 mg/kg/wk of ISIS 445569, ISIS 512497, ISIS 486178, ISIS 570808, ISIS 594292, ISIS 598768, ISIS 598769, ISIS 569473, ISIS 594300, and ISIS 598777 via subcutaneous injection. Thirteen weeks after the first dose, the animals were sacrificed and tissue analysis was performed. mRNA was isolated for real-time PCR analysis of rhesus monkey DMPK and normalized to RIBOGREEN®. Primer probe set RTS3164 (described above) was used to measure mRNA levels and the results are shown in Table 30 below. Additionally, further mRNA was isolated for real-time PCR analysis of rhesus monkey DMPK and normalized to RIBOGREEN® using primer probe set RTS4447 and the results are shown in Table 31 below. RTS4447 (forward sequence AGCCTGAGCCGGGAGATG, designated herein as SEQ ID NO: 20; reverse sequence GCGTAGTTGACTGGCAAAGTT, designated herein as SEQ ID NO: 21; probe sequence AGGCCATCCGCATGGCCAACC, designated herein as SEQ ID NO: 22).

TABLE 28

Plasma Chemistry & Urine Analysis in Sprague-Dawley Rats

| ISIS No. | ALT (U/L) | AST (U/L) | BUN (mg/dl) | Total protein (mg/dl) | T. Bil (mg/dl) | Creatinine (mg/dl) | Urine MTP/Creatine |
|---|---|---|---|---|---|---|---|
| Saline | 59.25 | 100.35 | 18.05 | 3.47 | 0.158 | 0.30 | 1.09 |
| 569473 | 101 | 198.25 | 25.9 | 2.74 | 0.195 | 0.4025 | 4.59 |
| 512497 | 211 | 240.25 | 19.32 | 3.58 | 0.17 | 0.39 | 6.18 |
| 598768 | 78.2 | 103.5 | 20.6 | 3.36 | 0.14 | 0.38 | 3.85 |
| 598769 | 84.5 | 104.5 | 18.6 | 3.52 | 0.15 | 0.34 | 3.02 |
| 570808 | 82 | 141 | 23.8 | 3.08 | 0.21 | 0.4 | 2.71 |
| 598777 | 109 | 119.5 | 21.65 | 3.79 | 0.22 | 0.37 | 2.56 |
| 445569 | 117.5 | 163.2 | 22.45 | 3.86 | 0.18 | 0.47 | 6.4 |
| 594300 | 66 | 80.75 | 17.53 | 3.59 | 0.12 | 0.29 | 4.72 |
| 486178 | 56.8 | 80.75 | 23.3 | 5.28 | 0.08 | 3.0 | 4.5 |
| 594292 | 64.5 | 80.5 | 19.62 | 3.38 | 0.098 | 0.29 | 5.17 |

TABLE 29

Plasma Chemistry & Urine Analysis in Sprague-Dawley Rats

| ISIS No. | Kidney (fold)* | Liver (fold)* | Spleen (fold)* |
|---|---|---|---|
| Saline | 1 | 1 | 1 |
| 569473 | 1.46 | 1.20 | 0.82 |
| 512497 | 1.03 | 1.22 | 1.94 |
| 598768 | 0.92 | 0.92 | 1.49 |
| 598769 | 0.93 | 1.04 | 0.98 |
| 570808 | 1.18 | 0.98 | 2.43 |
| 598777 | 1.07 | 0.93 | 2.31 |
| 445569 | 1 | 1.13 | 3.25 |
| 594300 | 1.03 | 1.04 | 1.94 |
| 486178 | 0.87 | 0.89 | 1.45 |
| 594292 | 1.08 | 1.01 | 2.04 |

*Fold change over Saline control group

TABLE 30

Dose-dependent inhibition of DMPK mRNA levels in Cynomolgus Monkeys using Primer Probe Set RTS3164

| ISIS No. | mg/ kg/wk | hDMPK mRNA levels (% PBS) | | | | | |
|---|---|---|---|---|---|---|---|
| | | TA | Quad (Left) | Gastroc | Kidney | Heart | Liver |
| PBS | 0 | 100 | 100 | 100 | 100 | 100 | 100 |
| 486178 | 40 | 26.1 | 30.8 | 49.3 | 55.3 | 45.8 | 44.9 |
| 445569 | 40 | 68.5 | 82.2 | 128.9 | 65.6 | 91.2 | 113.5 |
| 512497 | 40 | 60.3 | 58.7 | 66.7 | 61.9 | 74.2 | 68.1 |
| 598768 | 40 | 69.1 | 64.9 | 80.7 | 58.1 | 70.6 | 100.8 |
| 594300 | 40 | 73.6 | 80.2 | 106.0 | 57.9 | 97.5 | 91.6 |
| 594292 | 40 | 55.6 | 52.0 | 71.9 | 46.2 | 72.1 | 81.6 |
| 569473 | 40 | 44.8 | 31.7 | 61.6 | 44.0 | 58.7 | 28.0 |
| 598769 | 40 | 31.7 | 28.9 | 49.7 | 26.8 | 45.0 | 38.6 |
| 570808 | 40 | 2.5 | 4.4 | 6.4 | 29.7 | 17.5 | 7.2 |
| 598777 | 40 | 53.3 | 31.8 | 76.4 | 42.7 | 44.6 | 111.6 |

TABLE 31

Dose-dependent inhibition of DMPK mRNA levels in Cynomolgus Monkeys using Primer Probe Set RTS4447

| ISIS | mg/ | hDMPK mRNA levels (% PBS) | | | | | |
|---|---|---|---|---|---|---|---|
| No. | kg/wk | TA | Quad (Left) | Gastroc | Kidney | Heart | Liver |
| PBS | 0 | 100.0 | 100.0 | 100.0 | 100.0 | 100.0 | 100.0 |
| 486178 | 40 | 26.7 | 29.0 | 32.9 | 57.0 | 49.4 | 58.1 |
| 445569 | 40 | 85.4 | 87.4 | 147.1 | 77.1 | 97.2 | 93.6 |
| 512497 | 40 | 66.4 | 70.4 | 94.2 | 81.9 | 87.6 | 79.5 |
| 598768 | 40 | 48.3 | 76.4 | 106.7 | 73.7 | 81.0 | 85.1 |
| 594300 | 40 | 100.9 | 113.5 | 219.6 | 96.9 | 131.0 | 118.9 |
| 594292 | 40 | 76.5 | 75.7 | 151.7 | 86.6 | 107.1 | 108.6 |
| 569473 | 40 | 52.6 | 51.7 | 114.2 | 72.9 | 87.2 | 53.7 |
| 598769 | 40 | 45.2 | 57.6 | 86.3 | 56.6 | 65.4 | 72.5 |
| 570808 | 40 | 6.6 | 8.3 | 14.8 | 60.7 | 27.9 | 35.0 |
| 598777 | 40 | 55.1 | 56.8 | 124.1 | 78.6 | 88.9 | 131.2 |

Example 20: Thirteen (13) Week In Vivo Tolerability Study in Cynomolgus Monkeys Groups of cynomolgus male monkeys were administered 40 mg/kg of ISIS 445569, ISIS 512497, ISIS 486178, ISIS 570808, ISIS 594292, ISIS 598768, ISIS 598769, ISIS 569473, ISIS 594300, and ISIS 598777 via subcutaneous injection on days 1, 3, 5, and 7. Following administration on day 7, each monkey was administered 40 mg/kg/wk of ISIS 445569, ISIS 512497, ISIS 486178, ISIS 570808, ISIS 594292, ISIS 598768, ISIS 598769, ISIS 569473, ISIS 594300, and ISIS 598777 via subcutaneous injection.

48 hours after each monkey received a subcutaneous dose on days 28 and 91, blood and urine samples were taken for analysis. Some of the monkeys had blood and urine taken 48 hours after the dose given on day 56. Alanine aminotransferase (ALT), aspartate aminotransferase (AST), lactate dehydrogenase (LDH), and creatine kinase (CK) were measured for each animal in a treatment group and the average values are presented in the table below. Day of Sample values with a negative represent time point before treatment began. For example, a Day of Treatment value of −7 represents a sample taken 7 days before the first dose. Thirteen weeks after the first dose, the animals were sacrificed and tissue analysis was performed.

TABLE 32

Plasma Chemistry & Urine Analysis in Cynomolgus Monkeys

| ISIS No. | Day of Sample | ALT (U/L) | AST (U/L) | LDH (mg/dl) | CK (mg/dl) |
|---|---|---|---|---|---|
| Saline | −14 | 34.2 | 25.9 | 604.0 | 160.8 |
| | −7 | 38.8 | 27.8 | 861.3 | 249.0 |
| | 30 | 43.0 | 34.4 | 1029.0 | 300.0 |
| | 93 | 66.1 | 43.0 | 1257.3 | 898.8 |
| 486178 | −14 | 37.6 | 40.5 | 670.0 | 236.8 |
| | −7 | 49.8 | 55.0 | 1039.8 | 380.8 |
| | 30 | 47.0 | 41.2 | 875.4 | 415.0 |
| | 93 | 59.7 | 43.6 | 960.6 | 809.6 |
| 594292 | −14 | 38.9 | 32.0 | 776.3 | 375.8 |
| | −7 | 37.8 | 38.4 | 877.3 | 210.0 |
| | 30 | 35.4 | 39.6 | 666.0 | 93.8 |
| | 93 | 49.8 | 46.3 | 958.5 | 339.0 |
| 569473 | −14 | 49.4 | 49.8 | 1185.3 | 365.3 |
| | −7 | 50.4 | 59.7 | 1609.5 | 261.0 |
| | 30 | 46.7 | 52.5 | 1390.8 | 107.8 |
| | 93 | 56.3 | 49.8 | 1483.3 | 524.5 |
| 570808 | −14 | 47.1 | 46.8 | 896.0 | 448.3 |
| | −7 | 44.4 | 63.6 | 913.3 | 257.3 |
| | 30 | 47.1 | 57.7 | 660.5 | 125.0 |
| | 93 | 79.8 | 92.2 | 813.5 | 294.0 |
| 598768 | −14 | 37.9 | 41.6 | 666.3 | 253.8 |
| | −7 | 41.4 | 53.5 | 754.0 | 231.5 |
| | 30 | 37.2 | 38.9 | 652.3 | 106.3 |
| | 93 | 45.8 | 41.5 | 721.3 | 238.3 |
| 598769 | −14 | 44.2 | 36.1 | 1106.8 | 456.8 |
| | −7 | 45.7 | 41.5 | 1323.3 | 214.0 |
| | 30 | 40.3 | 42.0 | 981.0 | 147.8 |
| | 58 | 56.7 | 49.9 | 1101.5 | 552.3 |
| | 93 | 69.0 | 50.3 | 1167.3 | 749.5 |
| 512497 | −14 | 31.5 | 34.3 | 689.3 | 293.8 |
| | −7 | 39.0 | 45.4 | 1110.3 | 286.0 |
| | 30 | 47.2 | 60.2 | 960.5 | 202.5 |
| | 93 | 69.6 | 87.1 | 997.0 | 1118.5 |
| 594300 | −14 | 42.0 | 34.0 | 935.5 | 459.5 |
| | −7 | 42.1 | 53.6 | 1020.5 | 272.0 |
| | 30 | 28.0 | 34.6 | 620.8 | 124.5 |
| | 58 | 42.9 | 48.5 | 883.5 | 169.8 |
| | 93 | 45.7 | 45.7 | 835.5 | 252.3 |
| 598777 | −14 | 45.6 | 37.7 | 707.0 | 558.5 |
| | −7 | 43.3 | 50.0 | 705.8 | 200.3 |
| | 30 | 50.2 | 47.3 | 585.3 | 159.3 |
| | 93 | 79.2 | 56.1 | 1029.0 | 785.0 |
| 445569 | −14 | 40.2 | 44.2 | 835.8 | 404.0 |
| | −7 | 41.0 | 46.1 | 1074.3 | 305.5 |
| | 30 | 45.9 | 61.7 | 994.8 | 283.0 |
| | 58 | 51.6 | 85.1 | 739.0 | 117.8 |
| | 93 | 99.3 | 97.5 | 1583.5 | 2114.0 |

What is claimed is:

1. A compound comprising a single-stranded modified oligonucleotide consisting of 16-30 linked nucleosides and having a nucleobase sequence comprising a portion of at least 12 contiguous nucleobases 100% complementary to an equal length portion of nucleobases 10195 to 10294 of SEQ ID NO: 2, wherein the nucleobase sequence of the modified oligonucleotide is at least 90% complementary to SEQ ID NO: 2 as measured over the entirety of the modified oligonucleotide, and wherein the modified oligonucleotide comprises at least one modified internucleoside linkage and/or at least one modified nucleoside comprising a modified sugar.

2. The compound of claim 1, wherein the modified oligonucleotide comprises at least one modified internucleoside linkage.

3. The compound of claim 2, wherein each internucleoside linkage of the modified oligonucleotide is a phosphorothioate internucleoside linkage.

4. The compound of claim 1, wherein the modified oligonucleotide comprises at least one modified nucleoside comprising a modified sugar.

5. The compound of claim 4, wherein the modified oligonucleotide comprises at least two modified nucleosides comprising a modified sugar.

6. The compound of claim 4, wherein the modified sugar is a bicyclic sugar.

7. The compound of claim 6, wherein the bicyclic sugar is selected from cEt, LNA, α-L-LNA, ENA, and 2'-thio LNA.

8. The compound of claim 4, wherein the modified oligonucleotide comprises at least one 2'-substituted nucleoside.

9. The compound of claim 8, wherein the 2'-substituted nucleoside is selected from 2'-OCH3, 2'-F, and 2'-O-methoxyethyl.

10. The compound of claim 9, wherein the modified oligonucleotide comprises:

a gap segment consisting of 7-11 linked deoxynucleosides;

a 5' wing segment consisting of 2-6 linked nucleosides;

a 3' wing segment consisting of 2-6 linked nucleosides;

wherein the gap segment is positioned between the 5' wing segment and the 3' wing segment and wherein each nucleoside of each wing segment comprises a modified sugar.

11. The compound of claim 10, wherein the modified oligonucleotide consists of 16, 17, 18, 19, or 20 linked nucleosides.

12. A compound comprising a single-stranded modified oligonucleotide consisting of 16-30 linked nucleosides and having a nucleobase sequence comprising a portion of at least 12 contiguous nucleobases of any of SEQ ID NOs: 31 or 573-576, wherein the nucleobase sequence of the modified oligonucleotide is at least 90% complementary to SEQ ID NO: 2 as measured over the entirety of the modified oligonucleotide, and wherein the modified oligonucleotide comprises at least one modified internucleoside linkage and/or at least one modified nucleoside comprising a modified sugar.

13. The compound of claim 12, wherein the modified oligonucleotide comprises at least one modified internucleoside linkage.

14. The compound of claim 13, wherein each internucleoside linkage of the modified oligonucleotide is a phosphorothioate internucleoside linkage.

15. The compound of claim 14, wherein the modified oligonucleotide comprises at least one modified nucleoside comprising a modified sugar.

16. The compound of claim 15, wherein the modified oligonucleotide comprises at least two modified nucleosides comprising a modified sugar.

17. The compound of claim 15, wherein the modified sugar is a bicyclic sugar.

18. The compound of claim 17, wherein the bicyclic sugar is selected from cEt, LNA, α-L-LNA, ENA, and 2'-thio LNA.

19. The compound of claim 15, wherein the modified oligonucleotide comprises at least one 2'-substituted nucleoside.

20. The compound of claim 19, wherein the 2'-substituted nucleoside is selected from 2'-OCH3, 2'-F, and 2'-O-methoxyethyl.

21. The compound of claim 20, wherein the modified oligonucleotide comprises:

a gap segment consisting of 7-10 linked deoxynucleosides;

a 5' wing segment consisting of 2-5 linked nucleosides;

a 3' wing segment consisting of 2-5 linked nucleosides;

wherein the gap segment is positioned between the 5' wing segment and the 3' wing segment and wherein each nucleoside of each wing segment comprises a modified sugar.

22. The compound of claim 21, wherein the modified oligonucleotide consists of 16, 17, 18, 19, or 20 linked nucleosides.

23. A composition comprising the compound of claim 1 and a pharmaceutically acceptable carrier or diluent.

24. A composition comprising the compound of claim 12 and a pharmaceutically acceptable carrier or diluent.

25. A method of treating type 1 myotonic dystrophy (DM1) in an animal comprising administering to an animal in need thereof a compound according to claim 1.

26. A method of treating type 1 myotonic dystrophy (DM1) in an animal comprising administering to an animal in need thereof a compound according to claim 12.

* * * * *